United States Patent
Kimmel

(10) Patent No.: US 9,810,679 B2
(45) Date of Patent: Nov. 7, 2017

(54) INTELLIGENT PAD FOOT SOIL COMPACTION DEVICES AND METHODS OF USING SAME

(71) Applicant: COLORADO SCHOOL OF MINES, Golden, CO (US)

(72) Inventor: Shawn C. Kimmel, Lakewood, CO (US)

(*) Notice: Subject to any disclaimer, the term of this patent is extended or adjusted under 35 U.S.C. 154(b) by 0 days.

(21) Appl. No.: 14/677,587

(22) Filed: Apr. 2, 2015

(65) Prior Publication Data
US 2015/0316526 A1 Nov. 5, 2015

Related U.S. Application Data

(60) Provisional application No. 61/974,026, filed on Apr. 2, 2014.

(51) Int. Cl.
*G01N 3/08* (2006.01)
*G01N 33/24* (2006.01)
*E02D 1/02* (2006.01)
E02D 3/02 (2006.01)

(52) U.S. Cl.
CPC .......... *G01N 33/24* (2013.01); *E02D 1/022* (2013.01); *G01N 3/08* (2013.01); *E02D 1/02* (2013.01); *E02D 3/02* (2013.01)

(58) Field of Classification Search
CPC .. E02D 1/02; E02D 1/022; E02D 3/02; G01N 3/08; G01N 33/24
USPC ............................................ 73/84, 818, 760
See application file for complete search history.

(56) References Cited

U.S. PATENT DOCUMENTS

| 4,458,525 A | * | 7/1984 | Lutenegger | E02D 1/022 73/84 |
| 5,313,022 A | * | 5/1994 | Piroozmandi | G01L 1/2231 177/132 |
| 5,610,325 A | * | 3/1997 | Rajagopal | G01N 11/142 73/54.35 |
| 6,352,466 B1 | * | 3/2002 | Moore | B24B 37/013 257/E21.528 |
| 7,299,686 B2 | | 11/2007 | Briaud et al. | |
| 8,011,248 B2 | | 9/2011 | Troxler | |

(Continued)

*Primary Examiner* — Max Noori
(74) *Attorney, Agent, or Firm* — Dorsey & Whitney LLP

(57) ABSTRACT

Proper soil compaction is critical to providing structural support in any geo-construction project, particularly road construction. Described herein are devices, methods, and systems for intelligent soil compaction. In some embodiments, these disclosed systems, methods, and devices can provide up to 100% coverage with mechanistic measurements through machine integrated devices. These novel in-situ material characterization devices and methodologies enable continuous, mechanistic monitoring of soil compaction for use with a variety of geo-construction devices, including static pad foot soil compactors. In one embodiment, a strain gage instrumented pad is integrated into a pad foot soil compactor, and contact force is measured instrumented pad that is sensitive to soil compaction. In other embodiments, the disclosed device may allow for mechanistic measurements that may use a simplified geometry, and numerical and analytical modeling. In some embodiments, an inverse model, based on finite element modeling, may be used to extract constitutive parameters from plate strains.

16 Claims, 80 Drawing Sheets

(56) References Cited

U.S. PATENT DOCUMENTS

| | | |
|---|---|---|
| 8,393,223 B2 | 3/2013 | Delapierre et al. |
| 9,038,443 B1 * | 5/2015 | Pace .................... G01H 13/00 73/64.53 |

* cited by examiner

| Foam-Control EPS Geofoam Properties | | | | | | | | |
|---|---|---|---|---|---|---|---|---|
| Property | | ASTM D6817 | | | | | | |
| | | EPS12 | EPS15 | EPS19 | EPS22 | EPS29 | EPS39 | EPS46 |
| Density[1], min. | lb/ft³ (kg/m³) | 0.70 (11.2) | 0.90 (14.4) | 1.15 (18.4) | 1.35 (21.6) | 1.80 (28.8) | 2.40 (38.4) | 2.85 (45.7) |
| Compressive Resistance[1,2] @ 1% deformation, min. | psi psf (kPa) | 2.2 320 (15) | 3.6 520 (25) | 5.8 840 (40) | 7.3 1050 (50) | 10.9 1570 (75) | 15.0 2160 (103) | 18.6 2680 (128) |
| Elastic Modulus[1], min. | psi (kPa) | 220 (1500) | 360 (2500) | 580 (4000) | 730 (5000) | 1090 (7500) | 1500 (10300) | 1860 (12800) |
| Flexural Strength[1], min. | psi (kPa) | 10.0 (69) | 25.0 (172) | 30.0 (207) | 35.0 (240) | 50.0 (345) | 60.0 (414) | 75.0 (517) |
| Water Absorption[1] by total immersion, max. | vol % | 4.0 | 4.0 | 3.0 | 3.0 | 2.0 | 2.0 | 2.0 |
| Oxygen Index[1], min. | vol % | 24 | 24 | 24 | 24 | 24 | 24 | 24 |
| Buoyancy Force | lb/ft³ (kg/m³) | 61.7 (990) | 61.5 (980) | 61.3 (980) | 61.1 (980) | 60.6 (970) | 60.0 (960) | 59.5 (950) |
| Additional Properties for Compressible Applications | | | | | | | | |
| Compressive Resistance[1] @ 5% deformation, min. | psi psf (kPa) | 5.1 730 (35) | 8.0 1150 (55) | 13.1 1890 (90) | 16.7 2400 (115) | 24.7 3560 (170) | 35.0 5040 (241) | 43.5 6260 (300) |
| Compressive Resistance[1] @ 10% deformation, min. | psi psf (kPa) | 5.8 840 (40) | 10.2 1470 (70) | 16.0 2300 (110) | 19.6 2820 (135) | 29.0 4180 (200) | 40.0 5760 (276) | 50.0 7200 (345) |

[1] See ASTM D6817 Standard for test methods and complete information.
[2] Combined live and dead load stresses should not exceed the compressive resistance at 1% deformation.

FIG. 6

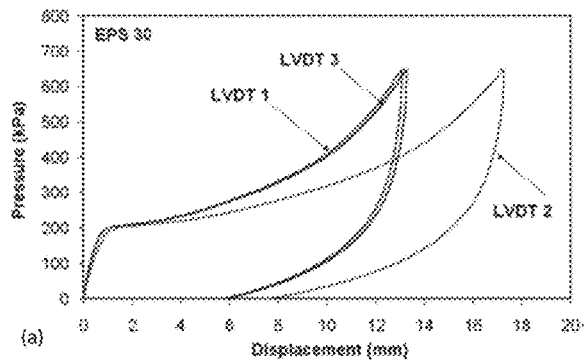 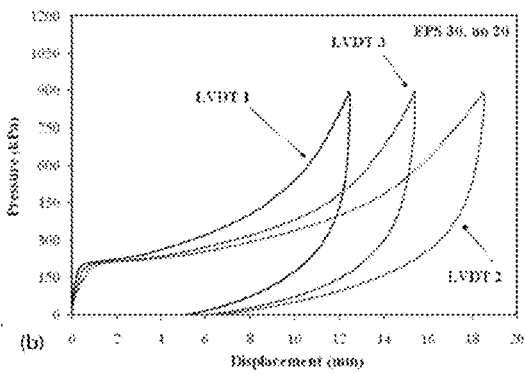
FIG. 9A  FIG. 9B
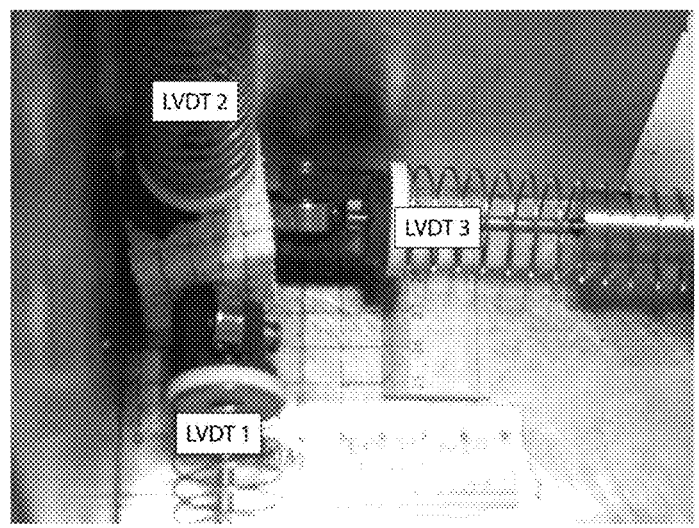
FIG. 10

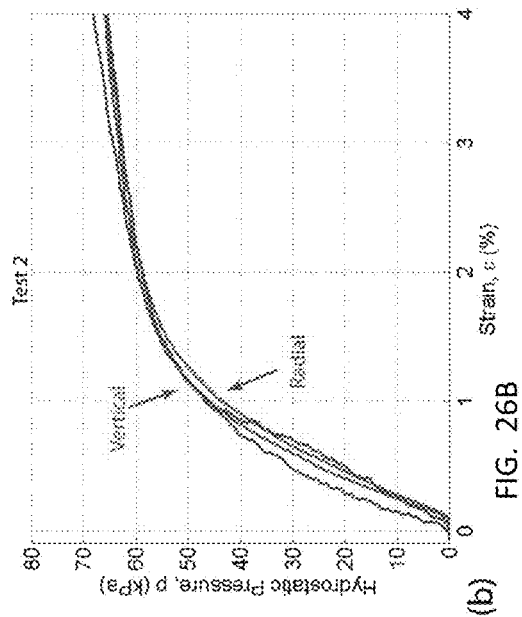
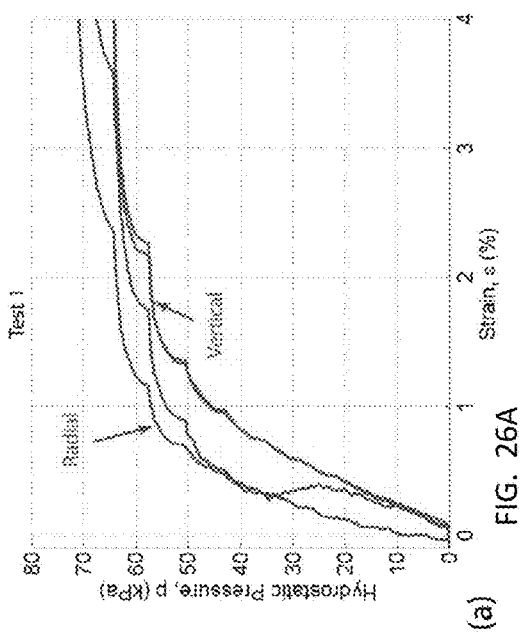
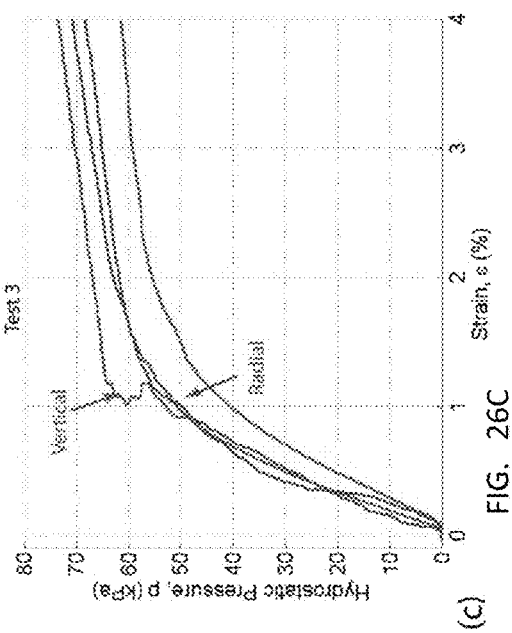
FIG. 26A
FIG. 26B
FIG. 26C

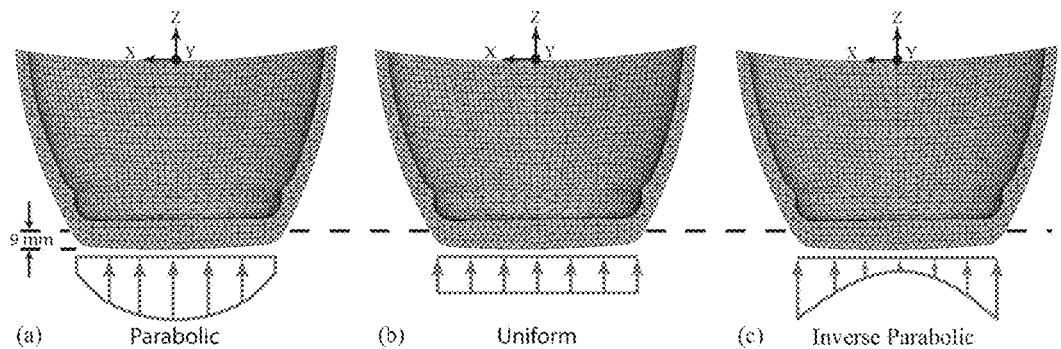
FIG. 36A   FIG. 36B   FIG. 36C
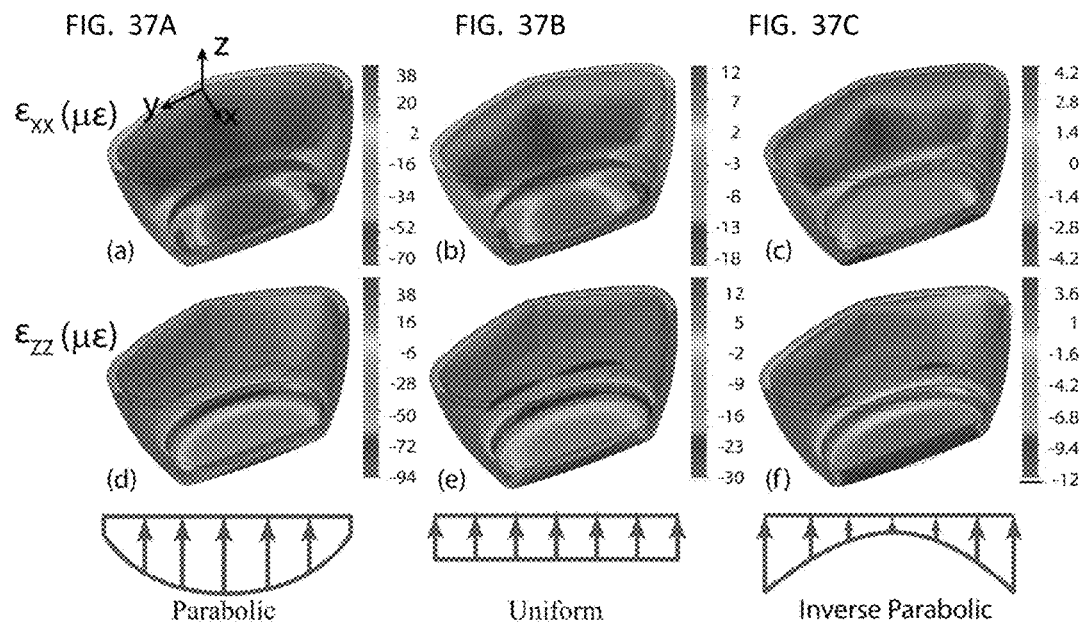
FIG. 37A   FIG. 37B   FIG. 37C
FIG. 37D   FIG. 37E   FIG. 37F

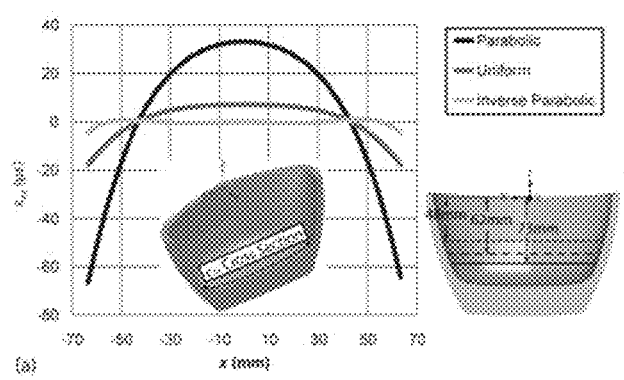
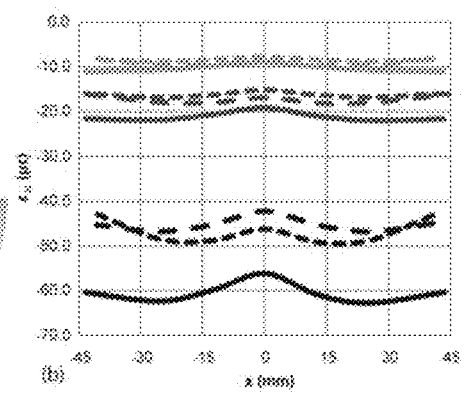
FIG. 38A              FIG. 38B
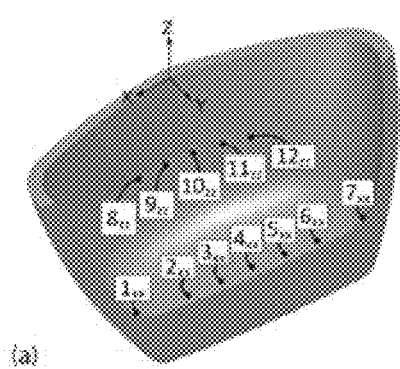
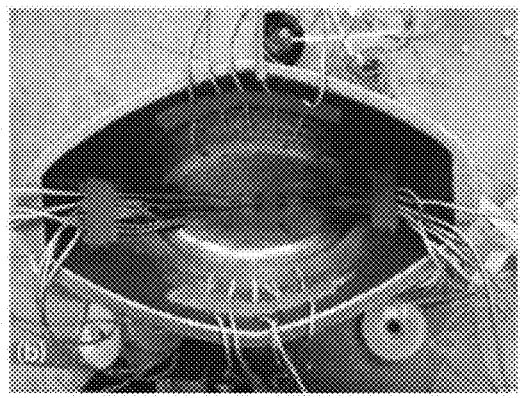
FIG. 39A              FIG. 39B

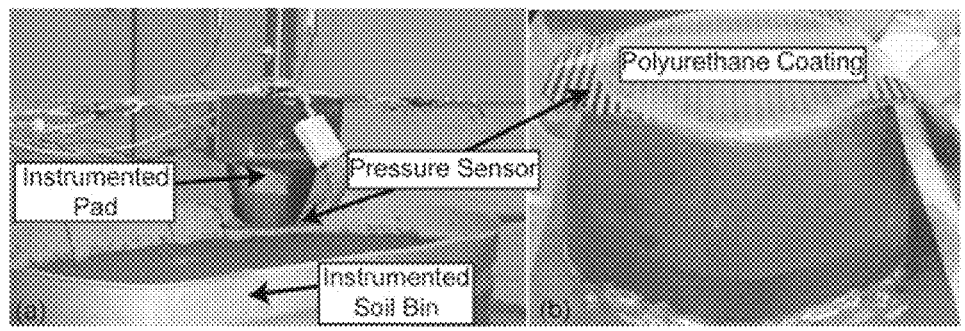
FIG. 40A          FIG. 40B
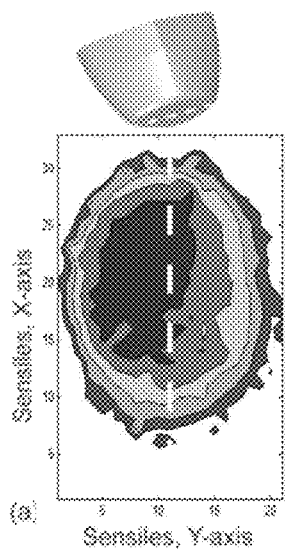  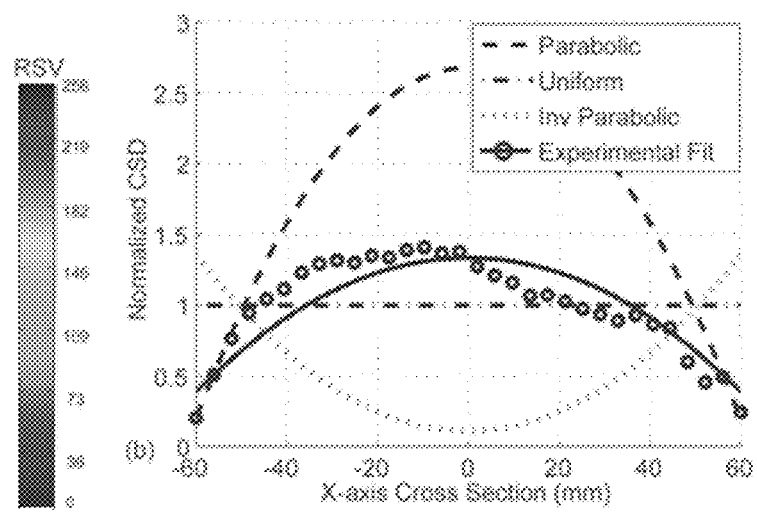
FIG. 41A          FIG. 41B

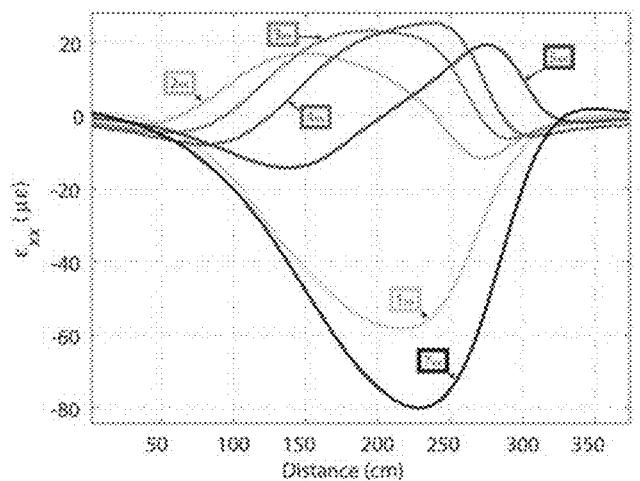
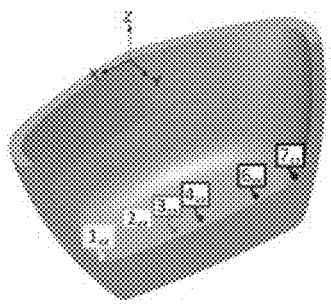
FIG. 44A
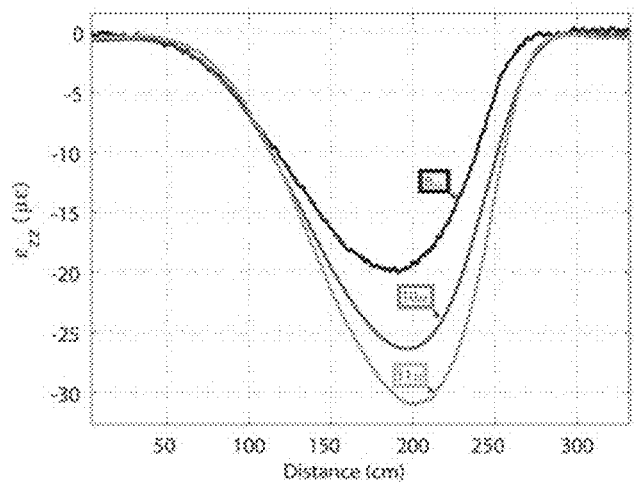
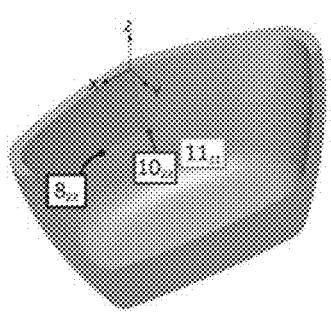
FIG. 44B
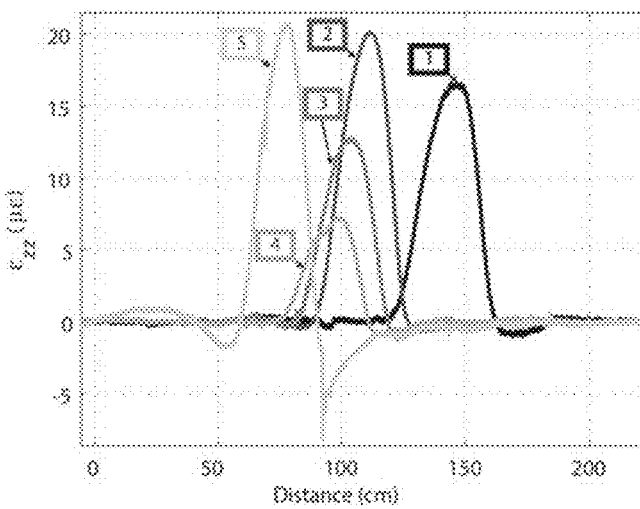
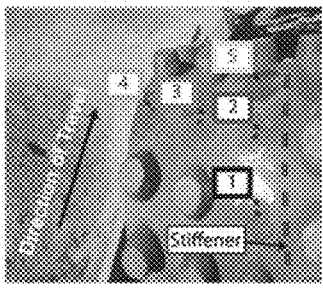
FIG. 45

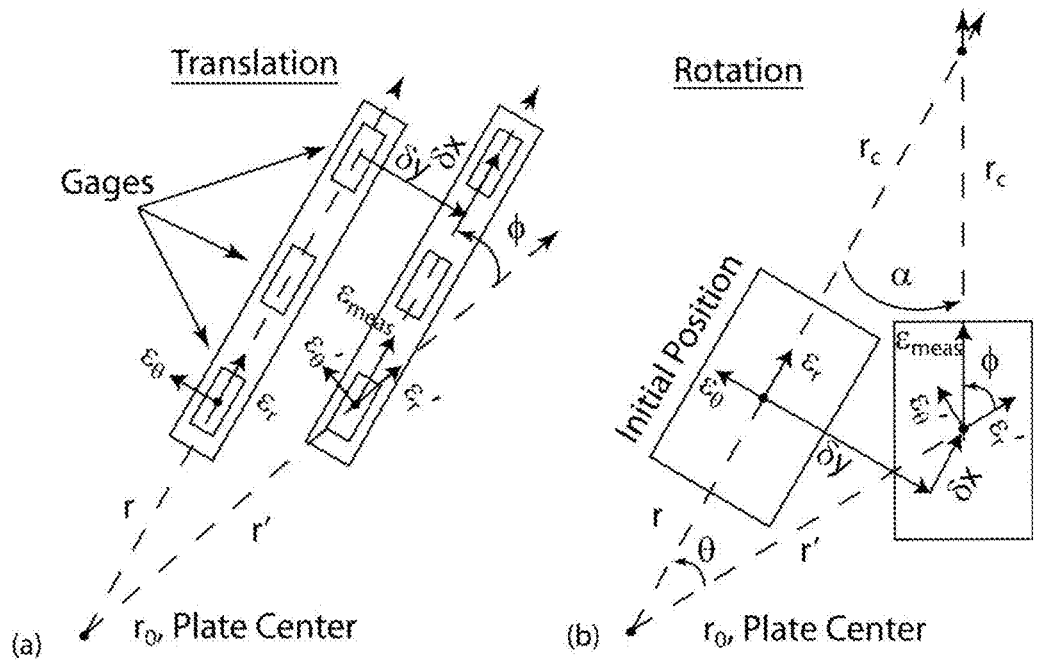
FIG. 55A
FIG. 55B
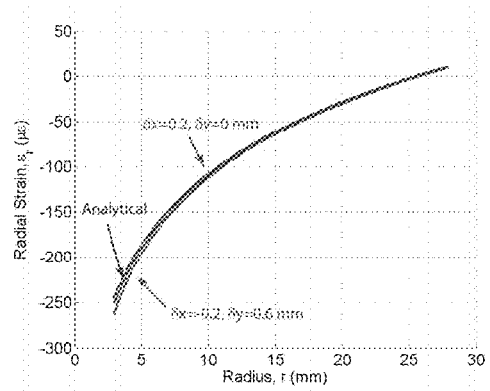
FIG. 56A
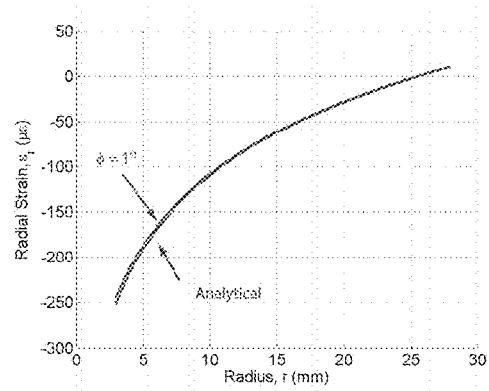
FIG. 56B

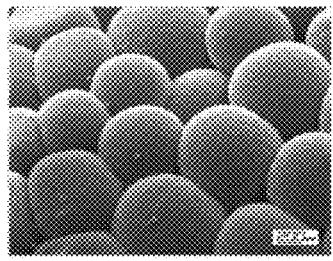
FIG. 91A
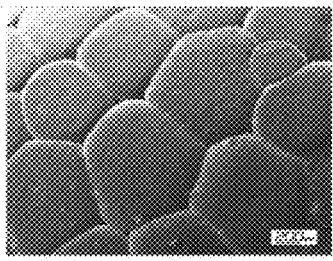
FIG. 91B
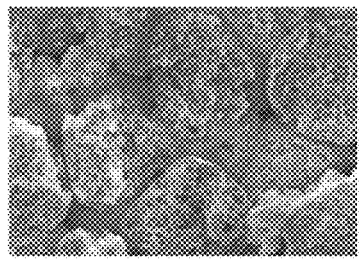
FIG. 91C
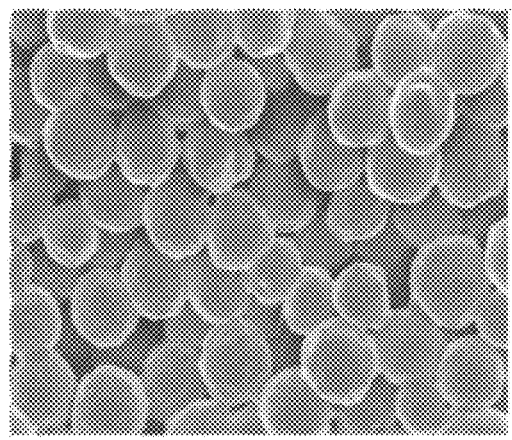
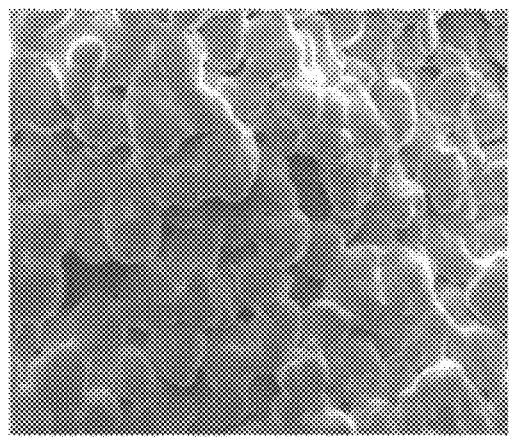
FIG. 92
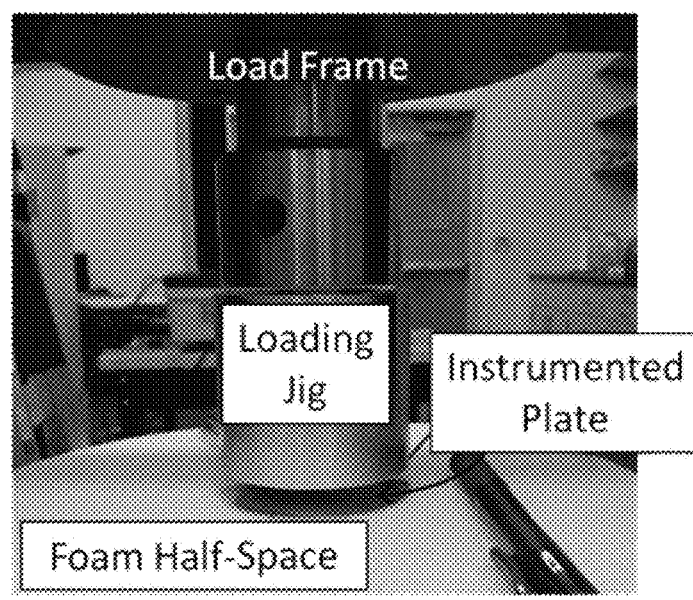
FIG. 93

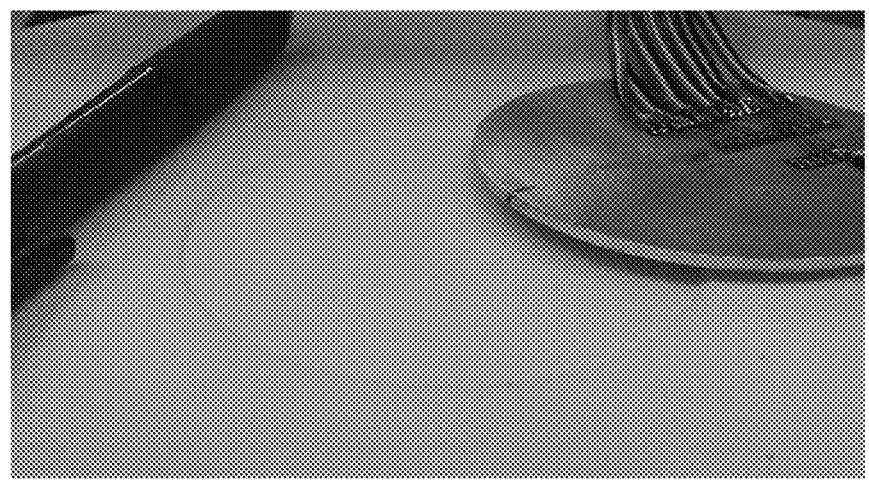
FIG. 116
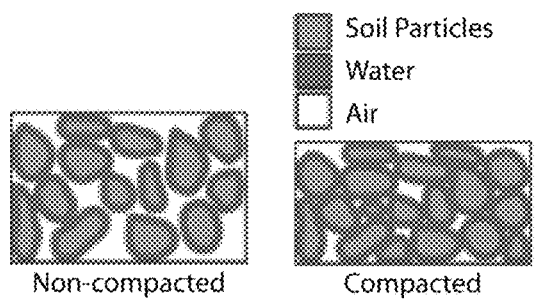
FIG. 117

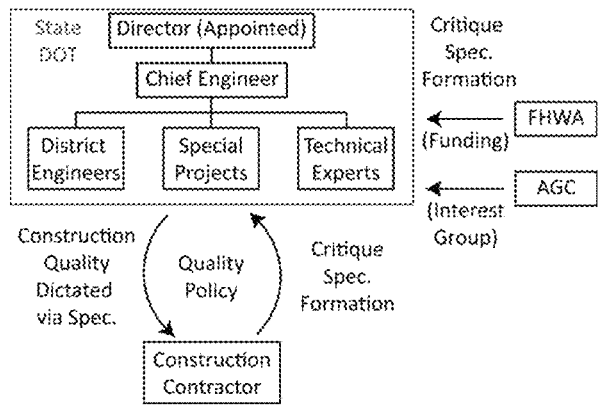
FIG. 118
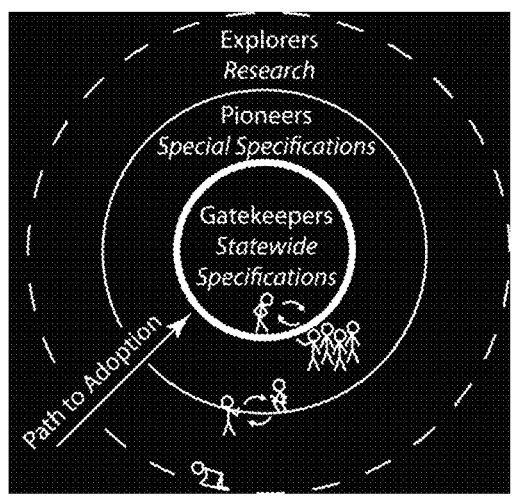
FIG. 119
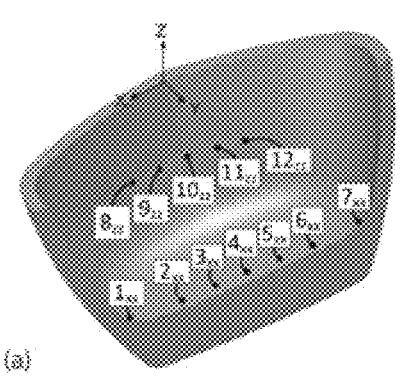 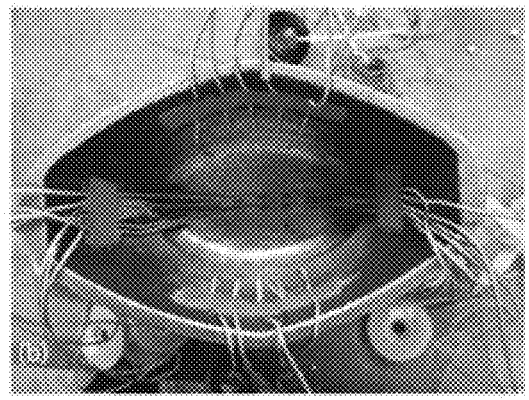
FIG. 120

INTELLIGENT PAD FOOT SOIL COMPACTION DEVICES AND METHODS OF USING SAME

CROSS REFERENCE TO RELATED APPLICATIONS

This application claims benefit of priority pursuant to 35 U.S.C. §119(e) of U.S. provisional patent application No. 61/974,026, filed Apr. 4, 2014, which is hereby incorporated herein by reference in its entirety.

FIELD

The disclosed processes, methods, devices, and systems are directed to real-time monitoring of compaction of an elastomeric material, such as soil.

BACKGROUND

Proper soil compaction is critical to providing adequate structural support in any geo-construction project, and is particularly relevant to road construction. The past decade has brought significant advances in earthwork compaction quality control/quality assurance (QC/QA). The most notable advance has been the introduction of roller compactor-integrated measurement of soil stiffness coupled with GPS-based documentation. Through measurement of drum vibration, roller-integrated measurement systems continuously report on the stiffness of the underlying soil. The combination of roller integrated measurement and GPS based mapping and documentation, referred to as continuous compaction control (CCC) or intelligent compaction (IC) presents a significant leap forward in QC/QA of embankment, subgrade, sub-base and base course compaction for pavements, airfields, and transit [2]. CCC and IC move earthwork QC/QA from less than 1% coverage provided by spot test methods (e.g., nuclear moisture density gage) to 100% coverage. CCC also offers the potential to measure soil stiffness or modulus, i.e., mechanistic parameters that enable the implementation of performance based specifications.

While vibration-based measurement has shown much promise on smooth drum vibratory rollers, subgrade soils are often compacted more efficiently with pad foot rollers (FIG. 1) operated without vibration or 'statically'. There is currently no CCC system for pad foot rollers that provides a measure of soil stiffness during static compaction. The only non-vibratory based measurement system is Caterpillar's machine drive power (MDP) approach that is based on propulsion power required to drive through soil during compaction. MDP has been empirically related to soil compaction [3, 4].

Current quality control/quality assurance practices often evaluate only 0.1% of the compaction area, which can be problematic for a heterogeneous material like soil. For example, in roadways, improper soil compaction can lead to potholes and cracking. The limitation in coverage is due to dependence on spot testing devices, such as the nuclear density gage or sand cone test. In addition to providing space coverage, these devices create a disparity between design and construction engineering by measuring density, whereas soil foundations are designed in terms of an elastic modulus and yield strength (i.e., stiffness and bearing capacity).

What is needed is a soil compaction device and methods for monitoring compaction with greatly increased coverage, using mechanistic measurements.

SUMMARY

Realizing that stiffness is a function of contact force and deformation, an envisioned system will estimate soil stiffness through a combination of force measurements from strain gage instrumented pads and soil deformation measurements from laser sensors (FIG. 1). In pursuit of this system, Chapter 3 develops a pad-based contact force measurement system.

While the instrumented pad system discussed in Chapter 3 correlated well with soil compaction levels, it had some limitations. In order to calculate elastic modulus, the instrumented pad readings must be combined with deflection measurements, and thus requires additional sensors. Furthermore, the pad-based contact force measurement was empirical in nature, i.e., the pad must be calibrated for each new soil. Different soils are known to exhibit varying contact behavior, which influences pad strain response. If the soil type could be identified, for example, through the identification of plasticity parameters, it may be possible to determine analyze pad strain results without a soil specific calibration procedure. Therefore, limitations of the pad may be summarized as (a) it cannot independently measure elastic modulus, and (b) it cannot independently adapt its measurements to various soil types.

Chapters 4 and 5 conceive approaches for addressing the above limitations by simplifying the geometry of the instrumented pad to an instrumented plate, as shown in FIG. 2. Chapter 4 addresses limitation (a) above by developing an inverse model that can estimate elastic modulus of a half-space directly from plate strains, i.e., there is no need for a deflection measurement. Chapter 5 addresses limitation (b) above by investigating plate strain sensitivity to plasticity parameters of a half-space and developing an inverse model to determine uniaxial compressive yield stress.

The experimental tests for Chapters 4 and 5 are conducted with expanded polystyrene (EPS) geo-foam. EPS geo-foam is used in various geotechnical applications and has similar elastic modulus to soils used in foundations. Additionally, EPS geo-foam offers the advantage of being a more repeatable and well-characterized elasto-plastic material than soil. Chapter 3 discusses the constitutive model used to characterize EPS geo-foam, and results from laboratory experiments carried out to obtain the elastic and plastic constitutive parameters.

The design and verification of the instrumented plate is introduced in Chapter 4. The simplicity of the instrumented plate allows for modeling of a plate on an elastic half-space in both numerical (i.e., finite element) and analytical models. An error analysis was conducted on the plate to investigate the influence of various instrumentation and experimental errors. The instrumented plate was then verified for accuracy by comparing experimental tests in a simply supported configuration (i.e., that introduces minimal experimental variables) to the error analysis.

Chapter 4 also introduces the first mechanistic in-situ measurement method for the instrumented plate. The plate strain sensitivity to elastic modulus of a half-space is addressed. An inverse model is developed to estimate the elastic modulus of a half-space based on plate strain measurements. The inverse model uses both the numerical and analytical models to provide estimates of elastic modulus. Through experimental testing of the instrumented plate on EPS geo-foam, the inverse model is evaluated.

A second mechanistic in-situ measurement method for the instrumented plate is discussed in Chapter 5. A FE model is developed that captures the elasto-plastic behavior of the EPS geo-foam under plate loading. Plate strain sensitivity to half-space plasticity parameters is investigated. According to findings of the sensitivity analysis, an inverse model is developed for determining the uniaxial yield stress of the half-space. This inverse model is evaluated with experimental plate loading tests on elasto-plastic EPS geo-foam.

Deviating from the traditional purely technical engineering thesis, I also investigate public policy dimensions associated with the implications of the technical research. The in-situ devices discussed in this thesis may be particularly beneficial to highway construction applications. However, it is recognized that the highway construction industry is notoriously slow to adopt innovations[5]. Researchers, practitioners, and public officials would benefit from a better understand of the pathways and barriers to innovation adoption. Chapter 6 investigates innovation in the US highway construction industry through interviews with a wide range of industry professionals. A case study is conducted on intelligent vibratory soil compaction, which is currently at varying levels of adoption in different US states. Through the lens of Kingdon's theory of decision agendas, key players are identified and the pathways and barriers to adoption are discussed. Chapter 7 provides concluding remarks and recommendations for future work.

Disclosed herein is a tool for estimating mechanical properties of a material comprising a plate configured to receive force; one or more measuring devices connected to the plate for measuring the force applied; one or more measuring devices connected to the plate for measuring mechanical strain in the plate; and a computing device for receiving the force and strain measurements and describing a mechanical interaction between the plate and material. In some embodiments, the plate can be a pad on a soil compression machine or device, or a pad on a pad foot roller, and the plate can be circular and defines a planar surface, and flexible and substantially thin, as to produce measurable mechanical strain. In some embodiments, the device for measuring applied force can be an electronic load cell, or selected from an electrical resistance strain gage, fiber-bragg grating, photo-stress, and combinations thereof. In some embodiments the devices can be mounted to a surface of the plate to provide measurements of plate strain during loading.

Also disclosed, is method for estimating mechanical properties of a material comprising positioning a plate on a material; applying a load to the plate to create an applied force; measuring the applied force with one or more force measuring devices; measuring mechanical strains of the plate with one or more strain measuring devices; modeling and describing a mechanical interaction between the plate and the material; and thereby estimating mechanical material properties of the material. In some embodiments, the modeling stem may include an analytical model that predicts plate strains as a function of applied force, and wherein a half-space elastic modulus is used to estimate elastic modulus from measured plate strains and applied force; a numerical model that predicts plate strains as a function of applied force, and wherein a half-space elastic modulus is used to estimate elastic modulus from measured plate strains and applied force; a numerical model that predicts plate strains as a function of applied force, and wherein a half-space yield strength is used to estimate yield strength from measured plate strains and applied force; and/or a numerical model that predicts plate strains as a function of applied force, and wherein a half-space plastic hardening curve is used to estimate plastic hardening curve from measured plate strains and applied force. In some embodiments, the force is applied force that can be applied at the center of the plate and/or around the edge of the plate; applied in a direction selected from vertically, diagonally, horizontally, and combinations thereof. In various embodiments, the plate is a pad on a soil compression machine or device; or a pad on a pad foot roller. In some embodiments, the plate is circular and defines a planar surface and/or can be flexible and substantially thin, as to produce measurable mechanical strain. In some embodiments, the device for measuring strain is selected from an electrical resistance strain gage, fiber-bragg grating, photo-stress, and combinations thereof, and the devices can be mounted to a surface of the plate to provide measurements of plate strain during loading. In some embodiments, the device for measuring applied force is an electronic load cell.

BRIEF DESCRIPTION OF THE DRAWINGS

FIG. 6 Properties of EPS foam.

FIG. 9A-B Hydrostatic compression results from EPS30 for 50×50×50 mm cubes [9a) from [14], 9b) from[1]).

FIG. 10 Hydrostatic compression experimental setup used by Ozturk with an EPS foam specimen at max load.

FIG. 26A-C Radial and vertical strain measurements versus hydrostatic pressure during three hydrostatic compression tests on EPS12. Note that two sensors collect data in each direction for each test.

FIG. 36A-C Loading on pad model. Contact stress distributions used in FE include: 36a) parabolic simulates cohesionless soils, 36b) uniform simulates an intermediate soil, and 36c) inverse parabolic simulates a cohesive soil. The dashed line shows the area below which loading is applied, simulating 9 mm of soil penetration.

FIG. 37A-F FEA results: normal strains in x and z directions for the three different loading cases. Positive strains are tensile.

FIG. 38A-B FEA results for normal strain distributions for 38a) $\epsilon_{xx}$ along inside bottom pad face for parabolic, uniform and inverse parabolic CSDs (9 kN loading) at y=0; 38b) $\epsilon_{zz}$ along the sidewall for parabolic, uniform, and inverse parabolic CSDs (9 kN loading) at −73, −62, and −48 mm from the top of the pad.

FIG. 39A-B Layout of strain gage instrumented pad

FIG. 40A-B 40a) Instrumented pad ready to pressed into an instrumented soil bin, 40b) Tekscan F-3000 TPS attached to pad with polyurethane coating.

FIG. 41A-B 41a) Typical TPS reading of contact stress distribution between the pad and granular soil. 41b) Cross section (along x-axis) of TPS results from compacted granular soil is compared to preliminary FE loading scenarios. Pressures are normalize to an average pressure of unity, including loading around the sidewalls of the pad, which are not shown. (F=4.7 kN)

FIG. 44A-B Strain time histories of bottom $\epsilon_{xx}$ gages 44a) and sidewall $\epsilon_{zz}$ gages 44b) for pad 1 during forward pass 9 of test bed 1. Gages $5_{xx}$, $8_{zz}$, and $9_{zz}$ malfunctioned during the tests; note: tensile strains are positive.

FIG. 45 Strains for Gage $10_{zz}$ from pads 1 through 5 of Test Bed 1; note: compressive strains are positive.

FIG. 55A-B Installation errors arise from 55a) translation of gages, and 55b) rotation of gages.

FIG. 56A-B The influence of installation errors on plate strains for 56a) translation, and 56b) rotation.

FIG. 91*a-c* Surface bead structure for polystyrene foam 91*a*) low fusion, 91*b*) high fusion, 91*c*) high fusion after fracture.

FIG. 92 Bead collapse and surface residue formation from heating of foam.

FIG. 93 Experimental setup for an elastic plate on a plastic half-space using an MTS load frame.

FIG. 116 Foam sample after testing, showing ~1 mm ridge created by the edge of the plate.

FIG. 117 Example of a roller compactor used on highway projects.

FIG. 118 Structure of highway construction specification formation and implementation.

FIG. 119 Depiction of three of the four roles required for innovation adoption in highway construction: explorers research potential innovations; pioneers apply promising innovations on projects through special specifications; and gatekeepers determine if an innovation is suitable for state-wide use. The fourth role, leaders, help to coordinate and motivate the interactions of the other roles.

FIG. 120 Layout of strain gage instrumented pad.

DETAILED DESCRIPTION

Chapter 2—Experimental Characterization of EPS GEO-Foam

In order to develop a monitoring device for determining mechanical properties of a material, it is useful to have a prototype material that is well behaved and whose mechanical behavior closely follows an established constitutive model. Ideally, such a material would have stiffness and strength properties similar to that of soil, and thus these tests could provide good insight into the new sensor's applicability to soil characterization. Fortunately, one such material exists that is both inexpensive and readily available: expanded polystyrene (EPS) foam. EPS geo-foam was used as the testing substrate for the research discussed in this thesis.

In this chapter, the structure and characteristics of EPS foams are introduced. The constitutive model used to characterize the foam is described. A section is devoted to discussing the experimental testing required to derive the mechanical properties of the foam. Finally, the results and discussion of the experimental testing are covered.

2.1 EPS Foams

EPS foam belongs to a family of cellular polymeric materials that are well suited for a number of applications because of their unique properties. EPS is a lightweight material, ranging from 10 to 50 kg/m3, with stiffness, energy absorption, and thermal resistance properties that make it useful for a number of applications. For example, EPS foam is used as structural fill for earthen structures, impact resistant packaging, and coolers[6-8].

The unique properties of cellular foams arise from their composition and structure, which are a result of their manufacturing process. According to ACH Foam [9], from whom the samples used in this research were obtained, EPS foam is manufactured from polystyrene resin beads containing pentane gas. First, a pre-expansion phase expands beads to nearly 50 times their original size through the release of the pentane gas in a heating process. The beads are further expanded and fused together inside a mold with the injection of pressurized steam.

Figure 1:
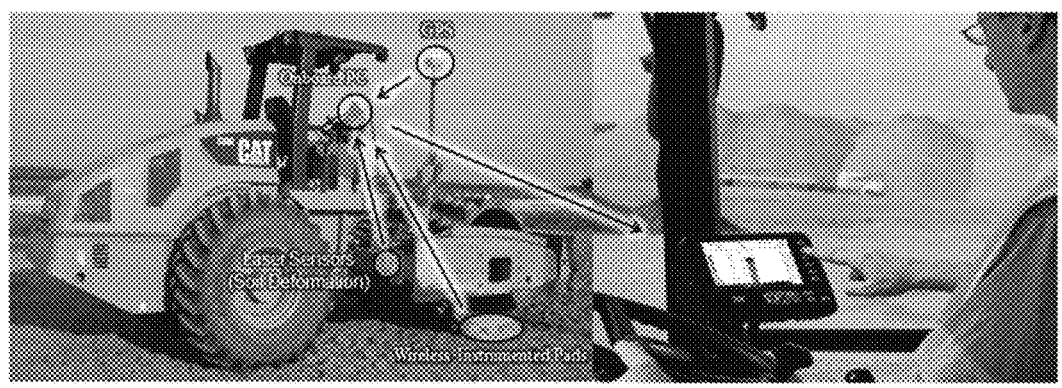
FIG. 1 Concept of stiffness monitoring pad foot soil compactor: stiffness is determined by force sensing pads and deflection sensing lasers FIG. 2 The instrumented pad was simplified to an instrumented plate.
Figure 2:
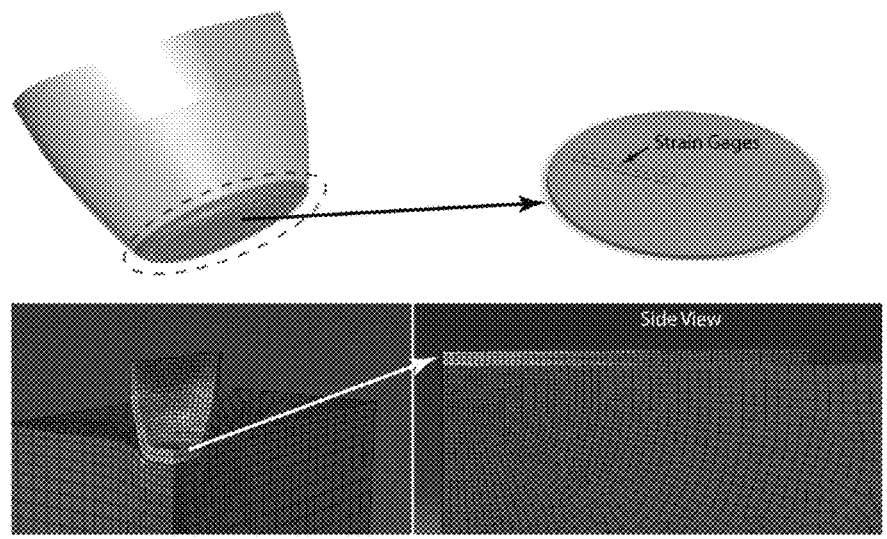
Figures 3A, 3B:
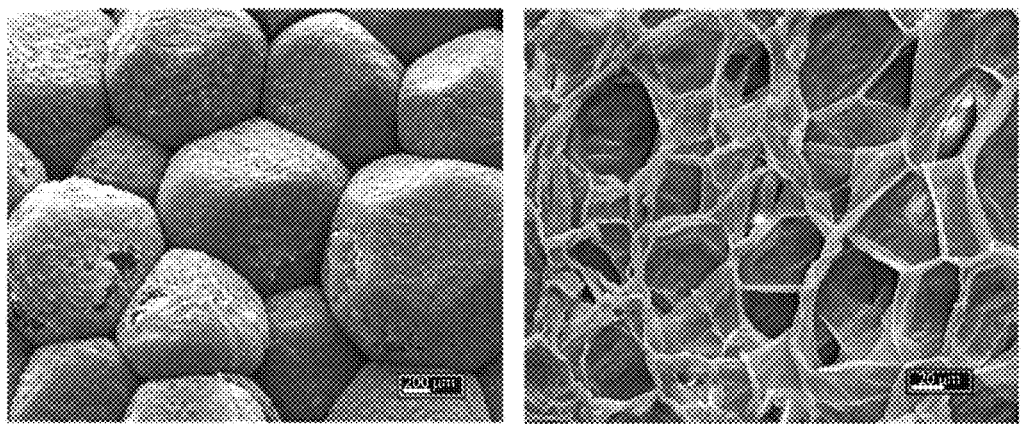
FIG. 3A-B Typical polystyrene foam structure: 3a) closed cell structure of expanded beads, and 3b) honeycombed cellular structure within a bead.

The typical structure of EPS foam can be visualized from scanning electron microscope imagery, as is presented in FIG. 3.

Figure 4:
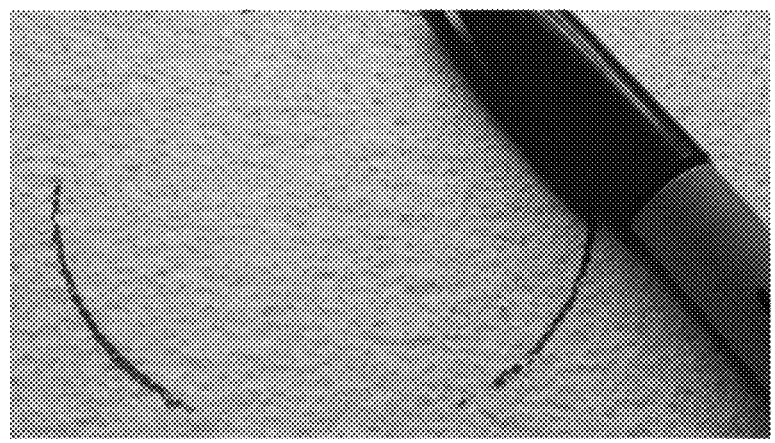
FIG. 4 Picture of the surface of EPS12 used in testing.

For this research, the foam used was ACH geo-foam, which are used as a replacement for structural fill in earthen structures. FIG. 4 shows a picture of surface of one of the foam samples. Foam samples were obtained in two different sized sheets, 101×305×305 mm and 610×1219×1219 mm.

Figure 5:
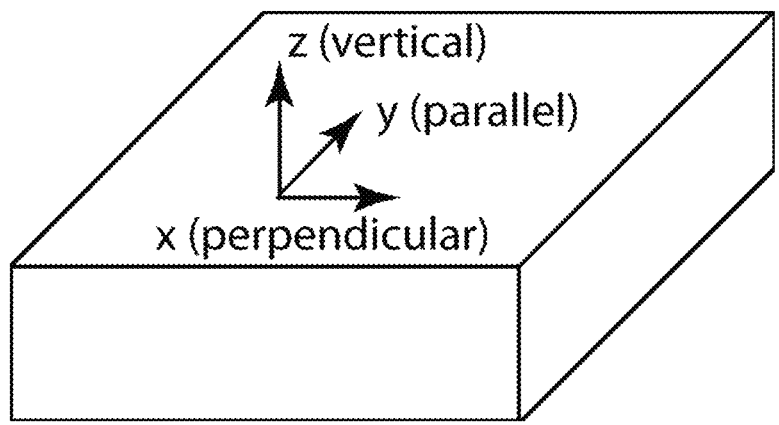
FIG. 5 Coordinate system for foam blocks.

The coordinate system for the foam sheets is shown in FIG. 5, with the z-axis being vertical during the manufacturing expansion process.

Figure 7:
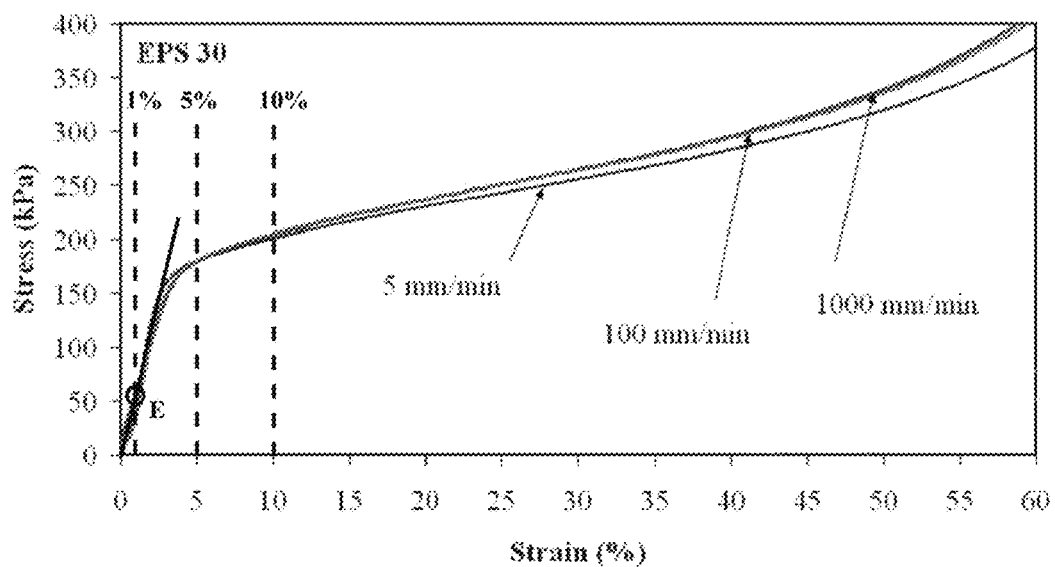
FIG. 7 Uniaxial compression test results for EPS30 foam at three different load rates. ACH foam publishes the minimum expected stress values at 1%, 5% and 10% strain, shown by dotted lines.

Mechanical properties of EPS foam can take on a range of values depending on the foam density. For example, FIG. 6 shows the properties for ACH's geo-foams. Properties given in this table are obtained using the ASTM 6817 standard. Several of these properties are obtained from a uniaxial compression test (ASTM 1621), an example of which is shown in FIG. 7. These tests are conducted in the z (vertical) axis. The stress at 1%, 5%, and 10% strain is shown by dotted lines in FIG. 7. The elastic modulus, E, is determined based on the stress at 1% strain, as shown by the circle and solid line in FIG. 7. The elastic modulus of these materials ranges from 15 to 128 kPa. The yield strength is usually close to the 'Compressive Resistance at 5% deformation', which ranges from 35-300 kPa. In my research, four foams were used: EPS12, EPS22, and two different batches of EPS29 (denoted EPS29A and EPS29B).

2.2 Foam Constitutive Model

EPS foam has shown good agreement between experimental testing and a constitutive model described as linear, elastic, isotropic, homogeneous, and with plastic behavior modeled by the Crushable Foam model[11-13]. This section describes the constitutive model and reviews literature that has characterized the elastic and plastic mechanical behavior of EPS foams.

Figure 8:
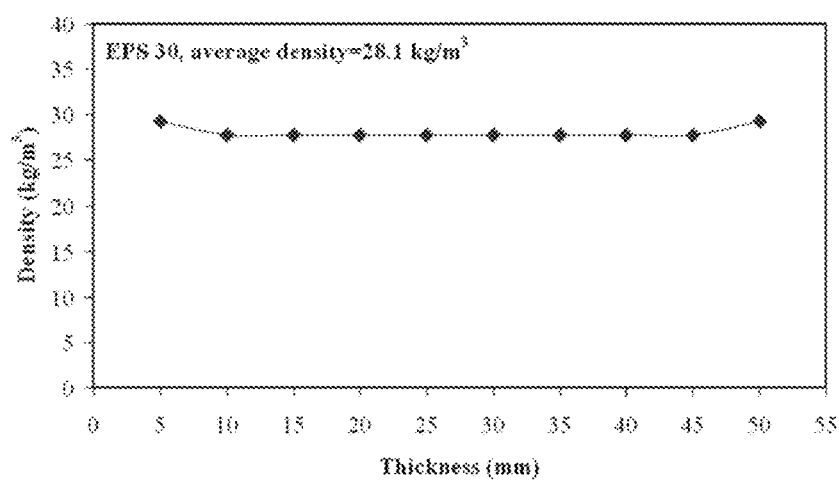
FIG. 8 Density of EPS 30 throughout the thickness of a specimen Ozturk.

Considerable work has been conducted on foams to characterize their mechanical behavior. While the material is clearly heterogeneous on a microscopic level due to variation in bead expansion (see FIG. 3), the macroscopic behavior can generally be considered homogeneous with the exception of a thin surface layer exhibiting increased density (see FIG. 8)[1]. This thin layer of higher density foam is a product of the manufacturing process.

In the elastic region, EPS foam shows good linearity, as shown by the stress-strain curve up to 2.5% strain in FIG. 7. Also shown in FIG. 7 is the minimal impact of loading rate between 5 to 1000 mm/s. The value for Poisson's ratio of EPS foam is suggested as 0.12 by the EPS Industry Alliance [17] and as an equation by the manufacturer EDO[18]

$$v = 0.0056\rho + 0.0024 \quad (2.1)$$

where $\alpha$ is the foam density in kg/m3. For the foams used in this research, this equation leads to a range of 0.1 to 0.17. A Poisson's ratio of 0.1 has been successfully used to achieve good agreement between experimental tests and numerical models[19-21]. In this research, a value of 0.1 will be adopted, as this is in line with both manufacturer specifications and academic literature.

Direct experimental characterization of the isotropy of EPS foam has not provided clear results. Extruded polystyrene (XPS), which is the same polymer as EPS but manufactured with a different process, has been found to be transversely isotropic due to the extrusion manufacturing process[20]. However, according to discussions with foam manufacturer ACH, the expansion manufacturing process of EPS foam produces an isotropic material[22]. Hydrostatic tests, i.e., when equal pressure is applied to all sides, can be used to characterize isotropy. The results of Ozturk's[1, 14] hydrostatic compression tests on 50×50×50 mm EPS foam cubes are shown in FIG. 9. In this figure, LVDT 2 is oriented in the z (vertical) direction, and LVDT 1 and 3 are perpendicular to the z-axis, although it is not specified which is in the x or y direction. Ozturk[14] claims that the EPS foam is transversely isotropic based on FIG. 9(a), yet the earlier work of Ozturk's thesis[1] using the same device appears less decisive in FIG. 9(b). A photo of Ozturk's experimental setup with a specimen at maximum pressure is shown in FIG. 10. The warping of the specimen may be a factor in the differences experienced between tests. A clear verdict on the isotropy of EPS foam is not found from these tests.

Despite the lack of direct experimental characterization of EPS foam isotropy, many experimentalists have found good agreement between isotropic EPS models and experimental tests in a number of uniaxial loading scenarios, e.g., block and cylinder indentation testing[1], helmet crash testing[23], and crushing of pyramids[20]. Considering the high quality of agreement found between isotropic FE models and indentation type testing, the research discussed in this thesis will assume that the material is isotropic. The tests conducted in this chapter further support the isotropic assumption.

In the elastic region, the EPS foam is modeled according to Hooke's Law, $$\epsilon = S : \sigma \quad (2.2)$$

where $\sigma$ is the Cauchy stress tensor, S is the fourth order compliance tensor, and $\epsilon$ is the infinitesimal strain tensor. This equation can also be written in matrix form:

$$\begin{bmatrix} \varepsilon_{xx} \\ \varepsilon_{yy} \\ \varepsilon_{zz} \\ \gamma_{yz} \\ \gamma_{xz} \\ \gamma_{xy} \end{bmatrix} = \frac{1}{E} \begin{bmatrix} 1 & -v & -v & 0 & 0 & 0 \\ -v & 1 & -v & 0 & 0 & 0 \\ -v & -v & 1 & 0 & 0 & 0 \\ 0 & 0 & 0 & 2(1+v) & 0 & 0 \\ 0 & 0 & 0 & 0 & 2(1+v) & 0 \\ 0 & 0 & 0 & 0 & 0 & 2(1+v) \end{bmatrix} \begin{bmatrix} \sigma_{xx} \\ \sigma_{yy} \\ \sigma_{zz} \\ \sigma_{yz} \\ \sigma_{xz} \\ \sigma_{xy} \end{bmatrix} \quad (2.3)$$

where E is Young's modulus and v is the Poisson's ratio.

Within the plastic region, EPS foam can be modeled with a Crushable Foam plasticity model. Combined with linear, elastic, isotropic, homogeneous behavior, the Crushable Foam model has shown good agreement with experimental tests subjected to a single monotonic loading cycle[1, 14, 20]. The proposed monitoring device uses a single monotonic loading cycle, which supports the use of the Crushable Foam model. In this research, the model was implemented with the Abaqus FEA commercial software package, which includes Crushable Foam as a standard model.

Figure 11:
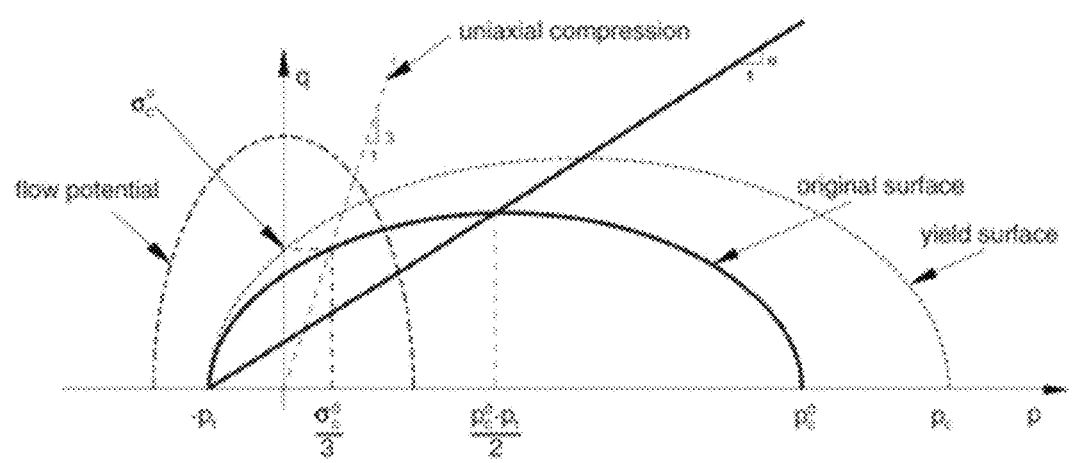
FIG. 11 Crushable Foam plasticity model in Abaqus, with original and post-yield yield surfaces, and flow potential.

This section defines the Crushable Foam plasticity model in terms of its yield surface, flow rule, and hardening rule. The Crushable Foam model has an elliptical yield surface in the deviatoric stress plane, as shown in FIG. 11. The yield surface is defined as $$F = \sqrt{q^2 + \alpha^2(p - p_0)^2} - B \quad (2.4)$$

where p is the mean normal stress $$p = -1/3 * \text{trace}[\sigma] \quad (2.5)$$

where $\alpha$ is the shape factor of the ellipse as a ratio of the vertical axis (B) over the horizontal axis (A), $$\alpha = B/A; \; B = \frac{p_c + p_t}{2} \quad (2.6)$$

where pc and pt are the yield stresses in hydrostatic compression and tension, respectively. The variable q is the von Mises stress given by the double dot produce of the deviatoric stress tensor, S, according to $$q = \sqrt{\frac{3}{2}S:S} \tag{2.7}$$

where S is $$S = \sigma - pI \tag{2.8}$$

where I is the identity matrix of same dimension as σ.

The yield surface is defined through two parameters, (1) the compressive yield stress ratio, k, and (2) the hydrostatic yield stress ratio, $k_t$. The first is defined by:

$$k = \frac{\sigma_c^0}{p_c^0} \tag{2.9}$$

where $\sigma_c^0$ is the initial uniaxial compressive yield stress and $p_c^0$ is the initial hydrostatic compressive yield stress. These values are identified as 'initial' in reference to the virgin state of the material. After yield, these values may change, e.g., increase in the case of hardening behavior. For the purposes of this research, the material is obtained in virgin form and it is loaded monotonically, so the yield stress values used to model the material are always the initial yield stress values. Therefore, in the rest of this thesis, the word 'initial' may be excluded. The second parameter defining the yield surface is $$k_t = \frac{p_t}{p_c^0} \tag{2.10}$$

where $p_t$ is the hydrostatic tensile yield stress, which does not change after yielding.

These two parameters give the shape factor of the yield surface, α, by $$\alpha = \frac{3k}{(3k_t + k)(3 - k)} \tag{2.11}$$

thereby fully defining the yield surface. Most of these plasticity parameters can be obtained by experimental characterization.

Uniaxial compressive tests give the uniaxial compressive yield strength. Determination of the hydrostatic compressive yield strength requires a hydrostatic compression apparatus, discussed further in the methodology section. However, hydrostatic tension is an extremely difficult test to achieve. A value for $k_t$ of 0.1 has been found to provide good agreement with experimental tests[1, 11, 13, 14]. Furthermore, this value has little effect on tests where the specimen is in compression, as is the case for the proposed material characterization device.

The flow rule for the Crushable Foam model is elliptical in the deviatoric stress plane, as shown in FIG. 11. The flow potential is centered on the p axis and defined by $$G = \sqrt{q^2 + \frac{9}{2}p^2} \tag{2.12}$$

which serves to grow the yield surface in a self-similar fashion, i.e., the shape factor, α, and pt remain constant. This flow rule is non-associative, i.e., plastic flow may occur non-perpendicular to the yield surface. There are no adjustable parameters in this flow rule, so no experimental characterization is needed to define it.

Abaqus has two options for hardening rules, volumetric and isotropic, for the Crush able Foam model. Both models behave similarly for compression dominated behavior, as is expected in the proposed experiments[13]. The volumetric hardening has been used by other experimenters[1, 11, 14, 15], and will be adopted in this research because of the good agreement found in these studies.

Abaqus defines volumetric hardening from uniaxial compression data. Building on the assumption that the yield surface expands in a self-similar fashion, we can describe the hardening behavior from uniaxial compression tests according to $$p_c(\varepsilon_{vol}^{pl}) = \frac{\sigma_c(\varepsilon_{axial}^{pl})\left[\sigma_c(\varepsilon_{axial}^{pl})\left(\frac{1}{\alpha^2} + \frac{1}{9}\right) + \frac{pl}{3}\right]}{p_t + \frac{\sigma_c(\varepsilon_{axial}^{pl})}{3}} \tag{2.13}$$

and the fact that $\varepsilon_{axial}^{pl} = \varepsilon_{vol}^{pl}$ in uniaxial compression, where $\varepsilon_{vol}^{pl}$ is the volumetric compaction plastic strain, σc is the uniaxial compressive yield stress that may change after initial yielding, and $\varepsilon_{axial}^{pl}$ is the uniaxial compacting plastic strain. The hardening behavior can therefore be described by tabulating uniaxial plastic strain and stress. The first point is the uniaxial compressive yield stress, which is associated with zero plastic strain. Any number of points from the uniaxial compressive test may follow.

2.3 Experimental Methods

Two laboratory tests were used to obtain the foam constitutive parameters: uniaxial compression and isotropic compression. Uniaxial compressive tests provide the elastic modulus, uniaxial compressive yield stress, and the hardening curve. Isotropic compression gives the hydrostatic compressive yield stress, $p_c^0$, which is necessary to calculate k. Technically, hydrostatic tension testing is required to determine $k_t$, but the value of $k_t$ was assumed to be 0.1 according to support from the literature and the considerable difficulty of conducting this test.

It is worth noting that the manufacturer's published specifications (see FIG. 6) are nearly sufficient for determining constitutive parameters. While it is tempting to use these specifications, discussions with manufacturers revealed that there can be considerable variation of material properties from batch to batch[8]. The results of my independent tests have confirmed this statement, and further support the need of independent tests to obtain accurate values.

Figure 12:
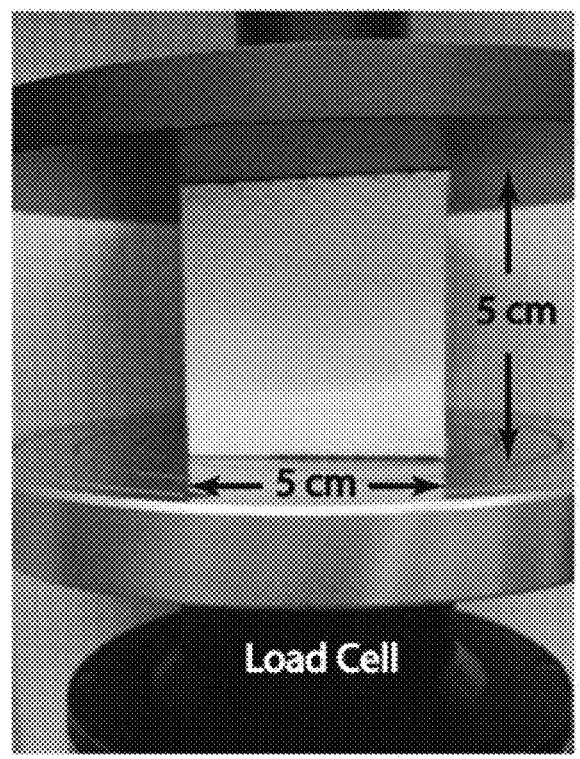
FIG. 12 Uniaxial compression setup with a foam block.

The uniaxial compression apparatus loads a foam specimen vertically between two platens, as is described in FIG. 12. These tests are conducted according to ASTM D6817. This testing requires the uniaxial loading of foam blocks of size 50 mm×50 mm×50 mm at a rate of 5 mm/min. The applied vertical force and vertical displacement are recorded while loading the block beyond yield. The maximum applied stress depended on foam yield strength, and ranged from 80-400 kPa. The testing was conducted on an MTS load frame with a 4448 N load cell with resolution of ±0.05 N and a displacement measurement device with resolution of ±0.005 mm.

Figure 13:
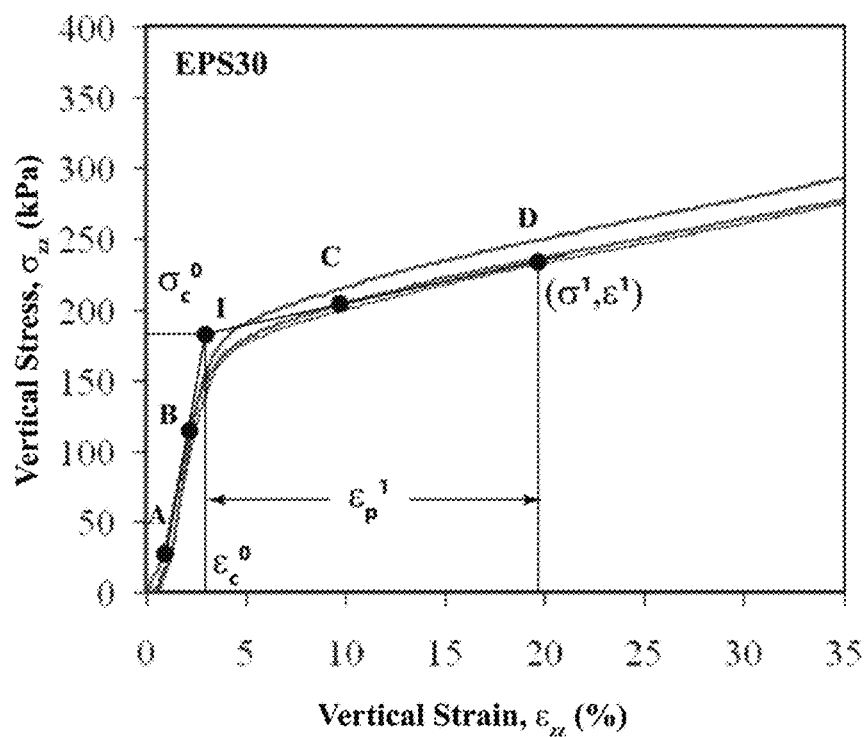
FIG. 13 Example results from uniaxial compression of EPS30. The $\sigma^1$ and $\epsilon^1$ shown here are equivalent to the $\sigma_p^1$ and $\epsilon_p^1$, respectively, used in this dissertation to describe the hardening curve.

The stress-strain curve from uniaxial compression tests provide three parameters for the constitutive model: uniaxial compressive yield stress, elastic modulus, and hardening curve. An example of stress-strain curves from uniaxial compression tests is shown in FIG. 13 for three independent samples of EPS30[1]. Parameter determination is explained here, using the red line in FIG. 13 as an example. According to the ASTM D6817 standard, the elastic modulus is determined by the steepest portion of the stress-strain curve, i.e., between points A and B. As the material reaches its yield stress, the stress-strain curve decreases in slope as it approaches the plastic plateau. The plastic plateau can be approximated as a linear line between points C and D. The yield stress, $\sigma_c^0$, is found at the intersection of the lines connecting AB and CD, labeled point I. The hardening curve can be defined by two points on the stress-strain curve: I and D. The hardening curve is defined in pairs of stress and plastic strain, ($\sigma p, \epsilon p$). Plastic strain is the amount of strain incurred after yield, e.g., for point D we take the total strain, $\epsilon^1$, minus the elastic strain, $\sigma_p^1$ to find the plastic strain, $\epsilon_p^1$. In this paper, the two points of the hardening curve are ($\sigma_c^0$, 0) and ($\sigma_p^1$, $\epsilon_p^1$), where the second point is taken at $\epsilon_p^1$ is 0.10 total strain.

Figure 14:
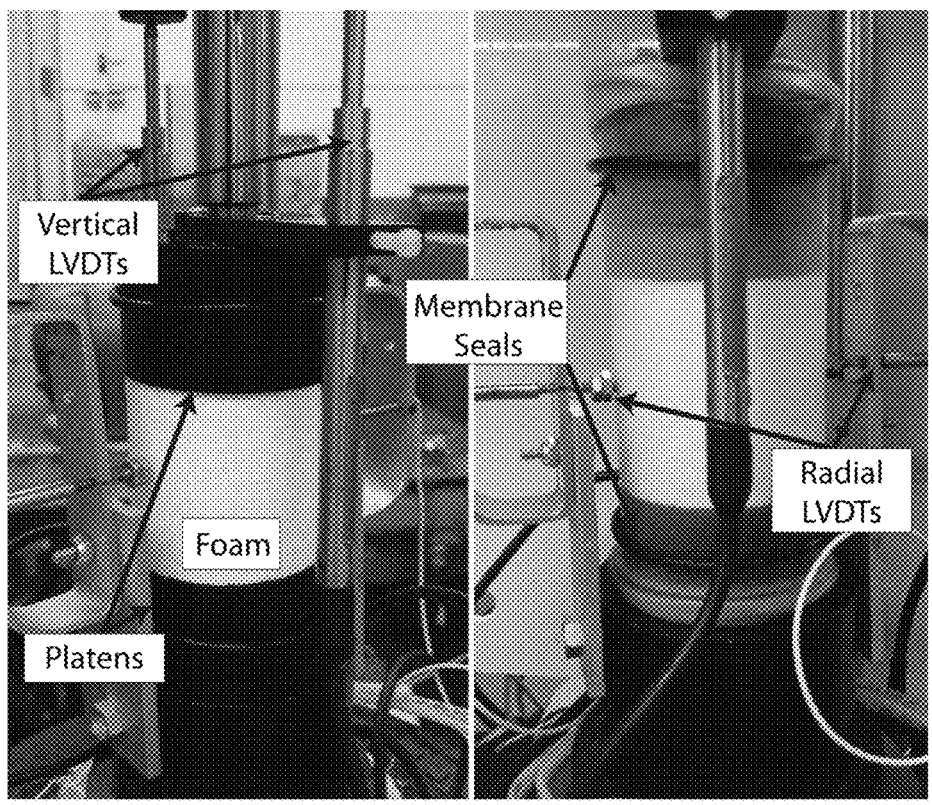
FIG. 14 Hydrostatic compression testing apparatus.

No ASTM standard exists for hydrostatic compression of foam, thus guidance on the equipment, sample size, loading rate, etc., was provided by existing literature. In my research, hydrostatic compression was conducted with the apparatus shown in FIG. 14, which is a tri-axial chamber used for hydrostatic and uniaxial compression of soils. The chamber is pressurized through a control valve on the top of the device, and is monitored with two separate pressure sensors inside the chamber to monitor uniformity. The foam was surrounded by an airtight membrane, because the porosity of the foam allows samples to be penetrated by surrounding fluid and apply pressure internally to the sample. Radial displacement was measured by two differential variable reluctance transducers (DVRT) positioned 180o from each other on the sample. Vertical displacement was measured by two LVDTs.

The cylindrical foam specimens were used, measuring 63.5 mm in diameter by 63.5 mm high. Cylindrical foam specimens were chosen because cylindrical samples are the standard shape for hydrostatic tests on soil (ASTM D4767-11), and have been used as the specimen shape for characterizing foams in other hydrostatic compression studies[15, 16]. This size was chosen for several reasons. It is similar in size to the foam cube used in uniaxial testing (50×50×50 mm), thus keeping consistent the ratio of the sample size to the foam bead size. This size sample is similar in size to specimens used in the literature, e.g., Kim et. al. used a cylinder 70 mm in diameter and 70 mm high, and Voit used a cylinder 25 mm in diameter and 20 mm high[15]. Finally, this cylinder size is supported by the test apparatus, i.e., platens, membranes, and sensor mounts support a 63.5 mm diameter sample. The specimen height was chosen to match the diameter, as in Kim's tests and as with the uniaxial test specimen.

Figure 15:
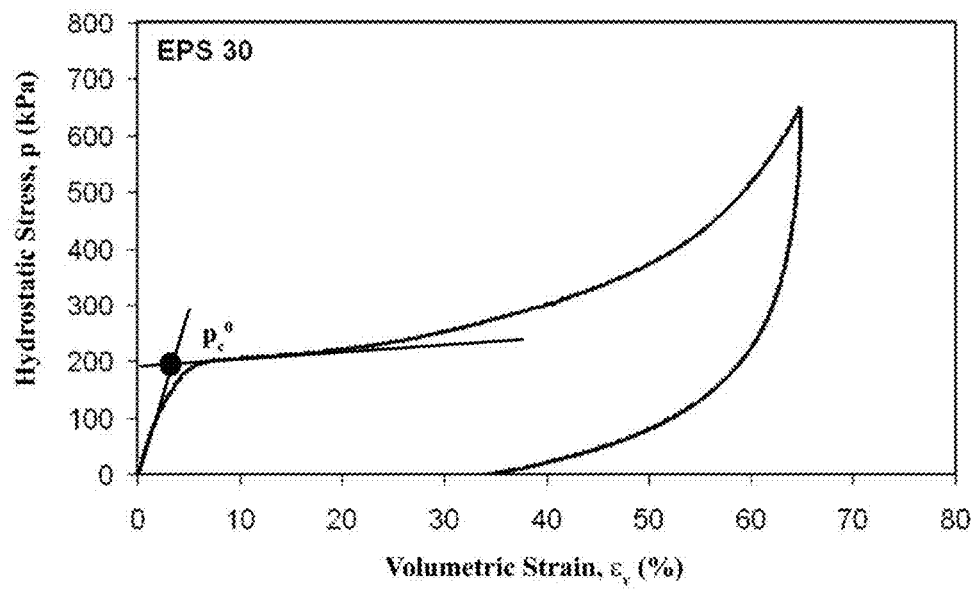
FIG. 15 Example of how the hydrostatic compressive yield stress is determined using hydrostatic compression results on EPS30 from Ozturk FIG. 16 Stress-strain curve under uniaxial compression for five tests on EPS12.

The value for isotropic compressive yield stress is obtained very similarly to uniaxial compressive yield stress, but based on a plot of volumetric strain rather than uniaxial strain. Volumetric strain, EV, can be calculated from the average of the two radial DVRT readings, DVRT1 and DVRT2, and the average of the two vertical LVDT readings, LVDT1 and LVDT2, using the equation $$\varepsilon_v = \frac{dV}{V_o} = 1 - \frac{\pi\left(r_o - \frac{DVRT1 + DVRT2}{2}\right)^2 * \left(h_o - \frac{LVDT1 + LVDT2}{2}\right)}{\pi r_o^2 h_o} \quad (2.14)$$

where dV is the change in specimen volume, $V_o$, is the initial specimen volume, $r_o$, is the initial specimen radius, and ho is the initial specimen height. This curve follows the same shape as the uniaxial stress-strain curve, as can be seen in FIG. 15. The hydrostatic compressive yield stress is found by the same methodology as the uniaxial compressive yield stress, i.e., at the intersection of the extrapolated elastic and plastic regions, as shown by the lines drawn on FIG. 15.

2.4 Uniaxial Compression Results

This section presents the results of uniaxial compression for foams of four different densities, EPS12, EPS22, EPS29A, and EPS29B. The two EPS29 foams were obtained from different manufacturing batches and had different densities, and are designated 'A' and 'B' throughout this paper.

The density of the foam samples were independently measured because the manufacturer only publishes minimum specifications. The samples were 50 mm cubes, the same size used in uniaxial compression tests. Four samples were measured for each type of foam, and the average is given in Table 2.1.

Figure 16:
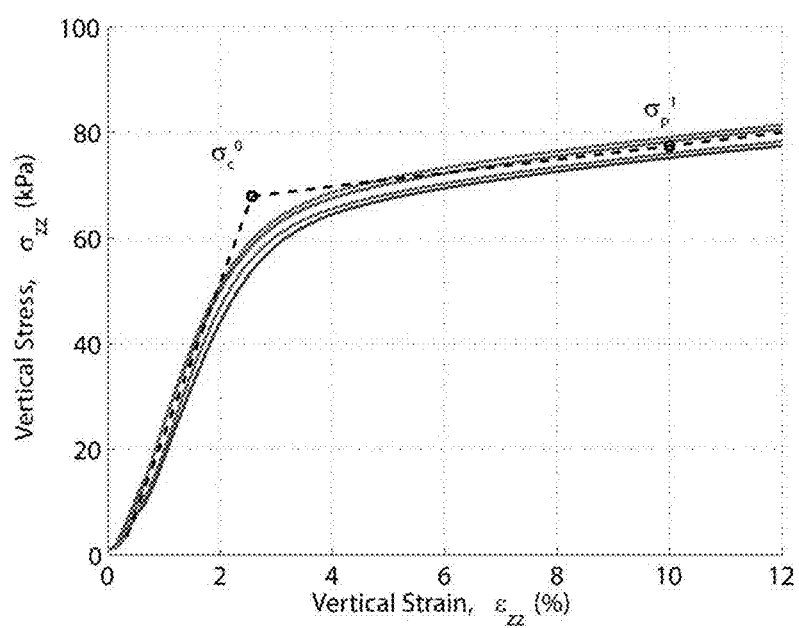

Five independent EPS12 samples were tested to determine the constitutive parameters. The uniaxial stress-strain curves from these tests are shown in FIG. 16. These tests exhibited repeatable stress-strain behavior. The yield stress and modulus were calculated for each individual test according to the method discussed in Section 2.3. The dashed lines show the average elastic and plastic slopes for all tests, and the intersection is the average yield stress. The average elastic modulus was 2.90 MPa, and the average yield stress was found to be 67.9 kPa. The final parameter determined from uniaxial tests is the hardening curve point, ($\sigma_p^1$, $\epsilon_p^1$), which is the point to the right on the plastic plateau in FIG. 16. For EPS12, this point is (77.4 MPa, 0.1).

TABLE 2.1

Experimentally measured densities for EPS geo-foams used in testing.

| ACH Rating | Density Measurements, ρ (kg/m3) | Density Average, ρ̄ (kg/m3) |
|---|---|---|
| EPS12 | 14.5, 14.9, 15.1, 14.9 | 14.9 |
| EPS22 | 30.9, 28.8, 29.8, 27.8 | 29.3 |
| EPS29A | 33.7, 34.3, 34.0, 34.5 | 34.1 |
| EPS29B | 36.2, 37.0, 35.6, 36.3 | 36.3 |

Table 2.2 summarizes the results for EPS12 tests. The results show good agreement among tests, with a coefficient of variation in the elastic modulus of 3%, and a coefficient of variation in the yield strength of 1%.

TABLE 2.2

Results from uniaxial compression tests on EPS12.

| Test | Elastic Modulus, E (MPa) | Compressive Yield Strength, $\sigma_c^o$ (kPa) |
|---|---|---|
| 1 | 2.71 | 67.2 |
| 2 | 2.96 | 67.3 |

TABLE 2.2-continued

Results from uniaxial compression tests on EPS12.

| Test | Elastic Modulus, E (MPa) | Compressive Yield Strength, $\sigma_c^o$ (kPa) |
|---|---|---|
| 3 | 2.87 | 67.8 |
| 4 | 2.93 | 68.2 |
| 5 | 3.01 | 69.1 |
| Avg | 2.9 | 67.9 |
| Cov | 0.03 | 0.01 |

Figure 17:
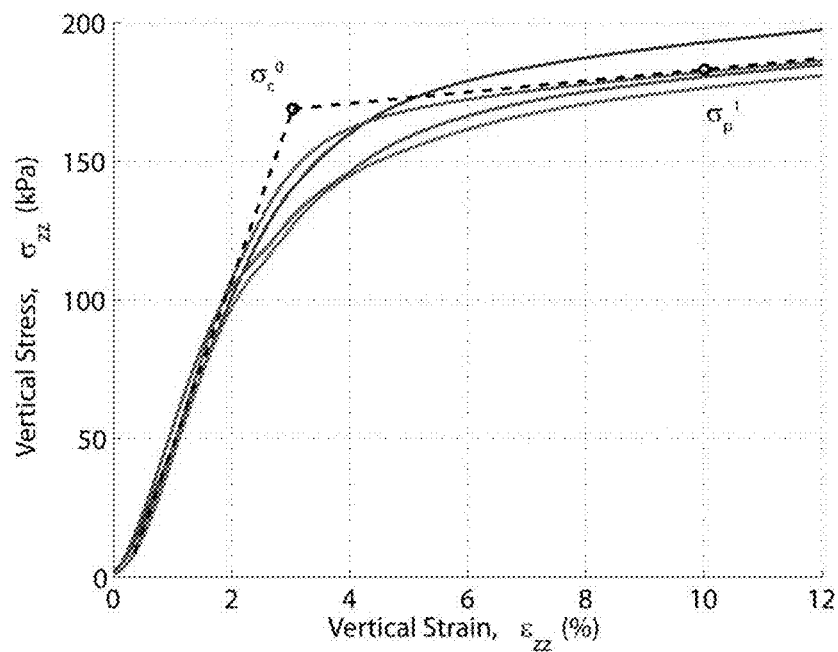
FIG. 17 Stress-strain curve under uniaxial compression for five tests on EPS22.

Four independent uniaxial tests were conducted on EPS22. The stress-strain curves from these tests are shown in FIG. 17. Similar to EPS12, there is good agreement between tests. For the EPS22 tests, the average yield stress, indicated by a circle, was found to be 169 kPa. The average elastic modulus was 5.99 MPa. The hardening curve point was found to be 183 MPa for $\sigma_p^1$ and 0.1 for $\epsilon_p^1$.

Table 2.3 summarizes the results for EPS22 tests. The results show good agreement among tests, with a coefficient of variation in the elastic modulus of 7%, and a coefficient of variation in the yield strength of 4%.

TABLE 2.3

Results from uniaxial compression tests on EPS22.

| Test | Elastic Modulus, E (MPa) | Compressive Yield Strength, $\sigma_c^o$ (kPa) |
|---|---|---|
| 1 | 5.46 | 179 |
| 2 | 6.37 | 168 |
| 3 | 6.06 | 166 |
| 4 | 6.05 | 162 |
| Avg | 6 | 169 |
| Cov | 0.07 | 0.04 |

Figure 18:
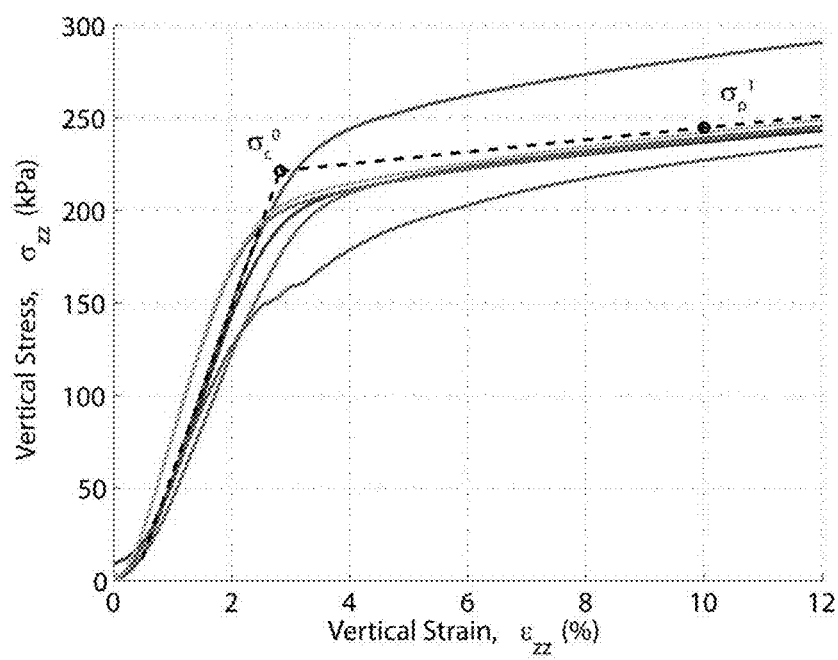
FIG. 18 Stress-strain curve under uniaxial compression for five tests on EPS29A.

Six uniaxial tests were conducted on EPS29A. The stress-strain curves from these tests are shown in FIG. 18. EPS29A showed greater variation in yield stress than EPS12 and EPS22. For the EPS29A tests, the average yield stress was 221 kPa, and the average elastic modulus was 9.0 MPa. The hardening curve point was found to be 245 MPa for $\sigma_p^1$ and 0.1 for $\epsilon_p^1$.

Table 2.4 summarizes the results for EPS29A tests. The coefficient of variation of the elastic modulus was 10%, and the coefficient of variation of the yield strength was 9%.

TABLE 2.4

Results from uniaxial compression tests on EPS29A.

| Test | Elastic Modulus, E (MPa) | Compressive Yield Strength, $\sigma_c^o$ (kPa) |
|---|---|---|
| 1 | 9.17 | 215 |
| 2 | 7.56 | 206 |
| 3 | 9.36 | 258 |
| 4 | 7.79 | 220 |
| 5 | 9.91 | 212 |
| 6 | 10.26 | 217 |
| Avg | 9 | 221 |
| Cov | 0.1 | 0.09 |

Figure 19:
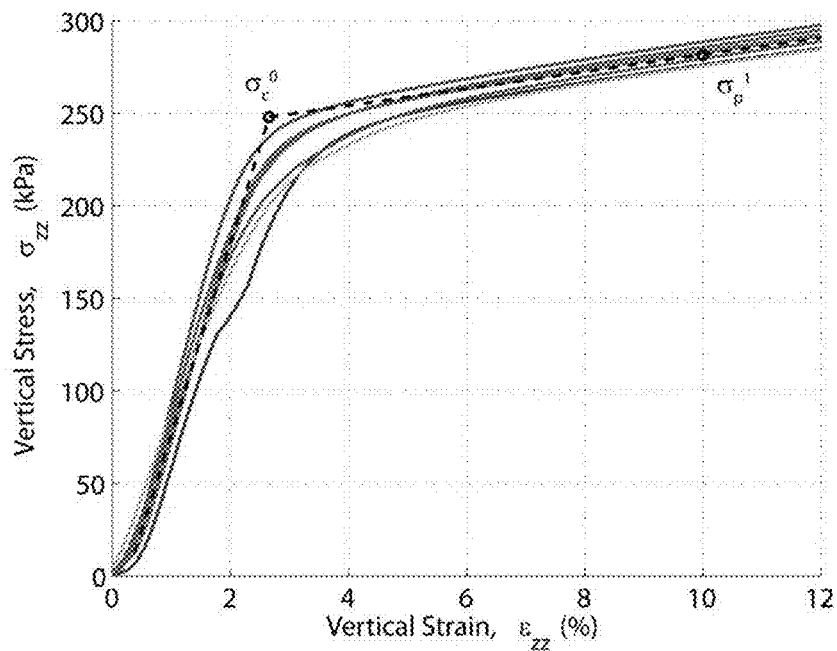
FIG. 19 Stress-strain curve under uniaxial compression for five tests on EPS29B.

Seven uniaxial tests were conducted on EPS29B. The stress-strain curves from these tests are shown in FIG. 19. These test results show good agreement. For the EPS29B tests, the average yield stress was 10 kPa, and the average elastic modulus was 248 MPa. The hardening curve point is (282 MPa, 0.1).

Table 2.5 summarizes the results for EPS29B tests. The results show good agreement among tests, with a coefficient of variation in the elastic modulus of 10%, and a coefficient of variation in the yield strength of 1%.

TABLE 2.5

Results from uniaxial compression tests on EPS29B.

| Test | Elastic Modulus, E (MPa) | Compressive Yield Strength, $\sigma_c^o$ (kPa) |
|---|---|---|
| 1 | 8.59 | 250 |
| 2 | 9.92 | 244 |
| 3 | 12.3 | 252 |
| 4 | 11.5 | 249 |
| 5 | 10.27 | 249 |
| 6 | 8.65 | 243 |
| 7 | 11.28 | 249 |
| Avg | 10 | 248 |
| Cov | 0.1 | 0.01 |

Figure 20:
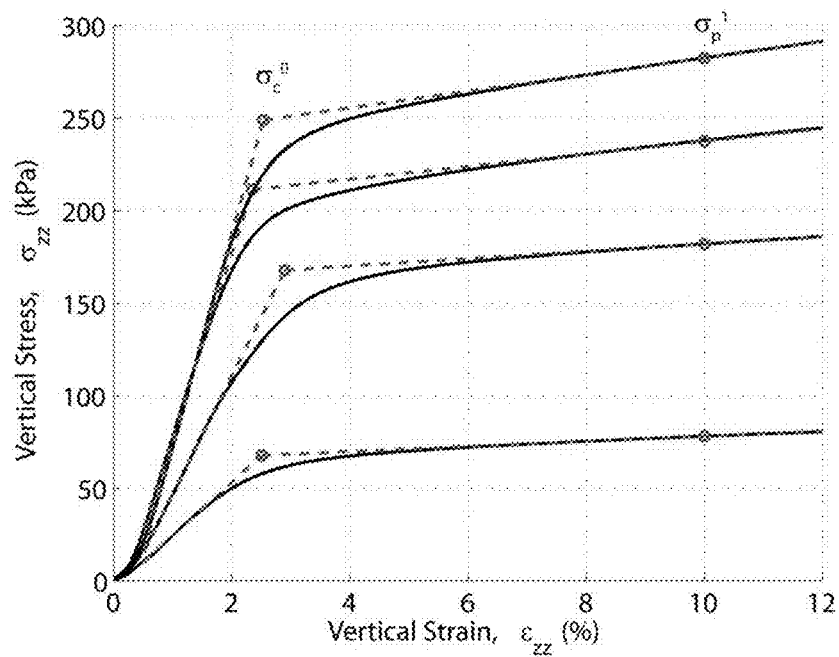
FIG. 20 Comparison of uniaxial stress-strain behavior of four EPS foams of different densities.
Figure 21:
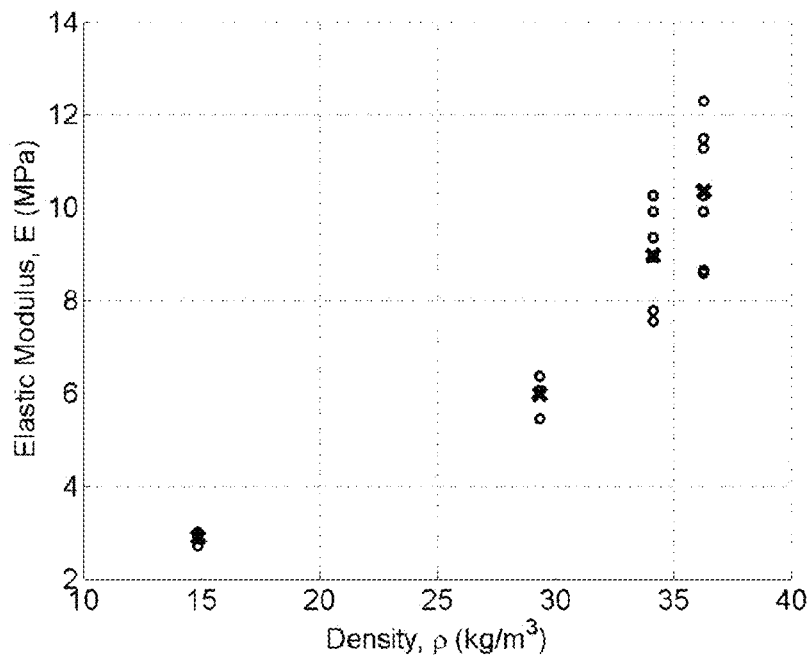
FIG. 21 Elastic modulus versus density for EPS foam of four different densities.
Figure 22:
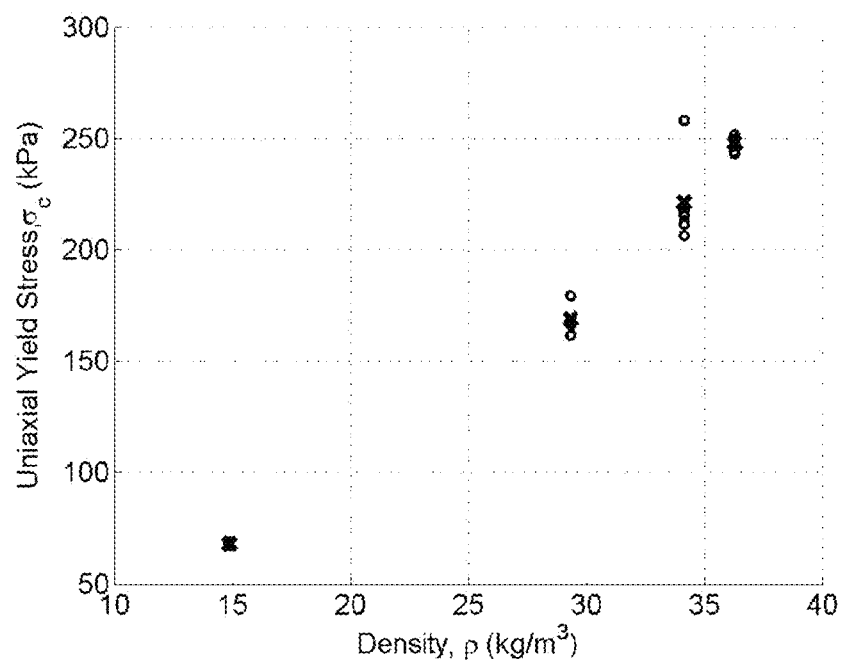
FIG. 22 Uniaxial compressive yield strength versus density for EPS foam of four different densities.

The uniaxial tests presented above characterize the elastic and plastic behavior of four different density EPS foams. Stress-strain behavior from the uniaxial compression tests are compared in FIG. 20, using the most representative test from each foam. FIG. 21 and FIG. 22 summarize the foam modulus and uniaxial compressive yield strength by density. Both parameters increase with density. The increasing trends appear linear in nature for both parameters. Table 2.6 summarizes all the results from the uniaxial compression tests. In addition to elastic modulus and uniaxial compressive yield strength, Table 2.6 also includes the hardening curve data point ($\sigma_p^1$, $\epsilon_p^1$). In determining this point, $\epsilon_p^1$ was chosen as 10% strain and $\sigma_p^1$ is calculated by extrapolating from the yield point using the average slope of the plastic plateau.

2.5 Hydrostatic Compression Results

In addition to uniaxial compression, hydrostatic compression is needed to fully characterize the foam constitutive model. In hydrostatic compression, a uniform compressive stress is applied to the sample and the hydrostatic compressive yield strength is determined from volumetric strain.

TABLE 2.6

Summary of uniaxial compression tests.

| Foam | Elastic Modulus, E (MPa) | Compressive Yield Strength, $\sigma_c^o$ (kPa) | $\sigma_p^1$ (kPa) | $\epsilon_p^1$ |
|---|---|---|---|---|
| EPS12 | 2.9 | 67.9 | 77.4 | 0.1 |
| EPS22 | 6 | 169 | 183 | 0.1 |
| EPS29A | 9 | 221 | 245 | 0.1 |
| EPS29B | 10 | 248 | 282 | 0.1 |

Figure 23:
FIG. 23 EPS12 specimen at peak hydrostatic pressure.

An example of a deformed specimen is shown in FIG. 23. As the sample compresses, the membrane wrinkles. The radial DVRTs use springs to keep the DVRT core in contact with the specimen, thereby preventing the wrinkles from affecting measurements.

Three hydrostatic compression tests were conducted on both EPS12 and EPS29B. The use of two foams instead of four was motivated by reducing the number of hydrostatic tests, which are time consuming to conduct and require the use of specialized and heavily utilized experimental equipment. The two foams selected for testing represent the most and least dense foams, providing the widest possible range of material properties.

Figure 24A:
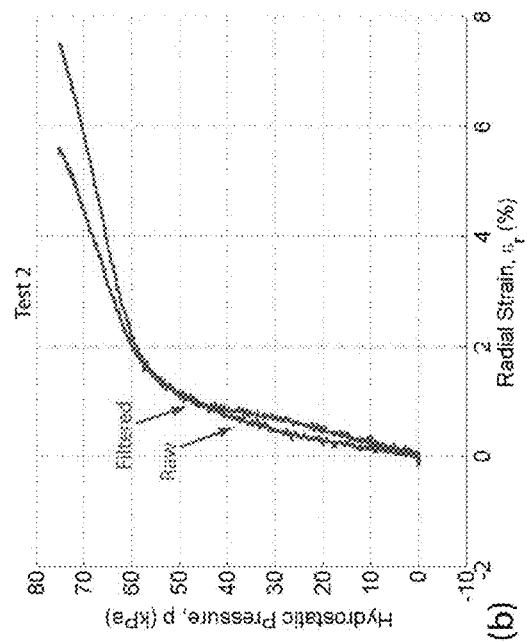
FIG. 24A-C Raw and filtered radial strain measurements versus hydrostatic pressure during three hydrostatic compression tests on EPS12. Note that two sensors collect radial measurements in each test.
Figure 24C:
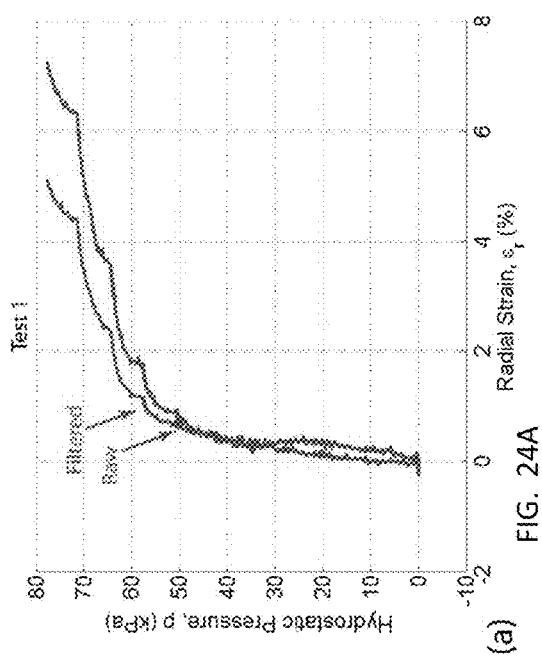
Figure 24B:
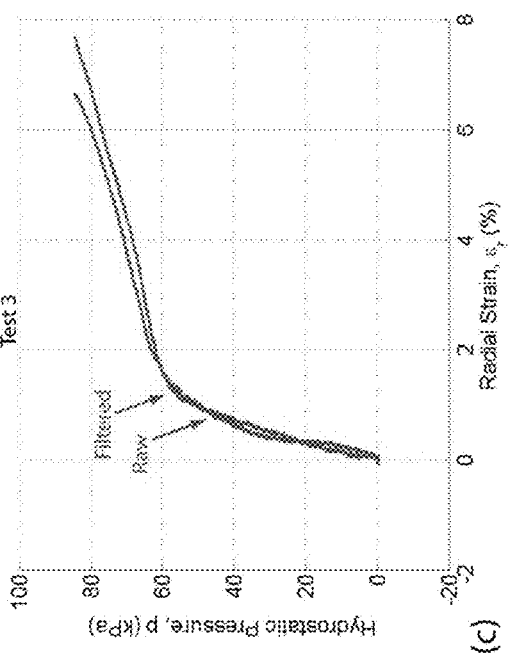
Figure 25A:
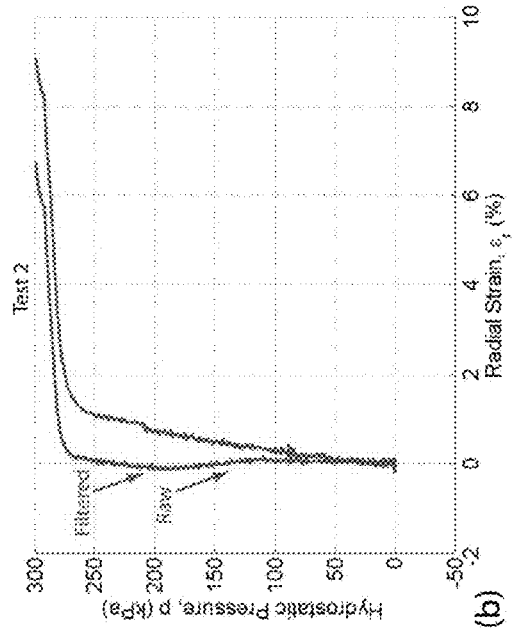
FIG. 25A-C Raw and filtered radial strain measurements versus hydrostatic pressure during three hydrostatic compression tests on EPS29B. Note that two sensors collect radial measurements in each test.
Figure 25C:
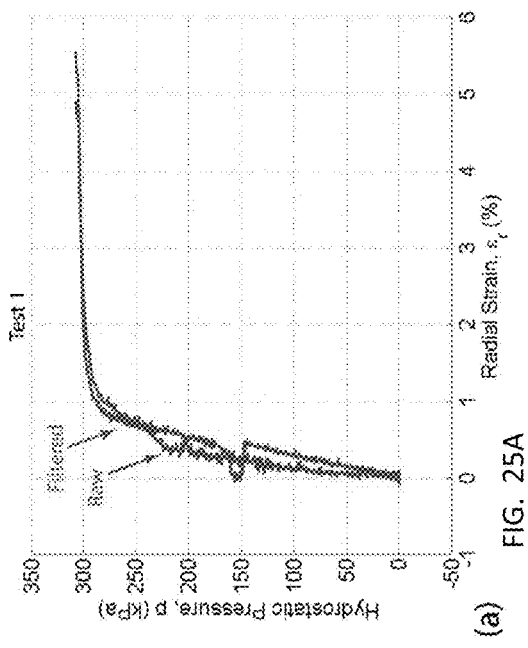
Figure 25B:
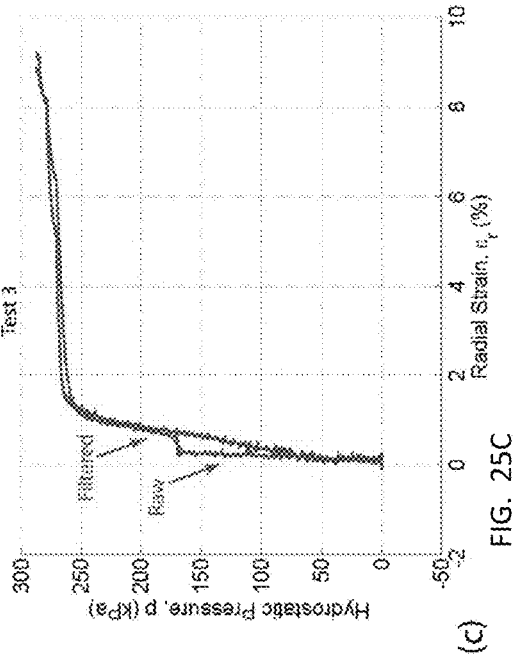

The radial DVRT measurements are shown in FIG. 24 and FIG. 25 for EPS12 and EPS29B, respectively. Three tests were conducted on each foam, with two radial sensors in each test. Measurements are presented in percent strain; for reference, the radius of the specimens was 31.75 mm. Readings from the DVRTs experienced high frequency noise, so a moving average filter was used to smooth the signal. The raw (blue) and filtered (red) signals are compared side by side. In FIG. 24(a), there are jumps in the curves above 50 kPa due to the fact that the pressure was increased in coarser steps during this test than in subsequent tests.

Figure 27A:
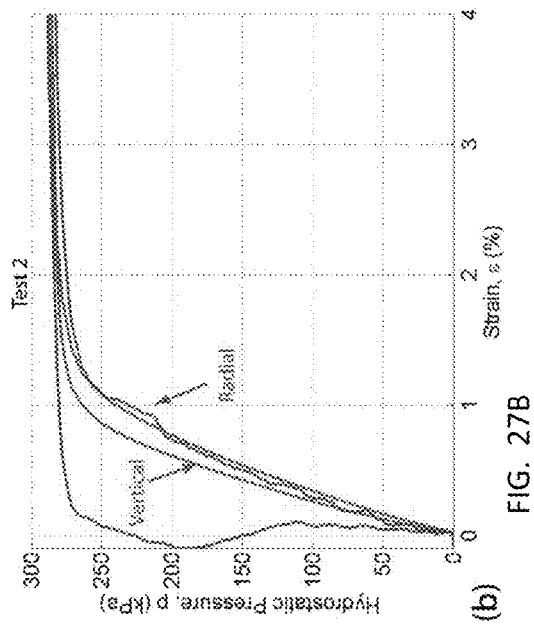
FIG. 27A-C Radial and vertical strain measurements versus hydrostatic pressure during three hydrostatic compression tests on EPS29B. Note that two sensors collect data in each direction for each test.
Figure 27B:
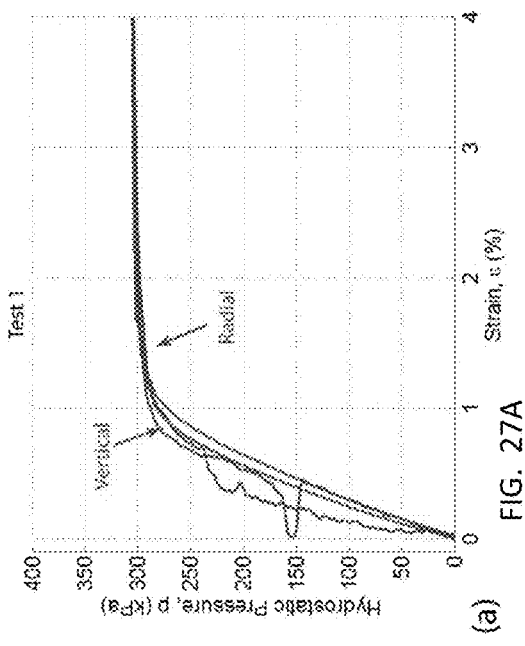
Figure 27C:
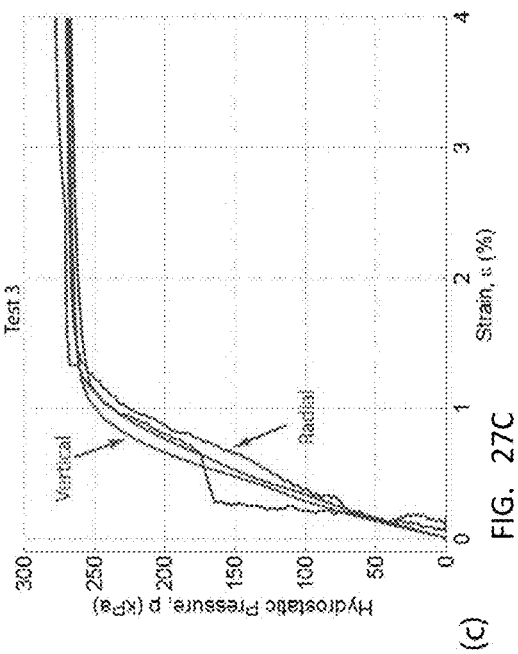

Experimental radial strain measurements are compared with vertical strain measurements in FIG. 26 and FIG. 27, giving strain for EPS12 and EPS29B, respectively. The strain values were calculated based on deformation measurements collected by two radial DVRTs (blue) and two vertical LVDTs (red). The jumps in the FIG. 26(a) curves are due to the fact that the pressure was increased in coarser steps during this test than in subsequent tests. There is generally good agreement between the strains along both of these axes, indicating that the EPS geo-foam is isotropic. One of the radial strain sensors in FIG. 27(b) does not agree with the remaining three sensors. The cause of this disagreement is unknown, but may have been caused by a particularly stubborn wrinkle in the membrane. This measurement was considered an anomaly and discarded in the volumetric strain calculation.

Figure 28:
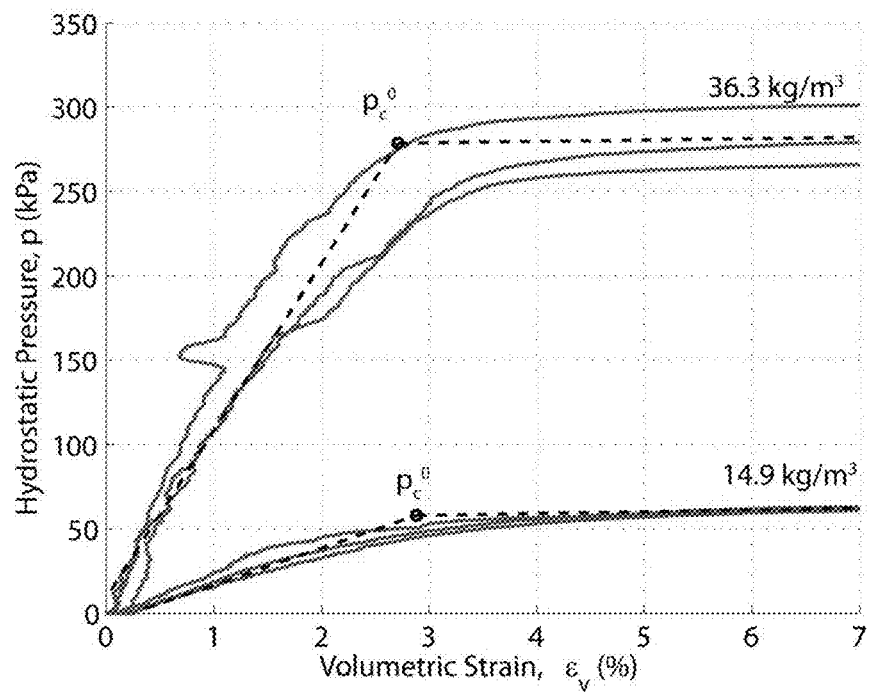
FIG. 28 Hydrostatic compression test results for EPS12 (14.9 kg/m3) and EPS29B (36.3 kg/m3).

Following the state of the art on characterizing foams, volumetric strain is used to calculate constitutive parameters from hydrostatic tests[14, 15, 20, 23]. Volumetric strain, $\epsilon v$, is calculated based on 2.14. The volumetric strain for the tests are shown in FIG. 28 for both foams. Both foams produced curves displaying the expected yield behavior following elastic loading.

The hydrostatic compressive yield stress for the tests on EPS12 and EPS29B are shown in Table 2.7 and Table 2.8, respectively. EPS12 averaged a hydrostatic compressive yield strength of 58.8 kPa, and EPS29B averaged 280 kPa. EPS12 shows excellent repeatability with a coefficient of variation of 0.3%, and EPS29B had good repeatability with a coefficient of variation of 6%. These low coefficients of variation provide confidence in the hydrostatic compressive yield stress results.

To provide comparison of the elastic parameters obtained through uniaxial compressive testing, the experimental bulk modulus, K, is given for both foams. The bulk modulus is the slope of the volumetric strain versus hydrostatic pressure curve shown in FIG. 28 in the elastic region. The bulk modulus can also be calculated independently from the uniaxial compression results by the equation $$K = \frac{E}{3(1-2v)} \quad (2.15)$$

According to this equation and the uniaxial compression results, EPS12 (i.e., with E=2.9 MPa, v=0.1) has a bulk modulus of K=1.2 MPa, and EPS29B (i.e., with E=10 MPa, v=0.1) has a bulk modulus of K=4.2 MPa. The bulk modulus values predicted by the uniaxial compression equation are lower than the experimental bulk modulus values by 35% for EPS12 and 51% for EPS29B. These differences are not unreasonable considering the relatively large coefficient of variation in bulk modulus values obtained by hydrostatic tests. The coefficients of variation for the bulk modulus from hydrostatic tests were 15% (EPS12) and 24% (EPS29B), and 3% (EPS12) and 10% (EPS29B) for elastic modulus from uniaxial compression tests. These variations highlight the ability of uniaxial compression tests to provide a more repeatable measurements of elastic parameters.

TABLE 2.7

Summary of hydrostatic compressive yield stress for EPS12.

| Test | $p_c^o$(kPa) | K(MPa) |
|---|---|---|
| 1 | 58.6 | 2.16 |
| 2 | 59.1 | 1.67 |
| 3 | 58.7 | 1.73 |
| Avg | 58.8 | 1.85 |
| Cov | 0.003 | 0.15 |

TABLE 2.8

Summary of hydrostatic compressive yield stress for EPS29B.

| Test | $p_c^o$(kPa) | K(MPa) |
|---|---|---|
| 1 | 298 | 11 |
| 2 | 279 | 7.66 |
| 3 | 262 | 7.19 |
| Avg | 280 | 8.62 |
| Cov | 0.06 | 0.24 |

2.6 EPS Foam Constitutive Model Verification

Figure 29:
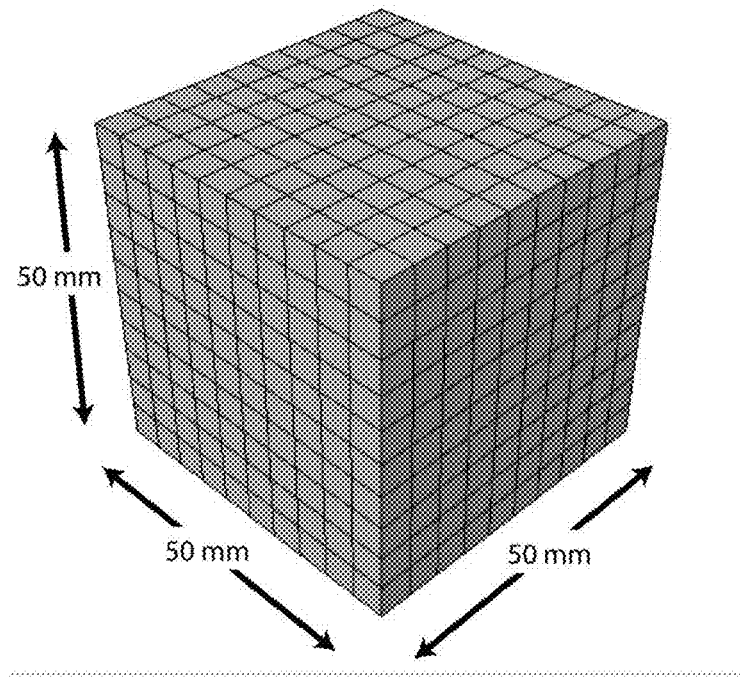
FIG. 29 Finite element model of uniaxial experiment.

The FE constitutive model was verified by simulating the uniaxial compression tests. FIG. 29 shows the FE model of the 50×50×50 mm uniaxial specimen. This model used 1000 elements, 10 on each side, of type C3D8R, i.e., 8node linear brick, reduced integration, hourglass control elements. The material properties of the block reflected the average properties obtained for each type of foam in the experimental tests. Uniform pressure was applied to the top of the block, while the bottom of the block was fixed in the z direction. One corner of the bottom of the block was fixed in the x and y directions.

Figure 30:
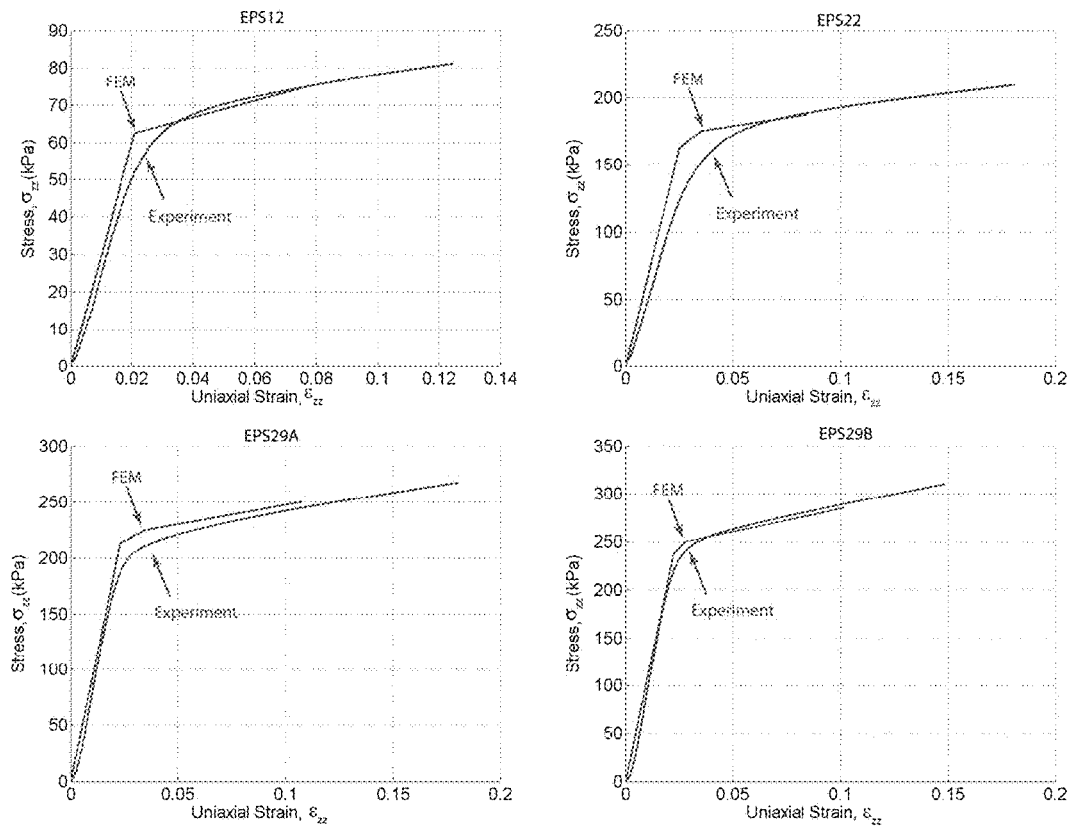
FIG. 30 Results of FE model verification for EPS12, EPS22, EPS29A, and EPS29B compared to representative experimental tests. Material properties in the FE model reflected the average values from experimental tests. The uniaxial compression test of a 50×50×50 mm cube was simulated in the FE model and compared to experimental strains.

A comparison of the FE model results to the experimental results for each type of foam is shown in FIG. 30. The FE model results and experimental results agreed very well. There is some disagreement at the yield point, which is to be expected. The FE model approximates the material behavior with a linear elastic region, and a plastic region that follows a linear hardening curve. The real-world material experiences a gradual onset of plasticity that does not exactly follow a linear hardening curve, although at higher strains (>0.05) the linear approximation of the hardening curve shows good predictive ability.

2.7 Discussion

Two types of laboratory tests were conducted to determine foam constitutive parameters. Uniaxial compression provides E, $\sigma_c^o$, and the hardening curve ($\sigma_c^o$, $\epsilon_c^o$), while hydrostatic compression gives $p_c^o$. The compressive yield ratio, k, is calculated from these parameters. Four foam densities were tested in uniaxial compression, and two foam densities (the least and most dense) were tested in hydrostatic compression.

Figure 31:
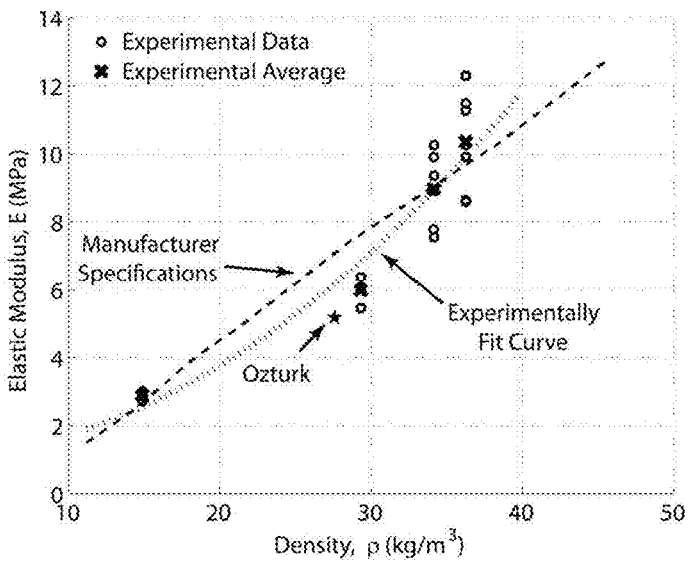
FIG. 31 Comparison of experimentally obtained modulus to other published values.

The experimentally obtained elastic modulus values generally showed good repeatability and agreed with published values. A comparison between experimentally obtained values and other published values is shown in FIG. 31 for elastic modulus. The experimentally obtained modulus values agreed very well with the manufacturers specifications (dashed line) and academic literature from Ozturk (star marker)[1]. The trend of the experimental results and Ozturk's data do not appear to be linear in nature. To capture the nonlinear trend, the average experimental modulus values for each foam were fit to a 2nd order curve. The linear term was set to zero to avoid a negative term from causing the modulus to decrease with increased density (as would happen without this requirement). The experimentally fit curve predicts the elastic modulus in MPa according to the equation $$E(\rho) = 6.7\rho^2 + 1.1 \text{ in MPa} \quad (2.16)$$

This curve fits with R2 value of 0.967. The curve still over-predicts for the EPS22 foam and Ozturk's data, but provides a much better fit than the linear curve. It is important to note that this equation can only be considered valid over the range of EPS foam densities evaluated here. This limitation is particularly relevant at lower densities, where the curve would reach a positive elastic modulus for a foam with zero density.

While it may appear that some measured modulus values fall below the manufacturer specifications, this is misleading. The experimental points are plotted with the true density, rather than the manufacturer's published value; and the true density always outperformed the published minimum density. For example, EPS22 has a published density of 21.6 kg/m3, but a measured value of 29.3 kg/m3. If the elastic modulus values for EPS22 were plotted at the published density value, they would all be above the manufacturer's specification. Therefore, the experimental modulus values meet the manufacturer's minimum specifications.

Figure 32:
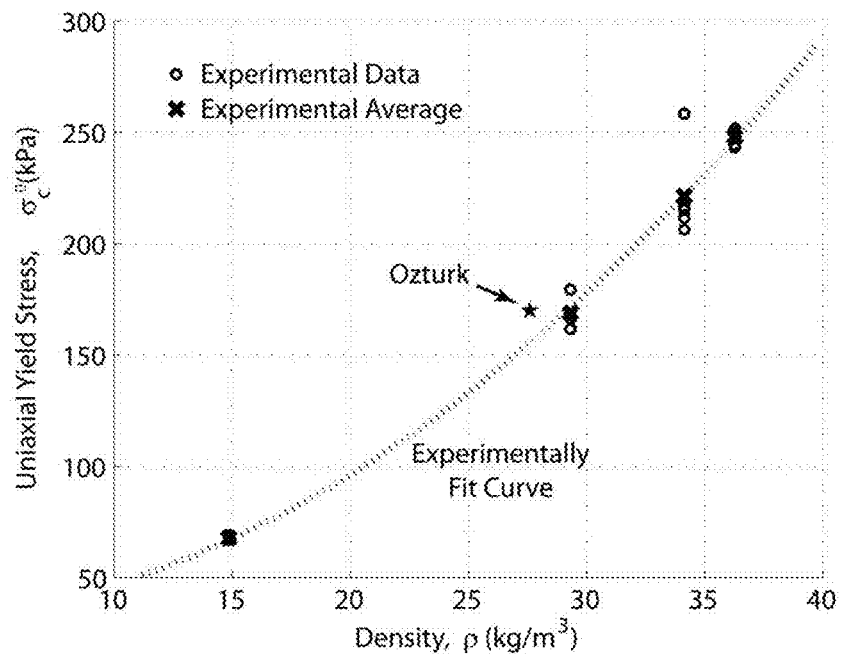
FIG. 32 Comparison of experimentally obtained uniaxial compressive yield stress to other published values.

The experimental results for uniaxial compressive yield stress also showed good repeatability and agreed with previous literature. FIG. 32 compares uniaxial compressive yield stresses from tests on each foam. Previously conducted tests from Ozturk are shown with a star marker. The results from Ozturk agree with the tests conducted in this thesis. The manufacturer does not provide a uniaxial compressive yield stress. As with the elastic modulus results, the $\sigma_c^0$ versus $\rho$ experimental data was fit to a curve. The experimentally fit curve predicts the elastic modulus in kPa according to the equation $$\sigma_c^0(\rho) = 0.164\rho^2 + 30.6 \text{ in kPa} \quad (2.17)$$

This curve fits with an R2 value of 0.999, indicating an excellent fit. Again, it must be noted that this curve is only valid over the range of densities investigated here.

Figure 33:
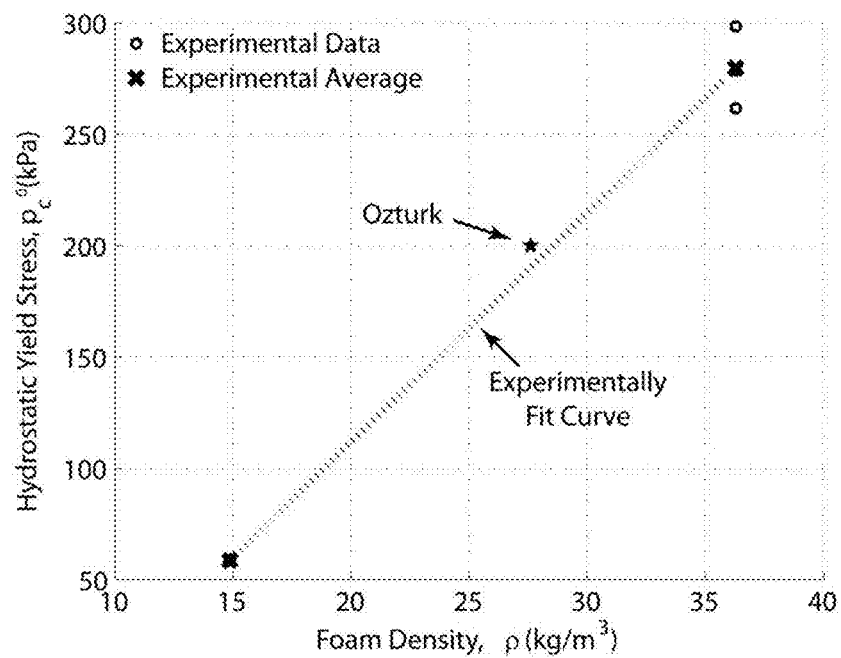
FIG. 33 Comparison of experimentally obtained hydrostatic compressive yield stress to other published values.

The hystrostatic yield stress from experimental tests show good repeatability and compare well to existing literature. FIG. 33 compares the experimental tests to results obtained by Ozturk[14]. While Ozturk's foam is not similar in density to the EPS12 and EPS29B tested here, it falls approximately along the linear trendline connecting the EPS12 and EPS29B test results. A linear curve was used for this data because there is only two densities at which to fit the curve. The linear trendline for hydrostatic compressive yield stress in kPa was found to be $$p_c^0(\rho) = 10.3\rho - 94.4 \text{ in kPa} \quad (2.18)$$

This curve is only valid over the range of densities investigated here, and may be even further limited in accuracy by the fact that only two densities were investigated.

The constitutive parameters for the foams tested are summarized in Table 2.9. Four of these parameters tended to increase linearly with density, including: elastic modulus, uniaxial compressive yield strength, bulk modulus, and hydrostatic compressive yield strength.

TABLE 2.9

Summary of foam constitutive parameters.

| Foam | E(MPa) | $\sigma_c^0$(kPa) | $\sigma_p^1$(kPa) | $\epsilon_p^1$(kPa) | $p_c^0$(kPa) | k | $k_t$ |
|---|---|---|---|---|---|---|---|
| EPS12 | 2.9 | 67.9 | 77.4 | 0.1 | 61.5 | 1.11 | 0.1 |
| EPS22 | 6.3 | 170 | 183 | 0.1 | X | X | 0.1 |
| EPS29A | 9 | 220 | 245 | 0.1 | X | X | 0.1 |
| EPS29B | 10 | 248 | 282 | 0.1 | 271.8 | 0.91 | 0.1 |

Chapter 3—In-Situ Determination of Soil Compaction Contact Force Via Instrumented Pad The following chapter was an article published in the Journal of Terramechanics, referenced as:

S. C. Kimmel, R. G. Bearce, R. V. Rinehart, and M. A. Mooney, "Development of a machine integrated strain-based contact force sensor for pad foot soil compactors," Journal of Terramechanics, vol. 51, pp. 31-41, February 2014.

As it pertains to this dissertation, the paper presented here serves as a central thread of my research. The development of a strain gage instrumented pad for monitoring soil compaction inspired the work of mechanistic in-situ characterization methods presented in Chapters-4 and 5, and illuminated the challenges of innovation adoption in highway construction investigated in Chapter 6.

This chapter lays the foundation for the strain-gage instrumented devices discussed in this dissertation. Established in this chapter is the potential for a machine integrated strain gage-based material characterization device, and the need to advance in-situ material characterization in the direction of mechanistic measurements. The utility for in-situ material characterization devices is found in many disciplines, but perhaps few as profoundly as in geotechnical engineering. Building on the successes of this chapter, Chapters 4 and 5 develop in-situ devices for mechanistic characterization of material elasticity and plasticity. Mechanistic measurements are valuable, because they provide parameters often used in the design of structures, thus allowing parity between quality assessment parameters and design parameters.

Considering that this paper has four authors, and is being presented in the dissertation of an individual, it is important to demarcate my personal contributions. I designed the strain gage instrumented pad, determining the gage locations and the method of interpreting strain readings. This design was based on my FE analysis of varying contact stresses on the pad (i.e., as a proxy for varying soil types). By analyzing the strain fields in the pad during different loading scenarios predicted by the FE model, I determined the ideal location for gages to measure contact force and provide insight on soil type.

Concerning the lab testing analysis, I conducted the comparison of FE pad strain results and contact pressure measurements. I used the contact pressure measurements from lab testing as the loading input to the FE model, and compared these results with the pad strain results used to design the pad. This FE analysis was important in verifying the design and predictive power of the FE model.

With regards to the field testing results, I conducted most of the pad strain analysis. I analyzed pad strain-time histories, which provided important insight into pad strain behavior as a pad rolls through the soil during compaction. I investigated pad strain versus pass data, which revealed that all pad strains were sensitive to compaction. The contact force calibration and subsequent comparison to field soil density measurements was a combination of efforts by Bobby Reinhart and myself. The contact force measurements were sensitive to compaction, indicating the value of this in-situ measurement device to compaction monitoring. It is worth noting that complimentary analysis of the soil behavior was conducted by Rick Bearce in his Master's Thesis[24].

3.1 Motivation

The past decade has brought significant advances in earthwork compaction quality control/quality assurance (QC/QA). The most notable advance has been the introduction of roller compactor-integrated measurement of soil stiffness coupled with GPS-based-documentation. Through measurement of drum vibration, roller-integrated measurement systems continuously report on the stiffness of the underlying soil. The combination of roller integrated measurement and GPS based mapping and documentation, referred to as continuous compaction control (CCC) or intelligent compaction (IC) presents a significant leap forward in QC/QA of embankment, subgrade, sub-base and base course compaction for pavements, airfields, and transit [2]. CCC and IC move earthwork QC/QA from less than 1% coverage provided by spot test methods (e.g., nuclear moisture density gage) to 100% coverage. CCC also offers the potential to measure soil stiffness or modulus, i.e., mechanistic parameters that enable the implementation of performance based specifications.

Figure 34:
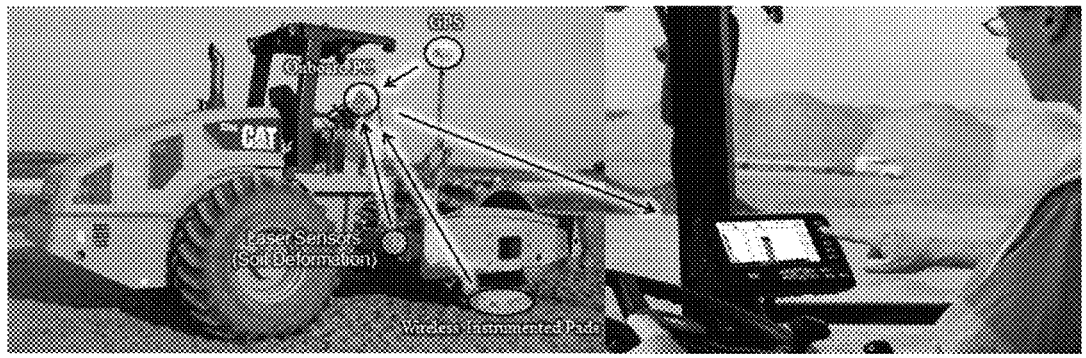
FIG. 34 Concept of stiffness monitoring pad foot soil compactor: stiffness is determined by force sensing pads and deflection sensing lasers.

While vibration-based measurement has shown much promise on smooth drum vibratory rollers, subgrade soils are often compacted more efficiently with pad foot rollers (FIG. 34) operated without vibration or 'statically'. There is currently no CCC system for pad foot rollers that provides a measure of soil stiffness during static compaction. The only non-vibratory based measurement system is Caterpillar's machine drive power (MDP) approach that is based on propulsion power required to drive through soil during compaction. MDP has been empirically related to soil compaction[3, 4]. Realizing that stiffness is a function of contact force and deformation, an envisioned system will estimate soil stiffness through a combination of force measurements from strain gage instrumented pads and soil deformation measurements from laser sensors (FIG. 34). In pursuit of this system, this paper develops a pad-based force measurement system.

Figure 35:
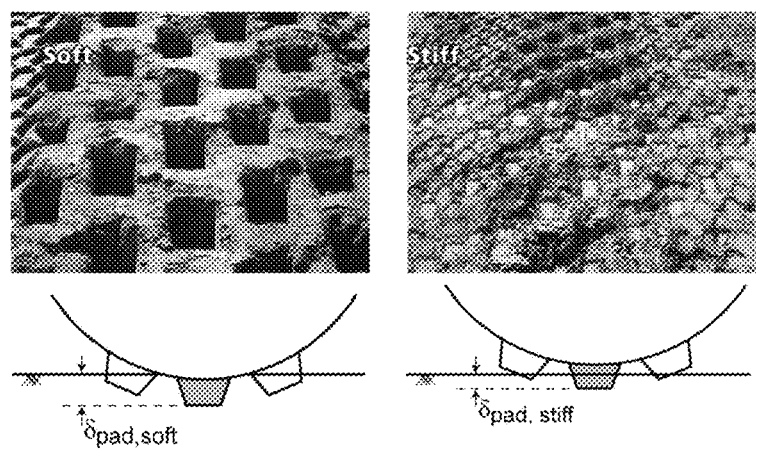
FIG. 35 Pad indentation depth changes with soil compaction.

The premise behind the strain gage instrumented pad approach is that the stress and strain fields experienced by each pad while rolling through the soil will evolve as the soil's strength and stiffness increase during compaction. This is illustrated in FIG. 35. When rolling through soft uncompacted soil, the load or weight of the drum is shared by many pads and the drum surface. When rolling through stiffer compacted soil, the load is transferred through a few pads only. As the soil is compacted with repeated roller passes, each pad penetrates the soil surface less, i.e., the pads walk out of the soil as compaction occurs. It stands to reason that as the pads walk out, the drum weight will increasingly concentrate within the pads and the load measured by the instrumented pad will increase.

Investigation of pad-soil interaction has received little attention in the literature, and rolling indenter problems in general have proven very difficult to characterize. The interaction between agricultural tyres and soil compaction has been modeled extensively using FE, for example[25-27]. However, these efforts focused on the soil response, and do not help us further understand how the machine reacts to changing conditions. Studies on the tyre response to soil loading have been conducted, focusing on deflection characteristics that aid in understanding and improving tyre design[28]. However, due to the different geometry and material of the pad, these studies are of little help in understanding the pad response. The grousers on tracked vehicles more closely resemble the geometry and material characteristics of the pads on a drum, but studies into this type of machine have focused on the soil response and traction, not the machine's mechanical response[29, 30]. Thus the machine's stress/strain response to various soil conditions is poorly understood.

The objective of this paper is to explore pad strain behavior during roller movement and compaction of soil. The design and implementation of the instrumented pads are discussed. Methods for determining total normal contact force are presented. The results of lab testing show pad strain response to uniaxial loading. Results from full scale field testing of the measurement system on a Caterpillar CP56 pad foot roller provide insight into pad strain behavior during single contact events and throughout compaction. Determination of contact force during field testing is discussed.

3.2 Finite Element Analysis and Design of Instrumented Pad

The design of the instrumented pad was determined via FE modeling. Pads from Cater pillar and Bomag were modeled in SolidWorks® 3D CAD software. Static FE analysis was performed with the SolidWorks® Simulation package. For brevity, FE analysis results from a single Caterpillar pad are presented in this paper (additional analysis is presented in [31]). However, the various pad designs (i.e., Bomag, Caterpillar, etc.) share common geometric elements, such as a trapezoidal profile and hollow center, and similar material properties, which allow the stress/strain findings to transport well between designs.

For the pad model, 4-noded tetrahedral elements with 4 Jacobian points were used. The element size averaged 4.5 mm, with a maximum and minimum size of 4.725 and 4.275 mm, respectively. This level of mesh refinement was chosen based on a mesh convergence study, which achieve high accuracy in areas of high strain gradient, e.g., the inside bottom face of the pad. The resulting mesh had 55,575 elements and 88,396 nodes. For reference, the pad dimensions are approximately 210×140×130 mm in the x, y, z-directions, respectively (FIG. 36). This meshing allowed for surface strains to be reported at no worse than a 4.725 mm resolution, which was helpful in comparing the modeling results to strain gage readings from experimental testing. The mesh achieved 97.3% of elements with an aspect ratio less than 3, and a maximum of 8.5. The pad is made of cast steel for which the modeling parameters were: elastic modulus=200 GPa, Poisson's ratio=0.32, and mass density=7800 kg/m3.

FE analysis simulated vertical loading of the pad rather than a rolling motion. This configuration is comparable to when the pad is oriented vertically directly below the center of the drum. One reason this configuration was chosen is that it is much simpler to replicate experimentally in a lab setting compared to rolling motion, thus allowing for easy comparison of results between modeling, lab testing, and a snapshot of field testing. To model this loading, the pad FE model was rigidly fixed around the rim that is welded to the drum (z=0 in FIG. 36) and variable loads were applied on the outer faces in contact with the soil (FIG. 36). The maximum load applied to the pad was 9 kN, which is an estimate of the weight applied to a pad by the drum in a fully compacted soil. The loading simulated a maximum soil deflection of 9 mm, which is representative of a highly compacted soil.

The FE model did not explicitly simulate soil, but rather used a range of pad loading scenarios to mimic pad interaction with different subgrade soils (i.e., sand, silt, clay).

This approach provides the necessary insight into the dependence of pad strain behavior on soil conditions without trying to address complex elasto-plastic constitutive soil modeling, which is an ongoing area of research. There is a base of theoretical and experimental knowledge regarding soil behavior that guided the selection of loading parameters in this regard. Soil type influences the distribution of contact stress on a surface. It has been suggested that when interacting with a rigid surface (such as a compactor pad), soils with cohesion impart an inverse parabolic contact stress distribution (CSD), i.e., contact stresses reach a maximum at outer edges and a minimum at the center[32]. Conversely, cohesionless soils impart a parabolic distribution, i.e., contact stresses reach a maximum at the center and dissipate toward the edges[32]. This theory was confirmed experimentally with the findings indicating that the maximum and minimum stresses could be as much as twice and one-half of the average contact stress, respectively[33, 34]. Additionally, the development of plasticity during loading has been shown to change the CSD[35], thus introducing a load and strength dependent factor to this problem.

Model simulations included three loading configurations known to mimic cohesionless, cohesive and mixed soil behaviors, by means of applying parabolic, inverse parabolic and uniform contact stresses, respectively. These loading configurations, illustrated in FIG. 36, represent a range of soil conditions per the findings in[33, 34]. The parabolic and inverse parabolic distributions have a maximum and minimum load of twice and one-half the average contact stress. An ellipsoidal equation was used to define the pressure, q, at x and y locations in millimeters, where x and y originate at the center of the face, i.e., $$q(x, y) = ax^2 + by^2 + c \qquad (3.1)$$

where coefficients a, b, and c are different for each distribution. For the parabolic distribution, a=4.23e-4, b=8.63e-4, and c=2; inverse parabolic distribution, a=4.23e-4, b=8.63e-4, and c=0.5; and for the uniform, a=0, b=0, and c=1. These values have been normalized to allow for an average pressure of unity, which can then be scaled by the desired load. The maximum applied force was 9.0 kN for each CSD, representing an estimate of the maximum axial force expected from the Caterpillar CP56 in the field[31]. The loading was applied normal to the bottom face and portions of the sidewall of the pad, simulating frictionless contact. Sidewall loading represented 9 mm of soil penetration. This level of penetration is admittedly arbitrary and is representative of a compacted stiff soil.

The FE analysis results, depicted in FIG. 37, showed measurable and complex stress/strain fields in the pad. In general, the three loading scenarios induce flexural strains in the inside bottom face ($\epsilon_{xx}$) comprised of tensile strains in the central bottom face and compressive strains in the inner fillet regions, as shown in FIG. 37(a-c). In addition, compressive vertical strains ($\epsilon_{zz}$) are induced in the sidewall, as shown in FIG. 37(d-f).

The nature of the externally-applied CSD has a profound influence on the observed normal strain magnitudes throughout the pad, i.e., Saint Venant's principle is not applicable over the length scale of the pad. FIG. 38a compares the strains across the inside bottom face of the pad for the different loading conditions. The 9.0 kN load applied via parabolic CSD induces tensile $\epsilon_{xx}$ in the inside bottom face that are much greater than those induced by uniform and inverse parabolic distributions. The maximum $\epsilon_{xx}$ occurs in the fillets (compression) and varies significantly with CSD. The central portion of the inside bottom face exhibits significant tensile strains during parabolic loading and very little strain during inverse parabolic loading (FIG. 38a). The very low normal strains incurred during inverse parabolic loading are a result of the nature of this CSD, i.e., there is far less flexure on the bottom face.

The vertical sidewall strains $\epsilon zz$ are also significantly influenced by the CSD as can be seen in FIG. 38b. No matter the vertical position on the sidewall, $\epsilon_{zz}$ magnitude depends on the CSD. The parabolic loading case induces the highest $\epsilon_{zz}$ magnitudes, which is somewhat counterintuitive because the inverse parabolic case applies the largest normal load directly in line with the sidewalls. However, the loading in the center of the bottom face creates a bending moment in the sidewalls that is far more influential to $\epsilon_{zz}$ in the sidewalls than loading directly in line with the walls. While the strain magnitude depends on CSD, the distribution of $\epsilon_{zz}$ in the x-dimension is very similar for all cases. The strain signatures for each case are essentially distinguishable by a scaling factor based on their CSD (described below).

FE analysis revealed that strains from both bottom face and sidewall are required to capture a clear picture of how the pad is being loaded and to estimate the normal contact force. Strains in the bottom face reveal how the contact stresses are distributed. Strains in the sidewall are proportional to total normal force, with the proportional constant being related to contact stress distribution. To this end, an empirical approach was developed in which the total normal force can be estimated from side wall strains using a calibration factor that is soil-specific. A soil-specific laboratory calibration effort is required for this approach.

Multiple pads were instrumented with strain gages, as shown in FIG. 39. Vishay Micro-Measurements foil gages were used on all pads (350 ohms, uniaxial, 0.125" gage length, model: CEA-06-125UN-350). Five vertically oriented strain gages measuring normal strain $\epsilon_{zz}$ were bonded on the inside face of the pad sidewalls (gages $8_{zz}$-$12_{zz}$ in FIG. 39a), and seven horizontally oriented strain gages measuring normal strain $\epsilon_{xx}$ were located on the inside bottom face (gages $1_{xx}$-$7_{xx}$ in FIG. 39). A second set of gages was placed symmetric to these 12 gages about the x-z plane that was expected to be a plane of loading symmetry (FIG. 39b). Measurements from the two sets of gages were combined in a complimentary Wheatstone half bridge configuration to double the signal to noise ratio (required due to small strain magnitude). Wired and wireless data acquisition systems were used (wired in lab and wireless in the field), for which the root mean squared (RMS) noise in a typical measurement was found to be 0.06 μc for the wired data acquisition, and 0.10 for the wireless data acquisition. This design was informed by finite element (FE) modeling described below. The specific locations of each gage, the installation procedure and the Wheatstone bridge/data acquisition system employed are described in detail in[36].

3.3 Laboratory Testing

Laboratory testing was conducted to experimentally characterize pad strain response under controlled loading conditions, measure contact stress distribution, calibrate the strain readings to the applied force, and validate the FE analysis. A series of cyclic uniaxial pad loading tests were performed on carefully prepared beds of compacted cohesionless soil (properties in Table 3.1). Cohesionless soil was employed to allow uniformly consistent and repeatable soil beds. The laboratory testing apparatus is illustrated in FIG. 40. An instrumented pad was fixed to an axial member and loading vertically via a hydraulic load frame. Load cells were employed to measure vertical and horizontal force. A tactile pressure sensor (TPS) system (Tekscan model F-3000) was employed to measure pad-soil CSD. Such sensors have been used previously in geomaterials research [37]. The TPS system was fixed to the pad with adhesive, and a polyurethane film was attached on top of the sensor to distribute point loads. Further details are discussed by Bearce[24].

The TPS captured the normal CSD between the pad and the soil during axial loading. A typical and representative result from the TPS system is shown in FIG. 41a for a 4.7 kN axial load. The pressure distribution is parabolic, which is to be expected from a cohesionless soil according to literature[32-34]. As discussed in Section 3.2, the preliminary FE analysis used three CSDs to simulate a wide range of potential soil conditions (FIG. 36). FIG. 41b shows how the experimental soil compared to these simulated loading conditions. The observed CSD falls between the parabolic and uniform CSD scenarios used in the preliminary FE analysis.

TABLE 3.1

Properties of soil used for lab testing

| Characteristic | Soil Value |
| --- | --- |
| USCS Classification | SW-SM |
| AASHTO Classification | A-1-b |
| % Passing #200 Sieve | 10.7 |
| Max Dry Unit Weight, $\gamma_{d,\,max}$[1] | 19.79 kN/m$^3$ |
| Optimum Moisture Content, $w_{opt}$ | 10.20% |

Figure 42:
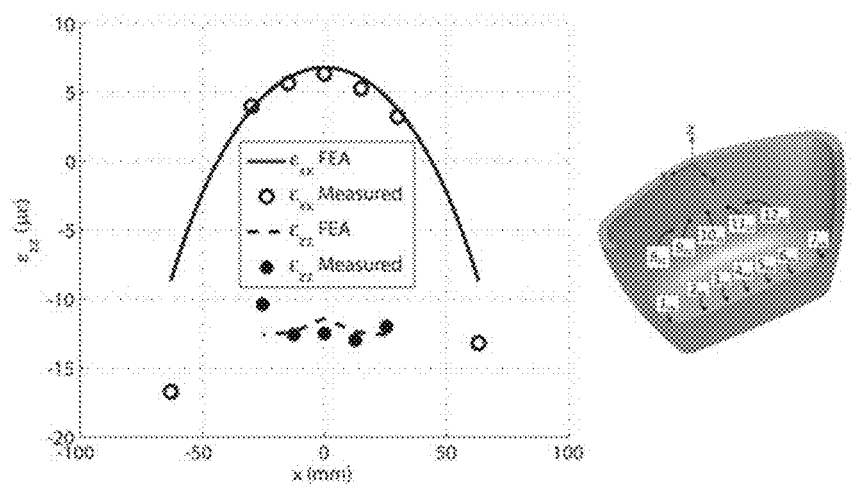
FIG. 42 Comparison of strains from lab measurements and lab-informed FE analysis for bottom $\epsilon_{xx}$ gages and sidewall $\epsilon_{zz}$ gages. Axial force=5 kN.

The measured CSD was used in Solidworks COSMOSWORKS®FE analysis to model realistic loading conditions on the bottom pad face and validate the FE model. The pad strains predicted by this FE analysis are shown as the curve in FIG. 42, and are compared to the laboratory measured pad strains. The lab testing measured 4 cm of soil penetration. As such, all the outer faces on the pad within 4 cm of the bottom were subjected to loading. The experimental and computational results match well, supporting the accuracy of the FE model. The experimental strains matched within 15% of the FE model strains, with the exception of two gages, $1_{xx}$ and $7_{xx}$, located at x=±63.5 mm. These two gages had poor agreement with the FE model. The strain gradient at $1_{xx}$ and $7_{xx}$ is very steep and the geometry is complex, being located at a fillet. These factors combine to make this the most challenging part of the pad to model and accurately instrument. With the exception of gages $1_{xx}$ and $7_{xx}$, there is good agreement with the FE model.

The laboratory data was used to calibrate the instrumented pads for field testing. This calibration process consisted of determining a soil specific strainforce sensitivity, whereby the pads could be used to measure contact force with the soil. With measured axial force and sidewall $\epsilon_{zz}$ values, a calibration factor was determined. Based on the results of 540 individual load cycles (multiple test bins; see [36] for detailed results), the calibration factor was determined to be 0.38 kN/µε. The average sidewall strain from gages $8_{zz}$ $12_{zz}$ was used during calibration. Gage averaging was used to increase the robustness of this measurement, and these gages were chosen because of the similarity in measurement values amongst these gages. Note that this calibration factor is soil-dependent and is only valid when the bottom pad face is parallel to the ground surface. Incidentally, the calibration factor from the FE analysis (FIG. 42) equaled 0.37 kN/µε and matched well with the experimentally determined value.

3.4 Field Testing

Figures 43A, 43B, 43C:
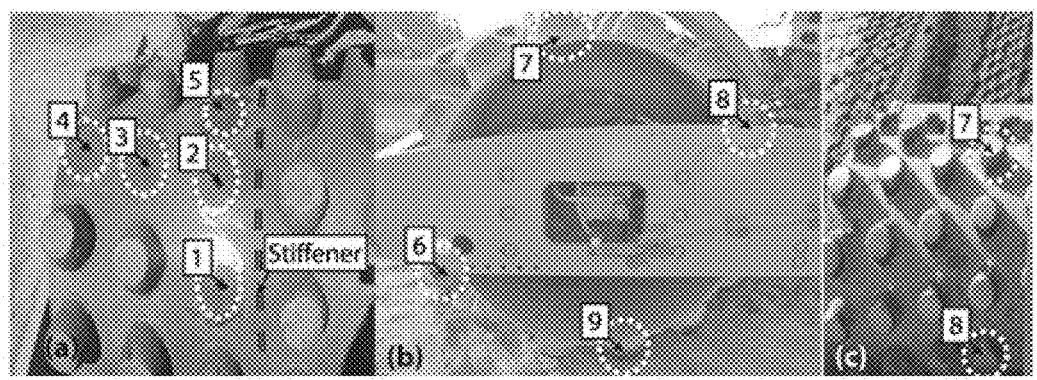
FIG. 43A-C Arrangement of the instrumented pads on the CP56 drum for right 43a) and left 43b) sides of the drum. The holes under each pad location are for the wires to feed through the drum.

The pad strain measurement system was mounted on a production scale Caterpillar CP56 pad foot roller and subjected to controlled field testing. Nine instrumented pads and a global position system (GPS) radio and receiver were mounted to the roller (FIG. 43). Measurements were processed with a wired DAQ (IOtech DaqBook 2001) and a wireless DAQ (custom in house device) and a Panasonic Toughbook PC running National Instrument's LabView. Installation details are provided in [36].

The roller compactor was outfitted with a GPS receiver and radio to continuously monitor the x, y, z position of the drum center. Real-time kinematic (RTK) GPS was employed providing position accuracies of ±1-2 cm in the horizontal plane and ±2-4 cm in the vertical direction. RTK GPS involves communication between the mobile roller and a fixed base station, and is commonly used on construction projects. RTK GPS forms an important component of roller-based monitoring for QC/QA purposes (e.g., [2]). Data from the GPS was transmitted to the computer for logging via a RS-232 connection. During the research phase of this project, the roller was operated at speeds of 0.25-0.5 m/s. The GPS temporal sampling (reporting) rate was 20 Hz. Therefore, the spatial resolution for data reporting ranged from 1.25-2.5 cm. This sampling rate was sufficient to estimate roller travel speed. With known y-offsets for each instrumented pad, the global x, y, z position for each pad measurement was recorded with 1-2 cm accuracy.

The test area was 7.5 m long by 3 m wide. Within this area, test beds were constructed with the cohesionless soil used in laboratory testing (see Table 3.1). The soil was placed in a single 30 cm thick lift via front-end loader and leveled by hand via rake. Moisture conditioning was performed as needed with a spray hose. A walk behind rototiller was used to mix the soil to promote homogenous conditions. The same soil was used for four individual test beds with water contents varying between 5.2% and 11.1% ($w_{opt}$=10.2%), as shown in Table 3.2. The intent was to explore pad strain evolution in soils dry of optimum, at optimum and wet of optimum. The free-draining nature of the granular soil made it difficult to achieve moisture significantly wet of optimum. The rototiller was used to loosen the compacted material between test beds. Dry unit weight (γd) and moisture content (w) were determined via the sand cone method and drying oven. Sand cone tests were performed to a depth of about 13 cm in accordance with ASTMD1556.

TABLE 3.2

Summary of test beds.

| Test Bed | No. of Roller Passes | $w_{init}$[2](%) | $\gamma_{d,\,init}$(kN/m$^3$) | $w_{final}$[3](%) | $\gamma_{d,\,final}$(kN/m$^3$) |
| --- | --- | --- | --- | --- | --- |
| 1 | 14 | 5.5 | 15.7 | 5.2 | 17.1 |
| 2 | 20 | 10.2 | 16.7 | 10.1 | 19.1 |
| 3 | 20 | 11.1 | 18.9 | 9.5 | 22.1 |
| 4 | 14 | 9.8 | 23.3 | 10 | 23.3 |

Pad strain response during a single roll through of the drum is presented in FIG. 44. FIG. 44a illustrates the bottom face $\epsilon_{xx}$ record from the seven gages ($1_{xx}$-$7_{xx}$) during a forward pass in test bed 1. Each temporal record was converted to a spatial record using the velocity provided by onboard GPS. Gages $1_{xx}$ and $7_{xx}$ experience compression throughout loading (peak $\epsilon_{xx}$ up to 90µɛ), while gage $4_{xx}$ experiences tension throughout loading (peak $\epsilon_{xx}$ up to 35µɛ). Gages $2_{xx}$, $3_{xx}$, and $6_{xx}$ experience a cycle of behavior including compression (up to 20µɛ) and tension (up to 20µɛ) as the pad rolls through the soil. Gage $5_{xx}$ malfunctioned. The location of the peak tensile $\epsilon_{xx}$ in the bottom face moves as the pad rolls through the soil, starting with gage $6_{xx}$ and ending with gage $2_{xx}$ for a forward pass. Conversely, very little time and spatial delay was observed between gages $1_{xx}$ and $7_{xx}$ suggesting that the entire fillet oval is compressionally engaged when one end of the pad makes contact with the soil. A symmetric $\epsilon_{xx}$ progression occurred during the reverse pass (not shown).

Sidewall $\epsilon_{zz}$ strain-time histories are shown in FIG. 44b. Gages $9_{zz}$ and $12_{zz}$ malfunctioned. The $\epsilon_{zz}$ responses from adjacent gages match each other reasonably well in shape, but can vary somewhat in magnitude. Peak $\epsilon_{zz}$ strain values in FIG. 44b ranges from 17 to 31µɛ. This amount of variation across passes was not uncommon, but some clear trends were observed, as will be discussed later. Throughout testing the sidewall $\epsilon_{zz}$ ranged from 6 to 48µɛ. The peak $\epsilon_{zz}$ values occurred in order of gages 8 to 12 for a forward pass and gages 12 to 8 for a reverse pass.

The strain time histories from gage $10_{zz}$ for pads 1 through 5 are shown in FIG. 45. The timing or position of the $\epsilon_{zz}$ peaks indicates when one pad comes into contact relative to another. The spatial interval between the pads easily identifies which pads are in similar and dissimilar rows (rows run along the width of the drum). The strain magnitudes appear to decrease as a pad is located closer to the edge of the drum, i.e., the progressive decrease in pads 2, 3 and 4. The drum is supported by a stiffener located between the 3rd and 4th circumference of pads, and as such pads 1, 2, and 5 experience the highest $\epsilon_{zz}$ magnitudes. Moving away from the stiffener, i.e., from pads 2 to 3 to 4, the $\epsilon_{zz}$ magnitudes in the pads decrease. This could be due to reduced stiffness of the drum as distance from the stiffener increases. Additionally, the soil is unconfined at the edges of the drum and could lead to a softer response to loading. It can then be inferred that the contact force of one pad is not representative of all pads, but instead is a function of the circumference on which the pad sits, and potentially other factors. A comparison of pad response along a similar circumference, e.g., pads 1, 2 and 5, illustrates the spatial heterogeneity in the soil.

Figure 46A:
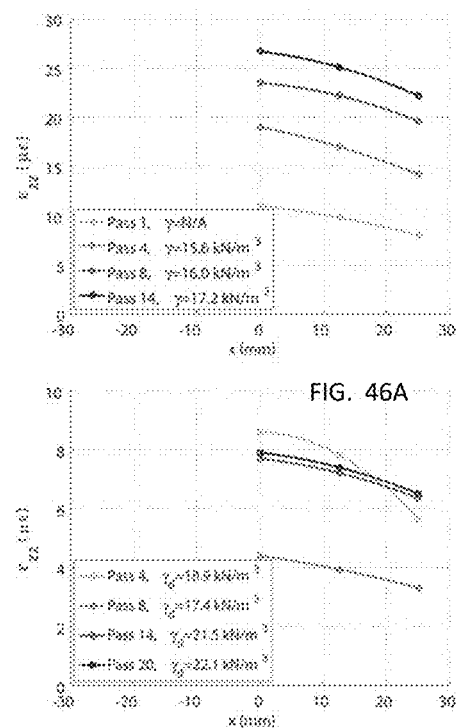
FIG. 46A-B Sidewall strains for pad 1 from test bed 1 46a) and test bed 3 46b). Strain magnitude increases with pass. Gages 8 and 9 malfunctioned during the tests; note: compressive strains are negative.
Figure 46B:
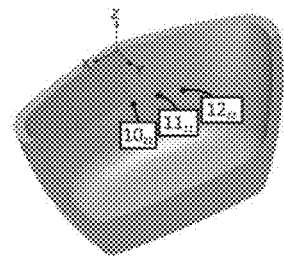

To investigate how pad strains change throughout compaction, pad strain results from test beds 1 and 3 are presented. The sidewall $\epsilon_{zz}$ magnitudes measured during test bed 1 and 3 forward passes are shown in FIG. 46. The $\epsilon_{zz}$ magnitudes were extracted when the pad was parallel with the soil surface as determined by the intersection of gage $2_{xx}$ and $6_{xx}$ response (gage $8_{zz}$ and $9_{zz}$ are unavailable due to malfunction). In test bed 1 (FIG. 46a), the magnitudes of $\epsilon_{zz}$ increased noticeably with pass as the soil was compacted (dry unit weights provided in the legend). The sidewall $\epsilon_{zz}$ magnitudes from test bed 3 (FIG. 46b) do not convey as clear an increase in $\epsilon_{zz}$ during compaction. Test bed 3 exhibited significantly different behaviors during early passes than during later passes. During initial passes, free water was visible and the soil demonstrated a pumping phenomenon-where very large elastic (recoverable) deformations were observed ahead of and behind the drum. This was likely caused by the high initial moisture content (Table 3.2). This behavior was not observed in later passes. Neglecting the pass 4 data, passes 8 through 20 exhibit increasing strain with compaction and a positive correlation between strain and γd. The considerable jump in density between pass 8 and pass 14 is reflected by a large increase in strain. Similarly, the minor change in density between pass 14 and 20 is reflected by a small change in strain. This trend supports the hypothesis that the contact force increase with compaction.

Figures 47A, 47B:
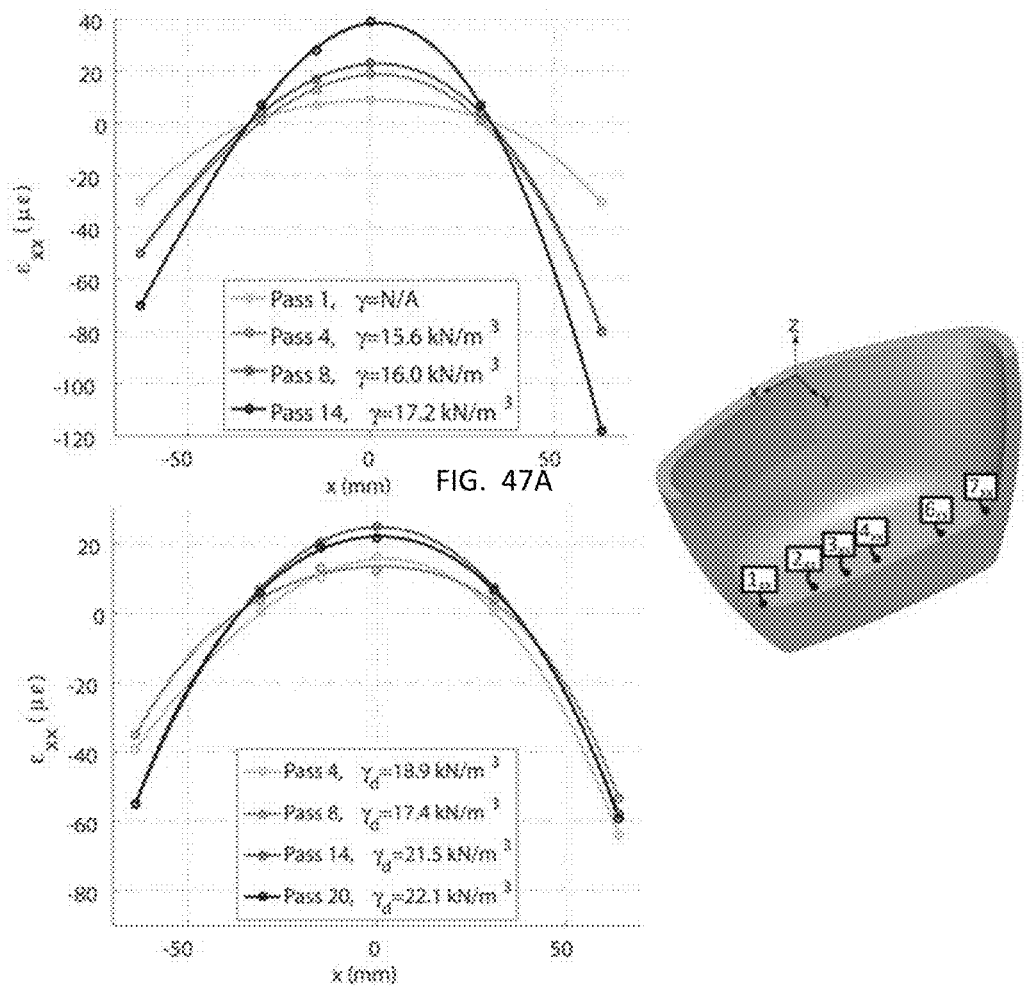
FIG. 47A-B Evolution of $\epsilon_{xx}$ in test bed 1 47a) and test bed 3 47b) for pad 1. Gage $5_{xx}$ malfunctioned during this test; note: tensile strains are positive.

The bottom pad face $\epsilon_{xx}$ magnitudes from test beds 1 and 3 are presented in FIG. 47. These strain snapshots were chosen at the point where gages $2_{xx}$ and $6_{xx}$ intersected, and are for passes immediately before density spot testing was performed. The $\epsilon_{xx}$ magnitudes generally increased (in compression and tension) with compaction. This increase in $\epsilon_{xx}$ magnitude is expected as the soil stiffens and the pad 'walks out' of the soil. The increase of $\epsilon_{xx}(x)$ in test bed 1 (FIG. 47a) is consistent with gradual increase in measured dry unit weight (γd) reflected in the legend. The slight increase in $\epsilon_{xx}$ from pass 4 to 8 is consistent with the small increase in γd, while the larger increase in pass 8 to 14 $\epsilon_{xx}$ is consistent with the greater increase in γd. The $\epsilon_{xx}$ distribution observed in test bed 3 (FIG. 47b) exhibited similar behavior to test bed 1. However, late pass strain magnitudes did not reach the same level of magnitude. The $\epsilon_{xx}$ distributions of passes 4 and 8 are similar, consistent with no measured increase in γd (in fact, the measured γd decreased). A noticeable increase in $\epsilon_{xx}(x)$ from passes 8 to 14 is consistent with a considerable increase in γd.

The magnitude of normal contact force can be determined based on the empirical calibration factor method (described earlier) that involves obtaining a soil specific relationship between sidewall strain (average of gages $8_{zz}$ $12_{zz}$) and applied force through controlled laboratory or field testing. Through laboratory testing (described above; see Mooney et al. 2011b for complete details), the calibration factor determined for the granular soil was 0.38 kN/µɛ.

Figure 48A:
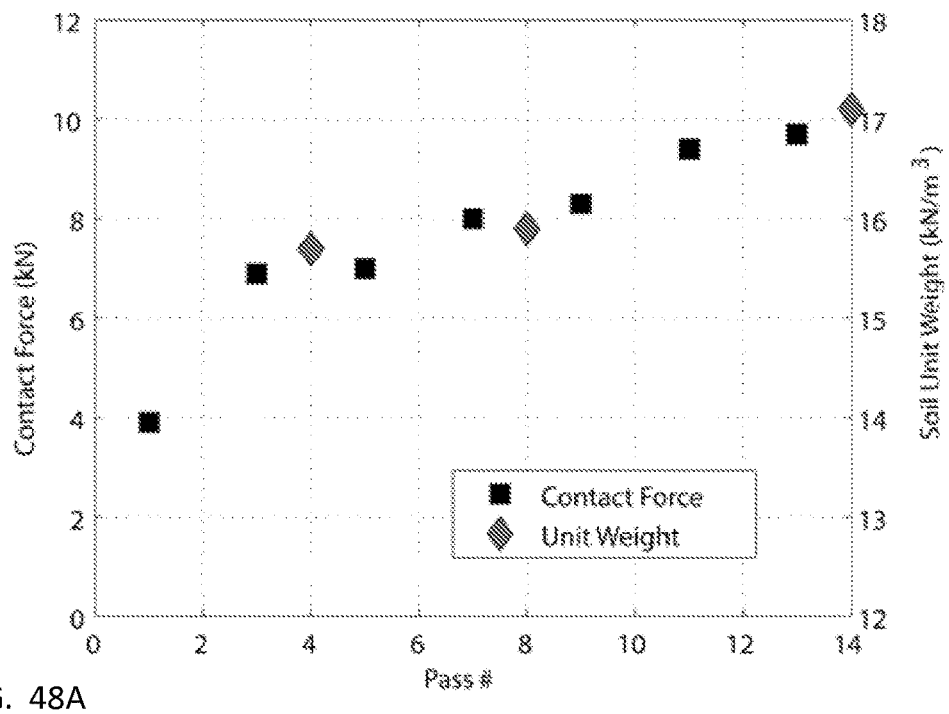
FIG. 48a-b Results from test bed 1 84a) and test bed 3 48b), relationships between contact force (kN) determined from vertical sidewall strains and soil unit weight.
Figure 48B:
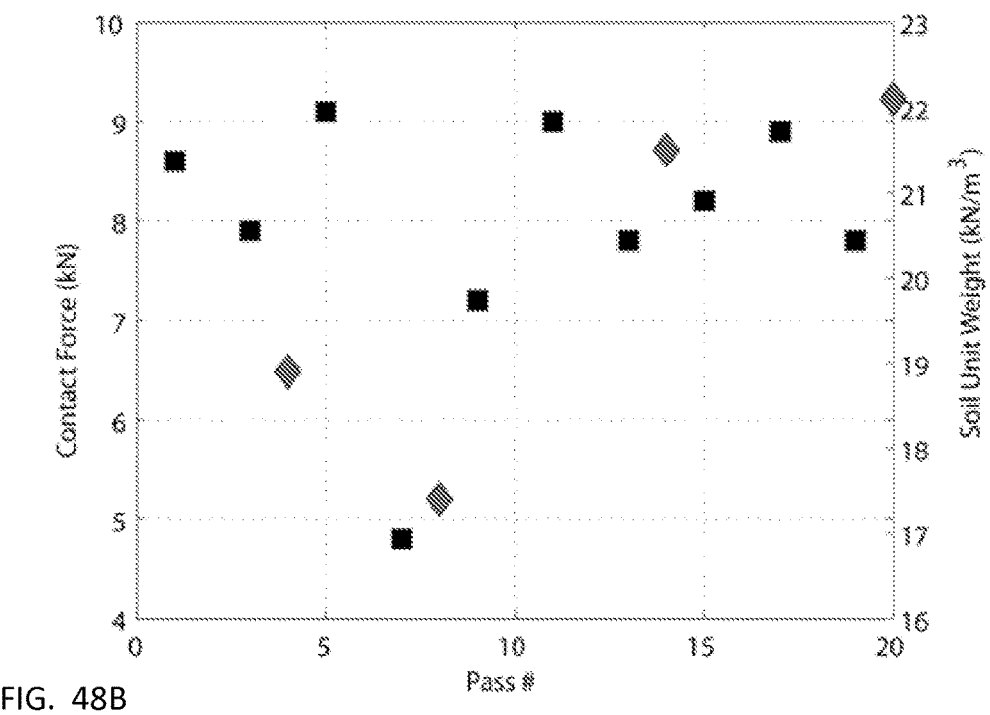

FIG. 48 shows the pad/soil contact force measurements for test bed 1 and 3 that were estimated using the granular soil calibration factor multiplied by the average of the peak sidewall $\epsilon_{xx}$ values (from gages $8_{zz}$ $12_{zz}$). Pad contact force measurements are shown as squares. There is a clear increase in peak contact force throughout test bed 1 passes, shown in FIG. 48a. The increase in contact force is significant—from 4 kN during pass 1 to almost 10 kN during pass 13—and trends well with the increase in measured γd. For test bed 3, shown in FIG. 48b, if the first 5 passes of data are neglected, the pass 6 through pass 20 data exhibit increasing contact force with compaction and a positive correlation between contact force and γd. In general, these results show support for an increasing contact force with compaction.

An investigation was undertaken to explore the use of measurable pad strains on a non-vibratory pad foot roller to provide real time continuous evidence of compaction and contact force. Individual pads were instrumented with 24 strain gages including bottom face $\epsilon_{xx}$ gages to characterize the distribution of contact stress along the direction of travel and sidewall $\epsilon_{zz}$ gages. This gage pattern was the result of computational modeling wherein finite element (FE) analysis revealed that pads undergo measurable strain fields during loading on soil and that the pad strain fields change as the applied force increases as a result of pad 'walk out' during compaction. The FE analysis revealed that the pad-soil contact stress distribution (CSD) has a significant influence on the observed pad strain field, including the sidewall vertical strains.

Results from uniaxial laboratory testing of pad/cohesionless soil interaction confirmed the findings from computational modeling, i.e., the estimated pad strains from the FE model matched well with experimentally measured strains. The CSD was measured using tactile pressure sensors and found to be moderately parabolic. An empirical calibration factor relating sidewall $\epsilon_{zz}$ strain to contact force was determined. For the cohesionless soil tested, the calibration factor was found to be 0.38 kN/µε. This calibration factor is soil-specific.

Field testing was performed on the cohesionless soil with multiple instrumented pads installed on a Caterpillar CP56 roller. Sidewall $\epsilon_{zz}$ and bottom pad face $\epsilon_{xx}$ magnitudes increased during repeated passes as the soil was compacted. Using the empirical calibration factor, the estimated contact force was shown to increase with compaction pass, correlating well with the independently-measured soil unit weight.

While the computational modeling and experimental testing demonstrate that pad strain sensing can be used to monitor compaction and estimate contact force, the findings in this study are based on limited data, i.e., a few test beds comprised of one soil type. It is therefore imperative to further explore pad strain response across a variety of subgrade soils spanning cohesive and cohesionless, as well as construction site conditions. With a rich database, one could explore and understand pad/soil interaction and the influence of various parameters such as plasticity, moisture, stiffness and density on pad response.

Chapter 4—In-situ Determination of Elastic Modulus Via Instrumented Plate

In geotechnical engineering, as well as other disciplines, in-situ material characterization is an important and challenging task. The instrumented pad foot roller compactor discussed in previous chapters represents an important step towards machine integrated in-situ material characterization for soil compaction. The capacity to characterize the mechanistic properties of the soil, e.g., elastic modulus, would represent an even greater contribution to earthwork monitoring. The work presented in this chapter takes the first step towards a rigorous understanding of strain-gage-based mechanistic property monitoring by predicting half-space elastic modulus with an instrumented plate.

An investigation was conducted to evaluate a thin circular plate instrumented with strain gages as a means to determine the elastic modulus of an expanded polystyrene (EPS) foam half-space. The plate and half-space contact was modeled with analytical and numerical models to create an inverse model for elastic modulus extraction. Using foam samples with four different moduli, plate radial strains were measured during compression tests on the foams. Experimental strains were used to predict a foam elastic modulus from the inverse models.

This chapter first reviews other plate devices used for determining elastic modulus of a half-space. Secondly, the two models used in this research to describe the behavior of the plate, namely an analytical and FE model, are discussed. The instrumented plate and experimental setup is described, which includes the independent measurement of foam elastic modulus, verification of the instrumented plate, and plate loading on the foam specimens. Finally, the results and conclusions from these tests are discussed.

4.1 Background

Indentation testing provides a means to characterize the in-situ elastic modulus of a half space. Indenters can take various shapes and sizes. The size of indenters ranges from nano-scale (e.g., the Berkovich indentor [38]) to micro-scale (e.g., Vickers or Knoop indenter[39]) to macro-scale (e.g., the Light Weight Deflectometer (LWD)[34]). Despite this range of scale, indenters typically share the same analysis approach.

The analysis required to determine elastic modulus from these indentation tests is based largely on the elastic contact problem described by Boussinesq [40] and Hertz [41], and extended by Sneddon [41]. Boussinesq solved the problem of a point load on an elastic half-space[40]. From this, solutions have been derived for a number of specific geometers, for example cylinders and cones[42, 43]. Sneddon showed how to extend this solution to any rigid punch profile that can be described by the revolution of a smooth function[44]. Hertz's contribution was to study the experimental contact stress distribution, which is a critical aspect of these formulations[41].

Of the devices discussed thus far, the LWD has the most similarity to the proposed measurement device. The LWD is a disk, assumed to be rigid, upon which a weight is dropped to induce deflection into soil. The elastic modulus of the soil measured by the LWD, ELWD, can be calculated with Boussinesq's analysis according to the equation $$E_{LWD} = \frac{(2P(1-v^2))}{awA} \tag{4.1}$$

where P is the vertically applied force, v is the poisson's ratio of the half-space, a is the radius of the plate, w is the vertical deflection under the center of the plate, and A is a factor that changes according to the contact stress distribution, i.e., A=4 for inverse parabolic, A=π for uniform, and A=3π/4 for parabolic[45].

Figure 49:
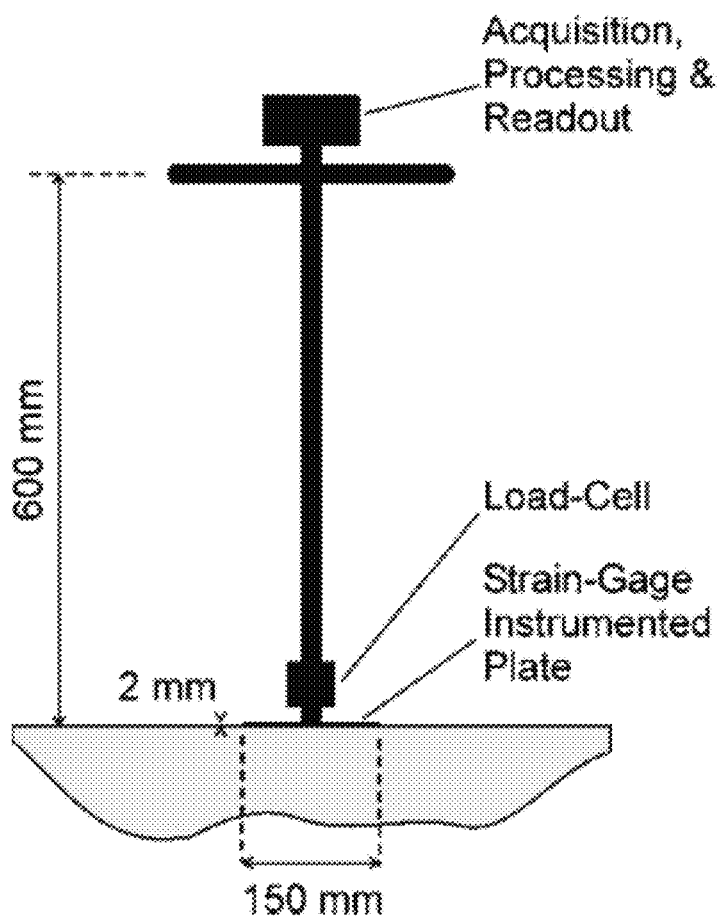
FIG. 49 Conceptual sketch of a Briaud Compaction Device (BDC).
Figure 50:
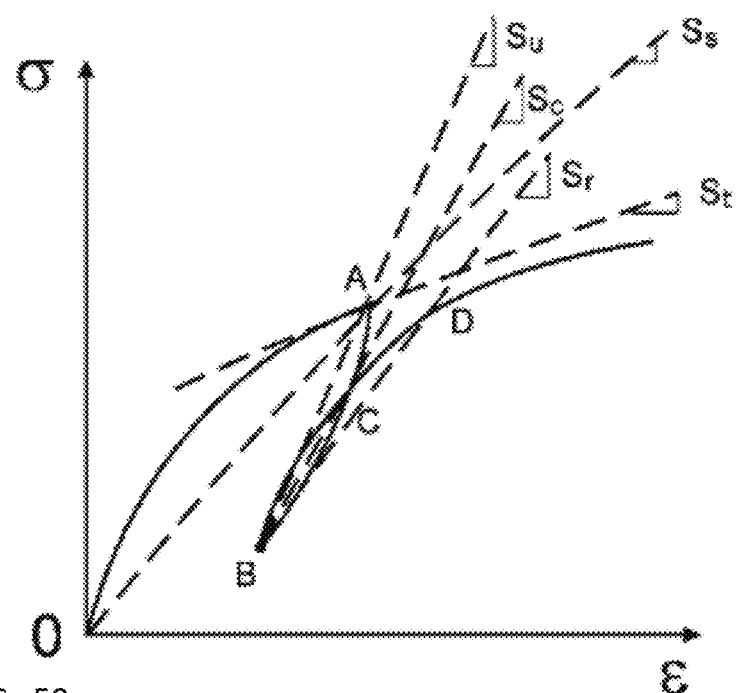
FIG. 50 Explanation for various moduli.

A device that estimates the elastic modulus of a homogeneous half-space with a flexible stainless steel plate is the Briaud compaction device (BCD), see FIG. 49. Instead of measuring the plate deflection, this device measures hoop strains on the plate following the logic that softer soils will produce higher plate strains due to increased bending in the plate. The hoop strains in the BCD plate were empirically correlated to soil reload modulus, ER. FIG. 50 shows an example of a stress-strain curve from repeated loading, and can be used to explain the different types of moduli. For example, the secant modulus, Es, is the slope between points O and A. The slope between points B and D, i.e., on the second loading, give Er. For moduli between ~5-50 MPa, the device achieved reasonable correlation between soil modulus and hoop strain at a specific measurement point on the plate, with an R2=0. in the field and R2=0.81 in the lab [46, 47]. Six soils were tested in obtaining this correlation, including what was described as clays and sands. The device gives a Briaud Compaction Device elastic reload modulus, EBCD, based on an empirical linear equation $$EBCD = 277.04 p/\epsilon - 16.37 \tag{4.2}$$

where p is the pressure under the plate created by the vertical load and ε is the hoop strain measured by a strain gage[48]. The location of the gage is unspecified, however, each BDC can be calibrated on a rubber block to ensure variation in gage location does not impact results [46, 47].

While the relationship between hoop strain and elastic modulus may be reasonably modeled as linear (i.e., Equation 4.2) for the range of elastic moduli investigated for the BCD (i.e., ~5-50 MPa), this type of contact problem is nonlinear in nature due to the evolving contact stress distribution and contact area [49]. The research discussed in this chapter captures the nonlinearity using analytical and numerical models as the basis for inverse models to predict half-space elastic modulus from arbitrary plate strains across a range of loads.

4.2 Analytical Model: Gladwell Plate Model

Plate theory can be used to establish a forward model for predicting plate strains under a wide range of physical situations. This section describes plate theory and its application to the experiments conducted in this research, namely a simply supported plate (used for verification of instrumentation) and a plate on an elastic half space.

Figure 51:
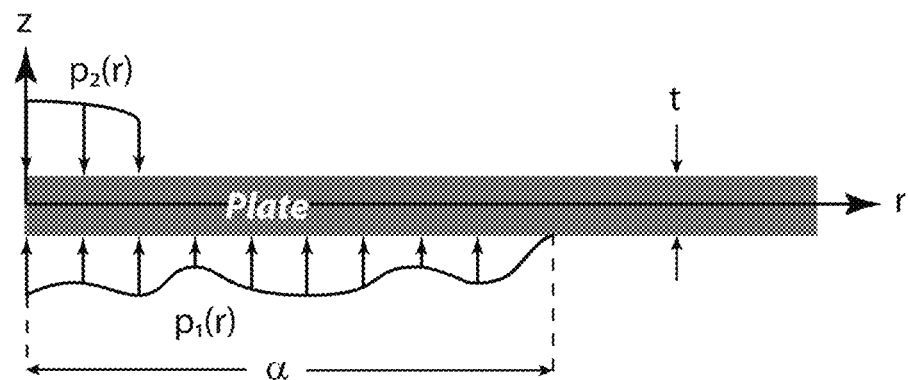
FIG. 51 Axisymmetric circular plate with coordinate system. Loading distribution is a function of r.

In plate theory, solving for normal deflection, w, provides the basis for all subsequent analysis, i.e. w is used to solve for moments, stresses, strains, etc. A diagram of a plate is given in FIG. 51. Axisymmetric plate deflection as a function of radius, $w1(r)$, is governed by the equation $$\nabla^4 w_1(r) = \left(\frac{d^2}{dr^2} + \frac{1}{r}\frac{d}{dr}\right)\left(\frac{(d^2 w)}{dr^2} + \frac{1}{r}\frac{dw}{dr}\right) = \frac{(p_2(r) - p_1(r))}{D} \quad (4.3)$$

where $\nabla$ is the Laplacian operator, p2 is the loading on the top of the plate as a function of radius, r, p1 is the loading below the plate as a function of r (for example the contact stress with a half-space), and D is the flexural rigidity, given by $$D = \frac{E_1 t^3}{12(1 - v_1^2)} \quad (4.4)$$

where E1 is the plate elastic modulus, t is the plate thickness, and v is the Poisson's ratio of the plate. The radial strain, $\epsilon r$, can be determined by the equation $$\varepsilon_r = -z\frac{\partial^2 w_1}{\partial r^2} \quad (4.5)$$

where z is the offset from the neutral axis, i.e., the center line depicted by the r-axis in FIG. 51. Tensile strains are positive and compressive strains are negative. Research on plate mechanical behavior has produced a number of viable analytical models suitable for describing plate strains. In particular, Kirchhoff plate theory was used as the basis for the forward model in this research. The plate schematic shown in FIG. 51 gives the coordinate system and loading convention for an axisymmetric plate. Kirchhoff theory applies to thin plates, which can be described as the thickness being at most 1/20 the smallest span, i.e., the diameter, and makes the following assumptions [50]:

1. The deflection in the mid-surface is small in comparison with the thickness of the plate. The slope of the deflected surface is much less than unity.
2. Straight lines initially normal to the mid-surface remain straight and normal to that surface subsequent to bending. This is equivalent to saying that the vertical shear strains, $\gamma_{rz}$ and $\gamma_{\theta z}$, are negligible. The deflection of the plate is thus associated principally with bending strains, with the implication that the normal strain, $\epsilon_z$, owing to vertical loading may also be neglected.
3. No mid-surface straining or in-plane straining, stretching, or contracting occurs as a result of bending
4. The component of stress normal to the mid-surface, $\sigma_z$, is negligible Two derivations of the plate equation are required to reflect the two plate tests conducted. First, the plate was tested with a center point load while simply supported circumferentially to verify the instrumentation. Second, the plate is loaded on an elastic half-space.

From Equation 4.3, the normal deflection of the plate can be found by the equation $$w_1(r) = \int \frac{1}{r} \int r \int \frac{1}{r} \int r \frac{p_2(r) - p_1(r)}{D} dr\, dr\, dr\, dr \quad (4.6)$$

In the case of a simply supported plate with a point load, the pressure distribution terms are set to zero, and the point load is factored in with a force balance applied later in this derivation. The integration of Equation 4.6 leads to $$w_1(r) = \frac{C_1 r^2}{4}(\ln(r) - 1) + \frac{C_2 r^2}{4} + C_3 \ln(r) + C_4 \quad (4.7)$$

where $C_1$, $C_2$, $C_3$, and $C_4$ are constants of integration. In order to ensure the function is defined at r=0, the term $C_3$ must be set to zero. The remaining three constants are solved using the boundary conditions and a vertical force balance. For the force balance, the point load P is set equal to the vertical shear stress at the edge of the plate, Qr ($\alpha$), where a is the radius of the plate and the vertical shear stress is given by $$Q_r(r) = -D\frac{d}{dr}\left(\frac{d^2 w_1}{dr^2} + \frac{1}{r}\frac{dw_1}{dr}\right) = \frac{-DC_1}{r} \quad (4.8)$$

leading to the force balance equation $$P = \int_0^{2\pi}\int_0^a Q_r(a)dr\, d\theta \quad (4.9)$$

From this equation, we can solve for the constant $C_1$=−P/(2πD). The simply supported plate gives two boundary conditions, namely the radial bending moment and plate deflection at the edge of the plate are zero:

$$M_r(\alpha)=0,\ w_1(\alpha)=0 \quad (4.10)$$

The radial bending moment of the plate is given by $$M_r(r) = -D\left(\frac{d^2 w_1}{dr^2} + \frac{v_1}{r}\frac{dw_1}{dr}\right) \quad (4.11)$$

From the boundary conditions, the other constants are solved for as $$C_2 = \frac{P}{2\pi D}\left(\ln(a) + \frac{1-v_1}{1+v_1}\cdot C_4\right) = \frac{P}{2\pi D}\left(\ln(a) + \frac{3+v_1}{1+v_1}\right) \quad (4.12)$$

Substituting in these constants, we obtain the plate deflection equation given by Timoshenko [45]

$$w_1(r) = \frac{P}{2\pi D}\left[\frac{1-v_1}{1+v_1}(a^2+r^2) + 2r^2 \ln\left(\frac{r}{a}\right)\right] \quad (4.13)$$

The radial and hoop strain, $\epsilon_r$ and $\epsilon_\theta$ respectively, are expressed as $$\varepsilon_r(r,z) = -z\frac{\partial^2 w_1}{\partial r} = -\frac{zP}{4\pi D}\left(\ln\left(\frac{r}{a}\right) + \frac{v_1}{1+v_1}\right) \quad (4.14)$$

$$\varepsilon_\theta(r,z) = -\frac{z}{r}\frac{\partial w_1}{\partial r} = -\frac{zP}{4\pi D}\left(\ln\left(\frac{r}{a}\right) - \frac{1}{2(1+v_1)}\right) \quad (4.15)$$

This equation can be used to provide the strain on the top of the plate where the strain gages are located at z=t/2.

For a plate on an elastic half-space, an approximate solution has been developed that couples the plate deflections to the deflection of the half-space[49]. The plate behavior is described by Equation 4.6 as before, with the contact pressure being described by $$p_1(r) = -2G_2\left\{\frac{g(\alpha)}{(\alpha^2 - r^2)^{1/2}} - \int_r^\alpha \frac{g'(t)dt}{(t^2 - r^2)^{1/2}}\right\}H(\alpha - r) \quad (4.16)$$

where $G_2$ is the shear modulus of the half-space (i.e., $G_2 = E_2/2[1+v2]$), $E_2$ is the elastic modulus of the half-space, v2 is the Poisson's ratio of the half-space, α is the contact radius such that α<a, and H is the Heaviside function. The function g(t) is the basic unknown function for which a solution is sought, and for this analysis is assumed to be of the form $$g(t) = \sum_{m=0}^{n} a_m t^m \quad (4.17)$$

In this research, a value of n=4 based on a comparison of contact stress distributions predicted by this model and FE model. Values of n=3,4,5 were investigated, and n=4 provided the contact stress distribution that matched best with FE predicted contact stress distributions. The boundary conditions applied at the free edge of the plate (r=α) are:

$$\nabla^2 w_1(r) = \frac{(1-v_1)w_1'(r)}{r}; \frac{d}{dr}\{\nabla^2 w_1(r)\} = 0 \text{ for } r=a \quad (4.18)$$

which leads to the plate deflection equation $$w_1(r) = -\int \frac{1}{r}\int r \int \frac{1}{r}\int r\frac{-p_1(r)}{D}dr\,dr\,dr\,dr + \quad (4.19)$$

-continued $$\left(\frac{(1-v_1)w_1'(a)}{4a}(r^2 - a^2) + w_1(a)\right)$$

Similarly, the half space deflection can be written in terms of the function g(t)

$$w_2(r) = -\frac{1-v_2}{G_2}\int_0^\infty J_\theta(\lambda r)2G_2 \int_0^\alpha g(t)\cos(\lambda t)dt\,d\lambda \quad (4.20)$$

where $J_0$ is a Bessel function of the first kind of order zero. The coefficients am are solved for according to Gladwell's [49] conditions:
1. The contact pressure is finite everywhere, i.e., $a_1=0$. This is due to the integral term in Equation 4.16, which leads to $$\int_r^\alpha \frac{a_1}{(t^2+r^2)^{1/2}}dt \quad (4.21)$$

2. The contact pressure is zero at r=α, which is equivalent to saying g(α)=0.
3. The total force applied by the contact pressure is equal to the applied load, P, so that $$\int_0^\alpha p_1(r)dr = \sum_{m=0}^{n} \frac{a_m \alpha^{m+1}}{m+1} = -\frac{P}{4\pi G_2} \quad (4.22)$$

4. The derivative of plate deflection at the edge of the plate, w1'(a), is given by $$w_1'(a) = \frac{2}{(1+v_1)Da}\left\{\frac{Pb^2}{16\pi} + G_2\sum_{m=0}^{n}\frac{a_m\alpha^{m+3}}{m+3}\right\} \quad (4.23)$$

5. Set $\omega_1(r)=\omega_2(r)$ for 0≤r≤α at n points, which approximates the condition that the plate and half-space are in contact within the contact region. With n points, this fully constrains the model with eight equations and eight unknowns ($\alpha_0, \alpha_1, \alpha_2, \alpha_3, \alpha_4, \omega_1(a), \omega'_1(\alpha), \alpha$).
6. The contact pressure is positive (compressive) in 0≤r≤α.

According to these conditions, the plate deflection, and therefore strain, may be solved for according to the material properties of the plate and half-space, and loading conditions.

4.3 Finite Element Model

Figure 52:
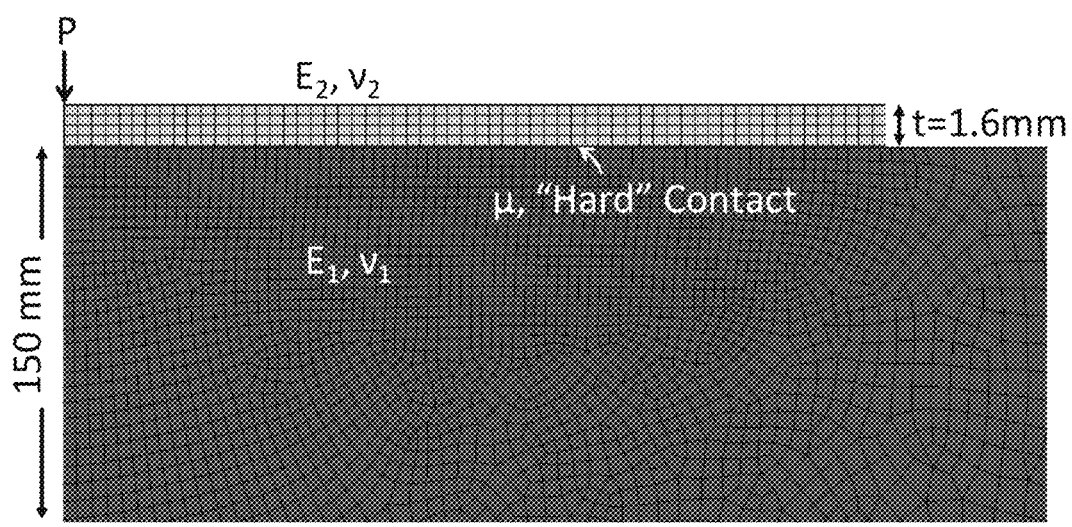
FIG. 52 Finite element model of an axisymmetric plate on a half-space.

In addition to an analytical model of plate strain, a FE model was used as the forward model for a second inverse model to predict foam elastic modulus. The FE model was constructed using Abaqus CAE, and run with the Abaqus Standard analysis package. The model, shown in FIG. 52, consisted of CAX4R elements (four node bilinear axisymmetric quadrilateral, reduced integration, hourglass control), and CAX3 elements (three node linear axisymmetric triangular). This model uses axisymmetry to reduce computation time.

The plate was 1.6 mm thick, with a 32 mm radius with all CAX4R elements. The average element size was 0.38×0.53 mm, thereby creating four elements through the thickness of the plate. The material properties were that of 6061-T6 aluminum, which has an elastic modulus of 68.9 GPa and a Poisson's ratio of 0.33.

The EPS foam was modeled as a 150 mm×150 mm body with an average mesh size 2.6 mm. There were 3892 elements, including 3828 CAX4R and 64 CAX3 elements. In order to ensure this model represented a half-space, the size of the foam was increased to a 300 mm by 300 mm body and resulted in <1% change in plate strains, and <2% change in von Mises stresses in the half-space directly under the plate. The mesh under the plate was refined considerably more than the rest of the foam to improve accuracy while decreasing runtime. This is sufficiently accurate because a 1% change in plate strains is insignificant when compared to the changes caused by half-space modulus, as discussed in Section 4.5. The elastic modulus was varied from 0.5 to 45 MPa and a Poisson's ratio of v=0.1 was used based on technical literature[17] and experimental literature[20].

The plate-foam interface was modeled with Abaqus's surface-to-surface contact and node-to-surface discretization. A coefficient of friction, μ, 0.3 was used because it lies halfway between the friction coefficient for foam on foam (0.5 [8]) and aluminum on aluminum (0.1 [51]). However, the selection of friction coefficient is not critical because varying this parameter (0<μ<0.9) had <2% influence on plate strains at a wide range of moduli and forces. The normal behavior was modeled with Hard contact and augmented Lagrange constrain enforcement. In this contact scheme, the FE model advances into a predicted mesh configuration at each new step, in which nodes from one body may overlap with another body. When an overlap is detected, a resistance force is calculated based on the depth of overlap, the associated mass, and the length of the time increment. In accordance with the augmented Lagrange method, the overlap is further reduced by an augmentation of the contact pressure.

4.4 Methodology

In this chapter, three phases of testing are discussed: independent characterization of foam mechanical properties, verification of plate instrumentation, and plate loading on foam. This section discusses the methodology for each of these tests.

4.4.1 Plate Instrumentation and Verification

Figure 53:
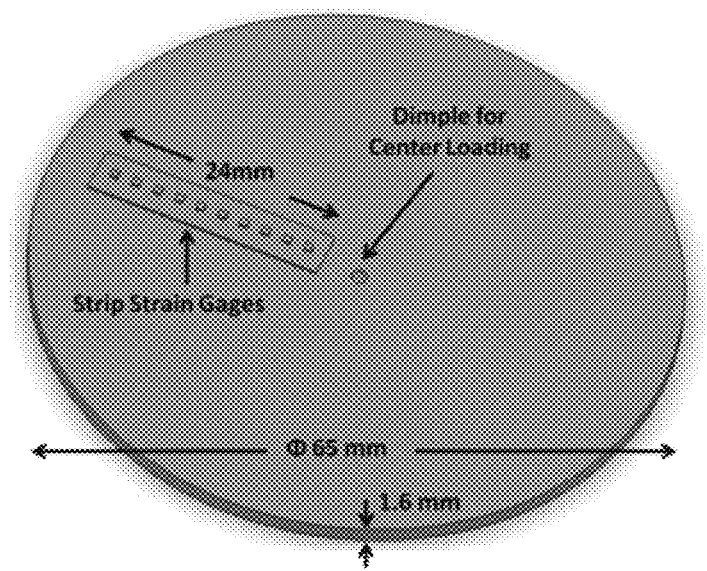
FIG. 53 Schematic of the instrumented plate.

An aluminum plate was instrumented with strain gages to measure plate response. The plate, shown in FIG. 53, was made of 6061-T6 aluminum and measures 65 mm in diameter and 1.6 mm thick. The ratio of thickness to diameter was kept below 1/20 in order to keep the plate within the guidelines for the analytical model. These dimensions were chosen based on analytical model calculations that ensured measureable strains when loaded on a half-space with the elastic modulus of the foam samples. A strip of ten strain gages was bonded to the plate to measure radial strain. Vishay Micro-Measurements part EA-13-031 MF-120 was bonded to the plate with M Bond 200 according to Vishay recommended procedures[52]. A small dimple was machined into the center of the plate with a ball end mill on a CNC matching the diameter (3.2 mm) of the loading ball used to apply the load. This arrangement ensures the load would be delivered directly to the center of the plate and have a small loading radius of approximately 1 mm, closely approximating a point load.

Figure 54:
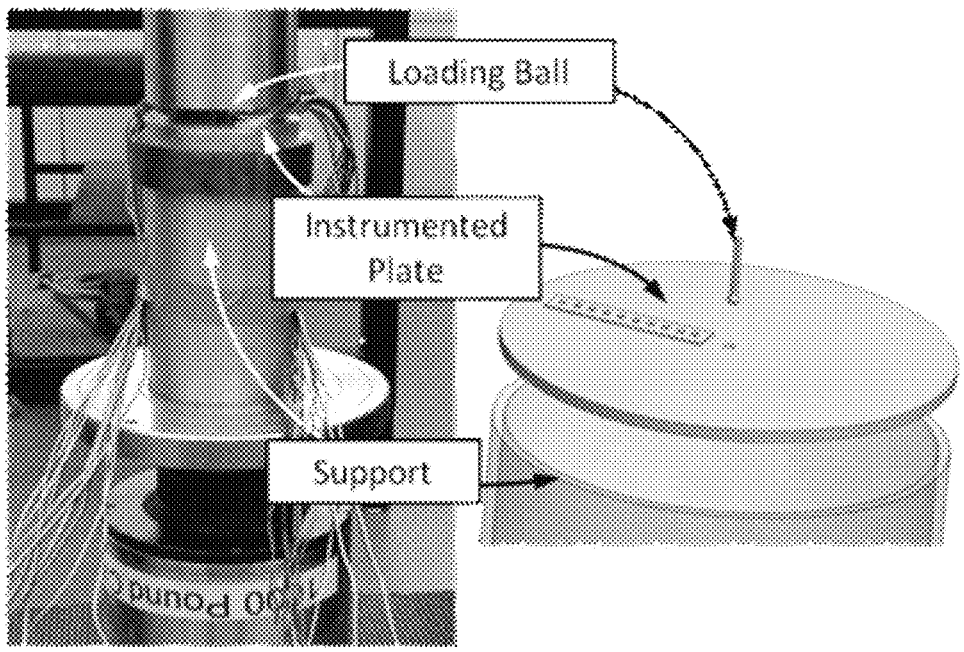
FIG. 54 Simply supported experimental setup.

The plate instrumentation was verified via tests with a center loaded, simply supported configuration, shown in FIG. 54. The plate is supported by a hollow aluminum tube 31.75 mm in diameter and 70 mm tall, and loaded in the center by a ball to approximate a point load. The wall thickness of the aluminum tube was 1.6 mm, but where the tube contacted the plate this was beveled to a point such that they only made contact along the outer radius. Samples were loaded up to 95% of the load at which plasticity was predicted by the FE model. The same MTS load frame used in the foam uniaxial compression tests was used here.

Experimental errors can originate from the gages themselves, from the DAQ system, or from the experimental setup. Errors from the gages include position and orientation errors associated with installation, and sensitivity to transverse strain. The following sections discuss contributions from each of these sources.

During installation, the position and orientation of gages can only be guaranteed to a certain accuracy. The associated installation errors translate to measurement errors, which depend on the strain field in the area of the gage. We will discuss the two cases, translation and rotation errors, separately.

FIG. 55a describes the case of translation. For this experimental setup, a strip of strain gages (including ten gages in the experiment, but only three are shown in the figure) is placed along a radius of a plate. We assume the gages are displaced by some δx (assumed to be in line with the radius of the plate) and δy (assumed to be perpendicular to the radius of the plate), related to the positioning accuracy of the installation method. In this particular case, the positioning accuracy was within ±0.2 mm in the x-direction and ±0.6 mm in the y-direction.

The error associated with translation will be different for each gage in the strip. We start by determining the new radial position of the gage $$r' = ((r+\delta x)2 + \delta y2)1/2 \quad (4.24)$$

and the angular shift of the gage relative to the radius of the plate, $$\phi = \tan^{-1}(\delta y/(r+\delta x)) \quad (4.25)$$

We can now calculate the radial and hoop strain at the new location, $\epsilon'_r$ and $\epsilon'_\theta$, substituting r' into Equations 4.14 and 4.15. To determine the strain measurement of the gage at the new position, $\epsilon_{meas}$, we need to perform a tensor transformation by angle φ with the transformation matrix T according to the equation $$\left\{ \begin{array}{c} \varepsilon_{meas} \\ \varepsilon_{meas,trans} \end{array} \right\} = T \begin{bmatrix} \varepsilon'_r & \gamma'_{r\theta} \\ \gamma'_{r\theta} & \varepsilon'_\theta \end{bmatrix} Tl =; T = \begin{bmatrix} \cos\phi & \sin\phi \\ \sin\phi & \cos\phi \end{bmatrix} \quad (4.26)$$

where $\epsilon_{meas,trans}$ is the transverse strain at the new gage location, $\gamma'_{r\theta}$ is the shear strain corresponding to $\epsilon'_r$ and $\epsilon'_\theta$, and TT is the transpose of T. Due to axisymmetry, $\gamma'_{r\theta}$ is zero. Solving for $\epsilon_{meas}$, this equation simplifies to $$\epsilon_{meas} = \epsilon'_r \cos^2\phi + \epsilon'_\theta \sin^2\phi \quad (4.27)$$

from which we can readily calculate the measurement error:

$$\Delta\epsilon_{pos} = \epsilon_r - \epsilon_{meas} \quad (4.28)$$

Errors arising from rotation of the gage placement can be calculated in a similar fashion. This scenario is depicted in FIG. 55b, with the critical parameters being the distance from the gage to the center of rotation, ro, and the rotation angle, φ. For this particular experiment, the center of rotation is assumed to be the center of the gage strip. We start by calculating the new position of the gage $$\delta x = r_o(1-\cos\alpha), \quad \delta y = r_o \sin\alpha \quad (4.29)$$

$$r' = \sqrt{(r+\delta x)^2 + (\delta y)^2} \quad (4.30)$$

The new orientation of the gage is given by $$\phi = \alpha + \tan^{-1}(\delta y/(r+\delta x)) \quad (4.31)$$

The strain at the new location can be calculated with Equations 4.14 and 4.15. The strain measurement requires a tensor transform by $\phi$, as given in equation (27), which allows for the calculation of the error produced by gage rotation:

$$\Delta\epsilon_{rot} = \epsilon_r - \epsilon_{mea,rot}$$

The influence of position and orientation gage errors on the radial strain is shown in FIG. 56 for an arbitrary force of 50 N. Gage position error is presented with the minimum and maximum error cases, corresponding to $\delta x=0.2$ mm and $\delta y=0$ mm and $\delta x=0.2$ mm and $\delta y=0.6$ mm respectively. Position error has a considerable impact, particularly in the positive direction. The positive error is strongly impacted by the $\delta y$, which causes the gage orientations to differ by as much as 6.7° at the first gage. Orientation error has a negligible impact.

Strain gages are subject to transverse error, which is caused by strain of the specimen in the direction perpendicular to the measurement axis of the gage. This transverse strain causes a change in resistance of the gage described by a transverse sensitivity, $\delta_{trans}$, or percent of transverse strain that contributes to the measurement. For the gages used in this experiment, the transverse sensitivity is 1.2%. The measurement error can be calculated by $$\Delta\epsilon_{trans} = \epsilon_\theta * \delta_{trans} \quad (4.32)$$

For this experiment, the transverse error will always increase the magnitude strain measurement because the hoop strain always has the same sign as the radial strain, as shown by Equations 4.14 and 4.15. It is worth noting that the percent error caused by the transverse sensitivity is increased if the gage has been rotated (i.e. due to installation errors). The radial strain is always greater than the hoop strain; therefore when the gage is rotated, the strain along the measurement axis decreases, while the strain in the transverse direction increases.

Figure 57:
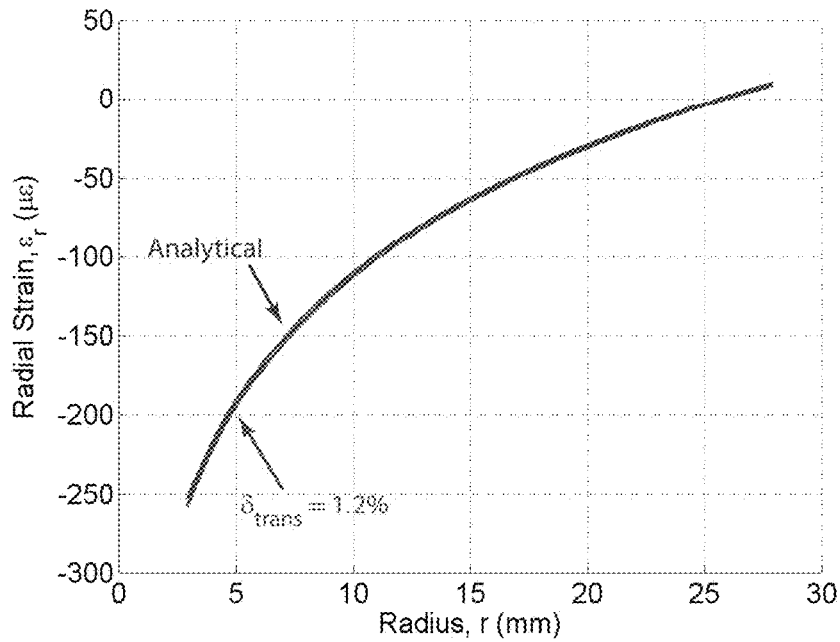
FIG. 57 The influence of transverse sensitivity on plate strain.

The influence of the transverse sensitivity on radial strain is negligible, as shown in FIG. 57.

The DAQ system is limited in its accuracy by the electronic components used. Errors arise from the accuracy with which the gain and excitation voltage, Vex, can be determined, as well as from the analogue to digital conversion.

To determine the influence of gain and Vex accuracy, we can conduct an error propagation analysis. The voltage measured by the DAQ (after analogue processing, i.e. gain) can be calculated by $$V_{meas} = \frac{\varepsilon * V_{ex} * F_g * \text{Gain}}{4} \quad (4.33)$$

The uncertainties in the DAQ system parameters are tabulated in Table 4.1.

TABLE 4.1

Uncertainties in the DAQ system.

| Field | Value |
|---|---|
| $V_{ex}$ | 5 ± 0.05 V |
| Gain | 200 ± 4 |

These errors can be propagated through the strain calculation.

$$\Delta V_{meas} = V_{meas}((\Delta)/V_{ex} + \Delta\text{Gain}/\text{Gain}) * \epsilon * F_g/4 \quad (4.34)$$

giving $V_{meas} \pm 0.0154 * V_{meas} * \epsilon$. Some example calculations are summarized in Table 4.2. The error is shown in $V_{meas}$ and in equivalent strain. The equivalent strain is calculated using Equation 4.33.

TABLE 4.2

Uncertainties in experimental setup.

| Strain (µε) | $\Delta V_{DAQ}$(mV) | $\Delta\epsilon$DAQ (µε) |
|---|---|---|
| 7036 | 0.39 | 0.76 |
| 5784 | 0.26 | 0.51 |
| 584.7 | 0.0027 | 0.0053 |

The DAQ has 16 bit analogue to digital conversion, which results in 216-1 possible digital values. For the DAQ's ±5 V input measurement, which corresponds to ±9756µε (from equation 7), this results in a quantization error of $$\Delta\epsilon_{A-D} = \epsilon_{FS}/N_{intervals} = (\pm 9756\mu\epsilon)/(2^{16}-1) = \pm 0.149\mu\epsilon \quad (4.35)$$

Figure 58:
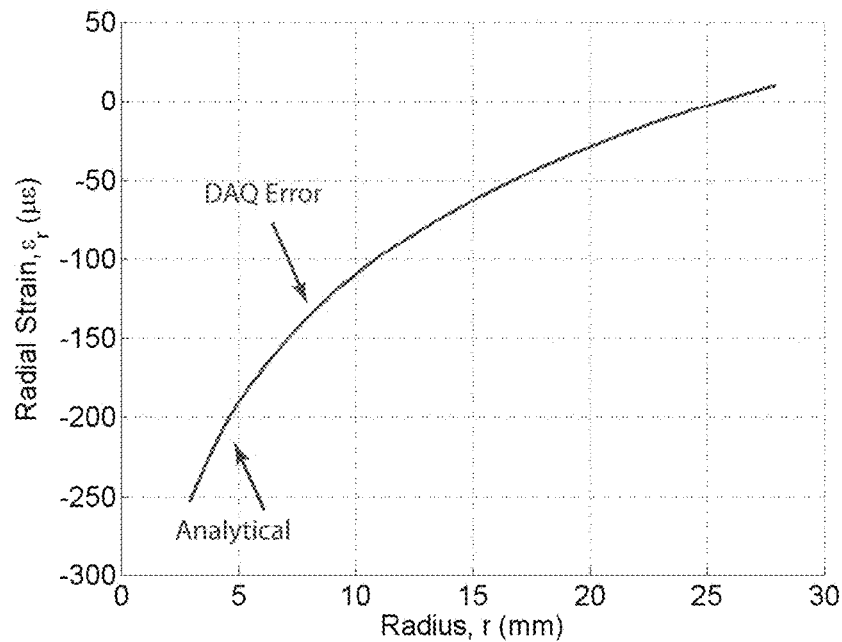
FIG. 58 The influence of data acquisition errors on plate strain measurements.

The total errors from the DAQ account for <1µε in the worst case scenario, which is negligible in the experiments being run. The radial strain with DAQ errors are shown in FIG. 58.

Figure 59:
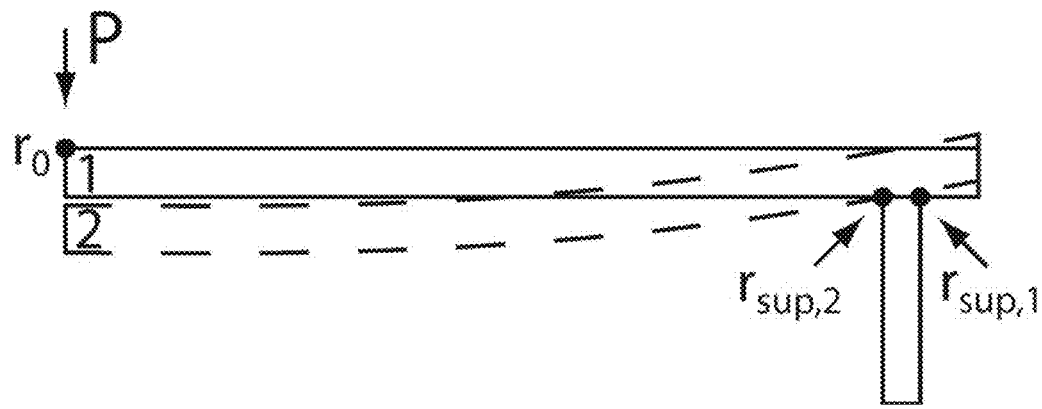
FIG. 59 Center loaded plate (P at r0) supported by a wall. Support may change position as plate is loaded from position 1 to 2

The ability of the physical setup to replicate the analytic model is limited in certain regards. In particular, the simple support for the plate is a hollow aluminum tube with a wall thickness of 2 mm. The position at which the plate is supported may change during loading, as shown in FIG. 59. To approximate the error caused by this shifting in the support, we can change the 'r' in Equation 4.14, leading to $$\Delta\varepsilon_{sup}(r) = \varepsilon_{r,sup1}(r) - \varepsilon_{r,sup2}(r) = \frac{-zP}{4\pi D}\left(\ln\frac{r}{r_{sup1}} - \ln\frac{r}{r_{sup2}}\right) \quad (4.36)$$

Figure 60:
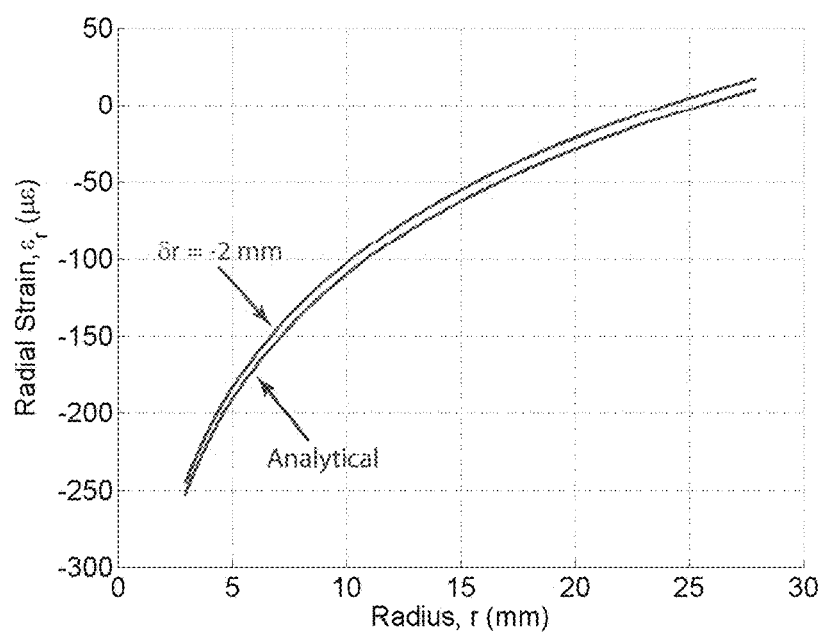
FIG. 60 Influence of moving simple support from 33 mm radius to 31 mm.

The change in radial strain caused by moving this support is shown in FIG. 60. These two lines represent a difference in the support of 2 mm.

Figure 61:
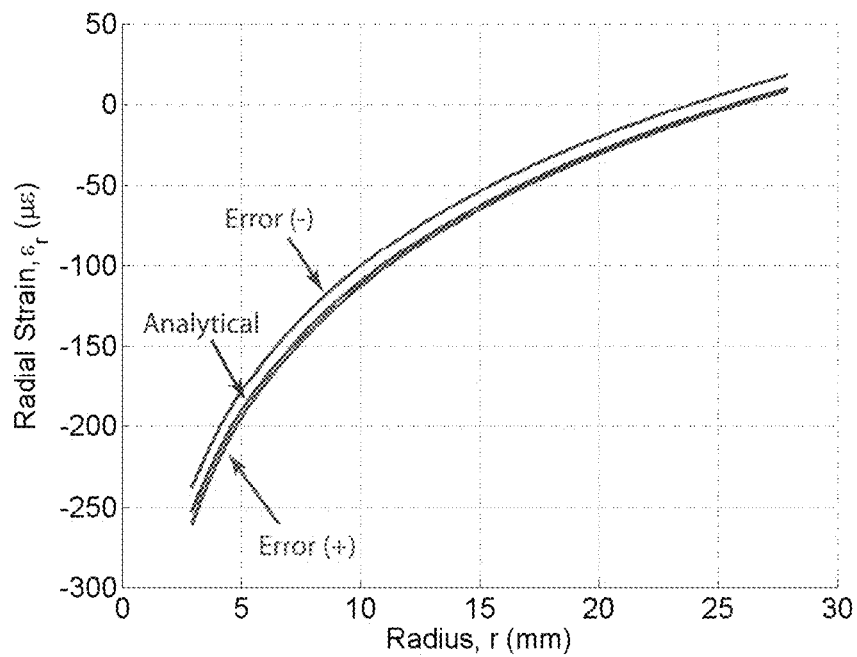
FIG. 61 Combination of experimental errors from gage position, gage orientation, gage transverse sensitivity, DAQ system, and experimental setup.

While the list of experimental errors in this section is not exhaustive, it has captured the majority of potential sources and should be able to explain most of the deviations between experimental results and the analytical model predictions. FIG. 61 shows the combination of all errors discussed in this section. The strain measurements from the plate verification tests should fit within these (−) and (+) bounds.

4.4.2 Plate on Elastic Half-space Testing

Figure 62:
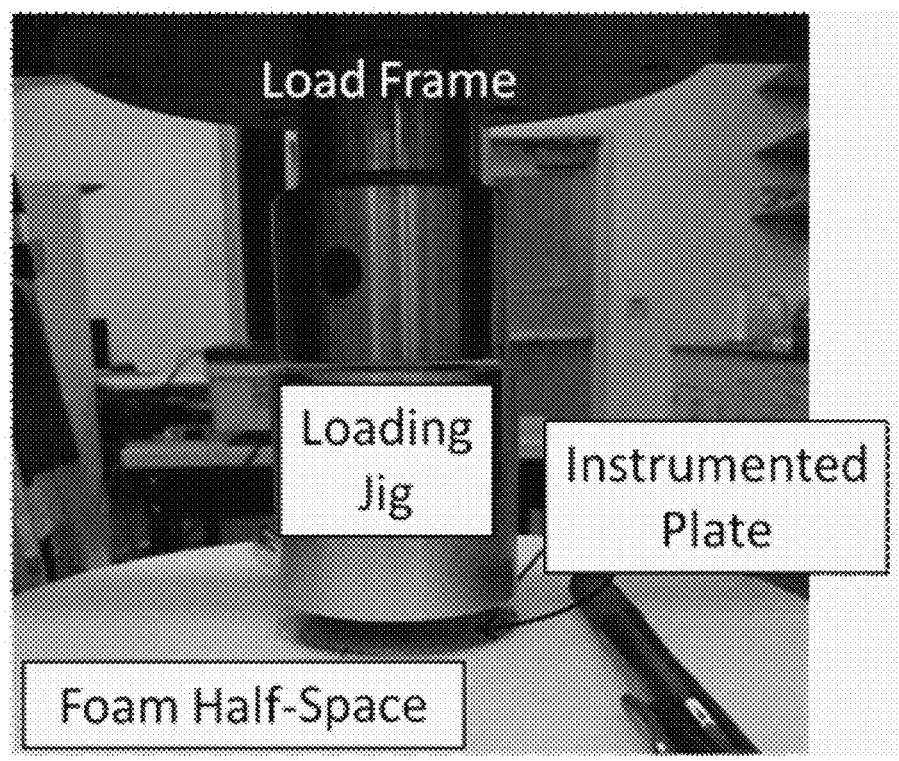
FIG. 62 Experimental setup for an elastic plate on an elastic half-space using an MTS load frame.

The instrumented plate was loaded onto a foam half-space to see if the elastic modulus of the half-space could be predicted. An MTS load frame, shown in FIG. 62, was used to load the instrumented plate onto the foam specimen with a designated loading cycle while plate strains were recorded. The load frame is equipped with a 4448 N load cell with resolution of ±0.05 N and a displacement measurement device with resolution of ±0.005 mm. The instrumented plate was loaded by a 3.2 mm spherical ball in the center of the plate. Ten strain gages were placed along the radius of the plate, measuring radial strain. The foam specimens measured 200 mm in diameter and 100 mm in height. These dimensions were chosen based on an FE analysis that concluded that boundary effects, e.g., stresses reflected at the material edges, are sufficiently negligible (<1% error in plate strains) at this size specimen.

Each foam type was subjected to six tests, where a test consisted of a single load cycle. Half of the tests sought to remove the effect of the inhomogeneous structure of the foam near the surface, i.e., increased density at the surface due to bead fusion during manufacturing. Three of the tests were conducted on the native surface of the foam, i.e., the surface created by the manufacturing mold. The second three tests were conducted after removing 1 mm from the foam surface via sanding. Sanding was conducted with 220 grit sand paper wrapped around a 2×4 wooden block moved in a circular motion to keep the sanding even across the foam surface. The thickness of material removed was periodically checked with the load frame vertical displacement measurement device, until 1±0.1 mm of material had been removed. The maximum force applied to the plate varied by foam density, according to the limitation of keeping stresses within the foam in the elastic range. The plate was loaded at 1 mm/sec onto the foam specimen.

4.5 Inverse Models for Plate on an Elastic Half-space

Two inverse models were developed for predicting half-space elastic modulus from plate radial strains based on two different forward models. A forward model predicts plate strain for a given half-space elastic modulus, while an inverse model predicts half-space elastic modulus from plate strains. The two forward models used here are an analytical model and a FE model, discussed in previous sections. The inverse model estimates elastic modulus of the half-space from experimental strains by minimizing the objective function:

$$\epsilon = \sum_{i=1}^{N} (\varepsilon_i^{EXP} - \varepsilon_i^{Model})^2 \quad (4.37)$$

where i is the gage, N is the total number of gages (N=10), $\epsilon_i^{EXP}$ is the experimental radial strain for gage i, and $\epsilon_i^{Model}$ is the model radial strain for gage i. The model strains are generated according to the forward model.

The half-space elastic modulus that minimizes the objective function is found using a lookup table, which is an approach used in other inverse modeling applications [53]. A look up table stores results from a large number of model simulations and allows quick calculation of plate strains for a given set of parameters. For example, several model simulations are run that systematically vary the elastic modulus parameter from 1.5 to 50 MPa and the applied force from 0 to 200 N, to represent the full range of physical conditions that were expected to be encountered in a test. For both forward models, the lookup table includes plate radial strains for all combinations of the following parameter values:

The plate radial strain values for an arbitrary set of parameters not explicitly listed in Table 4.3 can be estimated through linear interpolation or extrapolation. For example, the strain for gage 1 (r=5 mm) with a half-space elastic modulus of 15 MPa and a force of 25 N would be calculated based on the nearest points in the lookup table, i.e., between moduli of 10 and 20 MPa, and between forces of 0 and 50 N:

$$\epsilon_i^{Model}(E, F) = \epsilon_1^{Model}(15, 25) = ((\epsilon_1^{Model}(20, 50) + \epsilon_1^{Model}(10, 50))/2 + (\epsilon_1^{Model}(20, 0) + \epsilon_1^{Model}(10, 0))/2)/2$$

TABLE 4.3

Forward model parameter values used to populate plate radial strain lookup table.

| Parameter | Values |
| --- | --- |
| Radius of gages, r (mm) | [5, 7, 9, 11, 13, 15, 17, 19, 21, 23] |
| Half-space Elastic Modulus, $E_1$ (MPa) | [1.5, 5, 10, 20, 30, 50] |
| Force, F (N) | [0.50, 100, 150, 200] |

The resolution of the inverse model is therefore only limited by the error tolerance of the objective function. The inverse model accuracy is limited by the linearity of the forward models, which is discussed below.

Plate radial strains vary with location, material elastic modulus, and load magnitude. The linearity of each of these variables is discussed here because it is important to determining the discretization of the lookup table.

Figure 63:
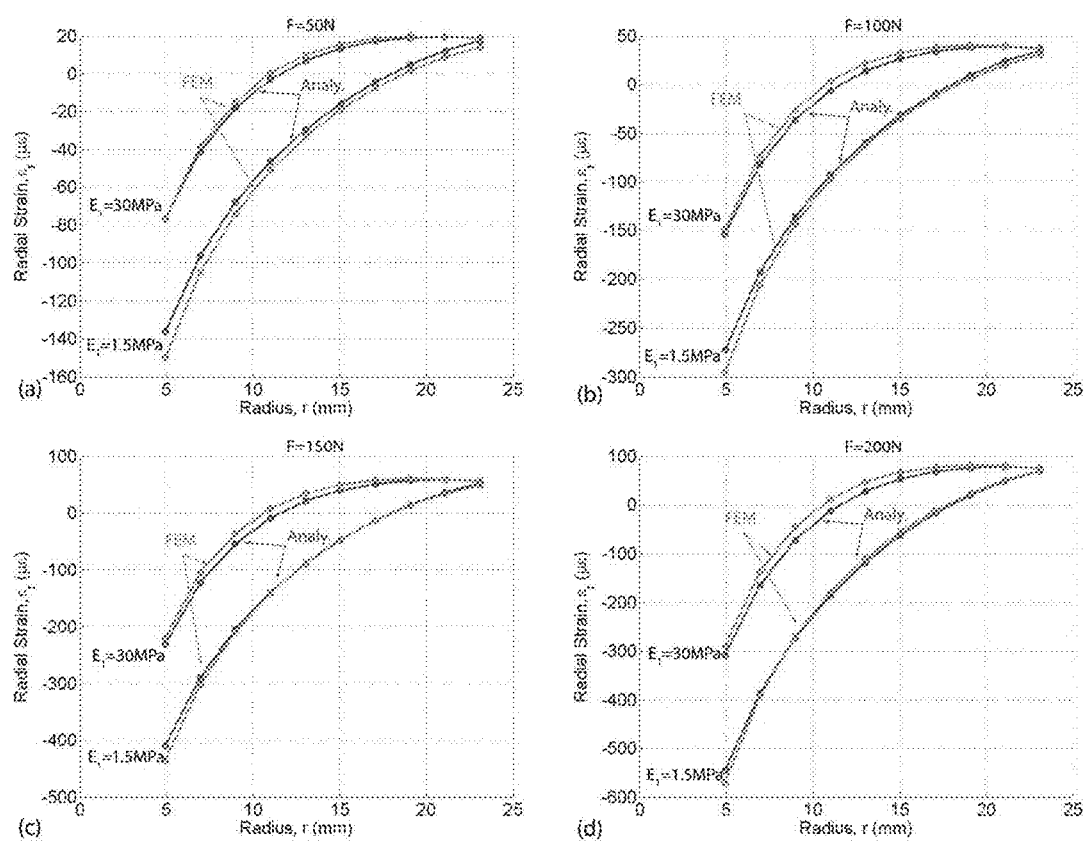
FIG. 63 Strain versus radius for an elastic plate on an elastic half-space. Comparison of analytical and FE models for various forces: 50, 100, 150, 200 N.

FIG. 63(a-d) compares the analytical model predicted and FE model predicted plate radial strains for a plate on a half-space. The comparison is made at four forces, 50, 100, 150, and 200 N, and two different foam moduli indicated in the legends. The 'o' on the strain curves shows the locations of the ten strain gages on the instrumented plate. Results from the analytical model and FE model agree well. These plots show the strains to be nonlinear with respect to radius. However, this nonlinearity in the spatial dimension (i.e., radius) is not problematic. In the analytical model, plate strain can be evaluated at any specified radius thereby not requiring any interpolation. The FE model has good spatial resolution, with a node located every 0.5 mm. Therefore, of the two points used for interpolating the strain at any given gage location, one point will be within at least 0.25 mm of the actual gage location.

To facilitate clear presentation of the model linearity, I focus on a single model at a time. As shown in FIG. 63, both models agree very well and, in fact, were found to yield the same conclusions for the linearity analysis. In this section, the results for the FE model linearity are presented. The analytical model linearity analysis is presented in Appendix B, and is nearly identical to the FE model results presented here. In this section, linearity of the FE model has been characterized with respect to half-space elastic modulus and applied vertical force.

Figure 64:
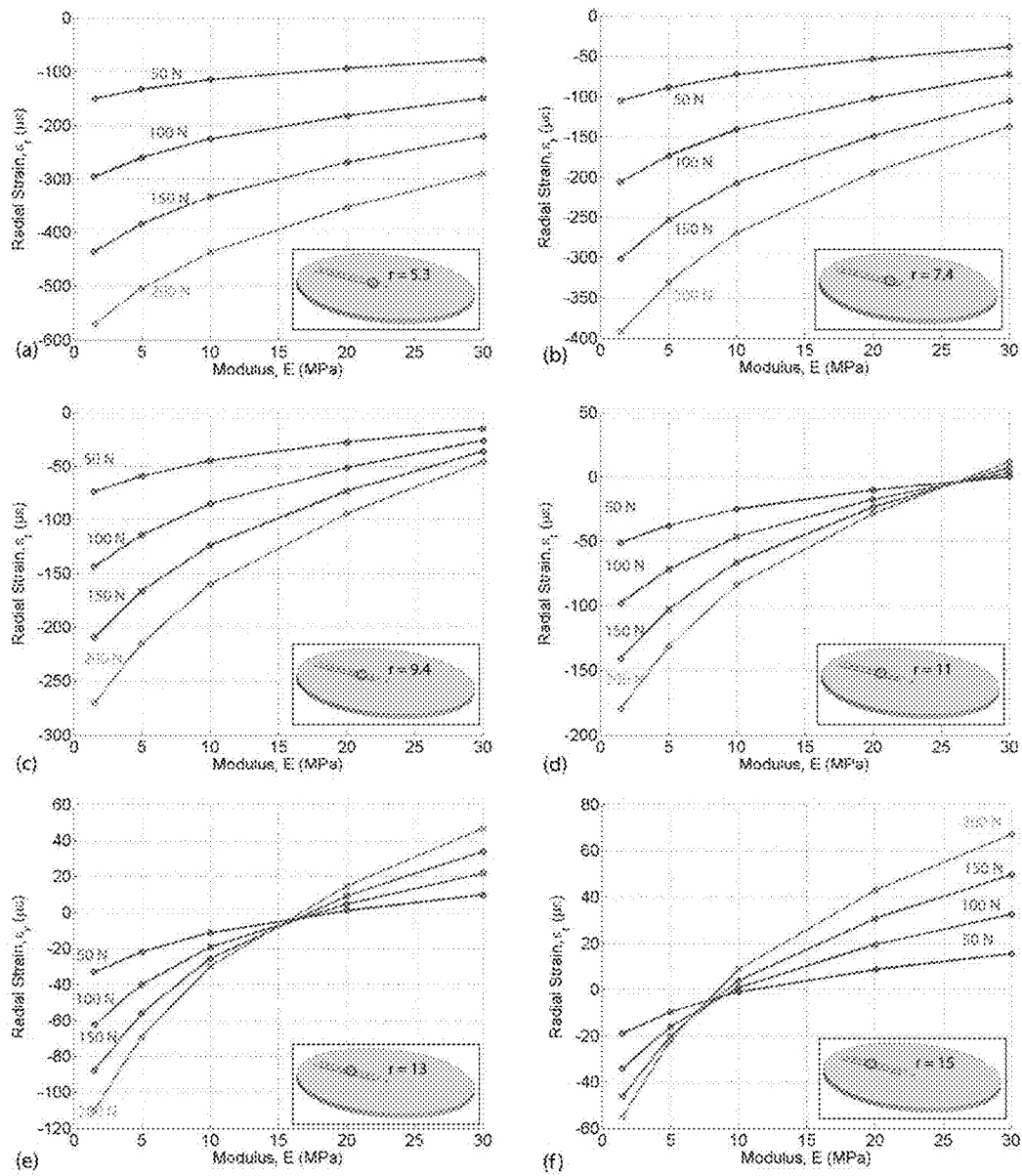
FIG. 64 Strain versus half-space elastic modulus for a plate on an elastic half-space for the six gages closest to the center of the plate, at F=50, 100, 150, 200 N for the FE model forward model.
Figure 65:
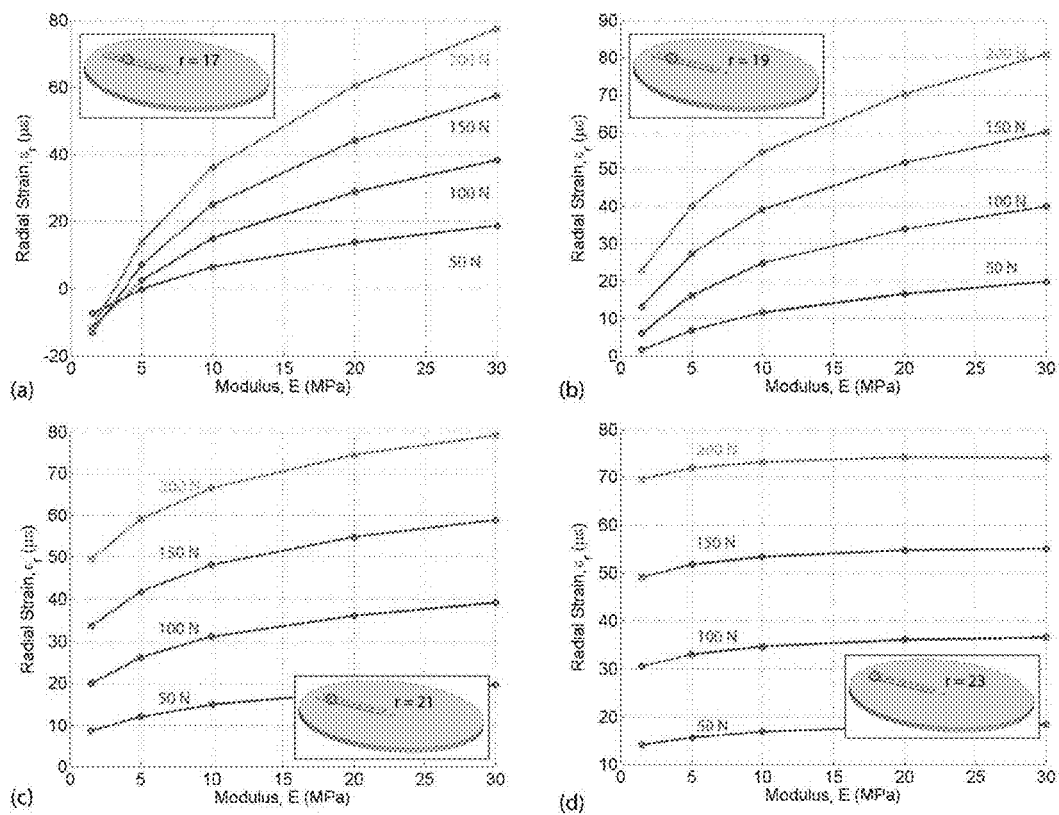
FIG. 65 Strain versus half-space elastic modulus for a plate on an elastic half-space for the four gages furthest from the center of the plate, at F=50, 100, 150, 200 N for the FE model forward model.

FIG. 64 and FIG. 65 show ten plots from FE model results, one for each strain gage location (r=5, 7, 9, 11, 13, 15, 17,19, 21, and 23 mm). The plots show plate strain versus half space elastic modulus at four forces shown in the legends: 50, 100, 150, and 200 N. The FE model strains are nonlinear with regard to half space elastic modulus, with the slope generally becoming less steep at higher moduli. The discretization of elastic modulus shown in these plots is able to capture this nonlinear strain behavior, and is used for the lookup table.

Figure 66:
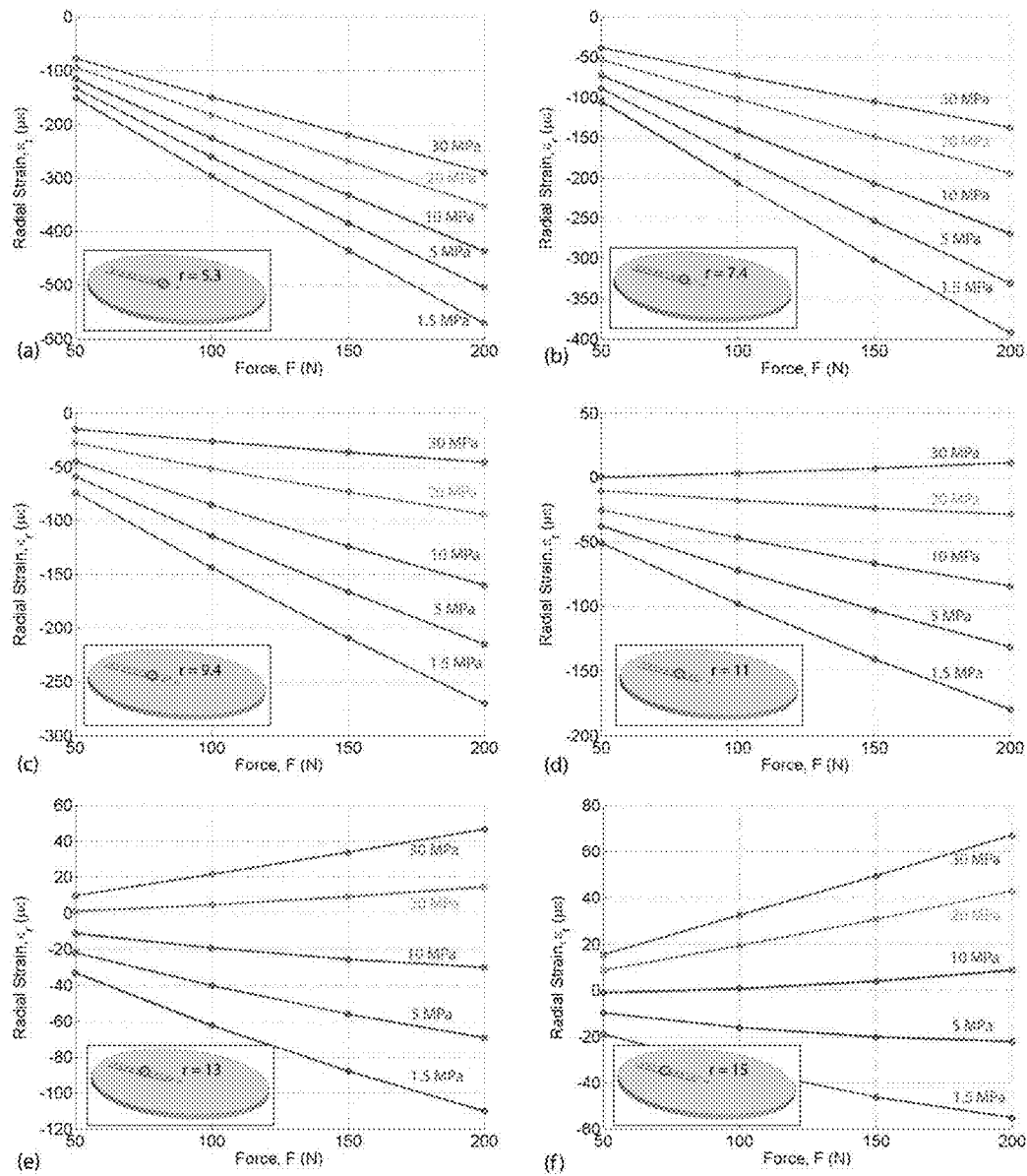
FIG. 66 Strain versus force for a plate on an elastic half-space for the six gages closest to the center of the plate, for multiple half-space elastic modulus values (1.5, 5, 10, 20, 30 MPa), from FE model results.
Figure 67:
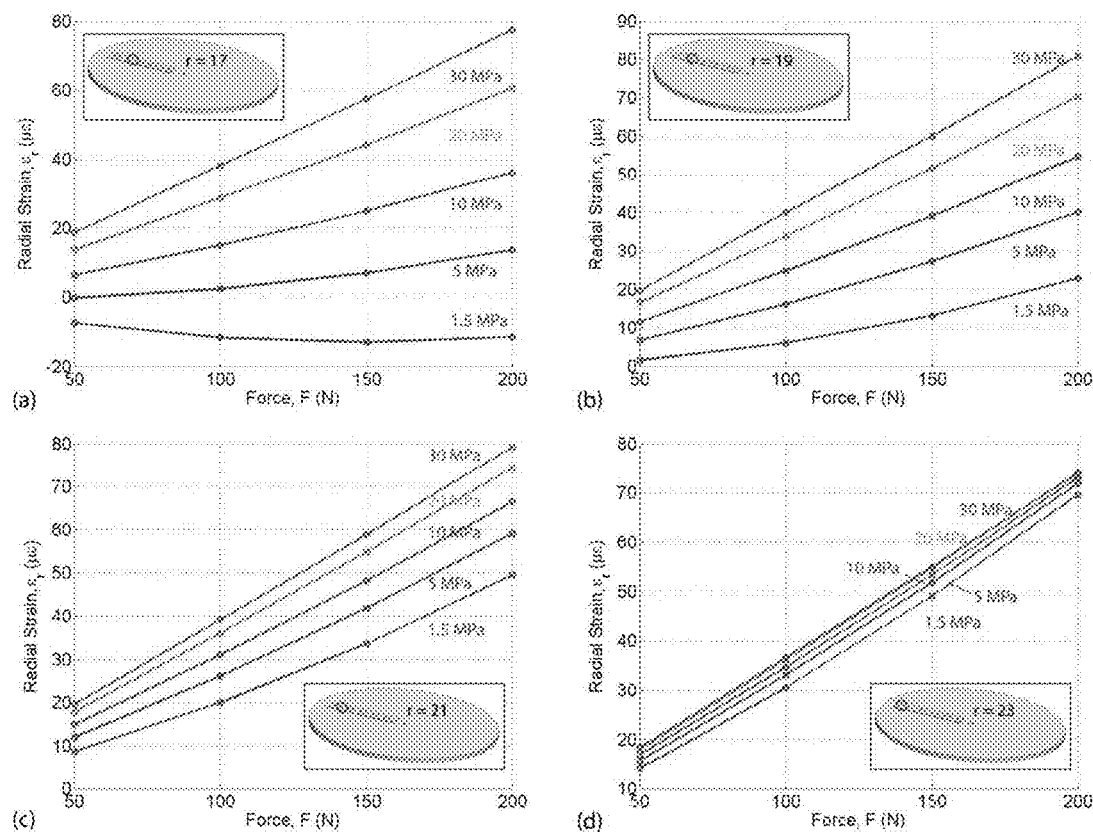
FIG. 67 Strain versus force for a plate on an elastic half-space for the four gages furthest from the center of the plate, at several gage locations for multiple half-space elastic modulus values (1.5, 5, 10, 20, 30 MPa), from FE model results.

FIG. 66 and FIG. 67 shows ten plots from FE model results, one for each strain gage location (5, 7, 9, 11, 13, 15, 17,19, 21, and 23 mm). The plots show the plate's radial strain versus load magnitude at five moduli. FE model strains are generally linear with regard to force. Gages towards the center of the plate experience some nonlinearity, particularly gages between 13 to 19 mm with a half-space elastic modulus of 10 MPa or lower. The good linearity of the force indicates that good accuracy can be achieved with 50 N increments in the lookup table.

The FE model results showed strains to be nonlinear with respect to plate radius (spatially) and material elastic modulus, and generally linear with respect to force magnitude. These same results hold for the analytical model. The discretization chosen for the lookup tables is sufficient to capture the nonlinearities in the strain behavior of the plate. A lookup table built from this set of parameters will be used as the basis of the two inverse models.

4.6 Results

The results from the laboratory experiments include verification of the plate instrumentation, loading of an instrumented elastic plate on an elastic foam half-space, and prediction of foam elastic modulus using an inverse model.

4.6.1 Platen Instrumentation Verification

The fidelity of measurements made by the strain gage instrumented plate were verified by testing the plate in a simply supported configuration. The plate was loaded in the center and simply supported by a hollow aluminum cylinder. This configuration allows for a comparison of plate strain measurements to an analytical model.

Figure 68:
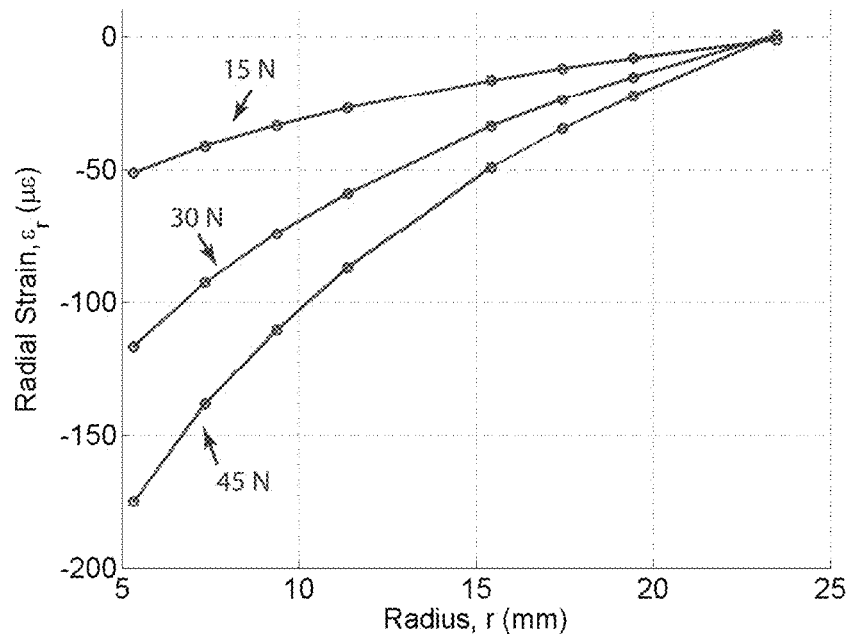
FIG. 68 Experimental plate strains for a simply supported plate at three center point loads, 15, 30, and 45 N.

Plate strain readings are shown in FIG. 68 for loads of 15, 30, and 45 N. Negative strains indicate compression. Strains generally increase with load, and are larger towards the center of the plate. Two of the gages were not functioning during these tests due to electrical issues (at r=13 and 21 mm).

Figure 69:
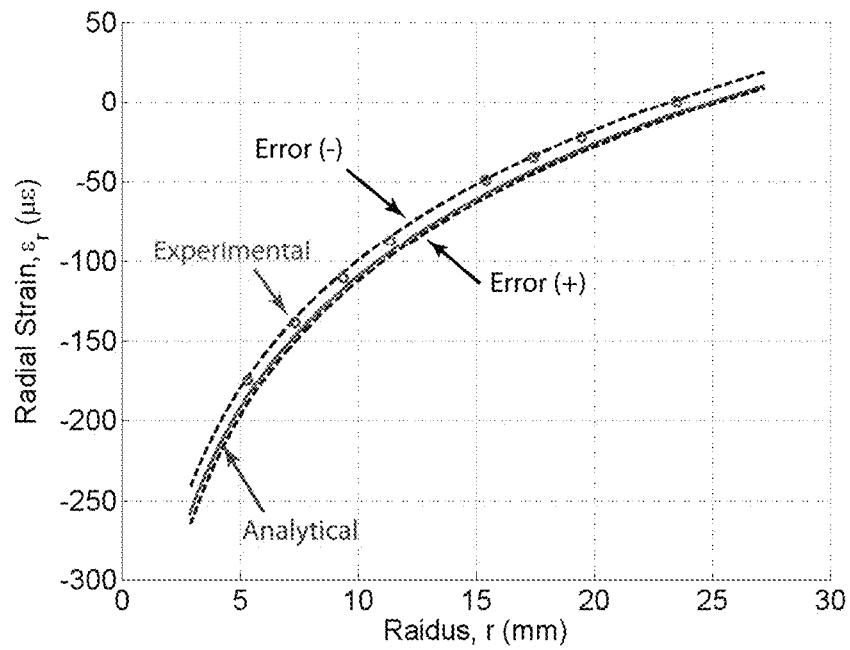
FIG. 69 Comparison of experimental plate strains to the analytical model for a simply supported plate. The dotted lines indicate error bounds. This data is for a load of 45 N.

Each set of plate strains measurement correlates to an applied vertical force and can be compared to the analytical model that has been developed. An example of a comparison between experimental and analytically predicted strains is shown in FIG. 69. The error bounds indicated by the dashed lines represent the range of experimental errors. At this force, all the experimental measurements are within the error bounds. The experimental results are larger than the ideal analytical model towards the center of the plate, and smaller towards the edge of the plate.

Figure 70:
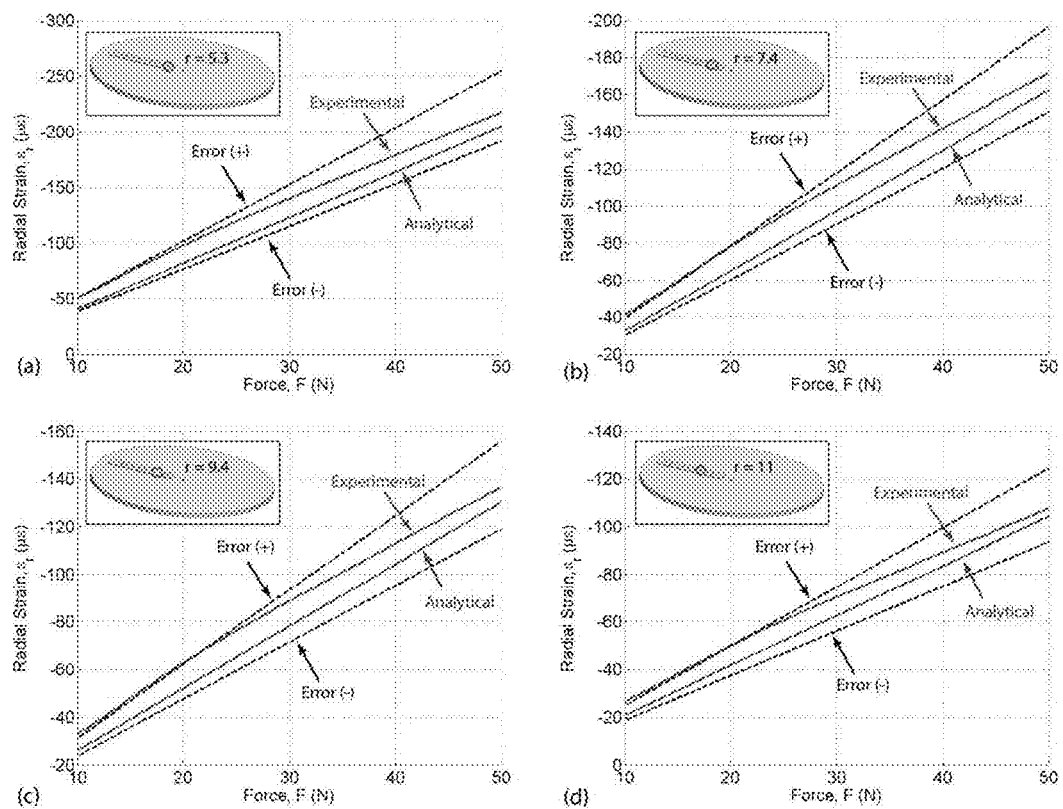
FIG. 70 Strain vs. force results from the four gages closest to the center of the plate from simply supported plate tests.
Figure 71:
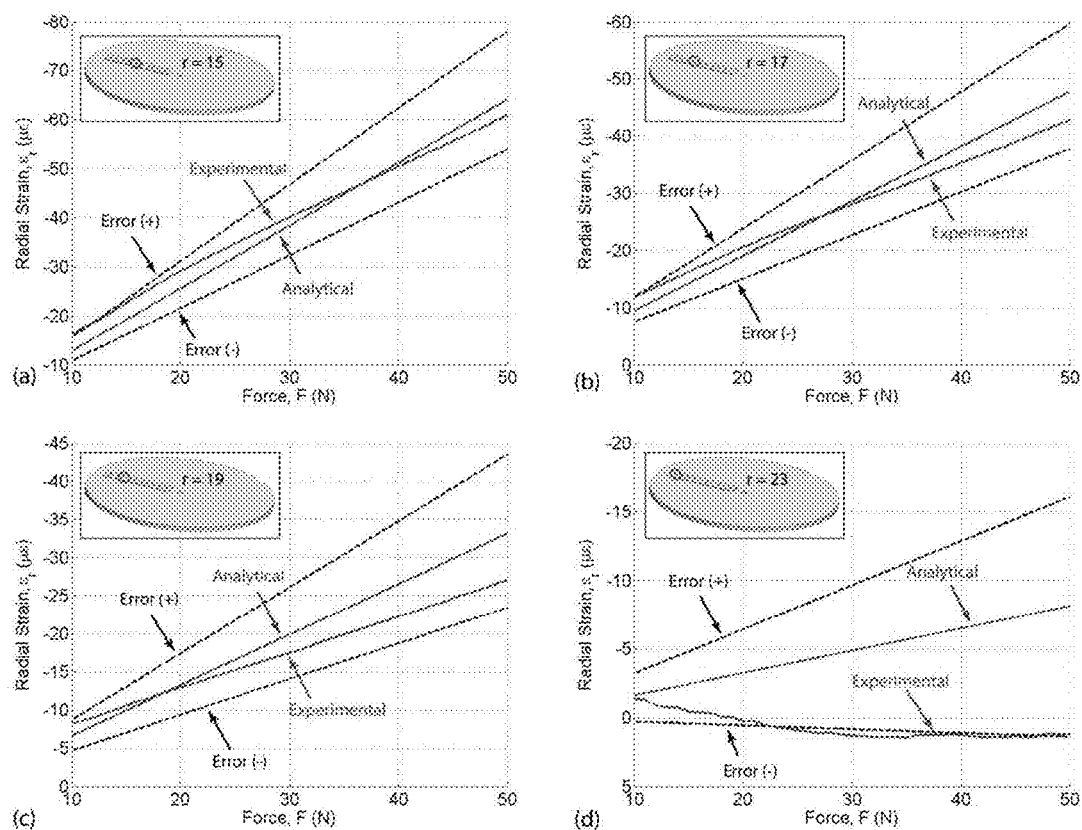
FIG. 71 Strain vs. force results from the four operational gages furthest from the center of the plate from simply supported plate tests.

A more complete way to look at the comparison of the experimental and analytical strains is with force-strain plots for each gage, given in FIG. 70 and FIG. 71. The analytical solution is given by a blue line, and the dashed lines indicate the error bounds. The experimental results mostly fall within the error bounds. At lower forces, i.e., below approximately 20 N, the gages towards the center of the plate fall above the upper error bound. The outermost gage at 23 mm shows strains slightly below the lower error bound for a portion of the loading curve. The strains that fall outside the error boundaries could be due to experimental errors that were not accounted for, such as friction at the support or non-uniform thickness of the plate. The largest differential between experimental strains and the error boundaries is $2\mu\epsilon$ at 10 N on the 9.4 mm gage. The elastic modulus extraction method presented at the end of this chapter is concerned with forces greater than 20 N, for which the differences between experimental strains and the error bounds shown in FIG. 70 and FIG. 71 are negligible.

The simply supported tests generally agree with the analytical model. The positive results from these tests verify the fidelity of measurements made by the instrumented plate.

4.6.2 Elastic Plate on an Elastic Half-space

The instrumented plate was loaded onto the surface of four EPS foam samples of different densities while plate radial strains were recorded. A total of six tests were conducted on each sample, with the plate being replaced prior to each test. Of these six tests, foam samples were tested three times on the native manufactured surface and three times after removing 1 mm of foam from the surface by sanding. This section discusses trends in the plate strain readings.

Figure 72:
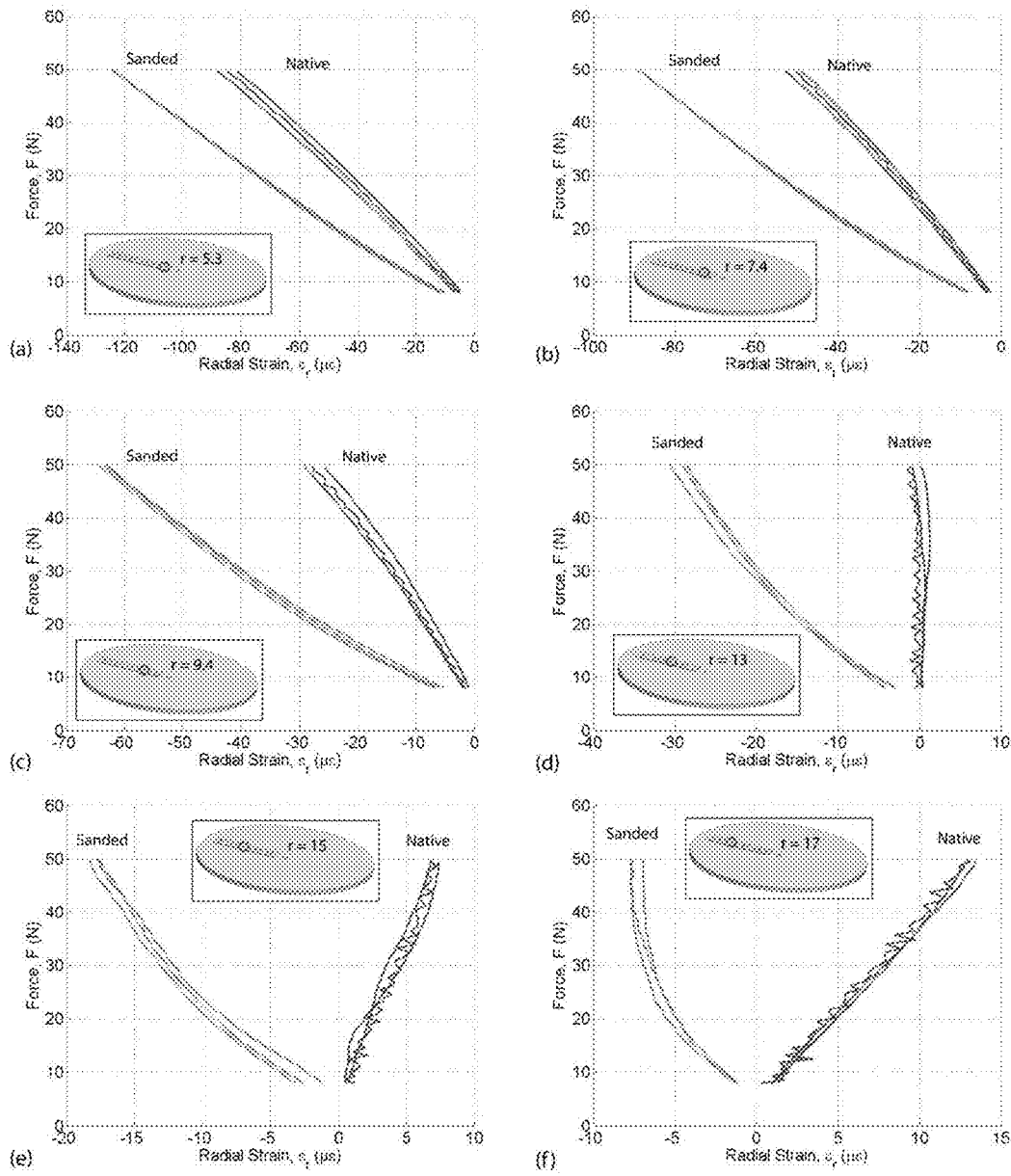
FIG. 72 Vertical force versus plate radial strain for three tests on the native surface and three tests on the sanded surface of EPS12 foam. Each plot is a different gage, as indicated by the inset plate diagram. Included are the three operational gages furthest from the center of the plate. Negative strains are compressive.
Figure 73:
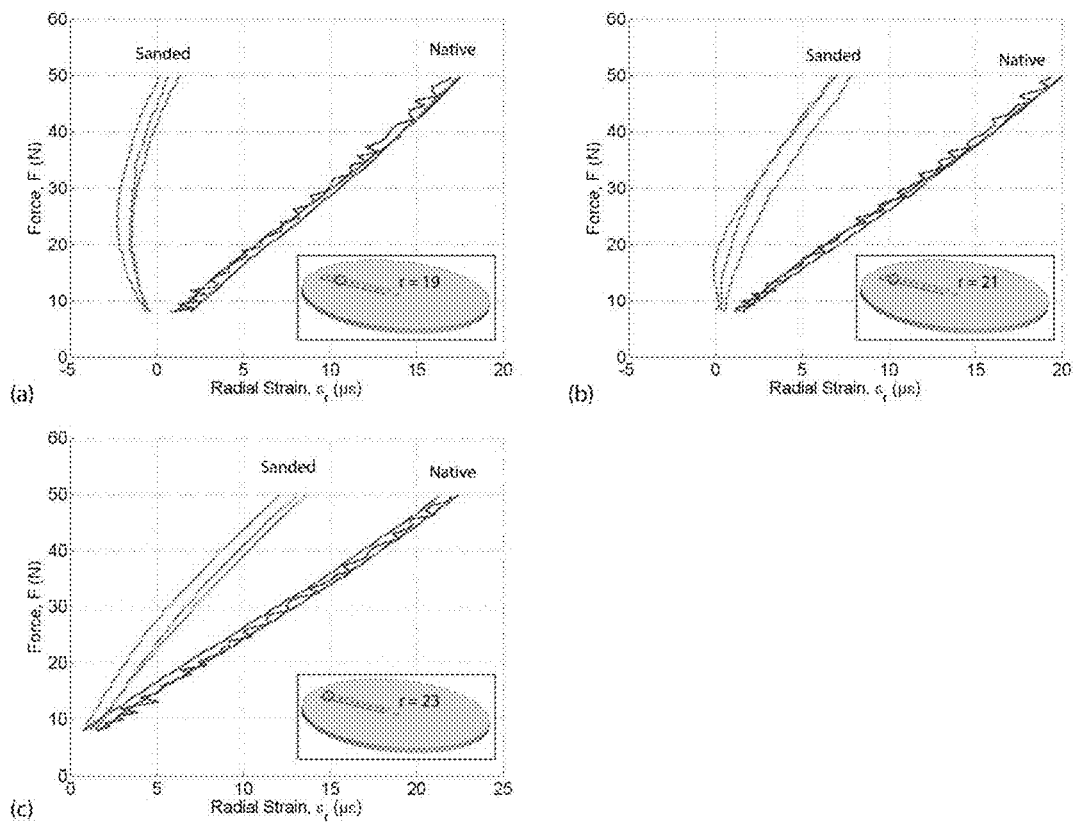
FIG. 73 Vertical force versus plate radial strain for three tests on the native surface and three tests on the sanded surface of EPS12 foam. Each plot is a different gage, as indicated by the inset plate diagram. Included are the three operational gages closest to the center of the plate. Negative strains are compressive.

The force versus strain relationship for individual gages in the tests on EPS12 is shown in FIG. 72 and FIG. 73. The native surface tests agree well with each other, as do sanded surface tests. However, results from these two different test conditions clearly differ from each other, indicating the strong influence of surface preparation on plate tests.

For EPS 12, sanded tests show larger compressive strains than in tests on the native surface. Towards the center of the plate, i.e., r≤9.4 mm, compressive strains are upwards of $40\mu\epsilon$ larger. Sanding of specimens removed a 1 mm layer of foam that is denser than the average foam density. Foam elastic modulus increases with density, therefore sanding removes a layer of stiffer foam. The larger compressive strains can be explained by the decreased stiffness of the foam from sanding. A half space with a lower stiffness will result in a larger displacement at the center of the plate. Larger plate displacements will lead to a steeper curvature at the center of the plate, and thus higher compressive strains.

Figure 74:
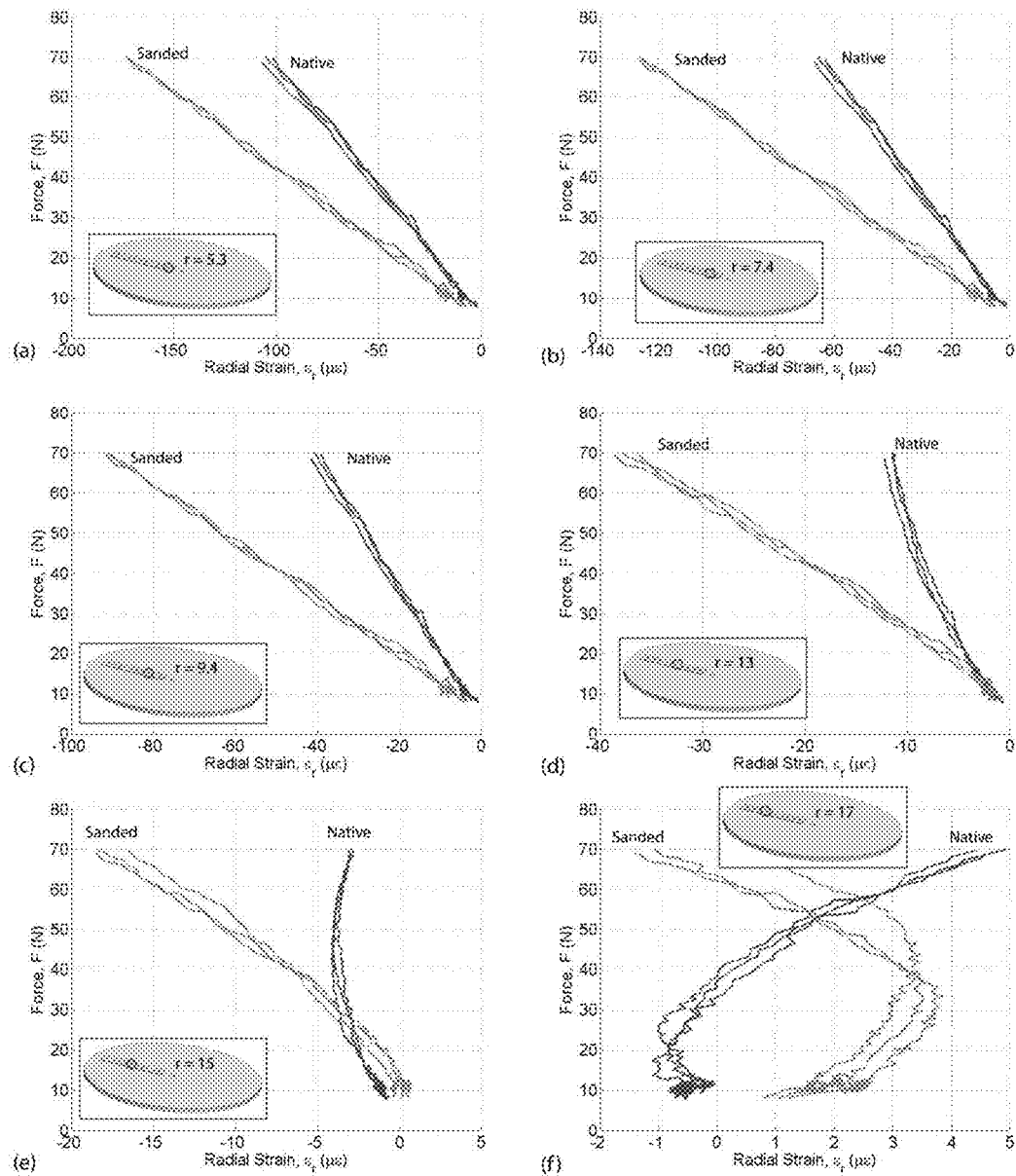
FIG. 74 Vertical force versus plate radial strain for three tests on the native surface and three tests on the sanded surface of EPS22 foam. Each plot is a different gage, as indicated by the inset plate diagram. Included are the six operational gages closest to the center of the plate. Negative strains are compressive.
Figure 75:
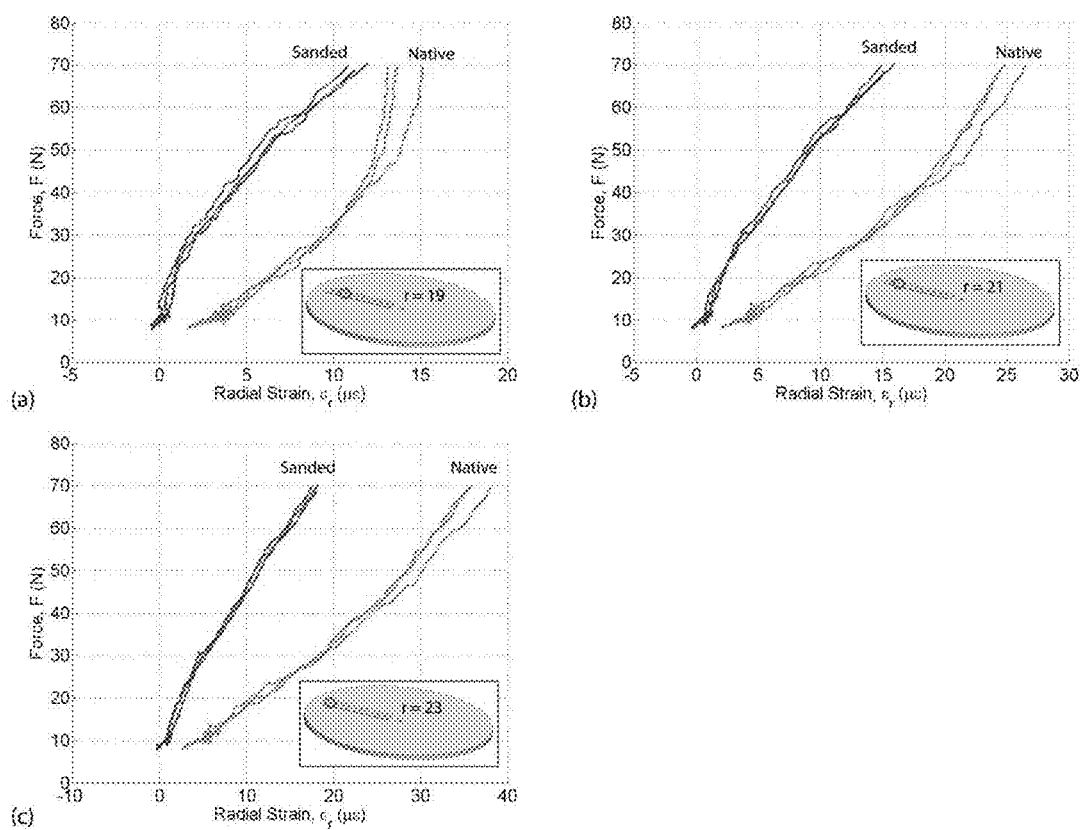
FIG. 75 Vertical force versus plate radial strain for three tests on the native surface and three tests on the sanded surface of EPS22 foam. Each plot is a different gage, as indicated by the inset plate diagram. Included are the three operational gages furthest from the center of the plate. Negative strains are compressive.
Figure 76:
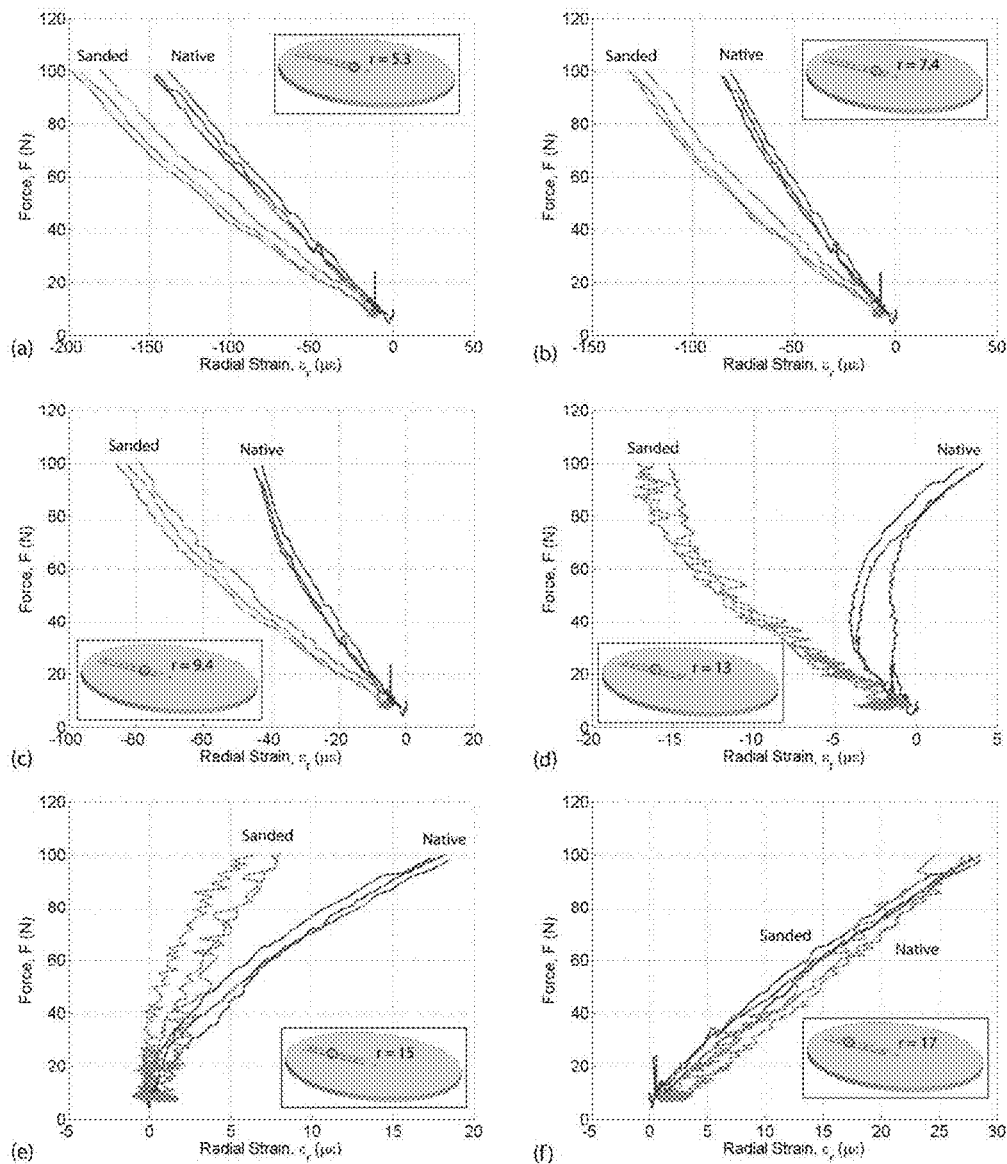
FIG. 76 Vertical force versus plate radial strain for three tests on the native surface and three tests on the sanded surface of EPS29A foam. Each plot is a different gage, as indicated by the inset plate diagram. Included are the six operational gages closest to the center of the plate. Negative strains are compressive.
Figure 77:
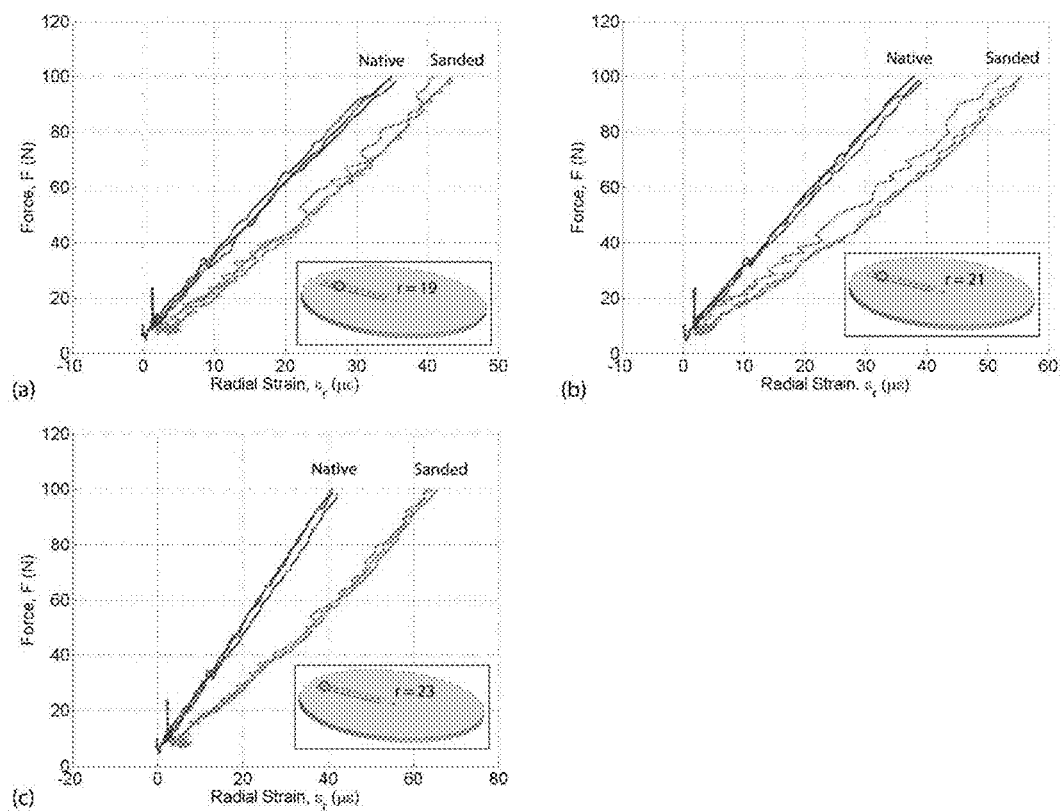
FIG. 77 Vertical force versus plate radial strain for three tests on the native surface and three tests on the sanded surface of EPS29A foam. Each plot is a different gage, as indicated by the inset plate diagram. Included are the three operational gages furthest from the center of the plate. Negative strains are compressive.
Figure 78:
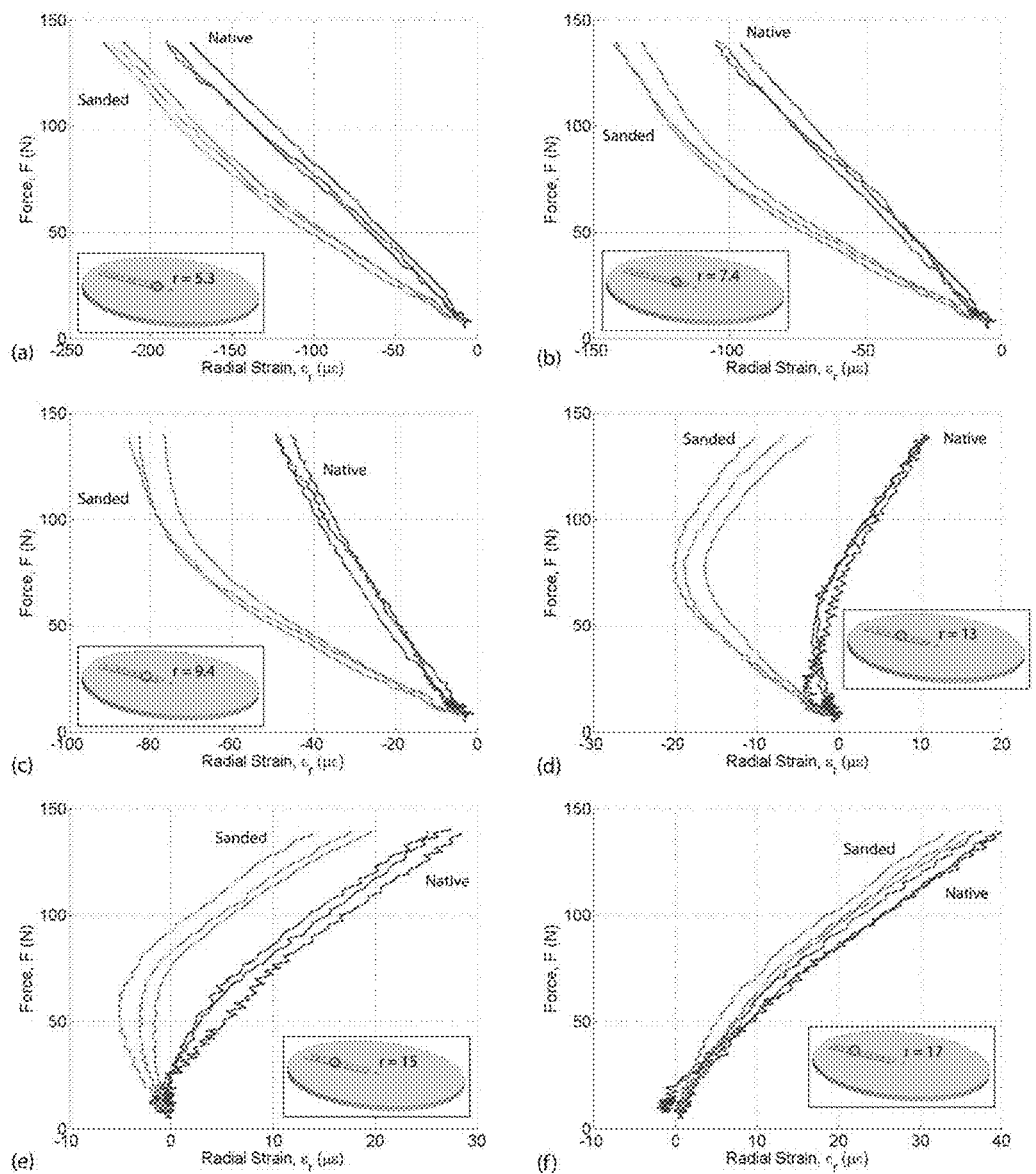
FIG. 78 Vertical force versus plate radial strain for three tests on the native surface and three tests on the sanded surface of EPS29B foam. Each plot is a different gage, as indicated by the inset plate diagram. Included are the six operational gages closest to the center of the plate. Negative strains are compressive.
Figure 79:
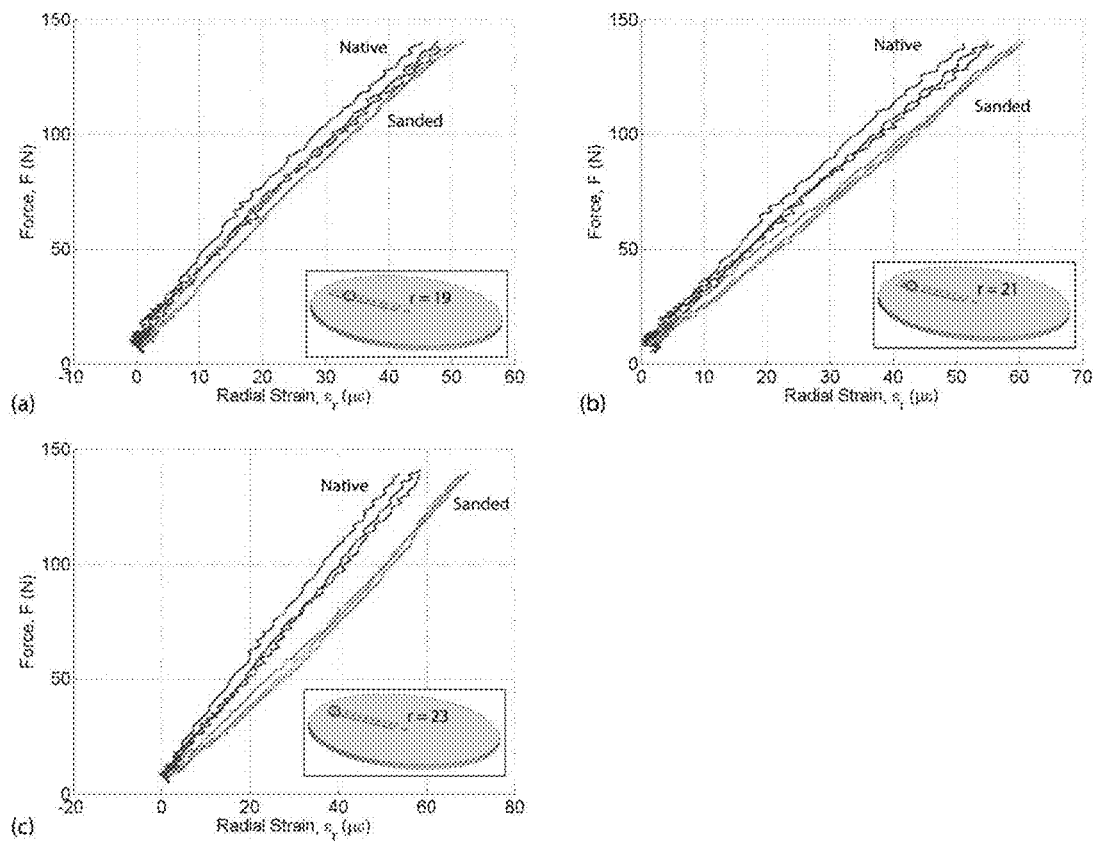
FIG. 79 Vertical force versus plate radial strain for three tests on the native surface and three tests on the sanded surface of EPS29B foam. Each plot is a different gage, as indicated by the inset plate diagram. Included are the three operational gages furthest from the center of the plate. Negative strains are compressive.

The force versus strain relationship are shown for the other three foams, EPS22 (FIG. 74, FIG. 75), EPS29A (FIG. 76, FIG. 77), and EPS29B (FIG. 78, FIG. 79). These figures split up test data from the same tests in order to provide a larger graphic. These foams show clear differentiation between sanded and native specimens, similar to EPS12. Compressive strains are generally larger in magnitude for sanded specimens than for native specimens. Tensile strains for EPS22, EPS29A, and EPS29B are larger for sanded specimens, which is different than the EPS12 results that show smaller tensile strains for sanded specimens. The force-strain behavior shows nonlinearity in tests on all the foams. For EPS22, EPS29A, and EPS29B, the nonlinear strain-force behavior is most pronounced near the transition from compressive to tensile strain, e.g., FIG. 74(*f*). The nonlinearity is likely due to contact between the plate and foam. We can discuss the contact nonlinearity in terms of a shifting contact stress distribution. In both the analytical model and FE model, the contact stress can change with force and half-space elastic modulus. The shift in contact stress distribution may also explain why EPS22 experienced smaller tensile strains with sanded specimens, while EPS22, EPS29A, and EPS29B exhibited larger tensile strains for sanded specimens.

Figure 80:
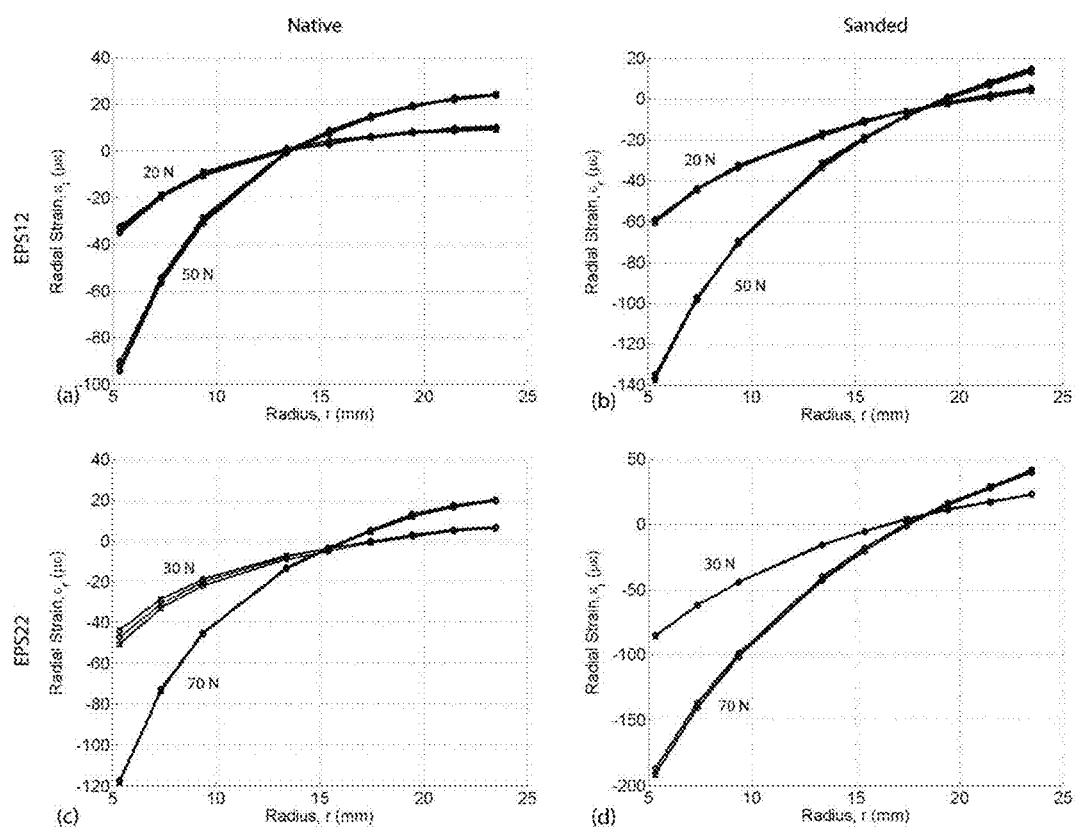
FIG. 80 Plate radial strains during plate loading tests at two forces. Foams EPS12 and EPS22 are shown with both native specimens (left) and sanded specimens (right). Negative strains are compressive.
Figure 81:
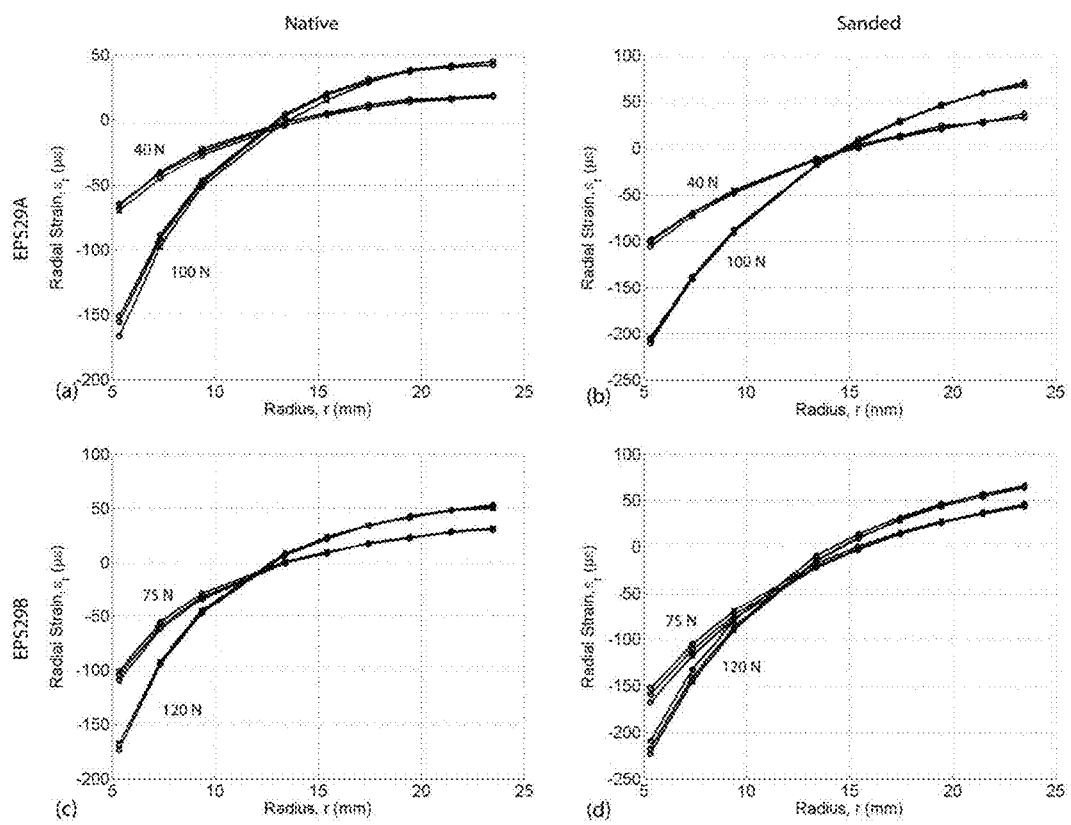
FIG. 81 Plate radial strains during plate loading tests at two forces. Foams EPS29A and EPS29B are shown with both native specimens (left) and sanded specimens (right). Negative strains are compressive.

To gain a better understanding of the plate strain behavior, the spatial distribution of radial strains along the radius of the plate is shown for each of the four foam densities in FIG. 80 and FIG. 81. Each line represents the radial strain at a different force in order to show the effect of load on strain distribution. Each of the three tests for a given foam and surface condition are plotted two different forces. It can be readily seen that these three lines at each force are in good agreement, further supporting the repeatability of the tests. The maximum force shown in these plots is approximately the maximum force applied to each type of foam.

As FIG. 80 shows, plate radial strains increased in magnitude with increasing force. Relatively large compressive strains are experienced towards the center of the plate, as this is where the plate incurs maximum deflection from the point load. As you move away from the center of the plate, strain magnitudes decrease until they become tensile. The zero crossing occurs at different radii depending on the foam density and force magnitude, but it is generally between 14-22 mm. The radial strain becomes tensile at the free edge in part because of the Poisson's effect. This can most easily be seen mathematically in the radial moment equation (also seen in Equation 4.11), which is proportionally equivalent to the sum of the radial strain and the hoop strain times the Poisson's ratio of the plate:

$$M_r(r)=-D((d^2w_1)/(dr^2)+v_1/r(dw_1)/dr)=-D/z(\epsilon_r(r)+v_1\epsilon_\theta(r)) \quad (4.38)$$

This balance between the moment, radial strain, and hoop strain exists throughout the radius of the plate. At the edge of the plate where the boundary condition species a free edge, i.e., the radial moment is zero at r=a. The hoop strain is compressive across the whole plate for all conditions discussed in this chapter. Therefore, the radial strain is tensile such that it balance out the compressive hoop strain.

4.6.3 Inverse Model Results

One goal of this chapter is to determine the efficacy of using plate strain measurements for determining half-space elastic modulus. This section discusses the elastic modulus predictions for four different foams, on native and sanded foam surfaces. Plate strain measurements taken during a test can be used to estimate half-space elastic modulus according to two in verse models. There is an inverse model based on an analytical model and a FE model. The inverse models estimate the half-space elastic modulus that predicts the best match to experimental plate strains at a given force.

Figure 82:
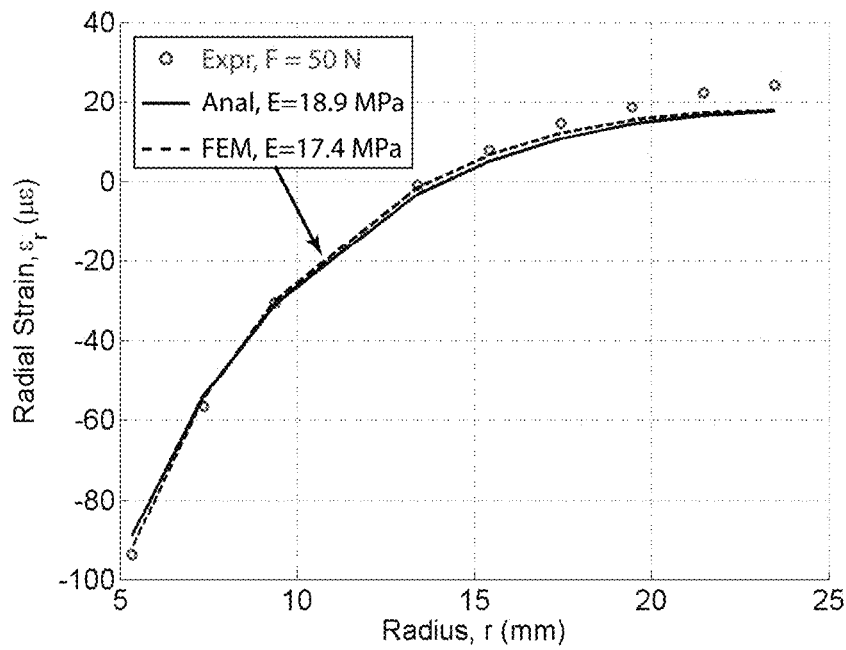
FIG. 82 Plate strains and elastic modulus values predicted by the analytical and FE inverse models for the first test on EPS12, native surface, loaded at 50 N.
Figure 83:
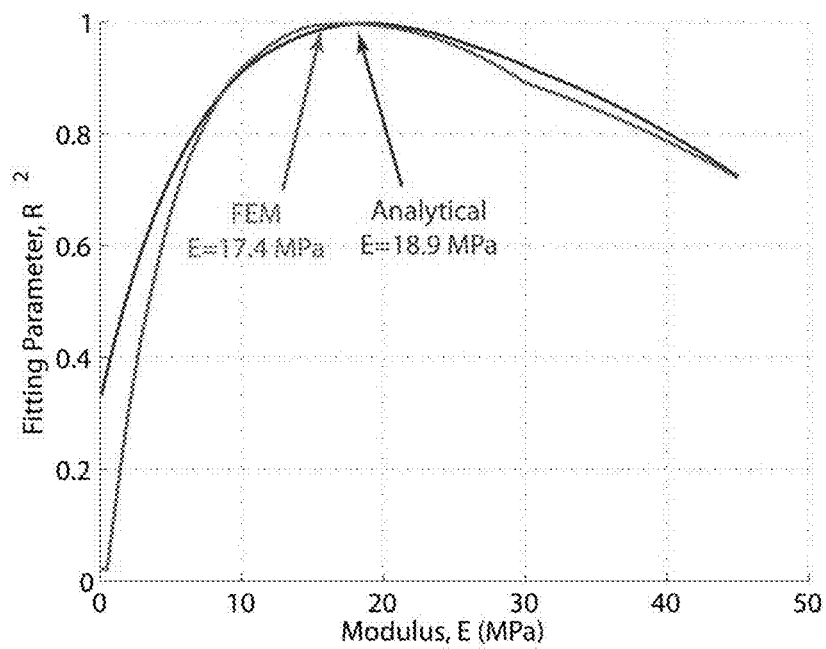
FIG. 83 Fitting parameter versus predicted elastic modulus for the two inverse models for the first test on EPS12, native surface, loaded at 50N.

An example fitting is show in FIG. 82. For each of the inverse models, the fitting algorithm calculates the fitting parameter, R2, between the experimental plate strains and the predicted plate strains at a large range of possible moduli. The variation of the fitting parameter versus predicted elastic modulus values is shown in FIG. 83. The elastic modulus value with the best fit for each model is used as the elastic modulus prediction for that inverse model. The best fitting elastic modulus values from FIG. 83 give the plate strain predictions shown in FIG. 82.

Figure 84:
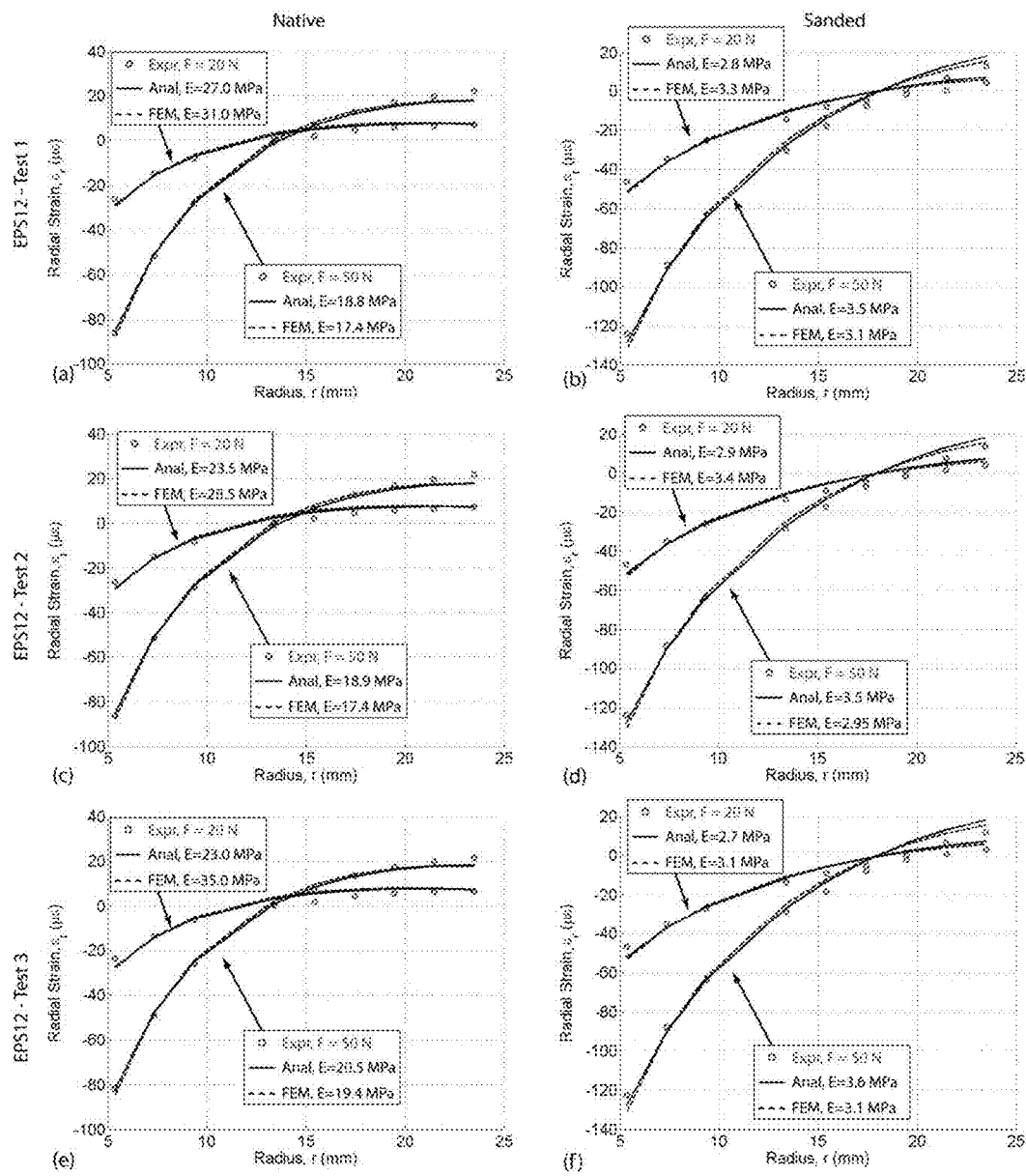
FIG. 84 Experimental strain measurements ('Expr' in plot legends) were used to predict the foam elastic modulus using analytical ('Anal' in plot legends) and FE inverse models. The results are shown at two forces. The left column is the native surface, and the right column is the sanded surface. This is EPS12 foam, with the test number shown on the left.

The strain fitting curves from the inverse models (i.e., FIG. 82) can vary by force and test condition. FIG. 84 shows the strain fitting curves for EPS12 at two forces for each test. Taking FIG. 84a for example, we can see that for the EPS12 native condition at a load of 20 N the analytical inverse model predicts an elastic modulus of 27.0 MPa and the FE model predicts 31.0 MPa, while at 50 N the analytical model predicts 18.8 MPa and the FE model predicts 17.4 MPa.

Figure 85:
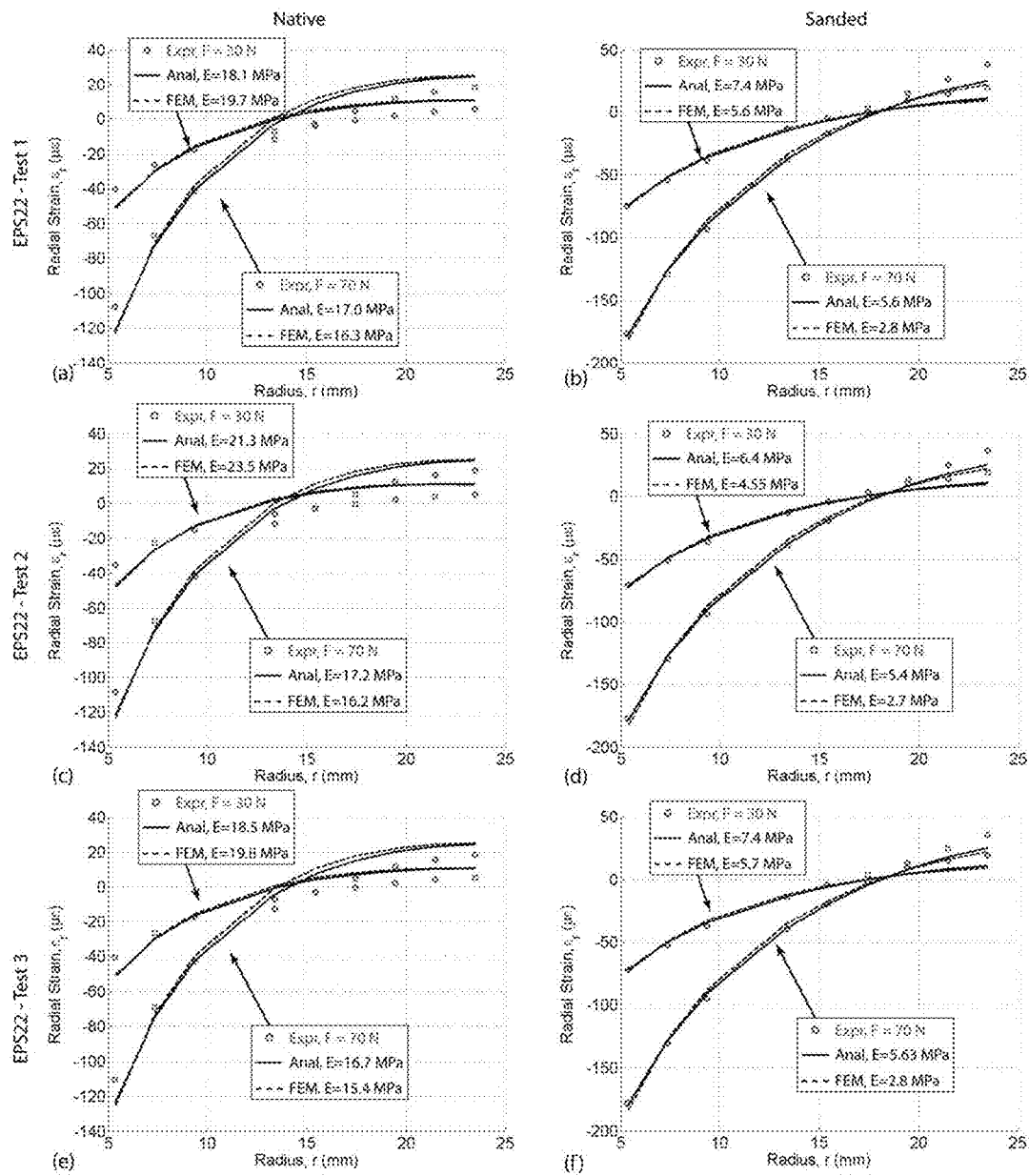
FIG. 85 Experimental strain measurements ('Expr' in plot legends) were used to predict the foam elastic modulus using analytical ('Anal' in plot legends) and FE inverse models. The results are shown at two forces. The left column is the native surface, and the right column is the sanded surface. This is EPS22 foam, with the test number shown on the left.
Figure 86:
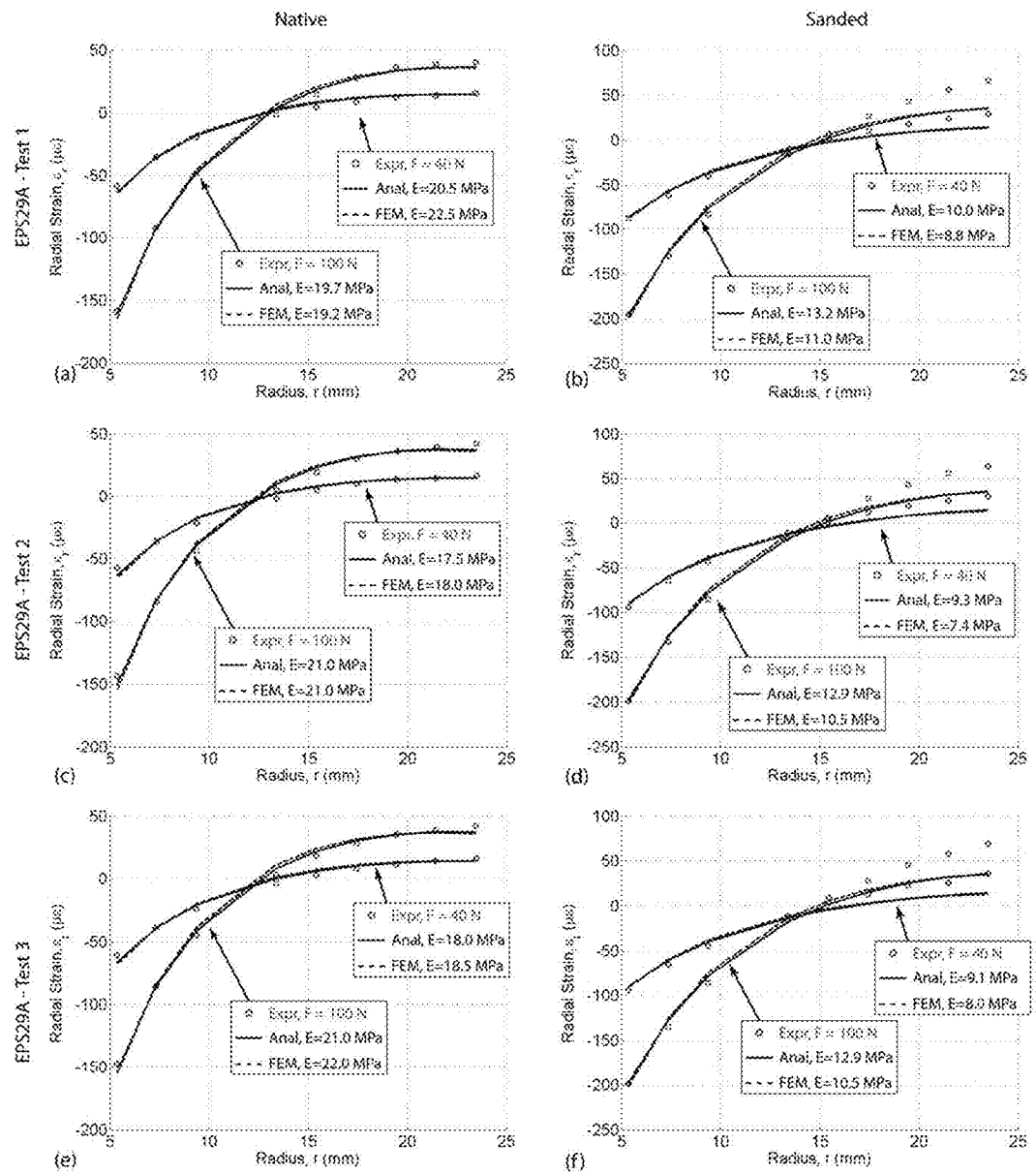
FIG. 86 Experimental strain measurements ('Expr' in plot legends) were used to predict the foam elastic modulus using analytical ('Anal' in plot legends) and FE inverse models. The results are shown at two forces. The left column is the native surface, and the right column is the sanded surface. This is EPS29A foam, with the test number shown on the left.
Figure 87:
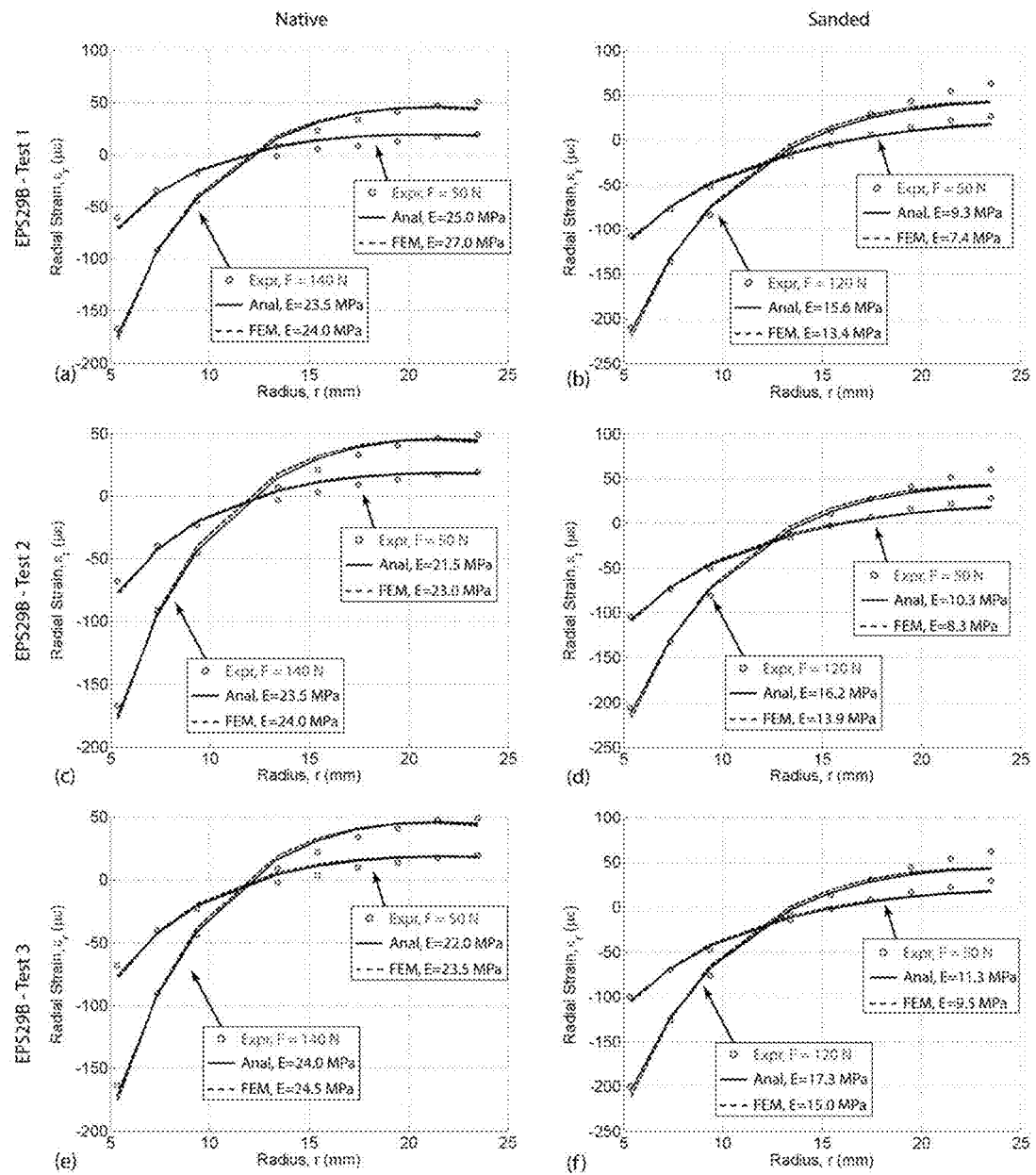
FIG. 87 Experimental strain measurements ('Expr' in plot legends) were used to predict the foam elastic modulus using analytical ('Anal' in plot legends) and FE inverse models. The results are shown at two forces. The left column is the native surface, and the right column is the sanded surface. This is EPS29B foam, with the test number shown on the left.

The results from the other foams are shown: EPS22 (FIG. 85), EPS29A (FIG. 86), and EPS29B (FIG. 87). For these different test conditions, there is a wide range of elastic modulus values predicted. In general, the FE model and analytical model predictions agree well.

The shape of the experimental strains and model strains tends to agree well, with a few exceptions. The strains towards the center of the plate, i.e., lower radius values, show good agreement between the experimental and model values. Towards the edge of the plate, the models under-predict strains for the sanded surface tests on EPS22 and EPS29A, and to a lesser extent EPS29B. In the EPS22 native and EPS12 sanded tests, the models over-predict strains towards the edge of the plate. The cause of these differences may be inhomogeneity in the foam, such as localized weaknesses in the foam structure or surface irregularities, i.e., uneven sanding and hot wire cutting.

The native surface test results show lower strains and higher elastic modulus predictions than the sanded surface tests. The one millimeter of foam removed in the sanded tests produces a considerable difference in elastic modulus prediction, sometimes by a whole order of magnitude. Plate strains are therefore highly sensitive to near surface conditions. To gain further insight into the differences between native and sanded conditions, we can evaluate the elastic modulus predictions throughout a whole test.

Figure 88:
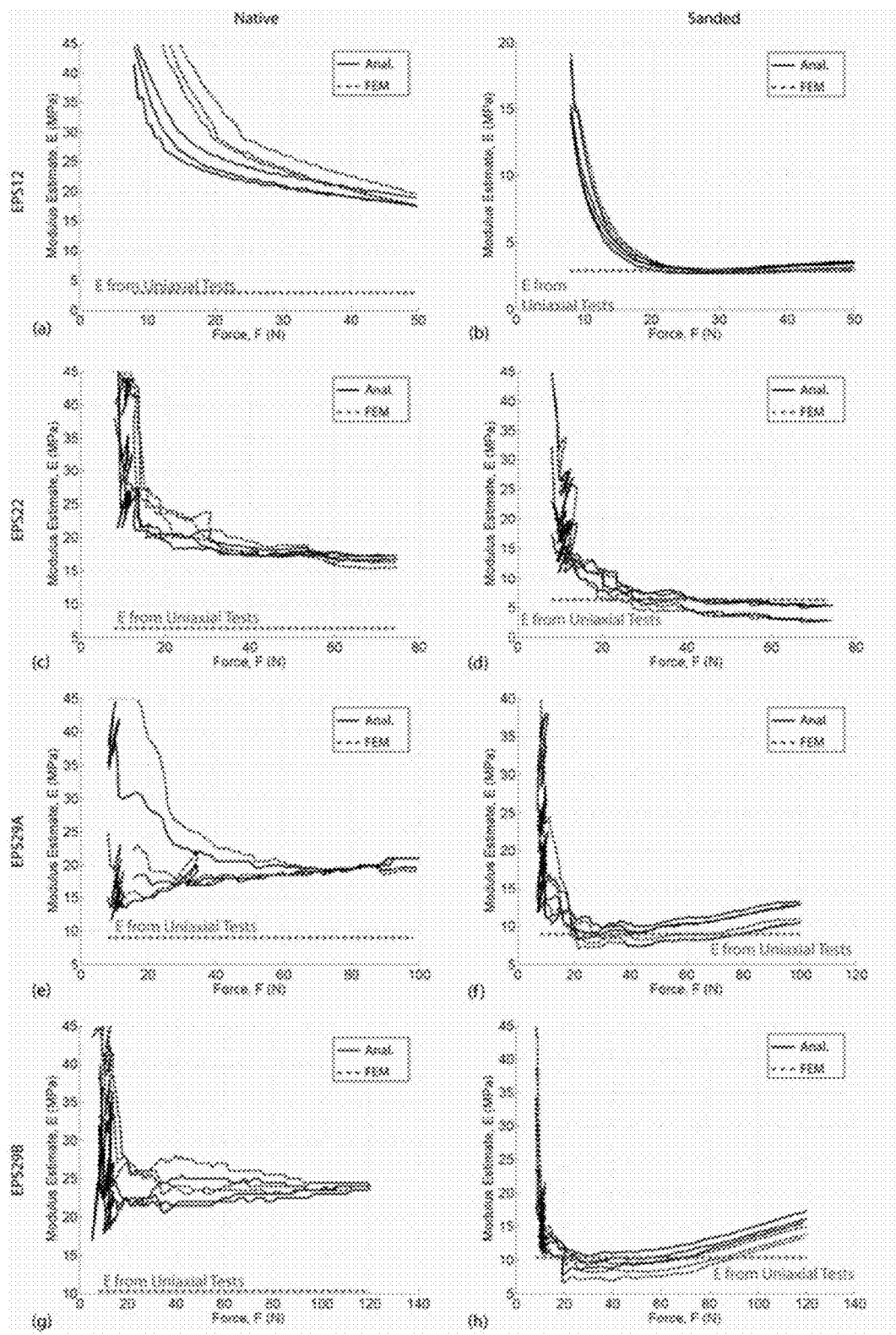
FIG. 88 Resulting elastic modulus prediction from the two inverse models (analytical and FE model) during loading of three tests for each condition. The left column is the native surface, and the right column is the sanded surface. The foam type is listed on the left.

The inverse model elastic modulus predictions throughout loading for each test is shown in FIG. 88. Results for a given surface condition, i.e., native versus sanded, generally agree with each other. The analytical model consistently predicts lower elastic modulus values for the sanded tests, yet there is not strong bias in the native tests. At low forces, the inverse models predict higher and irregular elastic modulus values. At higher forces, the elastic modulus predictions generally are lower and more consistent.

The force dependent nature of the elastic modulus predictions may occur due to material nonlinearity. In uniaxial compression tests (see Section 2.4), the rate of strain is clearly stress dependent prior to the yield stress. Foam specimens undergoing plate loading experience a wide range of stress conditions in the subsurface. Therefore, some force dependent behavior may be expected in the elastic modulus prediction models.

There is a distinct difference between native and sanded conditions. Native surface tests greatly over-predicted the foam elastic modulus compared to independently obtained foam elastic modulus values from uniaxial tests, while sanded surface tests were much closer to the expected elastic modulus values. The most likely explanation for this over-prediction is that the plate strains are highly sensitive to the top layer of the half-space, and foam is known to have a layer of denser, and therefore stiffer, material on the surface (see FIG. 8). Sanded tests removed this stiffer layer, thereby giving considerably lower elastic modulus predictions, often by more than half the native surface elastic modulus predictions.

Portions of the sanded tests agreed very well with the independently measured elastic modulus values. At loads between 20 to 40% of the maximum load, the elastic modulus prediction values approach the independently obtained elastic modulus from uniaxial testing. Towards the end of the sanded tests, the elastic modulus prediction value tends to increase again, with the exception of the EPS22 tests. The minimum elastic modulus value of the analytical model curves agree particularly well with the uniaxial elastic modulus for all foams. The test results in FIG. 88 indicate that sanded foam is better suited for predicting a representative foam elastic modulus.

Figure 89:
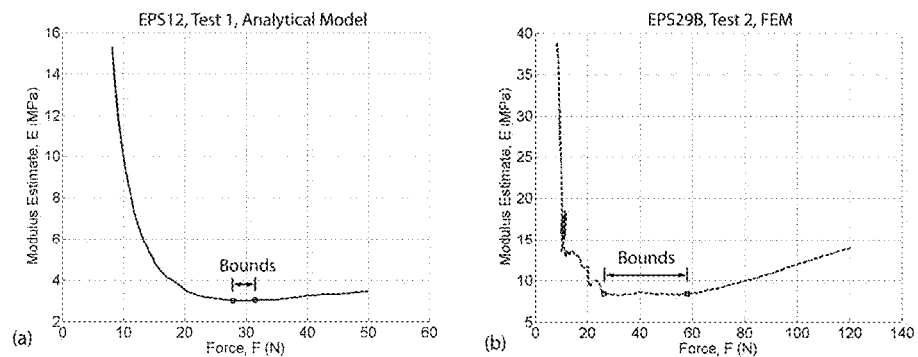
FIG. 89 Elastic modulus prediction curve with circles showing the bounds of the region used to determine the representative elastic modulus. First test on EPS12 sanded.

Here a method is proposed for determining the foam elastic modulus from the inverse model predictions in FIG. 88. The focus of this method is finding the minimum value of a curve, i.e., where the slope is zero. There is precedent for using the slope of a line to identify the region of a curve that best represents a material's elastic modulus. Elastic modulus is calculated from uniaxial tests by finding the maximum slope of the stress-strain curve. To help guard against outliers, the proposed method averages the elastic modulus prediction values across a region of minimum slope. This method is exemplified in FIG. 89 for two different samples. The analytical model results for test 1 on EPS12 show a relatively narrow region of minimum slope, whereas the FE model results for test 2 on EPS29B show a considerably larger region of minimum slope.

Figure 90:
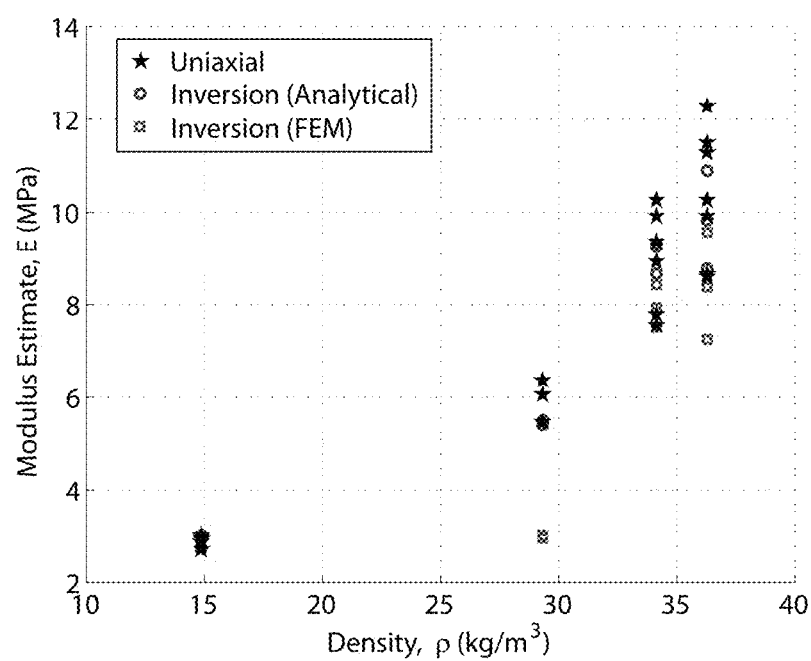
FIG. 90 Comparison of instrumented plate elastic modulus prediction using analytical and FE inverse models, and independently obtained elastic modulus from uniaxial tests for all foam types.

The results from the proposed elastic modulus determination method are summarized in Table 4.4. The results are also presented graphically by foam density in FIG. 90. In all tests, the analytical model predicts a higher elastic modulus than the FE model. Both analytical and FE models are within the spread of uniaxial results for EPS12 and EPS29A. The analytical model shows excellent agreement with the uniaxial average elastic modulus for these foams, arriving within 0.8% for EPS12 and 1.2% for EPS29A. For EPS22 and EPS29B, the inverse models under-predict compared to the uniaxial results. In particular, the FE model predictions are markedly below the uniaxial tests for EPS22. The reason for this disagreement is not readily apparent from the strain fitting curves in FIG. 85. The inverse models fit the experimental strain curves rather well for EPS22 at high force. There is abnormal behavior in FIG. 88*d*, in which the predicted elastic modulus versus force curve for EPS22 does not experience the same upswing as the other sanded specimens at higher forces. It is possible that this specimen of foam was an anomaly.

specimen. Native samples produced considerably higher elastic modulus predictions than sanded samples, which is likely due to the stiff layer of foam that exists along manufactured or hotwirecut surfaces. Thus, near-surface conditions are an important consideration when using the instrumented plate to characterize materials. With proper surface preparation, the results presented here show promise for the instrumented plate as a device for evaluating material elastic modulus.

TABLE 4.4

Results from instrumented plate elastic modulus prediction method for Analytical and FE inverse models on all foam types.

|  | EPS12 $E_{Analy}$ (MPa) | EPS12 $E_{FEM}$ (MPa) | EPS22 $E_{Analy}$ (MPa) | EPS22 $E_{FEM}$ (MPa) |
| --- | --- | --- | --- | --- |
| Test 1 | 3.01 | 2.71 | 5.50 | 3.00 |
| Test 2 | 3.01 | 2.83 | 5.48 | 3.01 |
| Test 3 | 2.73 | 2.71 | 5.40 | 2.95 |
| Mean | 2.92 | 2.75 | 5.46 | 2.99 |
| % Error Uniaxial | 0.8 | −5.1 | −8.8 | −50.1 |
| Uniaxial E | 2.9 | 2.9 | 6.0 | 6.0 |

4.7 Discussion

Testing of the instrumented plate revealed a number of insights. Sanding of the foam surface strongly impacted the plate strain results. Sanded foam tests resulted in elastic modulus predictions much closer to the independently obtained elastic modulus from uniaxial tests. This is thought to be due to the foam structure, which is discussed here.

Plate strains are highly sensitive to the foam surface. Sanded foam tests experienced up to a 60% increase in strain compared to the native surface. The foam elastic modulus predicted by the plate is similarly highly sensitive to the foam surface. With the native surface, the plate greatly over-predicts the elastic modulus of the foam, usually by at least twice the independently obtained value. However, on the sanded surface, the plate strains predict a range of moduli that typically include the independently obtained value from uniaxial tests.

The improvement in elastic modulus prediction after sanding may be explained by foam bead behavior at the surface. During the foam expansion process used in EPS manufacturing (see Chapter 2) the foam beads close to the mold wall fuse together [10]. The impact of increased bead fusion can be visualized by a scanning electron microscope, as shown in FIG. 91. The increased bead fusion at the surface results in a higher density than the rest of the specimen, as can be seen in the density variation with depth plotted in FIG. 8. Density correlates well with elastic modulus for EPS foams [1], which means that there is a layer of stiffer foam at the surface. A similar surface behavior may be expected from a foam surface created by hot wire cutting, which is how a number of native foam specimen surfaces were prepared. Foam beads collapse at temperatures above 160° C., and the foam cutter used in this research reached temperatures of 250° C. Foam bead collapse results in the formation of a residue on the surface, shown by scanning electron microscope images in FIG. 92. The improved elastic modulus prediction values in the sanded tests are likely the result of removing the highly fused beads and/or surface residue left from manufacturing and cutting processes.

These findings suggest that the instrumented plate is highly sensitive to material properties near the surface of a Chapter 5—In-Situ Determination of Plasticity Parameters Via Instrumented Plate This chapter builds upon the in-situ elastic property characterization method developed in Chapter 4 by extending it to the characterization of material plasticity. As in Chapter 4, a strain gage instrumented plate was loaded onto a material's surface, and the strain gage readings were used to characterize elastic behavior of the material. In this chapter, the plate strain readings will be used to characterize plastic behavior.

Characterizing the plastic behavior of materials is key for structural design and analysis. Plasticity describes a material's behavior once it has been loaded up to and beyond its yield strength, and begins undergoing permanent (plastic) deformation. Many applications must design materials for the potential, or even expected, advent of plastic behavior. For example, developing effective foam helmets and packaging depends on the accurate modeling of a foam's plastic behavior. Understanding the plastic deformation of soils is useful in the process of soil compaction, a critical task in the construction of structural foundations.

Plastic behavior can be described with constitutive models that require any number of parameters to be determined via laboratory or in-situ testing. Laboratory testing can require specialized equipment and tedious sample preparation. For example, see Chapter 2 describing the testing required for determining the hydrostatic compressive yield stress for EPS foams. in-situ testing can provide more flexibility in how and where tests are conducted, but in-situ methods do not exist for many plasticity parameters. This chapter includes an overview of other in-situ plasticity tests and evaluates a new method for characterizing EPS foam plasticity.

5.1 Background

Characterization of a material's plastic behavior for structural analysis and design can be conducted a number of ways, depending on the constitutive model being used. As discussed in Chapter 2, there are several constitutive models used to describe plasticity, and each has different parameters. Many of the parameters necessary for defining a plasticity model are traditionally obtained through laboratory tests that produce specific stress states in a sample. However, a number of in-situ tests have been developed to estimate plasticity parameters.

The field of Geotechnical engineering has produced a number of methods to measure plasticity parameters in situ. Parameters for the Modified Cam Clay plasticity model have been determined using the combination of laboratory testing, in-situ pressure meter testing (i.e., measuring volumetric strain in soil borehole due to applied pressure) and an inverse model[54]. However, a pure in-situ test based on this method has not been successfully developed. Cohesion and friction angle parameters, which describe the shear strength of many types of soils, were estimated based on pressure tunnel tests (i.e., applying pressure to tunnel walls while measuring the change in diameter) and an inverse model [55]. Plate loading has been used to characterize elastic nonlinear soil behavior, e.g., measuring high-strain and low-strain elastic modulus values by analyzing the surface waves created by plate loading[56]. However, methods for extracting plasticity parameters have not been developed, despite the fact that plastic behavior is known to influence plate loading tests[57].

One of the most common forms of in-situ testing for material plasticity characterization is indentation testing [58]. Indenters range in shape (cylinders, cones, pyramids, etc.) and in size (macro, micro, and nano)[58]. Young's modulus and yield stress can be inferred from indentation curves, i.e., force versus indenter penetration depth[58, 59]. As the realism and the interpretative capacity of plasticity models grow, the material parameters become more numerous and less amenable to direct separate measurement[59]. The combination of experimental results and simulations (e.g., numerical or analytical solutions) with inverse analysis provides an increasingly popular method for characterization[60, 61]. For example, elastic and plastic anisotropy parameters have been identified by imaging the indentation geometry (i.e., the residual vertical deflection) and applying an inverse model based on simulations of the classical Hill's model for anisotropic perfect elasto-plasticity[62, 63]. In another indentation geometry imaging technique, an inverse model was used to determine hardening parameters of Chaboche's associative elastic-plastic-hardening isotropic model using a finite element model[59, 64]. None of these indenter studies have recorded the deflection contours of the indenter or specimen surface in real-time, which represents a valuable piece of information during the indentation process. The in-situ method proposed in this chapter indirectly measures the deflection of the plate and specimen in real-time through plate strain measurements.

The characterization of polymer foam constitutive parameters remains largely based on lab testing[1, 14, 15, 20]. As discussed in Chapter 2, the typical methods for characterization are uniaxial compression and hydrostatic compression tests. Indentation tests have been used to inform foam design[65], and study impact deformation[21], but not as an in-situ method for estimating plasticity parameters. The method described in this chapter will be applied to foam plasticity parameter estimation.

5.2 Methodology

A strain gage instrumented plate was designed and fabricated for this in-situ material characterization method. The plate and strain gage configuration are the same as discussed in Chapter 4, with the exception of the plate thickness. In order to induce plastic deformation, the samples had to be loaded to higher forces. The thickness of the plate was doubled, from 1.6 mm to 3.2 mm, thereby ensuring the plate would remain elastic during the prescribed forces. The diameter of the plate and radial locations of the gages remained the same.

An experimental test consisted of a vertical monotonic loading cycle of the instrumented plate onto a foam specimens, as shown in FIG. 93. The foams tested include EPS12 and EPS29B, which are described in Chapter 2. Compared to the four foams tested in Chapter 4, only two foams were tested in this work due to the challenges associated with obtaining plasticity parameters. As discussed in Chapter 2, this pertains to the limited access to specialized equipment and the considerable duration of preparing and conducting tests for hydrostatic compression. This exemplifies the need for a device that can easily obtain plasticity parameters. EPS12 and EPS29B were selected because they provide the widest possible range of plasticity parameters. Five tests were conducted on each of these foams. The load frame is described further in Chapter 4.

The maximum vertical forces exerted on the plate were chosen based on the FE model discussed in Section 5.3. Above certain forces, excessive distortion in the elements describing the foam at the edge of the plate prevents the FE model from running to completion. The maximum forces for which the FE models were able to run to completion were 225 N for EPS12 and 800 N for EPS29B. Depending on the specific model being run, the maximum principal strain in the foam at the edge of the plate ranged from 5.0% to 12%. The experimental tests loaded the samples to vertical forces of 300 N for EPS12 and 900 N for EPS29B. The FE model predicted these forces would keep the plate stresses well within the elastic range. The experimental tests were run to slightly higher forces than the maximum FE forces to investigate plate strain response. For reference, the FE models predicted the onset of plasticity in the foam at a force of 100 N for EPS12 and 400 N for EPS29B.

The experimental plate strains and vertical force measurements were used to characterize the foam based on an inverse model. This inverse model operates on the assumption that plate strain measurements are sensitive to the applied vertical force as well as the plasticity parameters of the foam. This sensitivity was analyzed with a FE model capable of predicting plate strains for a given applied vertical force and set of foam plasticity parameters.

5.3 Finite Element Model

Figure 94:
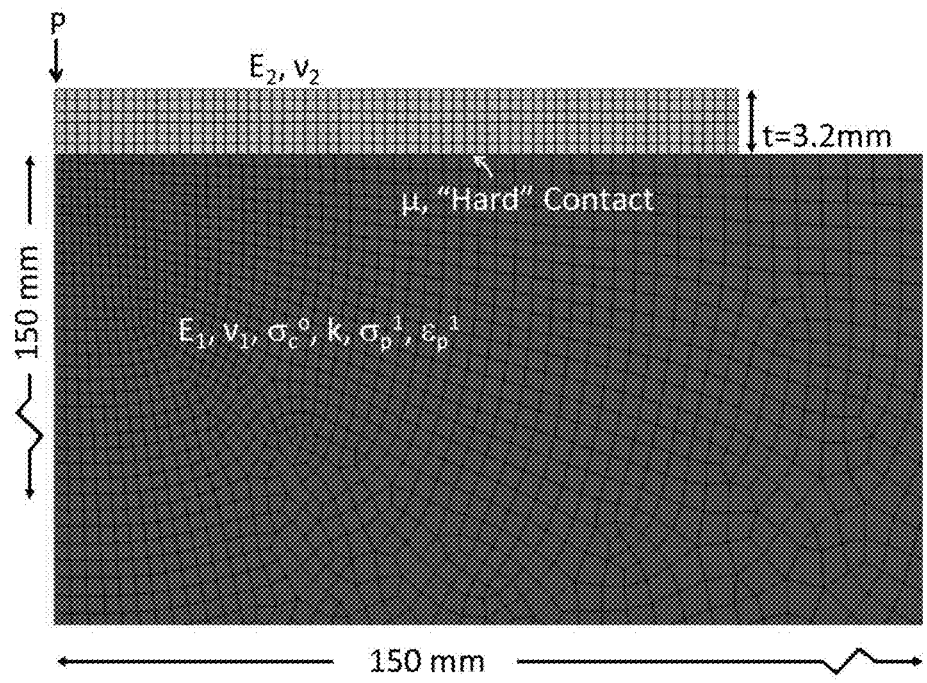
FIG. 94 FE model of an elastic plate on a plastic half-space.

A FE model was developed to predict plate strains for the experimental setup based on foam material properties. This FE model serves as the forward model for the inverse model used to predict plasticity parameters from plate strains. The FE model, shown in FIG. 94, places the aluminum plate on top of a foam half-space. The model was constructed using Abaqus CAE, and run with the Abaqus Standard analysis package. Axisymmetry was used to reduce computation time. The model consisted of CAX4R elements (four node bilinear axisymmetric quadrilateral, reduced integration, hourglass control), and CAX3 elements (three node linear axisymmetric triangular).

The plate was 3.2 mm thick, with a 32 mm radius with all CAX4R elements. The average element size was 0.53×0.53 mm, thereby creating six elements through the thickness of the plate, and a total of 360 elements. The material properties were that of 6061-T6 aluminum, which has an elastic modulus of 68.9 GPa and a Poisson's ratio of 0.33.

The EPS foam was modeled as a 150 mm×150 mm body with an average mesh size 2.6 mm. In order to ensure this model represented a half-space, the size of the foam was increased to a 300 mm by 300 mm body and resulted in <1.2% change in plate strains, and <2% change in Mises stresses in the half-space directly under the plate. The mesh can briefly be described as 3892 elements, including 3828 CAX4R and 64 CAX3 elements. The mesh had a bias, i.e., the mesh was more refined under the plate than at the edges of the half-space. This bias improves accuracy while decreasing run-time. The material properties of the foam were initially set to the values found in Chapter 2, also reproduced here in Table 5.1.

TABLE 5.1

Summary of foam constitutive parameters.

| Foam | E (MPa) | v | $\sigma_c^o$ (kPa) | $\sigma_p^1$ (kPa) | $\epsilon_p^1$ (kPa) | $p_c^o$ (kPa) | k | $k_r$ |
|---|---|---|---|---|---|---|---|---|
| EPS12 | 2.9 | 0.1 | 67.9 | 77.4 | 0.1 | 61.5 | 1.11 | 0.1 |
| EPS29B | 10 | 0.1 | 248 | 282 | 0.1 | 271.8 | 0.91 | 0.1 |

As part of the inverse model, the plasticity parameters of the FE model were varied. The following section discusses the plate strain sensitivity to variations in the plasticity parameters.

5.4 Plastic Parameter Sensitivity

The premise of the in-situ plasticity parameter estimation method developed in this chapter is that plate radial strains are sensitive to plasticity parameters of a foam specimen. This section investigates the sensitivity of plate strains to plasticity parameters. Based on the results from this investigation, an inverse model is developed.

In this analysis, the plate strain sensitivity to uniaxial compressive yield stress, $\sigma_c^0$, compressive yield stress ratio, k, and hardening parameters ($\sigma_p^1$, $\epsilon_p^1$) was investigated. As described in Chapter 2, k is defined by:

$$k = \frac{\sigma_c^0}{p_c^o} \qquad (5.1)$$

where $\sigma_c^0$ is the initial hydrostatic compressive yield stress. The set of parameters used in this analysis is shown in Table 5.2.

For k, the values ranged from 0.9 to 1.1, to reflect the range of values found for various foams in the literature[1, 14]. During the analysis on k, the other plasticity parameters assumed their experimentally determined values.

The range of values for $\sigma_c^0$ were chosen to be approximately 15% higher and lower than the yield stresses in Table 5.2. This range is admittedly arbitrary, but represents a range of yield stresses that might be experienced within a certain density of foam based on the "Compressive Resistance @ 5% deformation" listed in FIG. 6. The hardening parameters, $\sigma_p^1$ and $\epsilon_p^1$, were changed according to $\sigma_c^0$ such that the slope of the hardening curve remained unchanged, i.e., $\sigma_p^1$ was changed by the same value as $\sigma_c^0$. For simplicity, all discussion of the inverse model and results are in terms of the value of $\sigma_c^0$, but the value of $\sigma_p^1$ is easily found, i.e., $\sigma_p^1$ is always 10 kPa higher than $\sigma_c^0$ for EPS12 and 34 kPa higher for EPS29B. During the analysis on these parameters, k assumed its experimentally determined value.

TABLE 5.2

Parameters of plasticity parameter sensitivity analysis concerning plate strains.

| Parameter being Varied | EPS12 Values | EPS29B Values |
|---|---|---|
| k | k = [0.9, 1.0, 1.1] | k = [0.9, 1.0, 1.1] |
| $\sigma_c^o$ | $\sigma_c^o$ = [57.9, 67.9, 77.9] kPa | $\sigma_c^o$ = [218, 248, 288] kPa |

Figure 95:
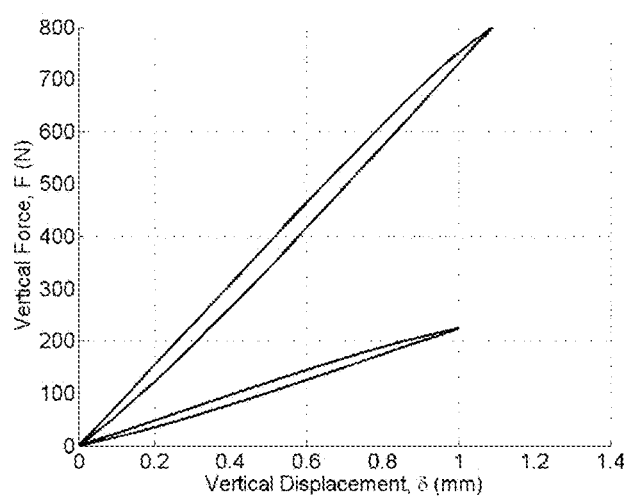
FIG. 95 Results from the FE model showing force versus displacement of the center of the plate for the two foams, using experimentally determined parameters FIG. 96 FE model of EPS12 at 225 N load, showing radial strain in the plate and von Mises stress in the foam half-space.
Figure 96:
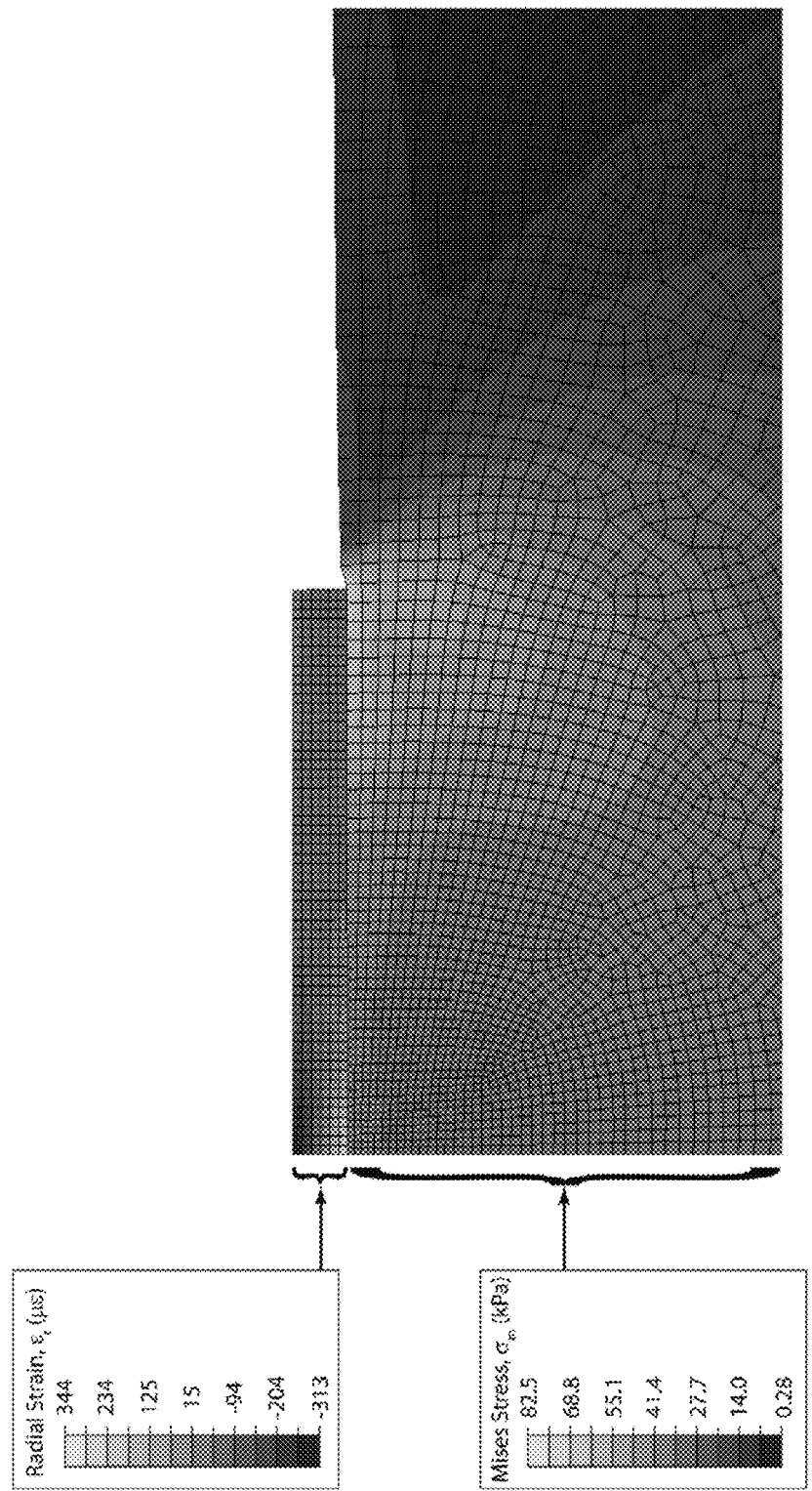

Before introducing the plate strain behavior, it is helpful to understand the behavior of the plate and foam half-space. The force versus displacement for EPS12 and EPS29B are shown in FIG. 95 for the load-unload cycle using the experimentally determined parameters in Table 5.1. The difference in displacement between load and unload was found to be 0.079 mm for EPS12 at 112.5 N, and 0.062 mm for EPS29B at 400 N (note that these forces are half the maximum applied force). There is very little permanent displacement under the center of the plate at these forces (i.e., <1 μm), due to the fact that the foam under the center of the plate generally stays elastic at these forces. A contour plot is given in FIG. 96, showing the radial strain in the plate and Mises stress (defined in Chapter 2) in the foam half space at 225 N. The foam experiences its highest von Mises stress towards the edges, which is consequently where plasticity develops. The plate experiences maximum radial strain towards its center, where the load is applied.

Figure 97:
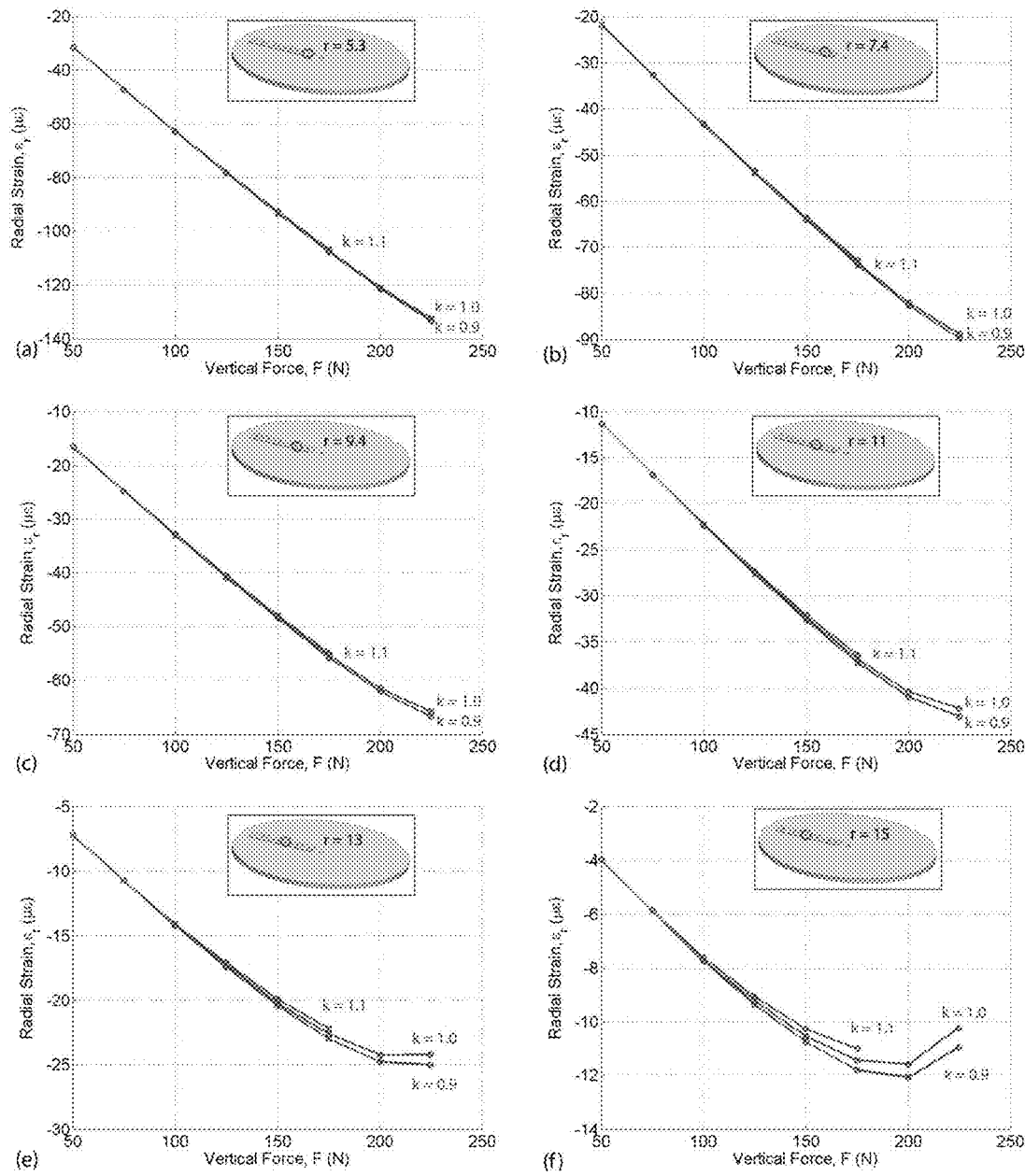
FIG. 97 Plate radial strain versus force for EPS12 using three different values of the compressive yield stress ratio, k. Each plot is a different radial location on the plate representing the six strain gages closest to the plate center.
Figure 98A:
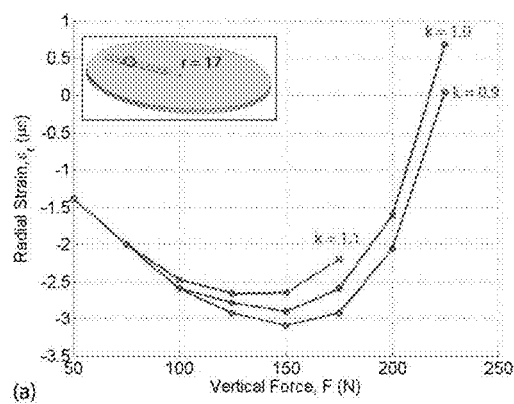
FIG. 98A-D Finite element results for plate radial strain versus force for EPS12 using three different values of the compressive yield stress ratio, k. Each plot is a different radial location on the plate representing the four strain gages furthest from the plate center.
Figure 98B:
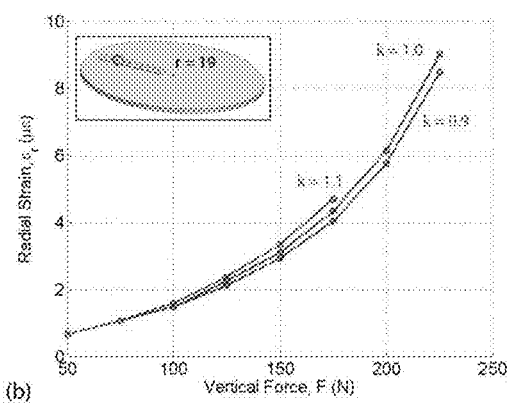
Figure 98C:
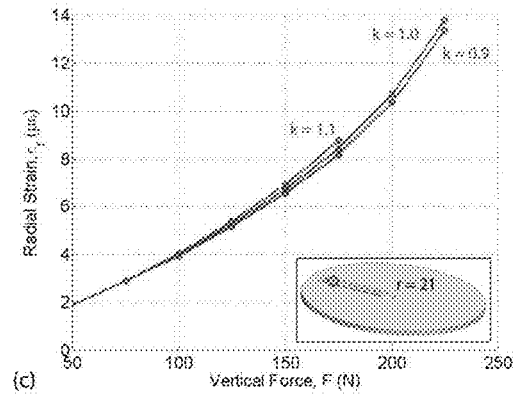
Figure 98D:
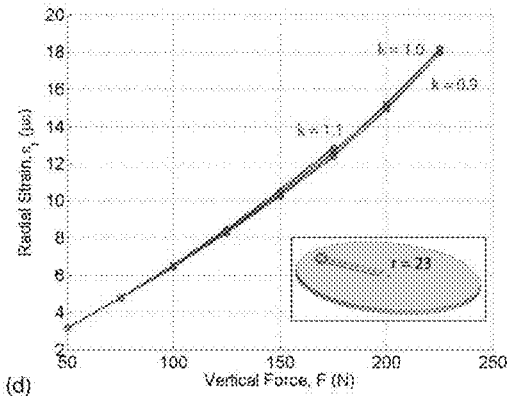
Figure 99:
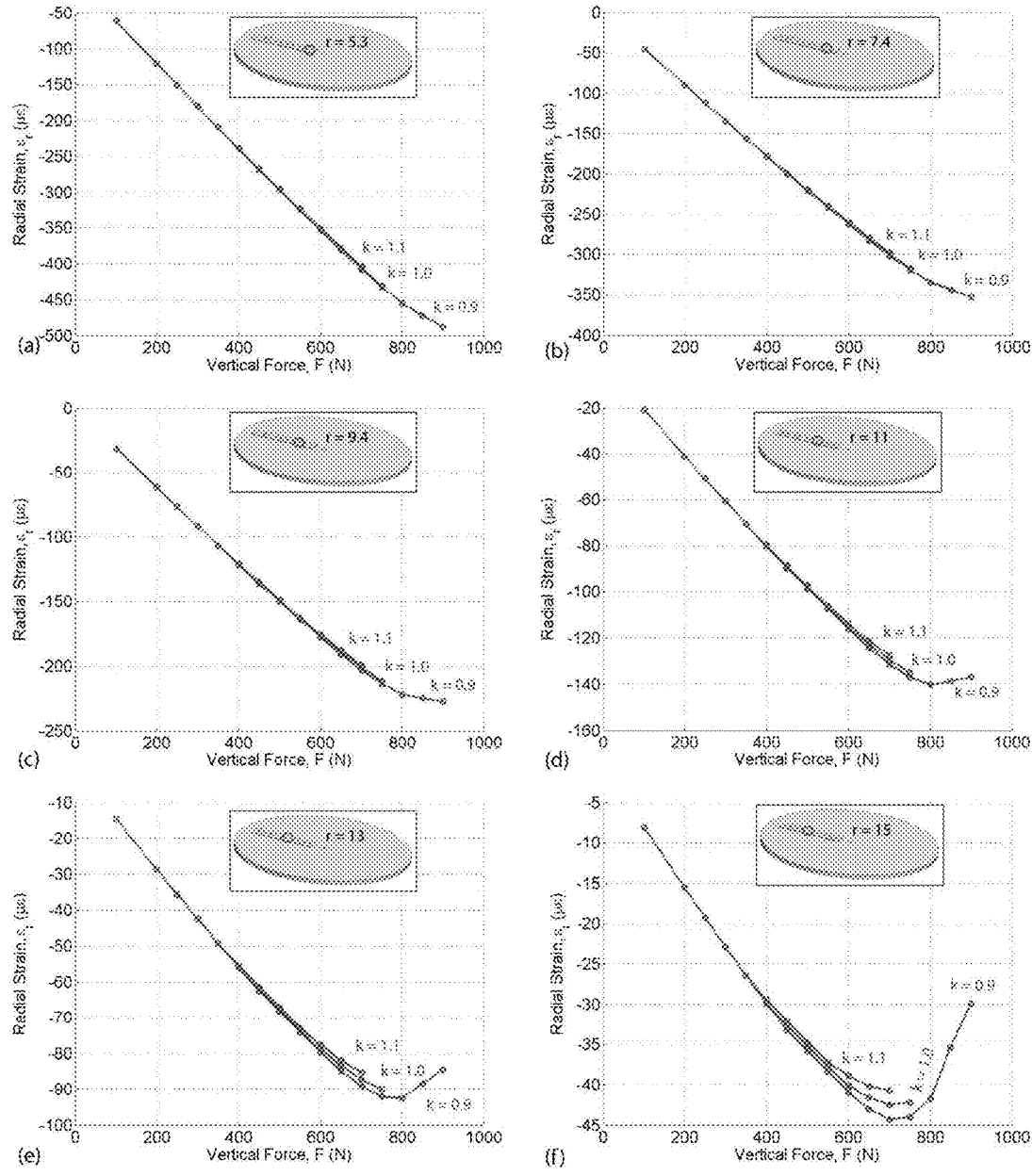
FIG. 99 Finite element results for plate radial strain versus force for EPS29B using three different values of the compressive yield stress ratio, k. Each plot is a different radial location on the plate representing the six strain gages closest to the plate center.
Figure 100:
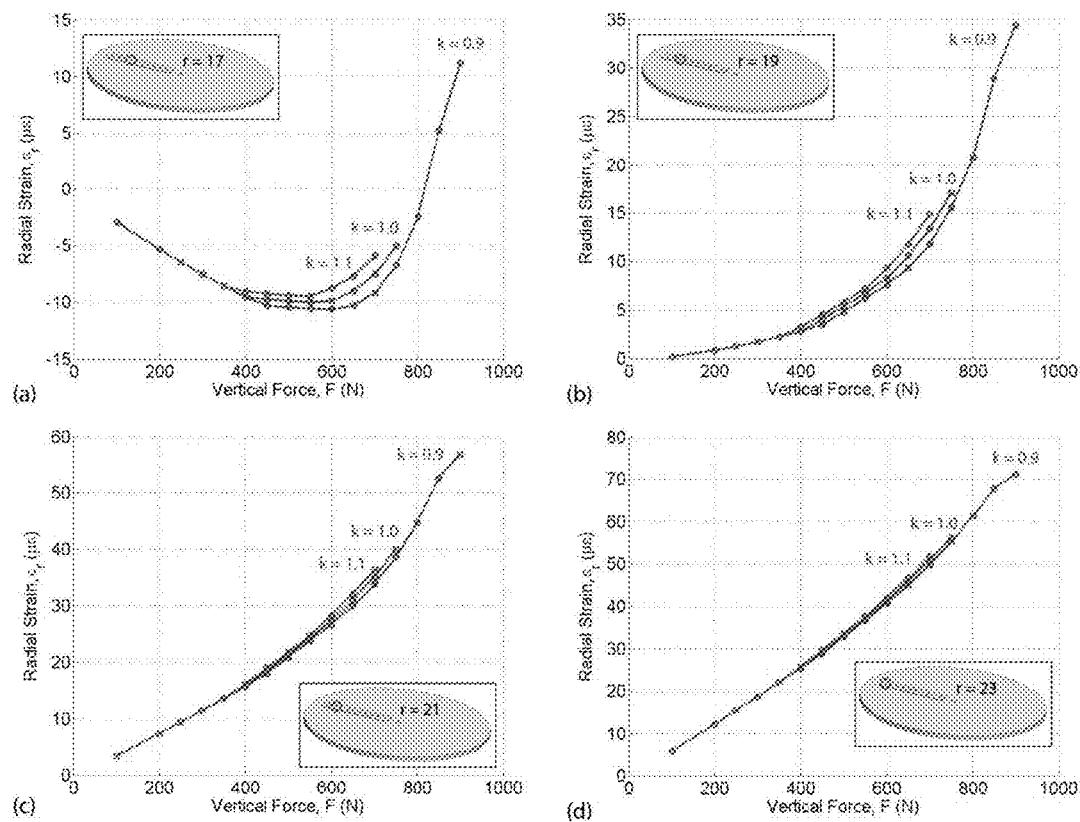
FIG. 100 Finite element results for plate radial strain versus force for EPS29B using three different values of the compressive yield stress ratio, k. Each plot is a different radial location on the plate representing the four strain gages furthest from the plate center.

The results of the analysis for k on EPS12 is shown in FIG. 97 and FIG. 98, where each plot shows the radial strain at one of the ten strain gage locations on the plate. Depending on the value of k, the FE model was able to solve up to different maximum forces. For example, the maximum force for the k=1.1 simulation was 175 N, while the other values of k solved up to 225 N. It can be seen that the radial strain at all gages remains same for all values of k until the force reaches 100 N, which is when the foam begins to deform plastically. The difference in strains between the various values of k increases with force. Variation in k shows more influence on plate strain towards the middle gages, i.e., r=13 mm through r=19 mm. The maximum variation in radial strain due to changes in k does not exceed 2με throughout this entire analysis. This small variation indicates that plate strains are not very sensitive to changes in k within this range of values The results of the analysis for k on EPS29B is shown in FIG. 99 and FIG. 100, where each plot shows the radial strain at one of the ten strain gage locations on the plate. The different values of k enabled the FE model to solve up to different maximum forces, i.e., k=1.1 solved up to 700 N. It can be seen that the radial strain at all gages remains same for all values of k until the force reaches 400N, which is when the foam begins to deform plastically. Similar as with the EPS12 foam, there is little variation in plate radial strains across these values of k. The influence is most pronounced towards the middle gages, i.e., r=13 mm through r=19 mm. However, the variation in radial strain due to changes in k does not exceed 6με throughout this entire analysis. For both EPS12 and EPS29B, plate strains are not very sensitive to this range of compressive yield stress ratios.

Figure 101:
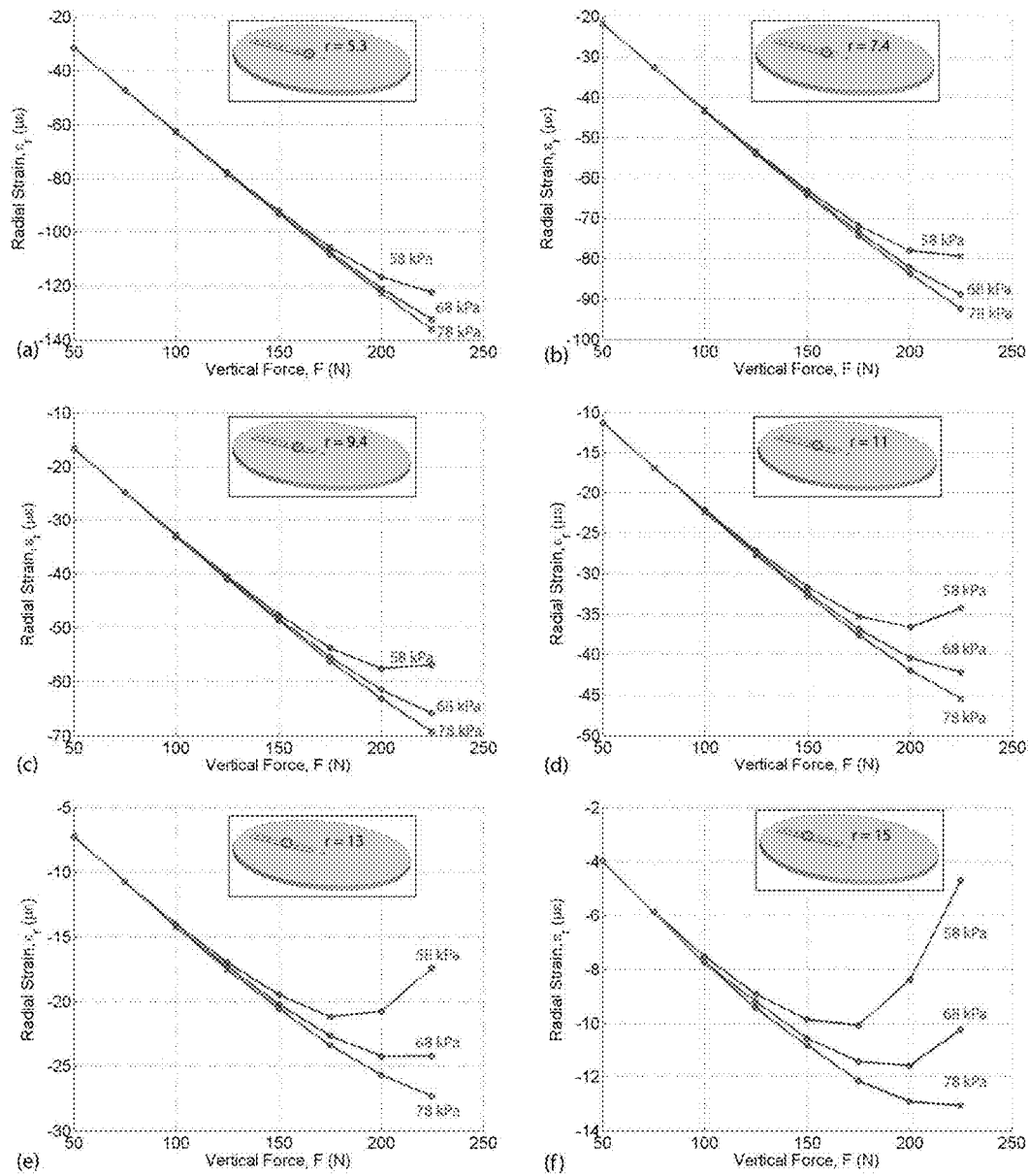
FIG. 101 Finite element results for plate radial strain versus force for EPS12 using three different values of the uniaxial compressive yield stress, $\sigma_c^0$. Each plot is a different radial location on the plate representing the six strain gages closest to the plate center.
Figure 102:
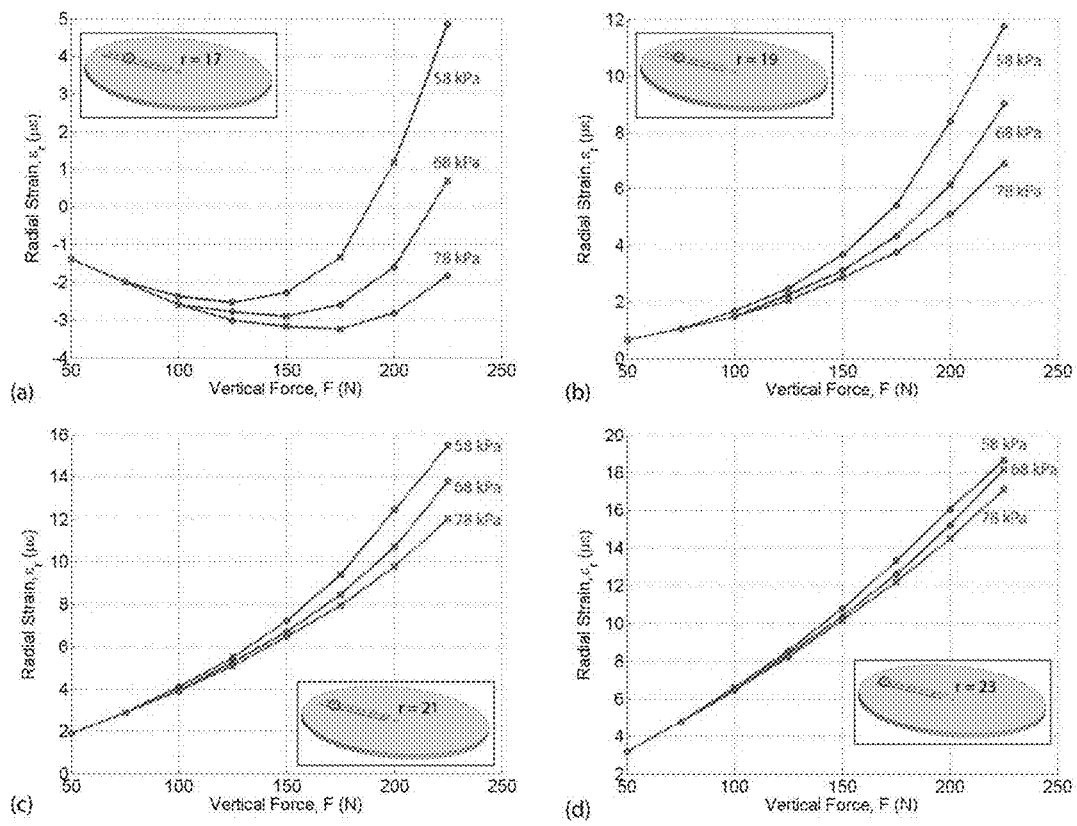
FIG. 102 Finite element results for plate radial strain versus force for EPS12 using three different values of the uniaxial compressive yield stress, $\sigma_c^0$. Each plot is a different radial location on the plate representing the four strain gages furthest from the plate center.

The results of the analysis for $\sigma_c^0$ on EPS12 is shown in FIG. 101 and FIG. 102, where each plot shows the radial strain at one of the ten strain gage locations on the plate. The lines are labeled with $\sigma_c^0$, although it should be noted that the hardening parameters are varied as discussed above. There is considerably more variation in plate strains due to these variations in $\sigma_c^0$ than due to the variations in k. Similar as with k, variation in $\sigma_c^0$ shows more influence towards the middle gages, i.e., r=11 mm through r=17 mm. In addition to variations in strain magnitude, these middle gages show differences in the slope of strain versus force. The variation in radial strains range up to 16με throughout this analysis. This level of variation in strain is much easier to detect with the strain gage measurement system than the 2με differences due to varying k for EPS12.

Figure 103:
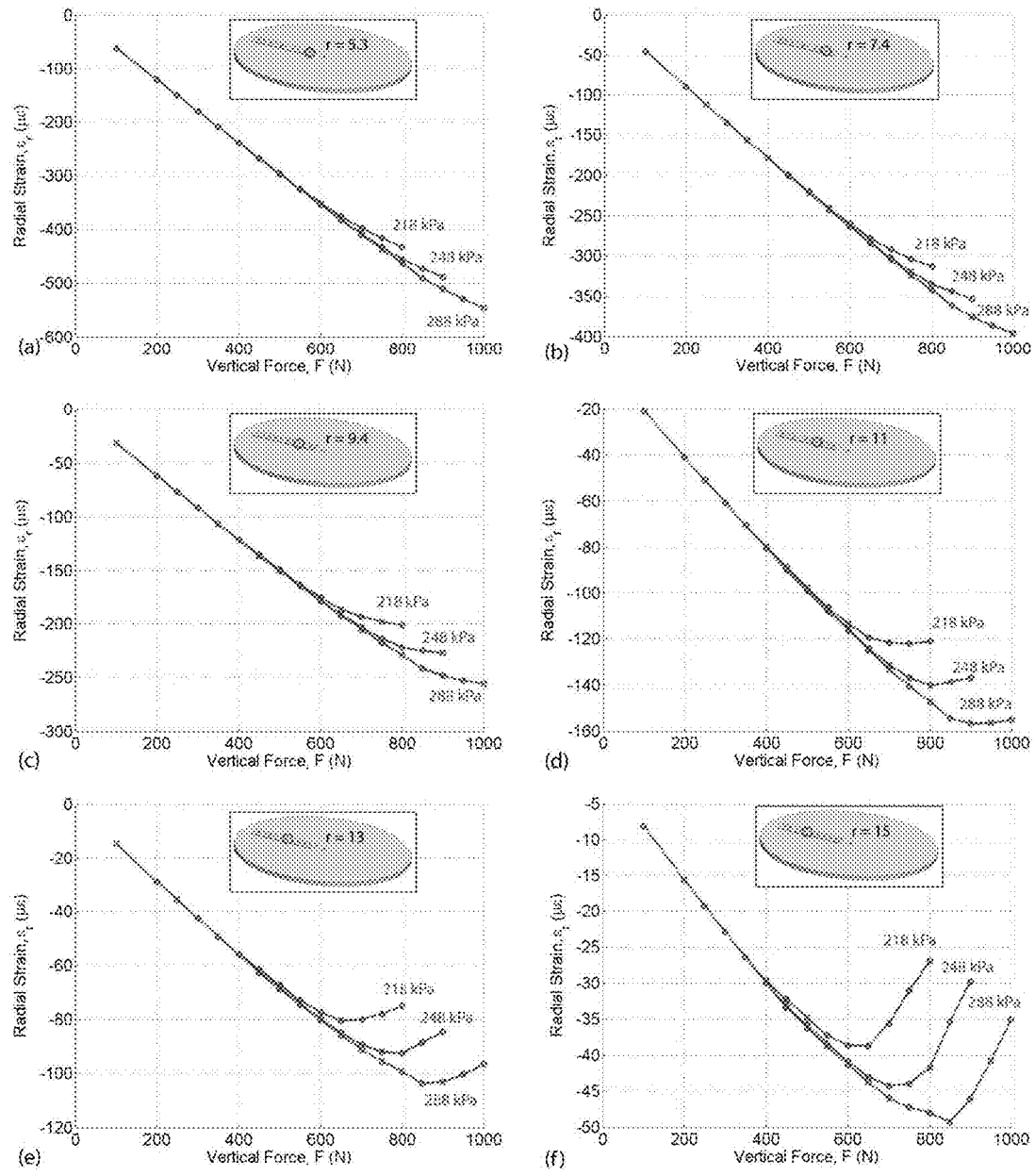
FIG. 103 Finite element results for plate radial strain versus force for EPS29B using three different values of the uniaxial compressive yield stress, $\sigma_c^0$. Each plot is a different radial location on the plate representing the six strain gages closest to the plate center.
Figure 104:
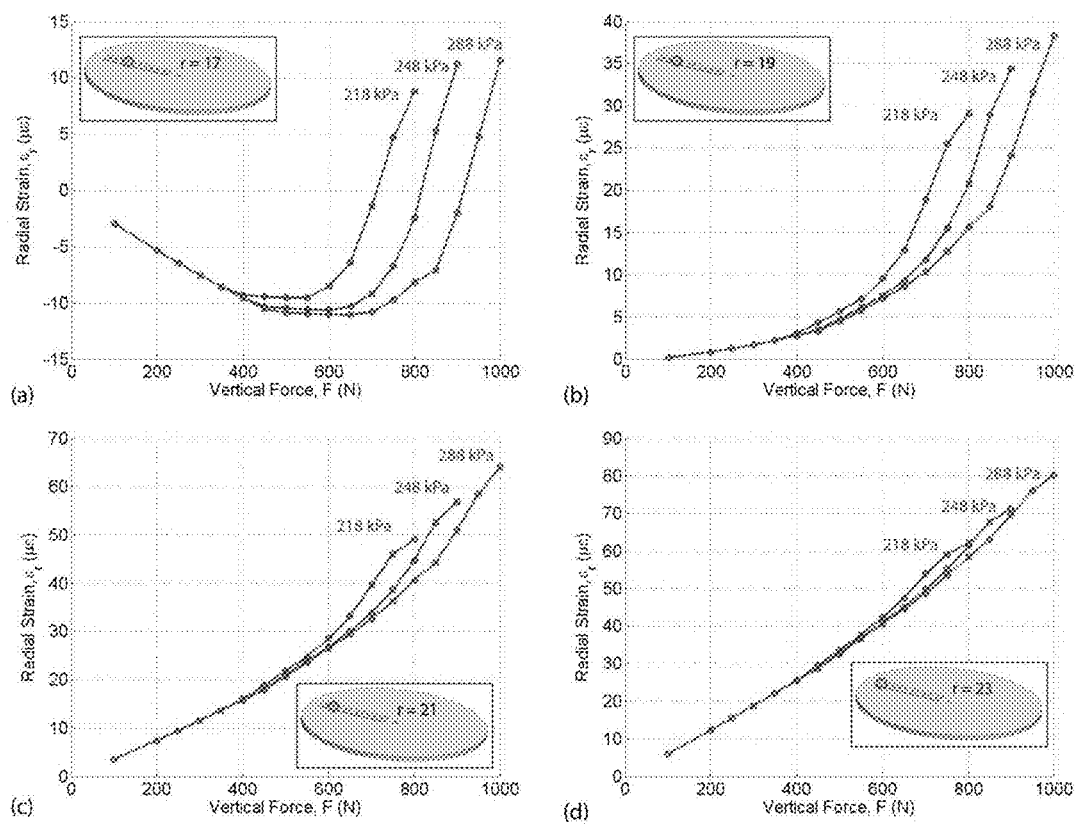
FIG. 104 Finite element results for plate radial strain versus force for EPS29B using three different values of the uniaxial compressive yield stress, $\sigma_c^0$. Each plot is a different radial location on the plate representing the four strain gages furthest from the plate center.

The results of the analysis for $\sigma_c^0$ on EPS29B is shown in FIG. 103 and FIG. 104, where each plot shows the radial strain at one of the ten strain gage locations on the plate. As with EPS12, there is considerably more variation in plate strains due to these variations in $\sigma_c^0$ than due to the variations in k. Also similar to EPS12, variation in $\sigma_c^0$ shows more influence towards the middle gages, i.e., r=11 mm through r=17 mm. The variation in radial strain range up to 31µε throughout this analysis. This level of variation in strain is much easier to detect with the strain gage measurement system than the 6µε variation in the k sensitivities for EPS29B.

Considering the lack of sensitivity of plate strains to k, and the much greater sensitivity to $\sigma_c^0$ (and associated change in hardening parameters), the approach developed in this chapter seeks an inverse model for determining $\sigma_c^0$.

5.5 Inverse Model

An inverse model was developed to estimate $\sigma_c^0$ from experimental plate strain data. This approach was chosen based on the sensitivity analysis in the previous section. The inverse model is based on the FE model introduced in this chapter. This section develops the inverse model.

Similar to the inverse model developed in Chapter 4, the inverse model developed here uses a lookup table based on FE model results. The values used to construct the look up table are defined in Table 5.3. The hardening parameters are changed in coordination with the $\sigma_c^0$, i.e., $\sigma_p^1$ is always 10 kPa higher than $\sigma_c^0$ for EPS12 and 34 kPa higher for EPS29B. For simplicity, all discussion of the inverse model and results are in terms of the value of $\sigma_c^0$, but the value of $\sigma_p^1$ is easily found.

The plate radial strain values for an arbitrary set of parameters not explicitly listed in Table 5.3 can be estimated through linear interpolation or extrapolation. Taking EPS29B for example, the strain for gage 1 (r=5 mm) with a $\sigma_c^0$ value of 268 MPa and a force of 425 N would be calculated based on the nearest points in the lookup table, i.e., between moduli of 248 and 288 MPa, and between forces of 400 and 450 N $$\varepsilon_i^{Model}(\sigma_c^0, F) = \quad (5.2)$$

$$\varepsilon_1^{Model}(268,425) = \frac{\left(\frac{(\varepsilon_i^{Model}(288,450) + \varepsilon_1^{Model}(248,450))}{2} + \frac{(\varepsilon_i^{Model}(288,400) + \varepsilon_1^{Model}(248,400))}{2}\right)}{2}$$

The inverse model finds the value of $\sigma_c^0$ that produces the least amount of error compared to the experimental results. As described in and Chapter 4, and reproduced here, the error is described by $$\epsilon = \Sigma_{i=1}^N (\epsilon_i^{EXP} - \epsilon_i^{Model})^2 \quad (5.3)$$

where i is the gage, N. is the total number of gages (N=10), $\epsilon_i^{EXP}$ is the experimental radial strain for gage i, and $\epsilon_i^{Model}$ is the model radial strain for gage i. The model strains are generated according to the forward model.

5.6 Results

This section presents the experimental results and the application of the inverse model to determine $\sigma_c^0$. The plate strains and spatial distribution of strains are presented. The application of the inverse model is introduced and applied to all the data sets.

Figure 105:
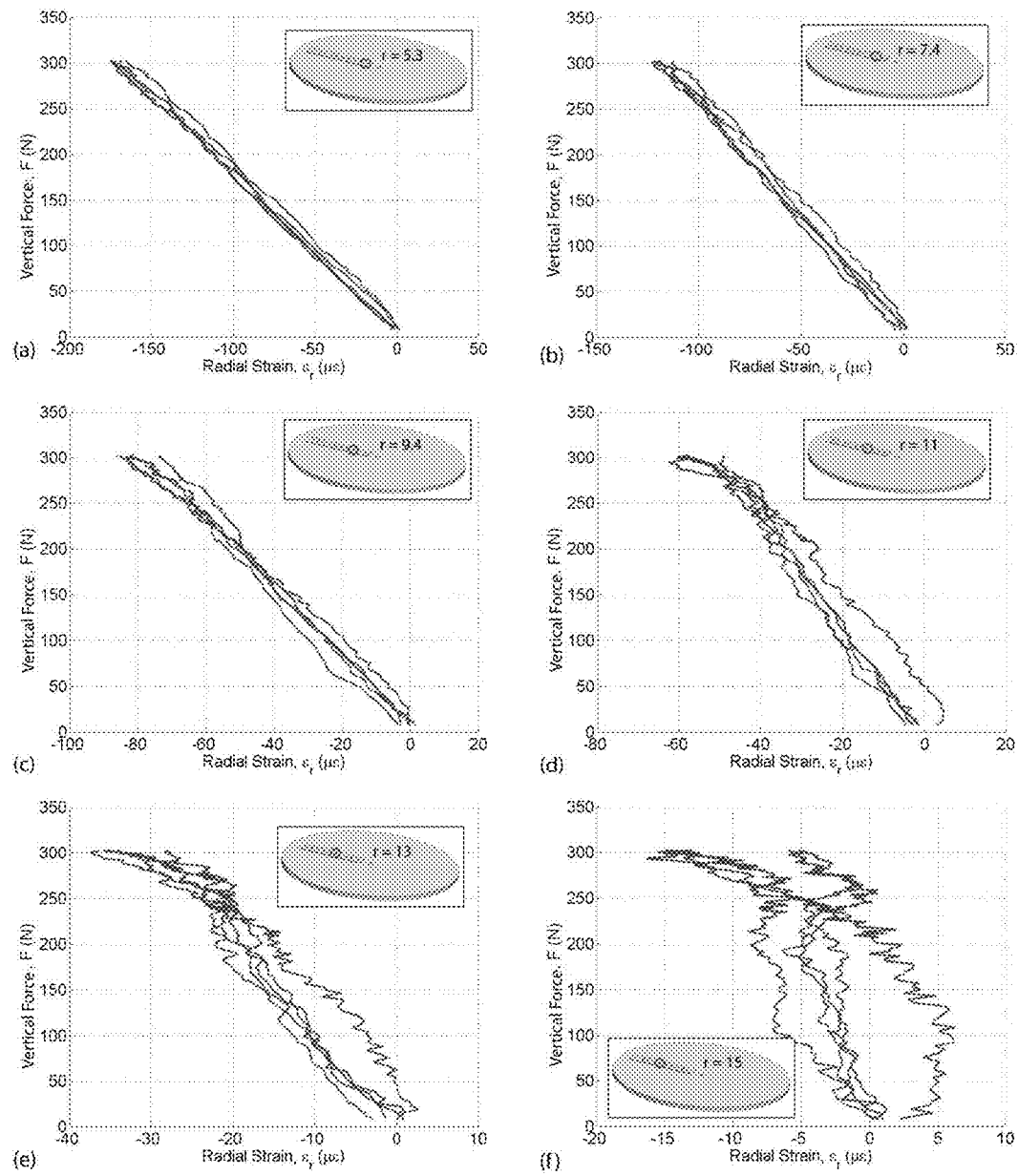
FIG. 105 Experimental plate strain results for EPS12. Each plot is a different radial location on the plate representing the six operational strain gages closest to the plate center.
Figure 106:
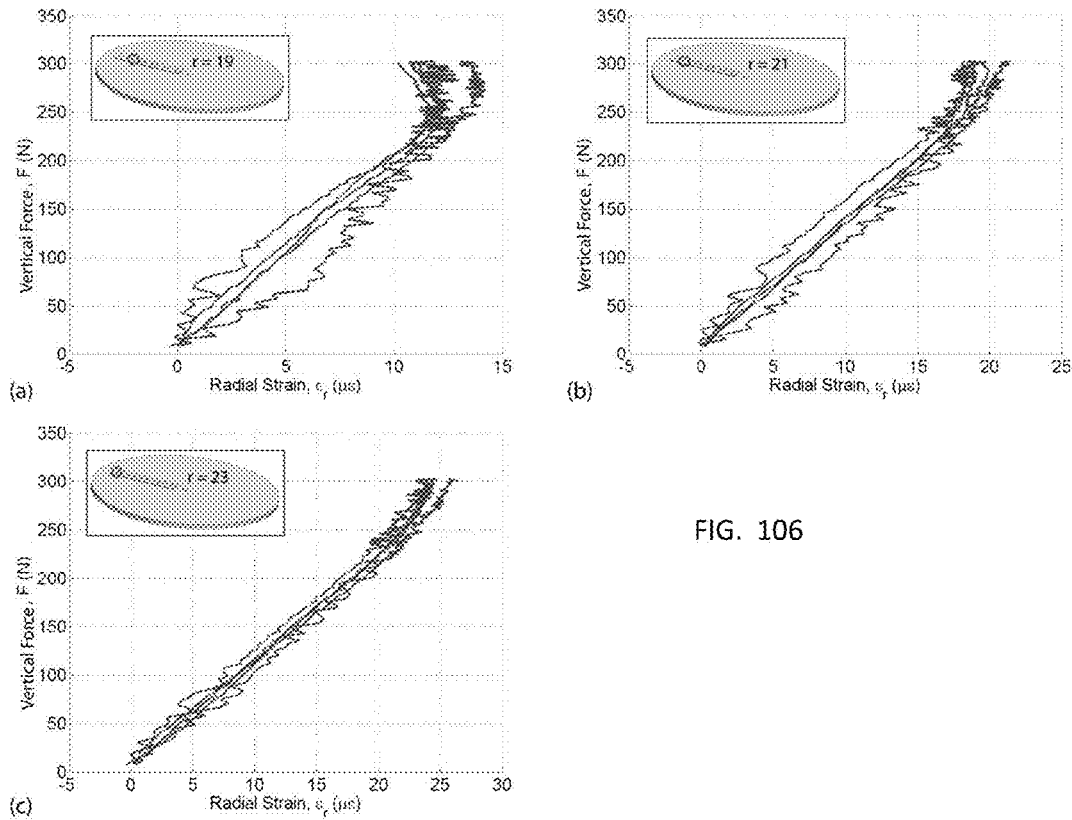
FIG. 106 Experimental plate strain results for EPS12. Each plot is a different radial location on the plate representing the three operational strain gages furthest from the plate center.

The plate strains results for EPS12 are presented in FIG. 105 and FIG. 106, plotted against the applied vertical force. Each plot shows the strain measurements of a single gage for five tests. During the tests, the gage at r=17 mm malfunctioned, so the results exclude data from this gage. These plots show good repeatability between tests, as seen by the degree with which each test overlaps the others. For loads up to 225 N, the strain curves are generally linear with the exception of gages r=15 and 19 mm. The nonlinearity of these gages during elastic loading was also seen in the tests in Chapter 4, and is discussed there. Above loads of approximately 225 N, there is a bend in the strain curves, seen especially well in gages r=13 through 19 mm. This bend is likely due to the development of plasticity in the foam, which can be verified by looking at the force-displacement graphs.

Figure 107:
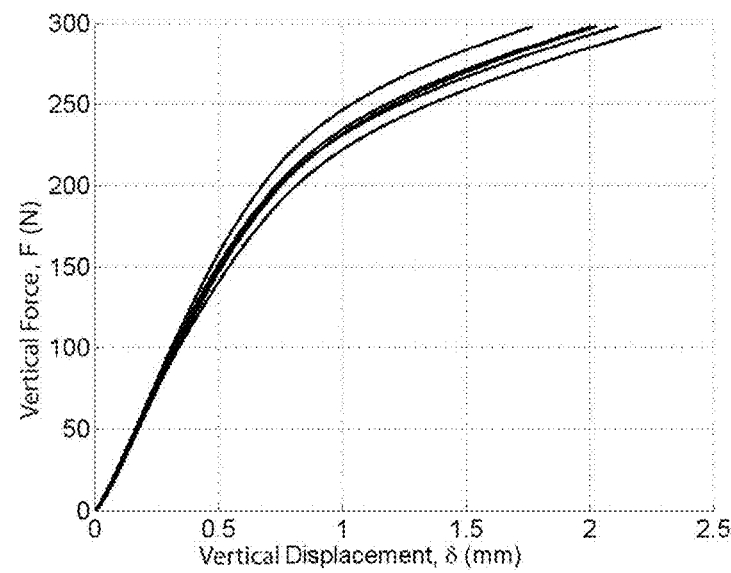
FIG. 107 Force versus displacement curve for five instrumented plate load tests on EPS12.

The curves for force versus the displacement at the center of the plate for EPS12 are shown in FIG. 107 for all five tests. Similar as with the plate radial strain curves in FIG. 105 and FIG. 106, there is a bend in the curve at approximately 225 N. The bend in the strain and displacement curves is due to the foam's plastic behavior. The average contact stress created by the plate at 225 N is 71.0 kPa, which is near the uniaxial compressive yield stress of the foam, 67.9 kPa. The FE model predicts localized failure at the edge of the plate at 100 N, but this small amount of plastic deformation does not greatly impact the plate strains or displacement until much higher forces.

Figure 108:
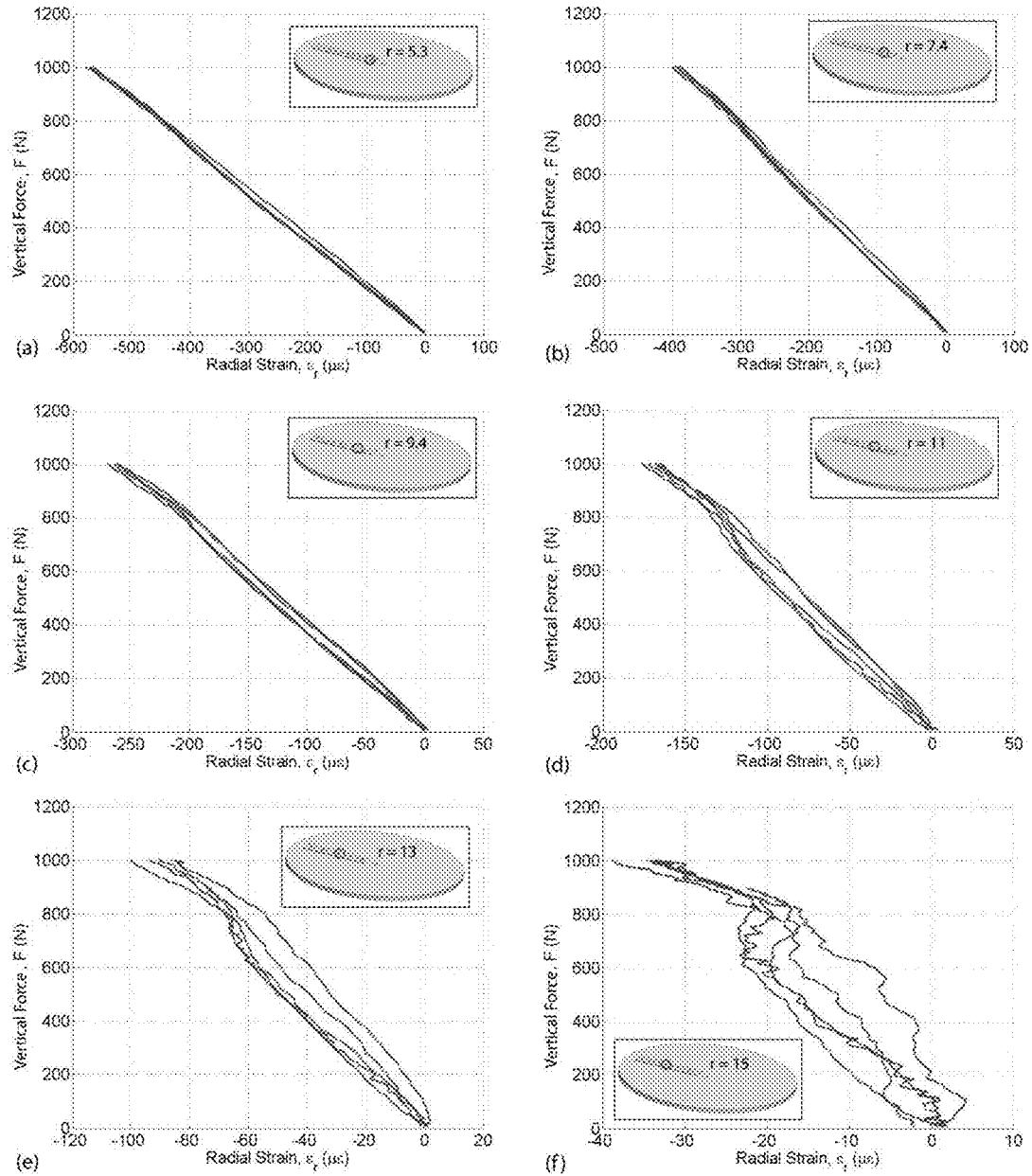
FIG. 108 Experimental plate strain results for EPS29B. Each plot is a different radial location on the plate representing the six operational strain gages closest to the plate center.
Figure 109:
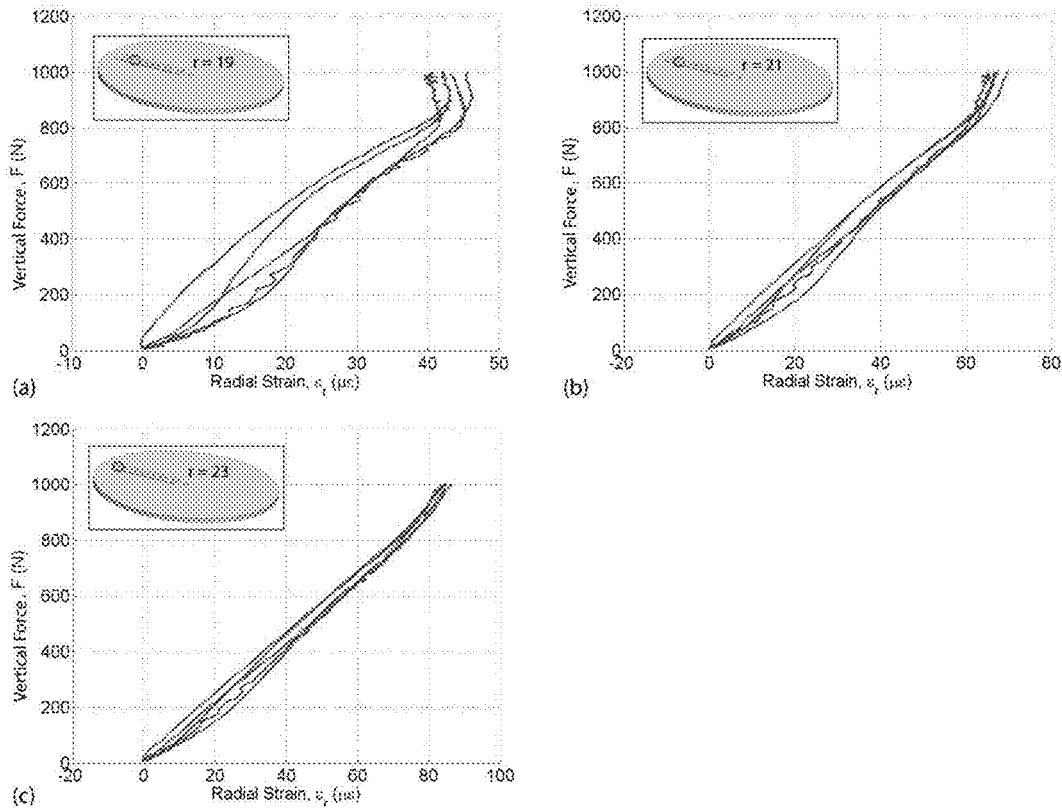
FIG. 109 Experimental plate strain results for EPS29B. Each plot is a different radial location on the plate representing the three operational strain gages furthest from the plate center.

The plate strains results for EPS29B are presented in FIG. 108 and FIG. 109, plotted against force. Each plot shows the strain measurements of a single gage for five tests. During the tests, the gage at r=17 mm malfunctioned, so the results exclude data from this gage. The EPS29B results are very similar to the EPS12 results, just at higher loads. There is good repeatability between tests. For loads up to approximately 800 N, the strain curves are generally linear with the exception of gages r=15 and 19 mm. Above loads of approximately 800 N, there is a bend in the strain curves, seen especially well in gages r=13 through 19 mm.

Figure 110:
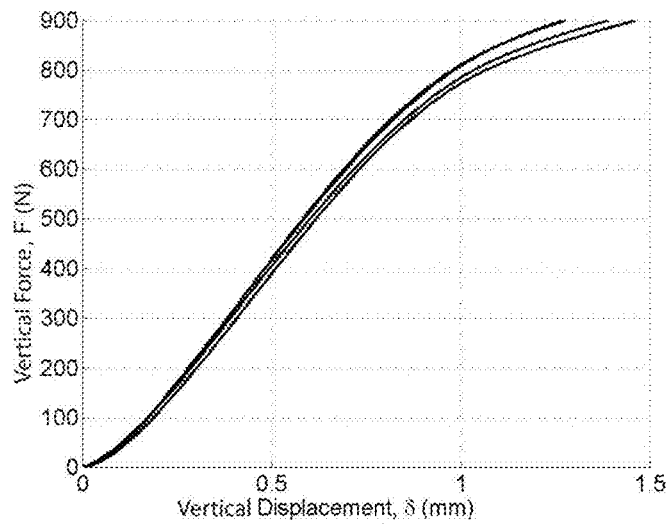
FIG. 110 Force versus displacement curve for five instrumented plate load tests on EPS29B.

The curves for force versus the displacement at the center of the plate for EPS19B are shown in FIG. 110 for all five tests. Just as with EPS12, there is a bend in the displacement

TABLE 5.3

Forward model parameter values used to populate plate radial strain lookup table for the plasticity inverse model.

| Parameter | EPS12 Values | EPS29B Values |
|---|---|---|
| $E_1$ (MPa) | 2.9 | 10 |
| v | 0.1 | 0.1 |
| k | 1.11 | 0.91 |
| r (mm) | [5, 7, 11, 13, 15, 17, 19, 21, 23] | [5, 7, 9, 11, 13, 15, 17, 21, 23] |
| F (N) | [100, 125, 150, 175, 200, 225] | [400, 450, 500, 550, 600, 650, 700, 750, 800] |
| $\sigma_c^0$ (kPa) | [57.9, 67.9, 77.9] | [218, 248, 288] |
| $\sigma_p^1$ (kPa), $\epsilon_p^1$ = 0.1 | [67.4, 77.4, 87.4] | [252, 282, 322] | curve at approximately the same force as in the plate strain curves, 800 N. The average contact stress created by the plate at 800 N is 253 kPa, which is near the uniaxial compressive yield stress of EPS29B, 248 kPa. The FE model predicts localized failure at the edge of the plate at 400 N, but the plastic deformation clearly does not greatly impact the plate strains or deformation until much higher forces.

Figures 111A, 111B:
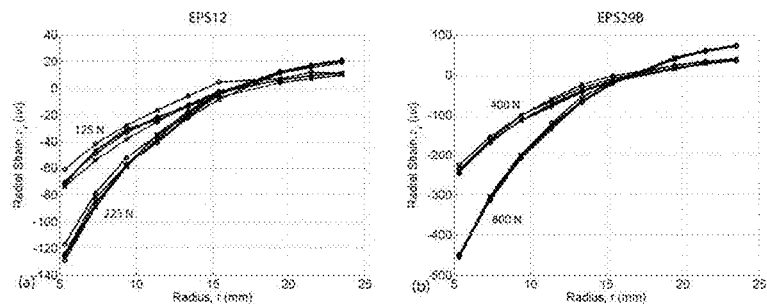
FIG. 111A-B Spatial distribution of plate radial strains for 111a) EPS12 and 111b) EPS29B. The strain distribution is shown for two forces for each foam, and the results from all five tests are shown at each force.

The spatial distribution of the plate strains can be seen in FIG. 111 for both EPS12 and EPS29B foams. The distribution of strain is shown at two forces for each foam, the lower force being when the foam is mostly elastic and the higher force being when plasticity has clearly begun to develop. The results from all five tests are shown at both forces. Both foams transition from compressive to tensile strain near 17 mm, indicating that the development of plasticity does not drastically change the transition point.

Figure 112:
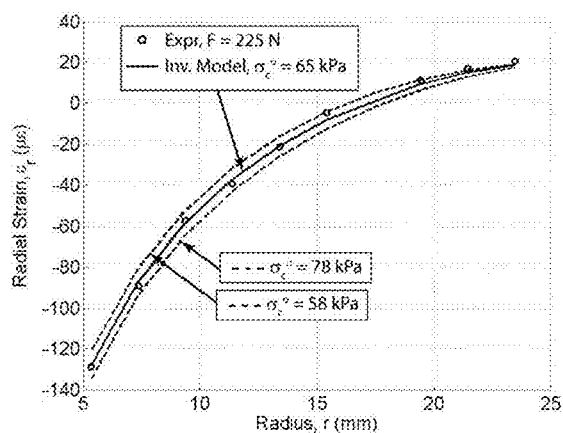
FIG. 112 Experimental plate radial strains, shown with circles, were analyzed using the inverse model. The inverse model predicted a uniaxial compressive yield stress of 65 kPa at a vertical load of 225N.

An inverse model was used to estimate uniaxial compressive yield strength from plate radial strain measurements. An example result from the inverse model is shown in FIG. 112 for a load of 225 N on EPS12. As with the inverse model applied in Chapter 4, the inverse model finds the value of the parameter (in this case $\sigma_c^0$ and the corresponding change in $\sigma_p^1$) that best fits the experimental results. For the experimental data shown in FIG. 112, a uniaxial compressive yield stress of 65 kPa was found to fit best. Per the discussion on inverse modeling, this corresponds to a value of 75 kPa for $\sigma_p^1$. In addition to the inverse model fit, FIG. 112 also shows dotted lines representing the minimum and maximum values for $\sigma_c^0$ used in this analysis, 58 and 78 kPa. This range of yield stresses presents an approximation of the spread that might be experienced for various batches of EPS12, which gives a relatively narrow band of strain values.

Figures 113A, 113B:
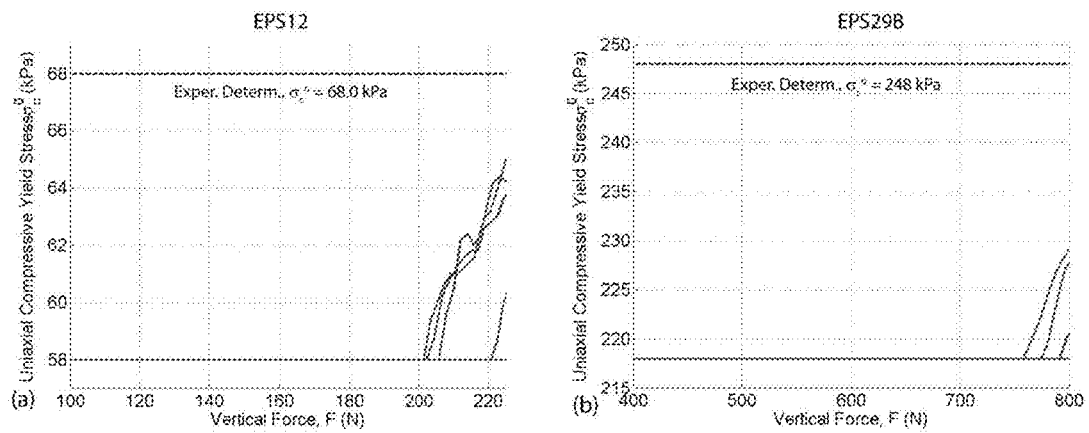
FIG. 113A-B Predictions for uniaxial compressive yield stress using the inverse model plotted by force for 113a) EPS12 and 113b) EPS29B.

The uniaxial compressive yield stress was predicted throughout each test by applying the inverse model to experimental data at each increment of force. The results of these predictions are plotted against force in FIG. 113, with the experimentally determined $\sigma_c^0$ shown by a dashed line. The range of forces shown represent the minimum force at which plastic deformation is seen in the FE model up to the maximum force for which the FE model could obtain a solution. The predictions of uniaxial yield stress remain constant at the minimum value (58 kPa for EPS12 and 218 for EPS29B) until the results from some of the tests show increased prediction values for $\sigma_c^0$ at just over 200 N for EPS12 and just over 750 N for EPS29B. These forces are similar to where the strain curves begin to bend in FIG. 105, FIG. 106, FIG. 108, and FIG. 109, i.e., where the plate radial strains show sensitivity to plastic deformation in the foam. Prior to this bend in the strainforce curve, the inverse model is unable to predict a meaningful value of $\sigma_c^0$.

Once the inverse model begins to predict values greater than the minimum yield stress, there is a range of values predicted. For EPS12, the values range from 58 kPa to 65 kPa. For EPS29B, the values range from 218 kPa to 229 kPa. None of the tests produced a prediction for $\sigma_c^0$ that matched the experimentally determined values of 68 kPa and 248 kPa for EPS and EPS29B, respectively. However, the prediction of $\sigma_c^0$ increases with force, suggesting that if the FE model could solve to higher forces the inverse model predictions may reach the independently obtained values.

Figure 114:
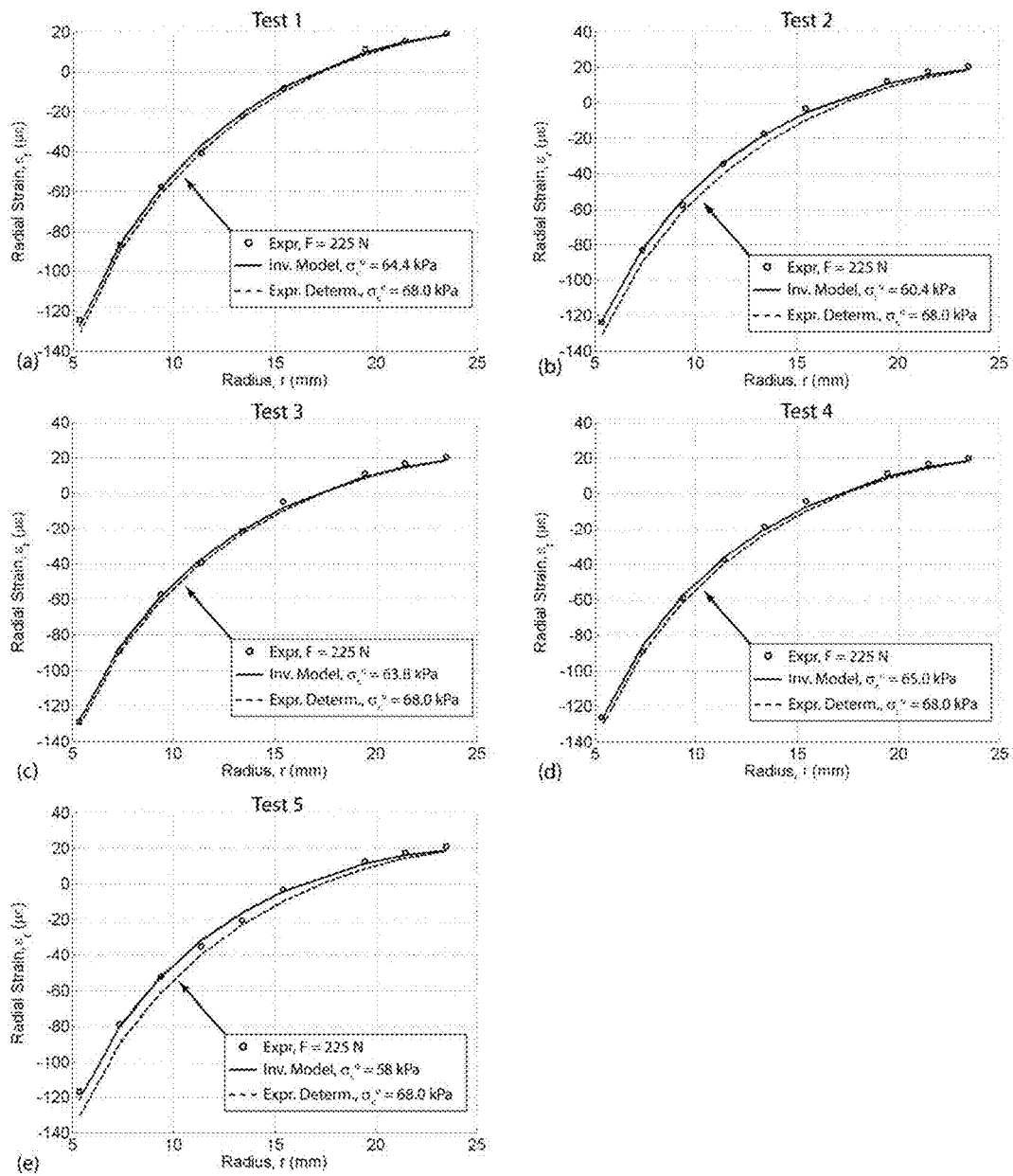
FIG. 114 Inverse model fits for the five tests on EPS12 at 225 N. Experimental results shown with circles, the model is shown with a dashed line.
Figure 115:
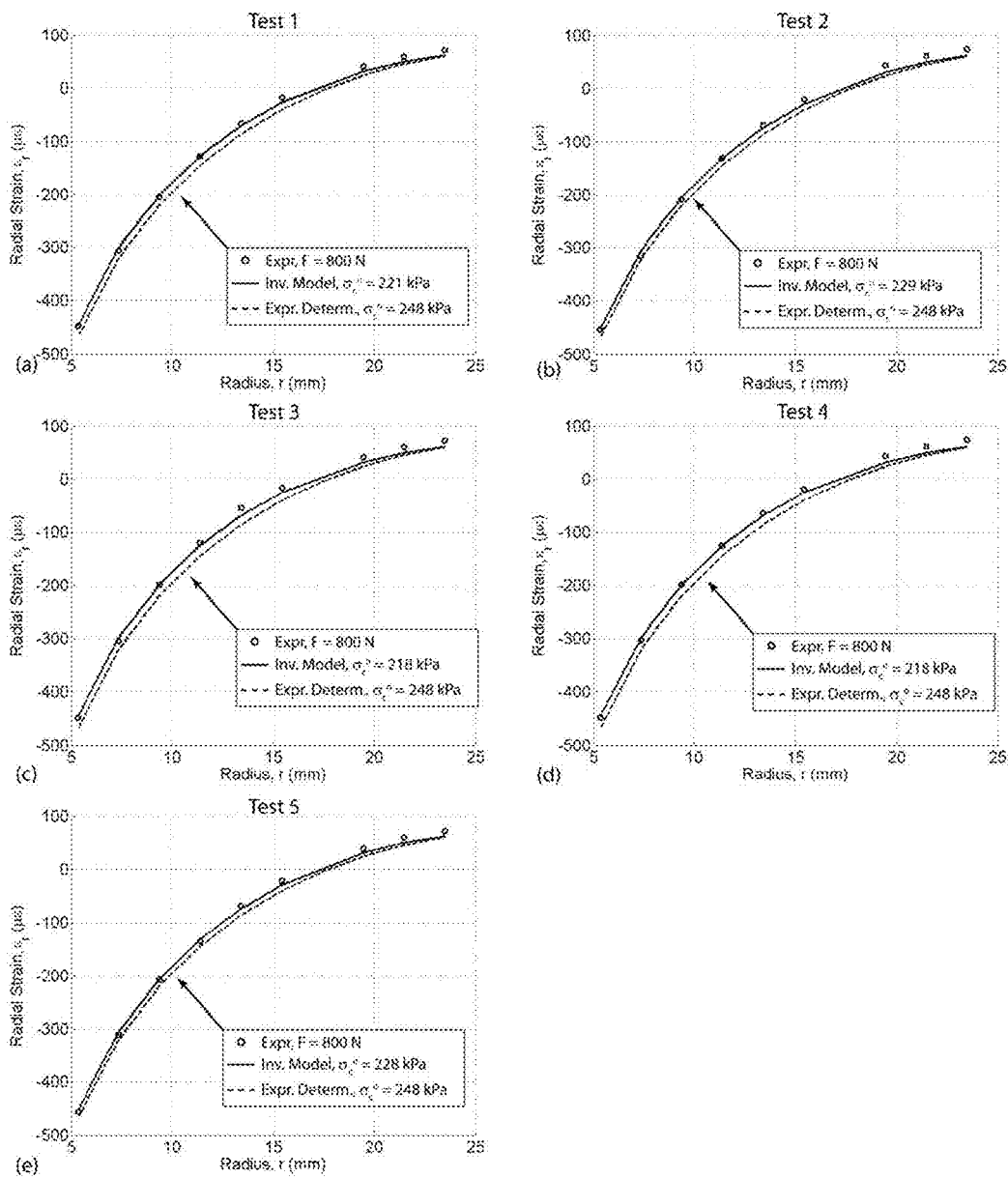
FIG. 115 Inverse model fits for the five tests on EPS29B at 800 N. Experimental results shown with circles, the model is shown with a dashed line.

The results of the plate strain fitting of the inverse model are shown at the maximum force in FIG. 114 for EPS 12 and FIG. 115 for EPS29B for all five tests on each foam. Simulated plate strains for the experimentally determined value of $\sigma_c^0$ are also plotted with a dashed line. All the results show a good fit of the inverse model to experimental strains, but show a range of predictions for uniaxial compressive yield stress. Predictions for EPS12 vary up to 7 kPa, or 12%, while predictions for EPS29B vary by 11 kPa, or 5%. Greater variation may be expected if some tests were not pinned at the minimum yield stress, i.e., Test 5 in FIG. 114, and Test 3 and 4 in FIG. 115.

5.7 Discussion

In this chapter, an inverse model was developed for estimating the uniaxial compressive yield stress of EPS foam using a strain gage instrumented plate.

A forward model was described, and a sensitivity analysis of this model to plasticity parameters was conducted. The forward model used as the basis for the inverse model was a FE model representing the aluminum plate on a plastic half-space described by the Crushable Foam constitutive model. The sensitivity of plate radial strains to plasticity parameters $\sigma_c^0$ and k found the model to be relatively insensitive to k. Therefore, an inverse model was developed to estimate the parameter $\sigma_c^0$.

The results of experimental tests were discussed, and showed that plate strains were sensitive to plastic deformation. Plate strains showed good repeatability on both EPS12 and EPS29B. These two foams showed a bend in the strainforce curves at around 225 N and 800 N respectively. The average pressure created under the plate at these forces corresponded well with the uniaxial compressive yield stress of the materials.

The results of applying the inverse model to the experimental plate strains show that the estimation of uniaxial compressive yield strength via a strain gage instrumented plate may be feasible, but would require considerable work to establish a robust method. The FE model greatly restricted the forces at which the inverse model could be applied. For EPS12, the FE model solved up to 225 N, which is the same force that experimental strains began showing sensitivity to plastic deformation. The FE model is limited by the interaction of the plate edge on the foam surface. In experimental testing, the edge of the plate created a 1-2 mm ridge in the foam surface at the maximum force, as seen in FIG. 116. The stress concentration created at the edge is not easily handled by continuous elements in FE models. A discrete element or hybrid discrete-finite element model would be better suited for handling this situation, and may allow higher forces to be reached.

Results show the inverse model to be highly sensitive to variations in plate strain measurements between tests. This sensitivity is a challenge for creating a robust inverse model. The experimental force versus plate strain curves show good repeatability of the plate tests, yet there are still large variations in the yield stress predictions. As with any ASTM testing standard, determining and controlling the possible sources of experimental error would be required. Furthermore, it is not clear from these tests how one would determine a representative uniaxial compressive yield stress. Typically, some type of feature in the force-strain curve is required, or some benchmarking force must be established. Neither of these can be suggested based on these tests.

Through these tests, it is evident that the inverse model for predicting uniaxial compressive yield strength may be feasible, but that considerably more work is needed. A forward model capable of predicting plate strains up to higher forces is needed, which would require implementing a model better suited to characterizing large localized deflections at the edge of the plate, e.g., discrete element modeling. The inverse model is highly sensitive to the variations in plate strains experienced between tests. Identifying and controlling for sources of experimental error would be helpful in increasing the robustness of this method.

Chapter 6—Roadblocks to Responsible Innovation: Exploring Technology Diffusion and Specification Reform in U.S. Public Highway Construction This chapter was submitted to the Journal of Responsible Research and Innovation, referenced as:

Kimmel, S. C., Toohey, N. M., Delborne, J. A. "Roadblocks to Responsible Innovation: Exploring technology diffusion and specification reform in U.S. Public Highway Construction." Submitted to Journal of Responsible Research and In novation.

The contributions of this chapter add a dimension of science policy to this dissertation. The technical developments discussed in previous chapters represent significant advances in in-situ testing that potentially face a path to practical adoption. The path to adoption requires consideration of a number of nontechnical issues that innovators would benefit from considering. This chapter discusses the paths to innovation adoption in the highway construction industry, which is particularly relevant to the in-situ devices developed this dissertation. Furthermore, this chapter provides a case study on intelligent compaction, which is directly applicable to the technology developed in Chapter 3, and very closely related to the application of technologies developed in Chapters 4 and 5.

As this paper is being presented in the dissertation of an individual and the paper presented in this chapter includes multiple authors, it is important to specify my personal contributions. I conducted a good deal of the background review on intelligent compaction and department of transportation structure. With regards to data collection, Nathan and I conducted the interviews jointly. The analysis was in large part conducted jointly with Nathan Toohey, but my personal contributions were more heavily focused on characterizing the influence of the DOT regulatory environment, defining the four key roles of key players along the adoption pathways (i.e. FIG. 119), and the joining of the streams, i.e., policy and political streams.

6.1 Background

The condition of the United States' highway system is deteriorating, with only 50% of roads in good condition, according to a recent report by the American Association of State Highway and Transportation Officials (AASHTO)[66]. The problem impacts not only state transportation budgets, but also individual motorists who spend on average $355 annually on vehicle maintenance due to poor road conditions [66]. One of the primary avenues for relieving this problem is technology innovation to deliver faster, cheaper and higher quality road construction [67]. However, the public road construction sector is notoriously resistant to adopting innovative technologies[5]. Responsible research and innovation in road construction requires a delicate balance between public safety and increasing demand, under unrelenting fiscal constraints.

This paper seeks to understand the innovation adoption process in the highway construction sector in the context of specification reform. Oftentimes technological innovations are incongruent with current specifications, thereby requiring alteration of current policy prior to adoption. In these situations, DOTs must effectively employ technology assessment techniques to drive responsible innovation adoption. Using a case study approach, we follow a specific soil compaction quality assurance (QA) innovation, Intelligent Compaction (IC), which requires specification reform in order to be implemented.

We use Kingdon's[68] theory of public policy agenda setting to investigate causal relationships behind technological innovation adoption through interviews with private and public sector professionals. In the application of Kingdon's theoretical framework, we consider the practical impact of IC on the highway construction community, in the context of owners, contractors and end-users. Ethical motivations and technological governance are addressed with respect to perceived societal obligations relevant to responsible research and innovation (RRI) adoption. By applying Kingdon's framework in the context of RRI, we are able to classify the dynamic processes of specification reform, identify the roles of key players in the diffusion process and illuminate the critical resources and personality traits that make these players influential.

We begin by broadly considering the nature of technological innovation adoption within the U.S. Highway Construction Industry, as it pertains to certain ethical and governance concepts applicable to an RRI assessment. We then provide a succinct description of the technological innovation chosen for a case study, IC, followed by a section explaining highway construction specifications and the organizational structure of this industry. Additionally, we detail the formal process by which specifications are changed. The third section reviews Kingdon's policy agenda setting theory in the context of highway construction specification reform. The fourth section discusses the methodology and analysis underlying this study. The final section presents insights gained through the application of Kingdon's framework and RRI concepts to the key people and processes that have played a part in the diffusion of IC.

6.1.1 Responsible Research and Innovation Adoption in US Highway Construction

The goal of RRI has been described as advancing the concept of "science for society, with society"[69]. RRI attempts to balance between fundamental research and a societal need for progressive and appropriate technological developments[70]. Such a balance requires ethical consideration with respect to social obligation and technological governance by engaging all actors within a given network [70]. Stilgoe[71] notes that "as the power of technology to produce both benefit and harm has become clearer, debates concerning [societal] responsibility have broadened"[72]. RRI expands the occupational role responsibilities of policy makers, scientists, and engineers to take the public's best interests into focus[73].

RRI concepts are particularly applicable to a public transportation institution such as the U.S. Highway Construction Industry. Seaden and Manseau[74] investigate governance roles in construction policy environments to gain insight into innovation systems and processes whereby the balance between public and private sector interests is paramount. This balance is maintained by policy negotiations between political appointees, career bureaucrats, industry leaders and the public. Gann[75] notes that the "built environment" is typically paid for, owned, used, maintained, and regulated by people from different institutions. Policy decisions must reflect the shared, and differing, objectives of all stake holders[71, 75]. Seaden and Manseau also specifically cite that a greater emphasis on construction performance against defined objectives (e.g., community values, construction economics and efficiency, long term sustainability, etc.) is likely to enhance innovation adoption proclivity. The present study highlights these RRI attributes with specific application to the U.S. Highway Construction Industry.

An important piece of responsible innovation is institutionalizing effective procedures for technology assessment: "institutionalization of established approaches of anticipation, reflection, and deliberation in and around research and innovation, influencing . . . associated policy" ([69], p 755).

The institutionalization process of technological innovation adoption within the U.S. Highway Construction Industry is particularly complex, involving various stages of adoption, including demonstration, validation and governance. The industry itself is notoriously resistant to adopting innovative technologies[5], in part because governance structures have been identified as significant obstacles to the successful integration of research and innovation[76]. This research investigates the processes internal to the U.S. Highway Construction Industry by which issues become prioritized, reach a decision agenda[68, 76], and ultimately become adopted into practice.

It is not yet clear what the specific application of RRI concepts to the highway construction technology adoption will yield. Are effective feedback and evaluation systems in place? Is the culture of technology adoption maximizing societal benefit, or does the industry suffer from overly conservative decision making? Of particular interest to this research is determining the ethical motivations of policy makers and engineers with respect to their perceived societal obligations. We also specifically seek to characterize the processes of technological innovation governance and how they ultimately influence adoption and institutionalization.

6.1.2 Intelligent Compaction

This paper focuses on the diffusion of IC, a technology used for monitoring soil compaction quality during soil compaction. We first describe the traditional practice of soil compaction and specification thereof that is common to nearly every highway project. We then explain how IC changes this activity not just by adding a new tool, but by improving efficiency and quality of roadway construction.

Every structure that interfaces with the earth must have a mechanically stable foundation. Roadways typically use compacted soil for this foundation. While there are several practices for compacting soil, highway construction often uses roller compactors (see FIG. 117) because of the speed with which they can compact large tracts of soil. On a highway construction project, soil compaction must meet certain specifications that seek to ensure a mechanically stable structure.

The specification of soil compaction is not entirely straightforward, due to the complex nature of soil. Highway design engineers specify foundations in terms of "stiffness." Soil stiffness reflects the resistance to vertical deflection under a given load or stress, and is measured in units of stress or force over deflection. Stiffness development through compaction is particularly important to ensure the mechanical stability of highway subgrade materials, as they are subject to repetitive traffic loading[78]. Due to soil's mechanical complexity, there is a multitude of ways to define its stiffness, only a few of which are used in pavement design (e.g., resilient or elastic modulus). A modulus value, however, is notoriously challenging to quantify in the field. IC presents one of the first opportunities to quantify the in-situ stiffness of a soil.

In current earthwork construction, soil compaction is typically specified in terms of target density and water content (per ASTM D698[79]), based on the assumption that there is a phenomenological correlation between these parameters and modulus. The relationship between modulus and density/water content is not fully understood, leaving an unresolved discrepancy between design, construction specifications, and operational performance.

There are several technologies for evaluating soil compaction. The most widely used are the Nuclear Density Gauge and Sand Cone, which measure density and water content at discrete locations on the roadway. These methodologies provide less than 0.1% spatial coverage of the constructed soil layer, and require stoppage of construction activities that can lead to considerable delays[80]. Poor spatial coverage can lead to acceptance despite the presence of areas with insufficient compaction or water content. Contractors attempt to avoid construction delays at all costs and generally perceive soil compaction monitoring as a hindrance to progress.

IC is a machine-integrated soil compaction evaluation method that reports in real-time during construction. IC vastly improves coverage of soil testing (i.e., from <0.1% to virtually 100%)[81] ensuring a more comprehensive performance evaluation. Furthermore, IC provides real-time measurements, eliminating the delays associated with conventional spot testing techniques.

Many IC systems, including those for vibratory compaction, are correlated to the stiffness of the soil, which is more congruent with mechanistic design characteristics. One problem is that the stiffness measurements provided by these systems are not standardized between manufacturers. Each IC manufacturer has a proprietary stiffness measurement value that does not replicate any widely used stiffness parameter[2]. This lack of standardization requires site specific calibration of IC and complicates the provision of standardized specifications for IC[2]. In effect, technology innovation (i.e., IC) requires policy innovation (i.e., a standard for stiffness measurement values that cross technological platforms). IC for vibratory compaction thus represents both a change in process and measurement quantity of a QA program specification.

Such dramatic procedural change can encounter significant resistance with respect to an institutional status quo. A NCHRP study[82] on the culture within the highway construction sector reported that institutional inertia poses a considerable barrier to innovation. This report goes on to say that several factors such as risk, economy and quality can serve to either enhance or inhibit such a process conversion.

In Colorado for example, the CDOT Field Materials Manual states that there is no intention to discourage contractors from developing and/or implementing 'better or faster methods of testing'[83] than those suggested as acceptable QA protocol or technologies. CDOT by no means, however, provides incentive to develop new testing technologies and in fact requires a complicated and rigorous approval process by both independent and federal regulatory committees[83]. This paper identifies specific pathways by which IC has begun to diffuse into becoming an accepted performance evaluation technology for QA program specification.

6.1.3 Highway Construction Specification

Specifications are the primary method used by highway construction project owners to ensure that the desired level of quality of construction is achieved. Simultaneously, specifications can be barriers to innovation because of their rigidity. Here we define specifications in the context of highway construction projects and the process by which they can be changed, e.g., to allow for the adoption of an innovation. We also discuss the key players in the highway construction industry that help shape these policies.

Construction specifications provide the basis for performance evaluation, and serve as a crucial link between a construction project owner (State DOT) and construction contractor. They are coincident to all infrastructure projects, typically involving the development of a Quality Assurance (QA) Program[83]. Through QA programs, 'materials, products, and workmanship'[83] are ensured to meet specifications by providing evidence and documentation for both acceptance and archival purposes[83]. Statewide manuals outline specifications that dictate almost every aspect of a project from the types of soils and concrete mixes used, to the spacing of rebar in bridges, to the degree of compaction of each layer of a roadway, etc.

There are several key players in the highway construction arena, as shown in FIG. 118, all of whom contribute to specification formation and implementation. State DOTs are the majority owners of almost all highway construction projects, and as such set and maintain the current specifications. Proposed changes to the current specifications must pass DOT review, in addition to review by several external parties. Supplementary funding for highways is often provided by the Federal Highway Administration (FHWA), giving them the power to review specification changes. Each state has local chapters of the Associated General Contractors (AGC) of America that represent the interests of the contractors in a given state. The AGC is consulted to ensure that new specifications are not too onerous on contractors. In the case of special specifications, the construction contractor on the project is a key player in shaping the new policy. Other parties may play various roles on a case-by-case basis, such as academic consultants, private financial investors, etc.

The state DOTs are the most important players in specification reform, often initiating reform as well as passing new policies. Therefore, it is critical to understand the state DOTs' decentralized organizational structure. State DOT organization is similar across the United States, with only minor variations from state to state. The DOTs geographically split their state into several districts that are run by district offices. These offices manage the majority of roadway construction projects, with the exception of special projects (e.g., large or complicated projects) that are managed by the central office. The central office handles specifications, research, and funding distribution. While the district offices receive funding from the central office, they have the freedom to manage projects largely at their own discretion; although these district offices will, at times, request technical guidance from the central office, for example, in the case of innovative technologies. As we will demonstrate, this operational independence turns out to be an important feature when considering the diffusion of innovation.

Certain innovations, such as IC are incompatible with current statewide construction specifications and require specification reform for implementation. New specifications are introduced in two phases: project specific pilot or special specifications and statewide specifications. Special specifications are a way to trial a new form of specification while limiting the risk of failure to a single project. These specifications may even be introduced as shadow specifications that are implemented in addition to existing specifications to further limit risk. Multiple special specifications may be created within a single state for a given innovation until a document general and successful enough emerges and can be adopted for statewide specification reform. Statewide specification revision differs in frequency from state to state, ranging from 1 year to 10 years. Both special and statewide specifications must be approved via a specification review committee, composed of high level officials including chief engineers and division heads.

To our knowledge, IC has yet to pass statewide specifications in any state, but special specifications for IC exist in at least 10 states. As a result, this research focuses mostly on the passage of special specifications, the crucial first step for any emerging technology in highway construction.

6.1.4 Kingdon's Theory of Public Policy Making

Scholars and other external observers have sought to understand the manner by which public policy manifests change (e.g., [84]). John Kingdon[68] presents a formalized theoretical framework in an attempt to characterize policy reform activities. Kingdon begins by identifying the plethora of topics associated with a given domain, which individually may or may not be paid serious attention. Of particular interest is the narrowing process by which specific issues and initiatives become selected to a decision agenda from what could otherwise be described as an infinite realm of possibilities. Kingdon's theory of public policy making establishes a framework that enables us to understand and identify the motivations and drivers behind setting the decision agenda within a given institution.

Kingdon's theoretical framework describes public policy agenda setting as a confluence of three streams: problem definition, policy solutions, and political environment. A problem must be defined to attract sufficient attention and ultimately warrant resolution. A number of policy solutions may evolve that fit certain criteria including demonstrating technically feasibility and aligning with specific problem related values. Finally, the prevailing political environment must be conducive to changes in the domain in question[85].

Kingdon's stream analogy exemplifies the dynamism associated with each of the three components of policy formulation. These processes develop and evolve coincidentally rather than according to a formal or linear progression [85], as borrowed from the Garbage Can model of Cohen et. al.[86]. Policy reform results from streaming confluence under a window of opportunity opened by both specific causality as well as probabilistic serendipity[84].

Kingdon conceptualizes the interaction of three streams in the context of decision agenda setting and policy making at the federal level. Scholars have suggested that Kingdon's framework may, however, apply more generally to all policy environments. Kingdon's analysis approach has been applied to policy environments such as state legislative bodies (e.g., [87]) and federal scientific-bureaucratic institutions[88]. In nearly all cases, authors have ultimately identified theoretical limitations with respect to specific application outside Kingdon's original lens.

Kingdon posits that problems are defined or punctuated in response to conditions that violate social values[87]. Due to the rather compartmentalized nature of the US highway construction sector, i.e., individual state DOT dominance, value identification and consensus is far from widespread. With respect to specific values, the emergence and diffusion of IC is largely in response to perceived problems with regard to product uniformity, design specification conformity, budgetary economy, and construction quality. In fact, a particular challenge in the highway construction industry is that the interpretation of these values is largely subjective. IC provides a solution that implies a particular problem that may or may not exist, depending upon whom you ask.

Kingdon conceptualizes how a problem may be defined by discussing several indicators[68]. Among others, problem punctuation by formal study is particularly appropriate to consider in the IC case study. He notes that research studies often serve to quantify the actual magnitude of a problem. Studies performed by academic, governmental, or nongovernment agencies can better characterize how the problem is defined and how significant it may or may not be. Kingdon specifically cites the effectiveness of systematic engineering studies in the case of highway and bridge repair ([68], p. 91).

With regards to soil compaction, there are no comprehensive studies quantifying the impact of conventional spot testing methods on highway lifecycle costs and quality. It is generally accepted that soil's heterogeneity can lead to considerable spatial variations in compaction, and that poor compaction leads to reduced roadway performance in the form of potholes, cracking, and other failures. Studies on IC have repeatedly shown the level of soil compaction to vary widely within test sites. Practitioners will admit that spot testing is highly sensitive to location. However, the extent to which monitoring related occurrences of subpar soil compaction lead to decreased performance has not been established.

The lack of a universally accepted assessment of the perceived problem associated with IC adoption critically impacts problem stream development among key players. Kingdon acknowledges that a lack of values consensus can at times trump even scientific evidence or documentation of a viable policy alternative. Our research has specifically targeted problem punctuation mechanisms in the case of IC. Additionally, the relationship between values consensus and personal character with respect to problem punctuation is evaluated.

Kingdon describes a policy "primeval soup," ([68], p. 116) in which many undeveloped ideas coexist, evolving until one or more policy alternatives gain prominence. These ideas are created by specialists within the "policy community", ([68], p. 117). The criteria for survival is based on their "technical feasibility" ([68], p. 131) and "value acceptability" ([68], p. 132), among other things[68]. Here we discuss idea generation and survival as it pertains to highway construction.

Idea generation in the highway construction policy community occurs hand-in-hand with the evaluation of technical feasibility, typically via research studies. These research studies, almost always conducted via pilot implementations, not only provide scientific evaluation of various policy ideas, many go so far as to provide explicit policy recommendations. In this regard, pilot studies become the most active contributors in the "primeval soup". For example, one of the most comprehensive research papers on IC listed as its second overall goal to provide "recommendations for using the compaction monitoring technology in practice"[4]. In another example, researchers state "Field spot tests are essential to IC implementation to provide correlation to IC measurements"[89], and go on to suggest methodologies for these correlations. The FHWA, a main funder of IC research projects, provided an example specification based on research they funded[90]. While these reports are building blocks for future policy, Kingdon's analogy of a primeval soup fittingly describes the evolutionary process by which finalized policies are formed.

While formation of IC policies in the primeval soup center on technical feasibility, values based negotiations are still very much a part of the process, perhaps trumping technical consideration in many cases. In IC policy, there are several points on which key players may disagree, including: calibration frequency and method, percent coverage that must pass a certain threshold, and the value of that threshold. Multiple solutions may have similar enough technical validity, ultimately resulting in a values-based decision making process.

The political stream describes the propensity for policy change in the current political environment. In Kingdon's analysis of federal legislative bodies, political environment typically refers to the distribution of political party affiliation[68]. However, he notes that this is not an exclusive interpretation of political environment, and in fact, within transportation regulation there is a distinct lack of political party affiliation. In this paper, we investigate surrogate ideological affiliations that may guide decision making processes.

In his theoretical formulation at the federal level, Kingdon locates primary decision making authority with political appointees. He prescribes only minor decision support to civil servants. However, in highly technical institutions such as DOTs it is possible that the balance of power between political appointees and civil servants may be distributed differently.

Policy entrepreneurs serve to raise awareness and garner support for issues, problems, and solutions within the surrounding network. Policy entrepreneurs are ultimately responsible for orchestrating the alignment of Kingdon's three streams. Kingdon identifies three categories of incentives pursuant of the entrepreneur: personal interest, values promotion, and pure enjoyment of the game[68]. Kingdon does not, however, discuss which incentives may be more or less likely to prevail in a given policy arena. Interestingly, it appears that the values promotion category of policy entrepreneur exemplifies many attributes associated with RRI, namely a strong ethical commitment to maximizing societal benefit.

Kingdon rightly identifies the critical role of the policy entrepreneur in the agenda setting process. The framework may however under appreciate inequalities in power and resources between various stakeholders and policy entrepreneurs assuming roles at different locations within a network. For example, Blackman[72] discusses the disproportionate weighting of financial power in the context of the tobacco industry lobby at state level. Further, Kingdon's theory does not characterize the different roles that policy entrepreneurs may assume with respect to their allocated resources. Interestingly, the IC case study identifies entrepreneurs at different levels of the network with markedly different roles and resources.

Policy issues reach the decision agenda via policy windows that are opened during the confluence of the three streams. According to Kingdon, the opening of these windows is due to a combination of serendipity and influence of policy entrepreneurs.

Kingdon ([68], p. 20) notes that the three streams typically couple during brief windows of opportunity. Kingdon suggests two primary mechanisms by which final stream coupling may occur, either via problem or political motivated policy windows. Problems may suddenly capture the attention of political figures, thereby pushing it into the forefront of decision making agendas. Conversely, a notable shift in the political stream, such as a turnover of administrations, can provide the alignment and momentum change necessary to open a policy window. We investigate the presence of both types of policy windows in our paper.

According to Kingdon, the three streams exhibit a dynamism that evolves independently and coincidentally to one another, coupling only at critical moments[72]. Several authors have noted a more connected relationship between stream developments. Kelly[87], applying the framework via examination of state level policy related to public schools, noted that state legislative bodies are not free to act as autonomously as federal entities, indicating that a purely independent development of the three streams is questionable. Harrison et. al.[88] found that for scientific-bureaucratic institutions, the problem and political streams exhibited a high degree of overlap. This study, in fact, identifies a strong coupling between the problem and policy streams.

Indeed, the confluence of the three streams relies upon several factors that vary with specific instance. One component, however, seems rather universal to bolstering convergence: the role of the policy entrepreneur. Nearly all of the supporting literature has identified the critical importance of individual champions within institutions to initiate various activities that ultimately coalesce to drive policy innovation (e.g., [87], etc.). Policy entrepreneurs exert their time, energy, reputation, and money to join together the three agenda-setting streams.

6.2 Methodology

We conducted interviews in order to investigate causal relationships and key players in the policy reform and innovation diffusion process. Interviewees included members from several state DOTs, comprising employees from both central and district offices, FHWA officials, construction contractors, and QC/QA contractors. The position of interviewees ranged from project managers, to research engineers, to materials engineers. Participants were initially selected by cold calling individuals connected to intelligent compaction by technical reports. Additional participants were identified in a snowball fashion, whereby interviewees were asked to suggest other candidates from their professional network. The process was considered complete once we had collected data from participants at all affiliations deemed important by the interviewees. Additionally, at this point, conclusions drawn from interview materials tended to converge.

Interviews were conducted face-to-face and over the phone, typically lasting about an hour. A predetermined set of questions formed the basis for about half of this time period, with the remainder of the interview being a freeform discussion allowing participants to direct the conversation into rich areas. All interviews were recorded for analysis purposes and coded using Dedoose (see www.dedoose.com). Dedoose is an online qualitative data analysis tool. We used this tool to facilitate the organization and quantification of interview results.

6.3 Analysis

We use Kingdon's theoretical framework[68] to analyze the policy environment surrounding the diffusion of IC. The framework generally applies well to the IC case study; however, coincident with the literature, the specific application of Kingdon's theory to the IC pol icy environment does reveal certain limitations. In tandem with Kingdon's framework, we consider various RRI concepts, e.g., ethical motivation and governance, with respect to IC diffusion and adoption within the highway construction community.

First, this research identifies the importance of personal character among key players, with respect to both problem definition and innovative championship. Second, regulation with state and federal departments of transportation (DOT) is a highly technical policy making environment, resulting in some deviation from Kingdon's original formulation. Third, while we found policy entrepreneurs to exist at all levels of the policy making environment, this research found the most predominate roles to be internal to a DOT. Policy entrepreneurs possess ideologies congruent with responsible research and innovation. Finally, we address certain limitations in applying Kingdon's theory to the joining of the three streams in the DOT regulatory environment. Contrary to Kingdon's general theory, we identify a tight coupling between the problem and policy streams in the case of IC diffusion at all times, rather than solely during the formation of policy windows. We also address the prevailing path by which IC policy is ultimately raised to the decision agenda.

6.3.1 Personal Character

The personal character of key players and stakeholders critically impacts innovation diffusion and acceptance in the IC policy environment. Kingdon[68] notes that personal character may play a role in explaining the motivations of policy entrepreneurs. However, we found this theme to run much deeper. Not only is personal character paramount in explaining the behavior of policy entrepreneurs, but it also defines ideological affiliations of participants in the political stream. Kingdon's theory minimally explores of the powerful impact of personal character, and its prevalence here is perhaps unique to the highway construction sector in which there is a distinct lack of external motivators for participants.

This section discusses how personal character applies to individuals in the network. Of particular importance is the degree to which individuals possess an intrinsic proclivity towards innovation. Furthermore, policy entrepreneurs demonstrate extremely unique personal quality by challenging the status quo, often enduring personal and professional risk to pro mote innovation. RRI speaks of the expanding occupational responsibilities of technologists to evaluate the societal benefits and risks of innovations[73]. Are individuals with a proclivity for innovation merely risk prone, or are they striving for the ethical guidelines being pioneered in RRI literature [71, 73]? This research indicates that, regardless, an individual's intrinsically felt obligation to improving societal quality stems from personal character, even in the face of significant risk or obstacle. In the following section, DOT Regulatory Environment, we discuss personal character in the more general context of the political environment.

Project level implementation of IC is very specific to the personal character of the participants involved. Personal character impacts how, and if, the problem is defined depending on whom is being asked. This study reveals that general tendencies toward innovation appear to be truly sustained at the personal level. This study ultimately identifies the importance of personal character over institutional character, with respect to both problem definition and innovation championship.

Nearly all participants in this study identified innovation proclivity as a critical driver to the acceptance of IC diffusion. Many study participants further related this characteristic to an individual's outlook on change in general. One participant stated, "Personalities, one word . . . ", when asked to comment on DOT climates that may foster or hinder innovation. There were references to individuals that were either innovators or "sticks in the mud". While there is likely to be a much smoother gradation of a person's level of innovation proclivity, this personal characteristic was a central theme.

In the case study on IC, there is hardly a clear distinction between a "situation" and a "problem". An individual's innovation proclivity impacts this distinction. In the case of IC, this personal characteristic can even serve as a more critical decision making factor than exposure to technical and visual evidence of performance improvements. In fact, one participant indicated that often times personal character can outweigh technical research and field validation of IC with disinterest and lack of acceptance. This statement indicates that, at least for some individuals in decision making for technology adoption, institutional inertia can be a stronger driver than the ethical criteria of societal benefit that an RRI framework places on technical decisions. At the very least, one's innovation proclivity impacts the way they interpret policy alternatives and problems, not to mention what values they base their decisions upon.

What makes an individual tolerant of innovation and risk? To answer this, we can leverage the large body of literature concerning innovation. Our study found a positive correlation between level of education and proclivity towards innovation, with 100% of participants with advanced degrees having specific examples of supporting an innovation. This concept concurs with prevailing literature, which suggests that individuals with an advanced structural organization of knowledge are better innovators[91]. We did not find any correlation between age and innovation, further supporting claims that innovation tendency is independent of age[91]. In interviews, supporters of innovation were often described as capitalizing on membership to sizeable professional networks, which agrees with research that shows a statistically significant correlation between one's personal network and diffusion of innovations in housing construction regulation[92]. Interviewees particularly emphasized the role of professional networks in providing exposure to a variety of ideas and demonstrations, and commanding a degree of credibility contributing to the capacity to spread ideas.

In addition, this research has identified cases where participants claimed to be innovative and open to new technologies such as IC, yet the practical reality appeared otherwise. No participant was, however, an explicitly, self-proclaimed hindrance to innovation.

Of the incentives for policy entrepreneurs that Kingdon discusses, the most pertinent to IC policy is that of values promotion. The policy entrepreneurs identified in this study had no personal gain from the success of IC and did not appear to be "policy groupies" ([68], p. 123). Beyond Kingdon, we identify this type (i.e., values promotion) of policy entrepreneur as the best reflection of RRI ideologies, in that they exemplify an ethical motivation to provide the most progressive and appropriate products and policy to society. This sense of social responsibility can be seen in their perseverance in the face of significant institutional inertia and lack of personal benefit.

Most important to understanding ideological stances, we look at motivation. An individual's stance on innovation and risk can be motivated either intrinsically or extrinsically. A study surveying eight DOTs found that the institutional incentives for innovation consisted solely of recognition [93]. Incentives that were mentioned included recognition in newsletters, and notoriety from technical conferences. Study participants reported that these extrinsic incentives do not drive policy entrepreneurs. Participants resoundingly attributed personal character, i.e., intrinsic motivation, as the dominant catalyst for policy change. Interviewees described champions of innovation as risking their short-term performance goals and professional reputations. One participant said of innovating, "You're swimming up Niagara falls, and your reputation is on the line". Yet, these individuals are the key to developing the political stream, and are active proponents of RRI principles.

6.3.2 DOT Regulatory Environment

The structure of the DOT has specific implications on RRI principles that are revealed through Kingdon's theory. The DOT regulatory environment is referred to herein as a scientific bureaucracy[88]. So-called scientific bureaucracies are said to privilege scientific research as the basis for bureaucratic policy output[88]. We find this feature to significantly impact the implementation of socially responsive innovation in two ways. Firstly, rather than political affiliations, which Kingdon discusses as the most relevant ideological affiliation guiding agenda setting, we found participants identified themselves along lines of their proclivity for innovation. In this regulatory environment, we found this proclivity for innovation to be deeply rooted in participants' perceived sense of social obligation. Secondly, the heavy weighting of scientific research in the decision making process creates additional barriers to societal feedback. For example, where Kingdon finds political appointees to have a strong influence on agenda setting, in DOTs we find career bureaucrats, with no explicit societal representation, to hold the majority of power and resources over regulatory reform. Further, this regulatory environment exemplifies the fact that senior policy makers work at some distance from the actual decision-making process at the regional level regarding the choice of innovative technologies and new organizational processes[75].

Proclivity to innovation and risk taking are the most relevant ideological affiliations to this case study, as opposed to political party as discussed by Kingdon[68]. Individuals throughout the network can either contribute to or impede the progress of a policy change related to IC. In interviews, the innovation proclivity characteristic appeared to be the strongest indicator of their support for adoption. The dominance, or lack thereof, of this ideology can vary highly from state to state, and within different networks in the same DOT. Changes in the political makeup of a DOT network depend primarily on turnover of positions. Some participants felt that long term shifts in political makeup were occurring due to promotion criteria and practices. While this phenomenon—seems possible, studying these changes was beyond the scope of this study, and would be worth further consideration.

Personal ideology underlies the discussion not just on innovation proclivity, but an individual's perceived societal obligation as well. As previously mentioned, policy entrepreneurs within the DOT regulatory environment appear to operate without expectation of personal gain. Instead, they are compelled by a sense of ethical responsibility to provide society with the most progressive and appropriate product and/or policy, despite significant institutional inertia and potential risk to their professional reputation.

Kingdon stresses the role of political appointees in defining the political environment, suggesting the existence of a top down power structure: "the appointees, not the career civil servants, are the movers and shakers" ([68], p30). Our findings, however, indicate that this model for federal policy agenda setting differs considerably from state transportation construction policy agenda setting. None of the study participants indicated the influence of the politically appointed DOT directors to be a significant factor in IC adoption, or innovation in general. DOT regulatory reform appears to occur outside the influence of appointed positions and in fact, civil servants tend to operate as policy entrepreneurs. This agenda setting structure is perhaps due to the highly technical nature of infrastructure construction. Specialists, in the form of civil servants, are disposed with more agenda setting power than appointees. Yet some DOTs are clearly the front runners in use of IC, suggesting the presence of unique conditions at these DOTs. Identifying the institutional positions within which these entrepreneurs act is the first step in understanding a political environment.

We propose a method for identifying a DOT's ideological distribution through a classification system based upon participant interviews. The manner in which a political environment becomes conducive to policy change involves strategic, albeit serendipitous, positioning of four key roles presented in FIG. 119. First, there are "policy explorers" that manifest problem awareness and demonstrate technical feasibility, often having to battle institutional inertia. Interviews revealed these individuals to exist as DOT research engineers, DOT district engineers, and construction contractors.

For an innovation to proceed to the next level, explorers must make a successful hand off to "policy pioneers". Pioneers are individuals willing to expend political leverage, energy and resources to implement a new technology, such as IC, on DOT projects. This entails passing a special specification for the project, requiring political influence that can typically only be exerted by a DOT District Engineer or a contractor. Special specification passage generally requires an iterative interchange between the these two key roles, i.e., explorers and pioneers.

Upon successful implementation of the innovation via the special specification, it can be considered for full adoption by the gatekeepers, whom often sit on a specification review committee. Gatekeepers provide a final interpretation of the overall innovation adoption impact to aid in the specification reform process. Specification review committees vary in composition between states, but often include chief engineers and division engineers. Gate keepers also include certain outside organizations, including funding agencies (e.g., FHWA) and professional organizations (e.g., AGC) that that participate in the specification review process. Finally, there must be leaders willing to endorse an unaccepted technology via a vast political network. Leaders are critical in coordinating and motivating the hand-off between the aforementioned levels. This power anecdotally resides in high ranking management positions. When there is ideological alignment of individuals in exploring, pioneering, gatekeeping, and leadership roles, the political stream is ripe for innovation-based policy agenda setting.

6.3.3 Key Roles of Policy Entrepreneurs

Coincident with Kingdon's theory, policy entrepreneurs can exist at any level or position within the political environment surrounding IC. However, the vast majority of policy entrepreneurs identified by participants in this study were DOT employees. This research has specifically identified policy entrepreneurs within a DOT in the roles of research engineers or district level engineers. These employees possess the resources to build support and ultimately promote the subject to a level of authoritative decision and specification. External contractors have also been carriers who brought IC into a project at their own interest and expense, but this appears to be the exception. Surprisingly, the IC equipment manufacturers, who perhaps have the most to gain from a policy change, appear to have no direct representation in the form of a policy entrepreneur.

The most common source of problem identification is via internal promotion within a governmental agency, be it a state DOT or federal authority. This research has identified policy entrepreneurs at various levels within both state and federal organizations. Whether a research engineer or district manager, all study participants indicated the necessity for policy entrepreneurs to bring the problem to the attention of key players. Entrepreneurs are responsible for actively raising awareness to convince colleagues in positions of power that IC was an endeavor worthwhile.

Research and district level engineers are each dispatched with distinct powers that enable them to be effective policy entrepreneurs. Research engineers are the technical experts of the DOT organization, making them a collection point for technical problems in the organization and giving them the credentials to suggest solutions to individuals across the DOT. Furthermore, these individuals are given funds to conduct research, including pilot projects, which we have identified as a key mechanism for spreading problem awareness and getting support for policy solutions. Research engineers are able to leverage their credentials and funds, in combination with their professional networks, to couple the problem and policy streams.

District level engineers possess considerable decision making power due to the decentralized nature of DOTs. Respondents unanimously agreed to the near autonomy of districts in conducting their projects. One interviewee said "the district is the customer," implying the central office provides services to the districts as opposed to managing them. If a district engineer decides he wants to use an innovation on a project, he holds the political power to put related policy issues on the agenda. Specifications still need to be approved by a committee that may contain other district engineers and high ranking officials in the central office, but the agenda setting for special specifications is controlled at the district level.

Policy entrepreneurs may also be external to the governmental agency, residing at the level of external contractors. In sparse cases, a contractor has taken initiative to suggest or integrate usage of IC on a specific project. As mentioned, the motivation here is achieving improved quality and/or cost efficiency. For example, one respondent cited a contractor using IC to provide additional as-built construction documentation in the advent of future litigation. Regardless of specific motivation, this form of diffusion appears less common without mandate or specification due to lack of incentive. In addition, self-promotion of IC use tends to be a luxury reserved for larger contractors responsible for larger projects.

Surprisingly, we did not identify any policy entrepreneurs from equipment manufacturers. It would seem that these companies would stand much to gain from IC reaching the decision agenda, thereby increasing market penetration. Representatives of manufacturers (and their dealers) seem to almost exclusively court contractors with this technology, despite the importance of DOT buy-in. It is worth noting that equipment manufacturers will contribute equipment and engineering time to pilot projects, but this typically results from partnerships with contractors or researchers. Their lack of interest in the policy realm appears a function of their business model, which does not promote interaction with governmental bodies.

6.3.4 Joining of the Streams

Kingdon discusses the confluence of streams as policy windows, critical points in advancing policy issues when an opportunity for the issue to reach the decision agenda exists. Yet, in our case the policy and problem streams are coupled very early in the process by policy explorers (and sometimes others). The political stream is often the last stream to join, resulting in what Kingdon identifies as politically activated policy windows[68]. The joining of the political steam, and thus the opportunity for the issue to reach the decision agenda, is conducted by policy pioneers (discussed in Section 6.3.2).

Pilot studies are the mechanism by which problem and policy streams become coupled. While the development of either of these streams may occur independently through other mechanisms, participants reported pilot studies as the predominant method for building both streams. The research aspect of pilot projects provides policy recommendations by establishing the technical validity of various implementations. Pilot projects often simultaneously invite members of the policy community for field demonstrations, which give firsthand experience that is particularly poignant in punctuating the problem to individuals. This tight coupling of problem and policy streams is not recognized in Kingdon's book[68], and may be a feature specific to highway construction.

We identify policy entrepreneurs and their critical role in punctuating the problems and promoting policy solutions connected with IC. The primary task for them becomes building awareness and the dissemination of knowledge and information to initiate the problem stream and couple the policy stream. This task is crucial to establish the status quo and its disconnect, or problem, with what improvements could be made through use of IC.

Field demonstrations were reported by all study participants as the most effective way to illuminate a problem and spread solution awareness. Field demonstrations provide direct empirical evidence of the potential improvements that a new technology such as IC can provide. Field demonstrations occur at various project levels. Despite the disjoint nature of state DOT operations, several participants were introduced to IC through field demonstrations both locally, nationally or internationally. International delegations, comprised of federal and state DOT employees, industry contractors and academics, perform scan tours to become exposed to new technologies in other parts of the world. This is particularly true in the case of IC, as the European highway community readily began research and development as early as the 1970s. European attention was undoubtedly a platform to foster U.S. interest in IC according to study participants. At the local or national level, several policy entrepreneurs within and even across state DOTs have diligently organized field demonstrations to raise awareness and garner support for IC.

In all cases, direct exposure to IC has been reported to be highly successful in coupling problem punctuation with policy solutions. One participant noted that direct exposure via field demonstrations brings a certain concrete interaction and awareness that is difficult to achieve by simply reading technical reports or specifications. Another participant recalled a rather telling response of a DOT official following an IC field demonstration: "Wow, I didn't realize . . . and I guess it's a no brainer, we ought to do this . . . ", and thus establishing the problem stream for IC in mind. Only once an idea takes hold in people's minds can it become institutionalized as policy reform[85].

According to Kingdon[68], issues reach decision agendas when the three streams are joined through a transformation in the political stream or novel problem identification. We define IC as 'reaching the decision agenda' when its usage on a project is suggested by either the DOT or a contractor resulting in initiating formation of a special specification. No states currently have a statewide specification for IC, so this case is not considered. This section discusses various aspects of the opening of policy windows. Our research shows that the joining of streams happens predominantly through politically activated windows. The individuals responsible for opening the policy window are policy pioneers (discussed in Section 6.3.2), who are typically district engineers. In rare instances, these policy pioneers could be external to the government, but this appears to be contingent on the contractual structuring of the project. We also discuss specific economic aspects of the IC technology that impact the opening of policy windows.

In the case of IC, proper alignment of ideologies between the four key roles discussed in the DOT Regulatory Environment section provides a critical window of opportunity. The key roles of exploring, pioneering, gatekeeping, and leadership represent the minimum support structure necessary to pass new specification. The problem and policy streams already pose a tight coupling in this industry. A political alignment is necessary because policy changes require individuals to place themselves at risk, which they will not do without an understanding that the necessary support exists.

Of particular note in this network is the role of policy pioneers, who again are the ones that exert their influence to formulate the use of IC on a project. These individuals' reputations are directly attached to the projects they work on, and we must stress the overwhelming sentiment of respondents that failure carries a much higher consequence than success. Study participants listed the most common position of IC policy pioneers to be in state DOT district offices, i.e. the ones in charge of executing the majority of highway construction and maintenance projects. The second most common position of policy pioneers for IC is engineers within general contracting firms. Policy pioneers can exist elsewhere within the DOT, including engineers overseeing special projects from a position in the DOT central office. Participants noted that in very rare cases, pioneers have been positioned in the FHWA and AGC, using political power to initiate policy reform.

Upon the opening of this politically activated policy window, it appears that the tight coupling of the policy and problem streams facilitated a rise of IC to the decision agenda. Field demonstrations provide this tight coupling and are used as a networking event where problem and policy streams are simultaneously illuminated to political participants. As one participant put it, "we had all the right people at the field demonstration. The ones [district engineers] that were interested were easily able to identify potential projects in their districts."

Interestingly, our study only found contractors as policy pioneers on Design-Build (DB) projects. DB is a contracting structure in which the contractor is responsible for designing the structure. This is in contrast to the more typical Design-Bid-Build (DBB), in which the design phase is conducted by another entity. Two aspects of contracting appear to make DB better suited for supporting contractor initiated innovation: award criteria and control over design. The awarding criteria for DBB projects is typically lowest cost, while DB often supports best-value evaluation. DB provides the opportunity for contractors to consider innovations like IC that provide added value at an added cost. Another advantage of DB is that it allows contractors to discuss novel ideas early in the design phase. This is critical for technologies like IC that impact the design of the structure through soil selection and placement guidelines. The DB structure expands the window of opportunity for contractors to act as policy pioneers and bring an issue to the policy agenda.

The upfront investment for a technology is also a critical factor in understanding the formation of viable policy windows. Multiple interviewees provided non-IC examples where contractors could often be more effective at implementing innovations at municipalities because there was a closer working relationship and less bureaucracy. However, innovations with a high initial investment, such as IC, would be unlikely candidates to appear first on small municipal projects. Implementation of these types of technologies therefore depends more heavily on the innovation-based policy reform practices of state DOTs discussed in this paper.

6.4 Discussion

U.S. DOTs face a tough road ahead with constricting budgets and deteriorating highway conditions. Technological innovation is one means to alleviate this pressure, but the highway construction industry is notoriously slow at adopting new innovations. In this paper, we have sought to understand this innovation adoption process through Kingdon's theory of agenda setting and in the context of responsible innovation adoption processes. Our intention was twofold: (1) to provide insights into DOT policy reformation processes that we hope the industry will find useful in streamlining adoption of future innovations, and (2) to use this case study to contribute to the body of literature applying Kingdon's theory to the dynamics of various policy setting environments. This paper highlights four critical points regarding the application of Kingdon's theory to the adoption of innovations in the highway construction industry, specifically in the case of IC.

First, perhaps the most critical factor driving innovation adoption is the personal character of the people involved; their risk tolerance and perseverance are what give an innovation a chance at adoption. This research identifies the importance that personal character plays in a general sense, i.e., with respect to an innate tendency of personnel in this industry to either accept or reject innovation. Coincident with the literature, personal character is duly noted as one of the primary motivators for policy entrepreneurs. Policy entrepreneurs in this industry appear to be of Kindon's values promotion category, exemplifying an ethical motivation to responsibly serve society with the most progressive and appropriate technological innovations. Analysis revealed that institutional incentives for supporting innovations were not the main drivers for adoption, and there exists a conservative culture that hinders change.

Second, the highly technical nature of DOT policy making creates a challenging environment for including societal feedback and complicates interpretation of Kingdon's original presentation of his framework. This technical policy environment results in a need to redefine ideological affiliations as a proclivity towards innovation, i.e., rather than political affiliation. Further, this environment promotes a reversal of Kingdon's idea that political appointees catalyze change, as opposed to civil servants. Instead it is clear that it is the career civil servants that need to be the movers and shakers for regulatory reform. In future applications of Kingdon's framework, the role of bureaucrats in agenda setting should be evaluated on a case-by-case basis. Third, we expand upon Kingdon's idea of policy entrepreneurs so far as to define four roles these entrepreneurs fulfill in the DOT technology adoption process, namely the policy explorers, policy pioneers, gatekeepers, and leaders. The identification of these roles may assist fellow policy entrepreneurs in advancing technology adoption through the alignment of these individuals. We suggest that future research investigates whether these roles generalize to other institutions.

Finally, rather than the convergence of the three streams at a single policy window as Kingdon suggests, we identify a tight coupling between the problem and policy streams that precedes IC reaching the decision agenda. This is in agreement with other literature that draws into question the dynamics of Kingdon's stream-coupling[88]. Kingdon's theory is, however, useful in addressing the prevailing path by which IC policy is ultimately raised to the decision agenda via a politically activated window. Stream coupling plays a defining role in policies reaching the decision agenda. In the case of IC, field demonstrations appear to be an effective mechanism for coupling streams suggesting that these efforts are crucial to innovation adoption.

It is our hope that these contributions will provide tools that help manage responsible research and innovation adoption in the highway construction industry.

Chapter 7—Conclusion

This thesis presents the development and evaluation of three material characterization methods for new strain gage based devices. These methods seek to characterize soil compaction, elastic modulus, and plasticity parameters. The material characterization devices investigated here make novel contributions to the in-situ measurement community, and have the potential to provide critical monitoring capabilities to enable intelligent systems. In addition to technical research, this thesis investigates public policy dimensions concerning adoption of these in-situ devices, e.g., in the US highway construction industry.

A strain gage instrumented pad was developed to explore the concept of real-time continuous monitoring of soil behavior during static pad foot soil compaction. The pad was instrumented with strain gages (i.e., as discussed in Chapter 3 and shown again here in FIG. 120), the locations of which were chosen through FE modeling of various loading configurations that simulated a range of soil conditions. Gage locations along the bottom pad face were most sensitive to varying contact stresses (and therefore varying soil conditions). Gage locations oriented vertically on the sidewall of the pad provide good indicators of con tact force. The instrumented pad was tested in the lab to establish a soil specific correlation factor between pad strain and contact force. Field testing, consisting of taking four test beds from a loose state to a compacted state, was conducted with the same instrumented pad and soil type. Results from field-testing indicated a positive correlation between test bed soil density, which is indicative of compaction level, and contact force measured by the instrumented pad. However, the pad was unable to directly estimate elastic modulus, and was unable to characterize different soil types, thereby requiring an empirical soil specific calibration procedure.

To investigate the capacity for strain gage based in-situ devices to provide mechanistic measurements (i.e., engineering parameters), the pad geometry was simplified to a plate to enable more robust analysis and testing. An instrumented plate was developed, and a method for estimating elastic modulus of an half-space from plate strain measurements was developed. In the geoconstruction however, soils do not behave as an ideal elastic material. Instead they elicit contact behavior that depends in part on their plasticity. In an effort to prevent the necessity of soil specific calibrations, thereby enabling a fully autonomous monitoring device, the ability of a strain gage instrumented plate to estimate plasticity parameters was investigated. It was found that plate strains were sensitive to uniaxial compressive yield stress, and so a method for estimating this plasticity parameter was developed.

Instead of testing on soil, the instrumented plates were tested on EPS geo-foam, which is a more reliable and well-characterized elasto-plastic material. The elasto-plastic constitutive model for EPS geo-foam was defined. EPS geo-foam is a cellular solid that generally exhibits linear, elastic, isotropic, homogenous behavior in the elastic region and can be described by the Crushable Foam constitutive model in the plastic region. Constitutive parameters were obtained experimentally for four foams: EPS12, EPS22, EPS29A, and EPS29B. Uniaxial compressive tests provided the elastic modulus, uniaxial compressive yield stress, and the hardening curve. Hydrostatic compression gave the hydrostatic compressive yield stress, $p_c^0$, which is necessary to calculate the compressive yield stress ratio, k. Chapters 4 and 5 then sought to determine these parameters independently with strain gage instrumented plates.

A strain gage instrumented plate was developed, and a method for predicting elastic modulus of EPS geo-foam from strain gage readings is evaluated. The instrumented plate included a strip of ten gages oriented in the radial direction. An inverse model was developed to estimate the elastic modulus of a half-space from plate strains based on two forward models: an analytical model and a FE model.

Laboratory tests were conducted to determine the efficacy of the elastic inverse model. The instrumented plate was loaded onto EPS12, EPS22, EPS29A, and EPS29B, with two surface conditions: native and sanded. The experimental tests showed good repeatability in plate strain measurements within each test condition, but much higher strains in the sanded condition. An elastic modulus was predicted by fitting the strain gage results with the inverse model. The native surface tests showed much higher than expected modulus estimates (i.e., compared to uniaxial compression tests), while the sanded tests predicted modulus values close to anticipated values. It is thought that the increased modulus prediction of native tests are due to a layer of stiff material on the outer surface of the EPS geo-foam created during manufacturing and hot wire cutting. Elastic modulus predictions were found to vary with applied force. A method was developed for extracting a representative elastic modulus based on the minimum predicted value of the inverse model. For sanded surface tests, the analytical-based inverse model agreed well with the elastic modulus obtained from uniaxial testing, while the FE model tended to under-predict the elastic modulus.

To expand the capabilities of the in-situ instrumented plate device, the applicability to plasticity parameters estimation was investigated. An FE model was developed to predict plate strains generated during loading onto an elastoplastic half-space of EPS geo-foam. An analysis investigated sensitivity of plate strains to uniaxial compressive yield stress revealed and compressive yield stress ratio, and revealed that that plate strains are sensitive to the uniaxial yield stress, but relatively insensitive to the compressive yield stress ratio. Therefore, an inverse model was developed to predict uniaxial compressive yield stress from plate strains based on the FE forward model. The inverse model was able to predict uniaxial compressive yield stress for forces up to 225 N for EPS12 and 800 N for EPS29B, and was limited from higher forces by mesh distortion caused at the edge of the plate.

The inverse model for uniaxial compressive yield stress was tested experimentally by loading the instrumented plate onto EPS12 and EPS29B. The force-displacement curves from the plate loading show the foam yielding at 225 N for EPS12 and 800 N for EPS29B, at which point the average pressure under the plate is similar to the uniaxial compressive yield stress. Force-strain curves for the strain gages also showed a bend at these forces, indicating their sensitivity to yield behavior. The inverse model was applied to plate strains to predict uniaxial compressive yield stress from experimental results. At forces above 200 N for EPS12 and 750 N for EPS29B, the values of uniaxial compressive yield stress predicted by the inverse model increased with applied force. At the highest forces accommodated by the inverse model (i.e., 225 N for EPS12 and 800 N for EPS29B), predictions of uniaxial compressive yield stress approached the values obtained from uniaxial compression tests in Chapter 2, but did not quite reach them. It is thought that the inverse model needs to be capable of reaching higher forces to provide more accurate predictions of uniaxial yield stress.

Findings from the instrumented plate methods stand to improve the capacity for mechanistic soil compaction monitoring, either with the instrumented pad, or with a geometrically different machine integrated device. The approach of the elastic inverse model developed for the instrumented plate can be applied to develop an elastic inverse model for the instrumented plate. A finite element model describing the pad-soil interaction could be developed as the forward model, and allow estimation of elastic modulus from pad strains. However, soil does not exhibit ideal elastic behavior even when fully compacted, thus greatly limiting the practical use of such an elastic inverse model for an instrumented pad. Soil plasticity must be considered. The approach of the inverse model for uniaxial compressive yield strength developed here may be applied to further characterize the soil and improve the potential for practical application. It should be noted that, while only uniaxial compressive yield strength was investigated, it is possible this inverse approach may be useful for other plasticity parameters in other constitutive models. The forward model would need more development for the plasticity parameter estimation to be effective. In particular, the forward model would have to produce accurate results at higher forces. Upon achieving an effective forward model, it is possible that instrumented pad strains would be able to characterize a soil's elastic and plastic constitutive parameters and provide a fully automated mechanistic monitoring device for soil compaction.

The instrumented pad is not the only possible device geometry that would facilitate mechanistic monitoring of soil compaction. For example, considerable work has already been conducted on instrumented plates in this thesis. It is feasible to implement instrumented plates as the monitoring devices by having them replace one or more pads on a pad foot roller. This presents a much simpler geometry and loading scenario, which would facilitate a more robust inverse model. Still, more work is needed to improve the plasticity parameter identification model. However, with a robust forward model, the potential for mechanistic monitoring of soil compaction is entirely possible.

Considering that each in-situ device developed in this thesis has applications in the geo construction industry, it is valuable to consider the policy dimensions that influence innovation adoption in this industry. An investigation was undertaken to examine the pathways and barriers to innovation adoption in the US highway construction industry through a case study on intelligent compaction. Several industry professionals were interviewed, and the results were analyzed through the lens of Kingdon's theory on policy agenda setting. Findings emphasize the importance of personal character of those surround the innovation adoption process. Additionally, four key roles are identified that create the pathway to innovation adoption, including policy explorers, policy pioneers, gatekeepers, and leaders. The coordination of these roles at a DOT provides an environment that facilitates adoption. Lastly, the importance of field demonstrations in the adoption process is highlighted. In Kingdon's terms, these field demonstrations provide an opportunity to couple the policy and problem streams, and thrust the issue of adoption onto the decision agenda.

7.1 Recommendations for Future Work

The scientific community would benefit from future work on these in-situ devices and policy topic. The instrumented plate research in Chapters 4 and 5 is ripe for application to the strain gage instrumented pad. By developing a sufficiently accurate forward model of pad-soil interaction, an inverse model that estimates soil elastic modulus, as well as other constitutive parameters, may be developed. The in-situ estimation of these parameters will enable a tighter coupling between engineering design and analysis, which uses these constitutive parameters, and construction. A more advanced forward model would be useful in the plasticity parameter estimation method. If a model that could reach higher applied vertical forces was used, there may be greater capacity for a strain gage instrumented plate to estimate plasticity parameters. It is conceivable that even the compressive yield stress ratio, k, that was found to be insensitive to plate strains at the forces modeled, may become considerably more sensitive to plate strains at higher forces.

Future work on the policy topic that may benefit the geo-construction industry includes more in-depth analysis into the distribution of ideological affiliations (i.e., innovation proclivity) within various departments, and their perceived level of innovation adoption. Hiring and promotion practices concerning innovation proclivity presents an area rich for investigation. Additionally, the relationship between the District Engineers and the central office concerning innovation adoption would clearly benefit from further characterization, as this appears to be a particularly important link in the pathway to innovation adoption.

The combination of technical and policy oriented research presented in this thesis provides technical innovations to advance in-situ testing, and therefore opportunities for intelligent systems, in addition to discussing pathways and barriers to adoption of these innovations. Hopefully, these contributions can improve the capabilities and adoption of future intelligent systems.

I claim:

1. A tool for estimating mechanical properties of a material comprising:
a plate configured to receive force, wherein the plate is a pad on a pad foot roller;
one or more measuring devices connected to the plate for measuring the force applied;
one or more measuring devices connected to the plate for measuring mechanical strain in the plate; and
a computing device for receiving the force and strain measurements and describing a mechanical interaction between the plate and material.

2. The tool of claim 1, wherein the plate is circular and defines a planar surface.

3. The tool of claim 1, wherein the plate is flexible and substantially thin, as to produce measurable mechanical strain.

4. The tool of claim 1, wherein the one or more measuring devices for measuring applied force is an electronic load cell.

5. The tool of claim 1, wherein the one or more measuring devices for measuring strain is selected from an electrical resistance strain gage, fiber-bragg grating, photo-stress, and combinations thereof, wherein the devices are mounted to a surface of the plate to provide measurements of plate strain during loading.

6. A method for estimating mechanical properties of a material comprising:
positioning a plate on a material, wherein the plate is a pad on a pad foot roller;
applying a load to the plate to create an applied force;
measuring the applied force with one or more force measuring devices;
measuring mechanical strains of the plate with one or more strain measuring devices;
modeling and describing a mechanical interaction between the plate and the material; and thereby
estimating mechanical material properties of the material.

7. The method of claim 6, wherein modeling uses an analytical model that predicts plate strains as a function of applied force, and wherein a half-space elastic modulus is used to estimate elastic modulus from measured plate strains and applied force.

8. The method of claim 6, wherein modeling uses a numerical model that predicts plate strains as a function of applied force, and wherein a half-space elastic modulus is used to estimate elastic modulus from measured plate strains and applied force.

9. The method of claim 6, wherein modeling uses a numerical model that predicts plate strains as a function of applied force, and wherein a half-space yield strength is used to estimate yield strength from measured plate strains and applied force.

10. The method of claim 6, wherein modeling uses a numerical model that predicts plate strains as a function of applied force, and wherein a half-space plastic hardening curve is used to estimate plastic hardening curve from measured plate strains and applied force.

11. The method of claim 6, wherein the force is applied force can be applied at the center of the plate and/or around the edge of the plate.

12. The method of claim 6, wherein the force is applied in a direction selected from vertically, diagonally, horizontally, and combinations thereof.

13. The method of claim 6, wherein the plate is circular and defines a planar surface.

14. The method of claim 6, wherein the plate is flexible and substantially thin, as to produce measurable mechanical strain.

15. The method of claim 6, wherein the measuring device for measuring strain is selected from an electrical resistance strain gage, fiber-bragg grating, photo-stress, and combinations thereof, wherein the devices are mounted to a surface of the plate to provide measurements of plate strain during loading.

16. The method of claim 6, wherein the measuring device for measuring applied force is an electronic load cell.

* * * * *